US005891870A

United States Patent [19]
Driedger et al.

[11] Patent Number: 5,891,870
[45] Date of Patent: *Apr. 6, 1999

[54] PROTEIN KINASE C MODULATORS Q

[75] Inventors: Paul E. Driedger, Boston; James Quick, Lexington, both of Mass.

[73] Assignee: Procyon Pharmaceuticals, Inc., Woburn, Mass.

[*] Notice: The term of this patent shall not extend beyond the expiration date of Pat. No. 5,716,968.

[21] Appl. No.: 472,871

[22] Filed: Jun. 7, 1995

Related U.S. Application Data

[63] Continuation-in-part of Ser. No. 664,396, Mar. 4, 1991, and Ser. No. 120,643, Sep. 13, 1993, Pat. No. 5,643,948, which is a continuation-in-part of Ser. No. 664,397, Mar. 4, 1991, abandoned, said Ser. No. 664,396, is a continuation-in-part of Ser. No. 537,885, Jun. 14, 1990, abandoned, Ser. No. 559,296, Jul. 30, 1990, abandoned, and Ser. No. 559,701, Jul. 30, 1990, Pat. No. 5,145,842, which is a continuation-in-part of Ser. No. 322,851, Mar. 13, 1989, abandoned, which is a division of Ser. No. 61,299, Jun. 10, 1987, abandoned, said Ser. No. 559,296, is a division of Ser. No. 322,881, Mar. 13, 1989, abandoned, which is a division of Ser. No. 61,299, Jun. 10, 1987, abandoned, said Ser. No. 537,885, is a continuation-in-part of Ser. No. 61,299, Jun. 10, 1987, abandoned, which is a continuation-in-part of Ser. No. 872,812, Jun. 11, 1986, abandoned.

[51] Int. Cl.⁶ ............... A61K 31/395; C07D 245/06
[52] U.S. Cl. .................. 514/183; 514/63; 514/410; 540/452; 540/460; 560/162; 560/249
[58] Field of Search ................. 560/249, 162; 514/63, 183, 410; 540/452, 460

[56] References Cited

U.S. PATENT DOCUMENTS

| | | | |
|---|---|---|---|
| 4,376,821 | 3/1983 | Braude | 435/68 |
| 4,376,822 | 3/1983 | Braude | 435/68 |
| 4,401,756 | 8/1983 | Gillis | 435/68 |
| 4,460,685 | 7/1984 | Vilcek et al. | 435/70 |
| 4,560,774 | 12/1985 | Petit et al. | 549/267 |
| 4,716,179 | 12/1987 | Hecker et al. | 514/691 |
| 5,089,517 | 2/1992 | Choi et al. | 514/411 |
| 5,145,842 | 9/1992 | Driedger et al. | 514/63 |
| 5,643,948 | 7/1997 | Driedger et al. | 514/533 |
| 5,716,968 | 2/1988 | Driedger et al. | 514/323 |
| 5,750,568 | 5/1998 | Driedger et al. | 514/533 |

FOREIGN PATENT DOCUMENTS

| | | | |
|---|---|---|---|
| 87/07599 | 12/1987 | WIPO | A61K 31/00 |

OTHER PUBLICATIONS

Sakata, K. et al., "Structure and Stereochemistry of Huratoxin, A Piscicidal Constituent of *Hura crepitans*," *Tetrahedron Letters* 16: 1141–1144 (1971).

Kupchan, S. et al., "Gnididin, Gniditrin, and Gnidicin, Novel Potent Antileukemic Diterpenoid Esters from *Gnidia lamprantha*," *JACS* 97: 672–673 (1975).

Kupchan, S. et al., "Gnidimacrin and Gnidimacrin 20–Palmitate, Novel Macrocyclic Antileukemic Diterpenoid Esters from *Gnidia subcordata*," *JACS* 98: 5719–5720 (1976).

Kupchan, S.M. and Baxter, R.L., "Mezerein: Antileukemic Principle Isolated from *Daphne mezereum L.*," *Science* 187: 652–653 (Feb. 21, 1975).

Stout, G. et al., "The Isolation and Structure of Daphnetoxin, The Poisonous Principle of Daphne Species," *JACS* 92(4) : 1070–1071 (Feb. 25, 1970).

Coetzer, J. et al., "The Isolation of 12–Hydroxy–Daphnetoxin, A Degradation Product of a Constituent of *Lasiosiphon burchellii*," *J. South Afr. Chem. Inst.* 24: 241–243 (1971).

Fürstenberger, G. et al., "New Highly Irritant Euphorbia Factors from Latex of *Euphorbia tirucalli L.*," *Experientia* 33: 986–988 (Feb. 15, 1977).

Thielmann, H.W. and Hecker, E., "Die Flaschensträger Reaktion," *Liebigs Ann. Chem.* 728: 158–183 (1969).

Thielmann, H. –W. and Hecker, E., "Beziehungen zwischen der Struktur von Phorbolderivaten und ihren entzündlichen . . . " In: C.G. Schmidt and O. Wetter (eds.), *Forschritte der Krebsforschung* vol. VII, pp. 171–179, NY; Schattauer (1969).

Hecker, E., "Structure–Activity Relationships in Diterpene Esters Irritant and Cocarcinogenic to Mouse Skin," In:T.J. Slaga, A. Sivak and R.K. Boutwell (eds.), *Carcinogenesis 2. Mechanisms of Tumor Promotion and Cocarcinogenesis*: 11–48, NY; Raven Press (1978).

Schmidt, R. and Evans, F., "Skin Irritant Effects of Esters of Phorbol and Related Polyols," *Arch. Toxicol.* 44: 279–289 (1980).

Harada, H. et al., "The X–Ray Structure Determination of Dihydroteleocidin B Monobromoacetate," *Bull. Chem. Soc. Japan* 39: 1773–1775 (1966).

de Laszlo, S. et al., "Synthetic Approaches to the Teleocidin–Related Tumour Promoters: A Total Synthesis of (±) — Indolactam V.," *J. Chem. Soc., Chem. Commun.* 344–346 (1986).

Adolf, W. et al., "Structure–Activity Relations of Polyfunctional Diterpenes of the Daphnane Type I. Revised Structure for Resiniferatoxin and Structure–Activity Relations of Resiniferonol and Some of Its Esters" *J. Natural Prod.* 45(3): 347–354 (1982).

Adolf, W. and Hecker, E., "On the Active Principles of the Thymelaeaceae" *J. Med. Plant Res.* 45: 177–182 (1982).

Seip E. and Hecker, E., "Skin Irritant Ingenol Esters from *Euphorbia esula*,"*J. Med. Plant Res.* 46: 215–218 (1982).

Opferkuch, H. et al., "On the Chemistry of Ingenol, I, Ingenol and Some of Its Derivatives," *Z. Naturforsch* 36: 878–887 (1981).

Sorg, B. and Hecker, E., "On the Chemistry of Ingenol, II[1], Esters of Ingenol and $\Delta^{7,8}$–Isoingenols," *Z. Naturforsch* 37: 748–756 (1982).

(List continued on next page.)

*Primary Examiner*—Richard L. Raymond
*Attorney, Agent, or Firm*—Hamilton, Brook, Smith & Reynolds, P.C.

[57] ABSTRACT

Compositions with anti-inflammatory and other activitites are disclosed. The compositions are derived from phorboids of the diterpene- and benzolactam-classes.

39 Claims, No Drawings

OTHER PUBLICATIONS

Sorg, B. and Hecker, E., "On the Chemistry of Ingenol, III, Synthesis of 3–deoxy–3–oxoingenol, Some 5–esters and of Ethers and Acetals of Ingenol," *Z. Naturforsch* 37: 1640–1647 (1982).

Jeffrey, A. and Liskamp, R., "Computer–Assisted Molecular Modeling of Tumor Promoters: Rationale for the Activity of Phorbol Esters, Teleocidin B, and Aplysiatoxin," *Proc. Natl. Acad. Sci. USA* 83: 241–245 (Jan. 1986).

Nishizuka, Y., "The Role of Protein Kinase C in Cell Surface Signal Transduction and Tumour Promotion," *Nature* 308: 693–698 (Apr. 19, 1984).

Liskamp, R. et al., "Cellular Uptake and Localization of Fluorescent Derivatives of Phorbol Ester Tumor Promoters," *BBRC* 131(2): 920–927 (Sep. 16, 1985).

Driedger, P. and Blumberg, P., "Quantitative Correlation Between in Vitro and in Vivo Activities of Phorbol Esters," *Cancer Research* 39: 714–719 (1979).

Driedger, P. and Blumberg, P., "The Effect of Phorbol Diesters on Chicken Embryo Fibroblasts," *Cancer Research* 37: 3257–3265 (1977).

Dunn, J.A. and Blumberg, P.M., "Specific Binding of [20–$^3$H]12–Deoxyphorbol 13–Isobutyrate to Phorbol Ester Receptor Subclasses in Mouse Skin Particulate Preparations," *Cancer Res.* 43:4632–4637 (1983).

Sugimura. T., "Synthesis of Optically Active Teleocidin Derivatives. Absolute Configuration of Telecidin B and Olivoretin A," *Gann* 73: 499–507 (1982).

Endo, Y. et al. "Synthesis of Optically Active Teleocidin Derivatives. Absolute Configuration of Teleocidin B and Olivoretin A," *Chem. Pharm. Bull.* 32: 358–361 (1984).

Hecker, E. and Schmidt, R., "Phorbolesters –The Irritants and Cocarcinogens of Croton Tiglium L.," *Fortschritte D. Chemie Organischer Naturstoffe* 31: 377–467 (1974).

Evans, F.J. and Soper, C.J., "The Tigliane, Daphnane and Ingenane Diterpenes, Their Chemistry, Distribution and Biological Activities. A Review," *Lloydia* 41 (3) : 193–233 (1978).

Schmidt, R. and Hecker, E., "Untersuchungen über die Beziehungen Zwischen Struktur und Wirkung von Phorbolestern," *In: Lettré* and G. Wagner (eds.), *Aktuelle Probleme aus dem Gebiet der Cancerologie* III, Third Heidelberg Symposium, pp. 98–108. Berlin: Springer Verlag, 1971.

Uemura, D. et al., "Isolation and Structures of 20–Deoxyingenol New Diterpene Derivatives and Ingenol Derivative Obtained from *kansui*," *Tetahedron Letters* 29: 2527–2528 (1974).

Uemora, D. et al., "New Diterpene, 13–Oxyingenol, Derivative Isolated from *Euphorbia Kansui* Liou," *Tetrahedron Letters* 29: 2529–2532 (1974).

Hirata, Y., "Toxic Substances of *Euphorbiaceae*," *Pure and Appl. Chem.* 41: 175–199 (1975).

Kupchan, S. et al. "Antileukemic Principles Isolated form *Euphorbiaceae*Plants," *Science* 19: 571–572 (1976).

Evans, F.J., The Irritant Toxins of Blue Euphorbia (*Euphorbia Coerulescens HAW.*) *Toxicon* 16: 51–57 (1978).

Ganong, B., et al., "Specificity and Mechanism of Protein Kinase C Activation by sn–1,2–diacylglycerols," *Proc. Natl. Acad. Sci. USA* 83: 1184–1188 (1986).

Schmidt, R. and Hecker, E., "Simple Phorbol Esters as Inhibitors of Tumor Promotion by TPA in Mouse Skin," *Carcinogenesis* 7: 57–63 (1982).

Horiuchi, T. et al., "Studies on Olivoretins Indicate a Requirement for a Free Hydroxyl Group for Teleocidin B Activity," *Gann* 75: 837–840 (1984).

Irie, K. et al., "Structure–Activity Relationship in the Induction of Epstein–Barr Virus by Teleocidin Derivatives," *Int. J. Cancer* 36: 485–488 (1985).

Wender, P. et al., "Analysis of the Phorbol Ester Pharmacophore on Protein Kinase C As a Guide to the Rational Design of New Classes of Analogs," *Proc. Natl. Acad. Sci. USA* 83: 4214–4218 (Jun. 1986).

Irie, K. et al., "Epstein–Barr Virus Early Antigen Inducing Activity of 14–0–Derivatives of (–)–Indolactam V," *Agric. Biol. Chem.* 49(5) : 1441–1446 (1985).

Evans, F.J., "Phorbol: Its Esters and Derivatives," In: F.J. Evans (ed.), *Naturally Occuring Phorbol Esters*, pp. 171–215. CRC Press (1986).

Schmidt, R., "The Daphnane Polyol Esters"In: F.J. Evans (ed.), *Naturally Occuring Phorbol Esters*, pp. 217–243. Boca Raton: CRC Press (1986).

Schmidt, R., "The Ingenane Polyol Esters"*In:* F.J. Evans (ed.), *Naturally Occuring Phorbol Esters* pp. 245–269. Boca Raton: CRC Press, 1986.

Aldaz, C.M. et al., "Cutaneous Changes During Prolonged Application of 12–0–tetradecanoylphorbol 13–acetate on Mouse Skin and Residual Effects after Cessation of Treatment," *Cancer Res.* 45(6) : 2753–2759 (1985) (Abstract No. 103: 136798 CA).

Baxter, C.S. et al., "Interaction of Tumor–Promoting Agents with Immunofunctional Cells in vitro and in vivo," *IARC Sci. Publ.* pp. 305–317 (1984) (Abstract No. 103: 136812).

Marshall, G.T. et al., "Short–Chain Phorbol Ester Constituents of Croton Oil," *JAOCS,* 61(7) : 1220–1225 (Jul. 1984).

Ohno, M. et al., "Desiged Molecules Reproducing the Two Conformations of Teleocidins," *Tetrahedron Letters,* 34(50) : 8119–8122 (1993).

Kozikowski, A.P. et al., "Synthesis, Molecular Modeling, 2–D NMR, and Biological Evaluation of ILV Mimics as Potential Modulators of Protein Kinase C," *J. Am. Chem. Soc.,* 115(10): 3957–3965 (1993).

Paquette, L.A. et al., "Ingenane Synthetic Studies. An Expedient Approach to Highly Oxygenated ABS Subunits of Ingenol via Reductive Dialkylative Annulation and α,β–Epoxy Ketone Photoisomerization" *J. Am. Chem. Soc.* 106: 1446–1454 (1984).

Ross, R.J. et al., "Ingenane Synthetic Studies. Stereocontrolled Introduction of All Oxygenated and Unsaturated Centers in an Ingenol Prototype," *J. Am. Chem. Soc.* 52: 5497–5498 (1987).

Uemura, D. et al., "Isolation and Structures of Irritant Substances Obtained From Euphorbia Species (Euphorbiaceae)," *Tetrahedron Letters* 11 pp. 881–884 (1973).

PROTEIN KINASE C MODULATORS Q

RELATED APPLICATIONS

This application is:

(i) a continuation-in-part of application Ser. No. 07/664,396, filed Mar. 4, 1991, which is a continuation-in-part of:

(a) application Ser. No. 07/537,885, filed Jun. 14, 1990 (abandoned), which is a file-wrapper continuation-in-part of application Ser. No. 07/061,299, filed Jun. 10, 1987 (abandoned), which is a continuation-in-part of application Ser. No. 06/872,812, filed Jun. 11, 1986 (abandoned); and (b) application Ser. No. 07/559,296, filed Jul. 30, 1990 (abandoned) and application Ser. No. 07/559,701, filed Jul. 30, 1990 (now U.S. Pat. No. 5,145,842, issued Sep. 8, 1992), which are, respectively, a division and a continuation-in-part of application Ser. No. 07/322,881, filed Mar. 13, 1989 (abandoned), which is a division of application Ser. No. 07/061,299, filed Jun. 10, 1987 (abandoned); and (ii) a continuation-in-part of application Ser. No. 08/120,643, filed Sep. 13, 1993, (now U.S. Pat. No. 5,643,948) which is a continuation-in-part of application Ser. No. 07/664,397 filed Mar. 4, 1991 (abandoned);

all of which are herein incorporated by reference in their entirety.

BACKGROUND

Protein kinase C (also known as "calcium/phospholipid-dependent protein kinase", "PKC" or "C-kinase") is a family of very closely related enzymes; one or more members of the protein kinase C family are found in nearly all animal tissues and animal cells that have been examined. The identity of protein kinase C is generally established by its ability to phosphorylate certain proteins when adenosine triphosphate and phospholipid cofactors are present, with greatly reduced activity when these cofactors are absent. Protein kinase C is believed to phosphorylate only serine and/or threonine residues in the proteins that are substrates for protein kinase C. Additionally, some forms of protein kinase C require the presence of calcium ions for maximal activity.

Protein kinase C activity is also substantially stimulated by certain 1,2-sn-diacylglycerols that bind specifically and stoichiometrically to a recognition site or sites on the enzyme. This site is called the diacylglycerol binding site, and it is located on the amino-terminal portion of protein kinase C, the so-called "regulatory domain". The carboxy-terminal portion of protein kinase C carries the site at which protein phosphorylation is effected, and this portion thus called the "kinase domain".

Thus, the rate at which various protein kinase C family members carry out their enzymatic phosphorylation of certain substrates can be markedly enhanced by the presence of the cofactors such as phospholipids, diacylglycerols and, for some protein kinase C family members, calcium ions. This stimulation of protein kinase C activity is referred to as protein kinase C "activation", and the activation of protein kinase C by the binding of diacylglycerols to the regulatory domain of protein kinase C is of particular importance in the normal and pathological functions of protein kinase C.

In contrast to the activation of protein kinase C, some chemical compounds have been shown, when added to protein kinase C enzyme assays, to reduce the rate at which protein kinase C phosphorylates its substrates; such compounds are referred to as protein kinase C "inhibitors" or, in some cases, "antagonists". In some circumstances, protein kinase C inhibitors are capable of inhibiting various cellular or tissue phenomena which are thought to be mediated by protein kinase C.

Activation of protein kinase C by diacylglycerols has been shown to be an important physiological event that mediates the actions of a wide variety of hormones, neurotransmitters, and other biological control factors such as histamine, vasopressin, α-adrenergic agonists, dopamine agonists, muscarinic cholinergic agonists, platelet activating factor, etc. [see Y. Nishizuka, Nature 308: 693–698 (1984) and Science 225: 1365–1370 (1984) for reviews].

The biological role of protein kinase C is also of great interest because of the discovery that certain very powerful tumor promoting chemicals activate this enzyme by binding specifically and with very high affinity to the diacylglycerol binding site on the enzyme. In addition to diacylglycerols, there are at present six other known classes of compounds that bind to this site: diterpenes such as the phorbol esters; indole alkaloids (indolactams) such as the telcocidins, lyngbyatoxin, and indolactam V; polyacetates such as the aplysiatoxins and oscillatoxins; certain derivatives of diaminobenzyl alcohol; macrocyclic lactones of the bryostatin class, and benzolactams such as (−)-BL-V8-310. The phorbol esters have long been known as powerful tumor promoters, the teleocidins and aplysiatoxins are now known to have this activity, and it appears likely that additional classes of compounds will be found to have the toxic and tumor promoting activities associated with the capability to bind to the diacylglycerol site of protein kinase C and thus activate the enzyme. Other toxicities of these agents when administered to animals include lung injury and profound changes in blood elements, such as leukopenia and neutropenia.

Representative examples of these seven classes of previously known protein kinase C-activating compounds, collectively referred to herein as "phorboids", are depicted below:

TYPICAL DITERPENE-TYPE PHORBOID AGONISTS
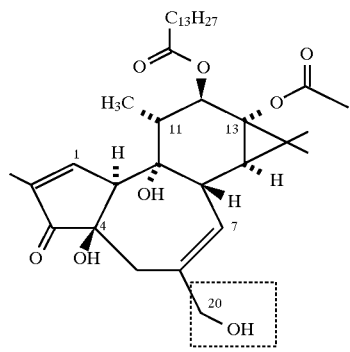
Phorbol 12-Myristate 13-Acetate (PMA)
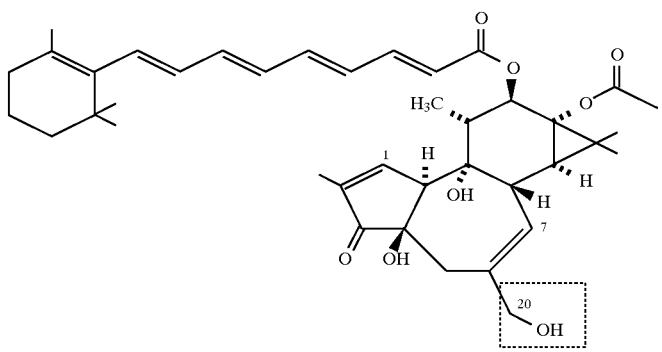
Phorbol 12-Retinoate 13-Acetate
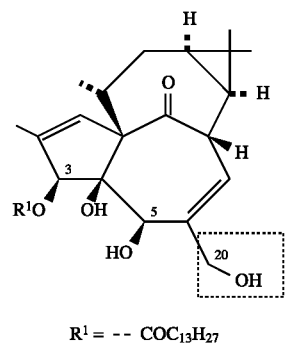
$R^1 =$ -- $COC_{13}H_{27}$
Ingenol 3-Tetradecanoate
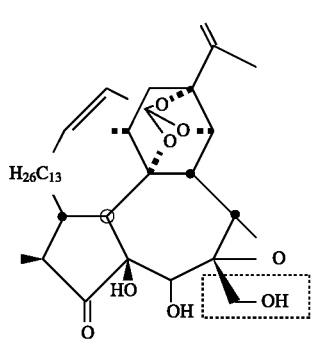
Synaptolepis Factor $K_1$
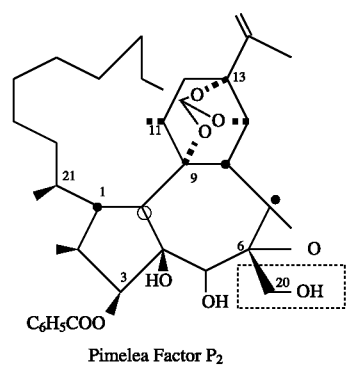
Pimelea Factor $P_2$
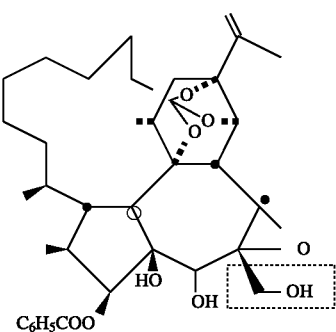
Daphnopsis Factor $R_6$ -continued
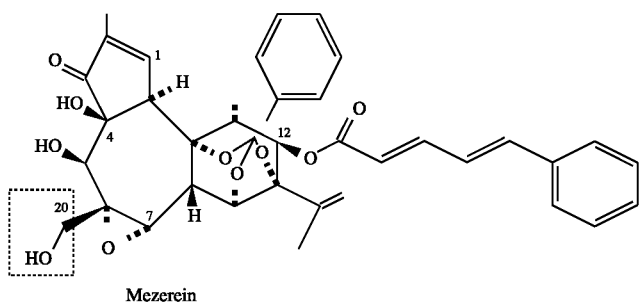
Mezerein
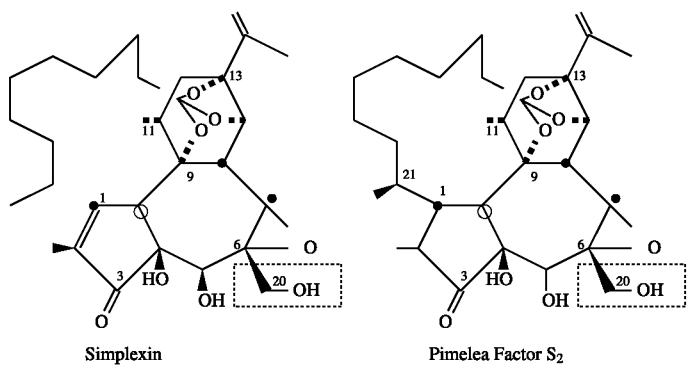
Simplexin  Pimelea Factor S₂
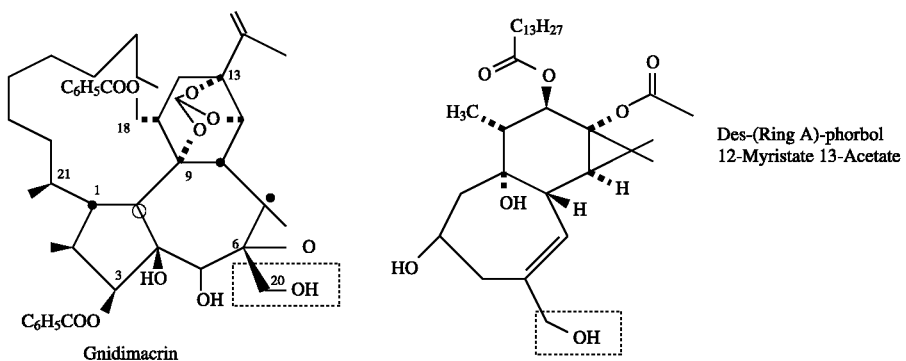
Gnidimacrin  Des-(Ring A)-phorbol 12-Myristate 13-Acetate
TYPICAL INDOLACTAM-TYPE PHORBOID AGONISTS
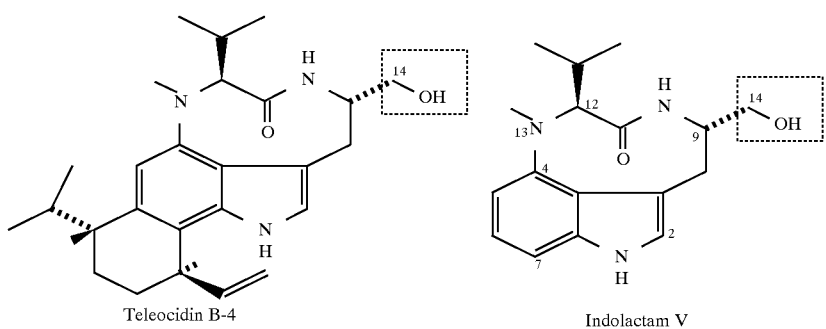
Teleocidin B-4  Indolactam V -continued
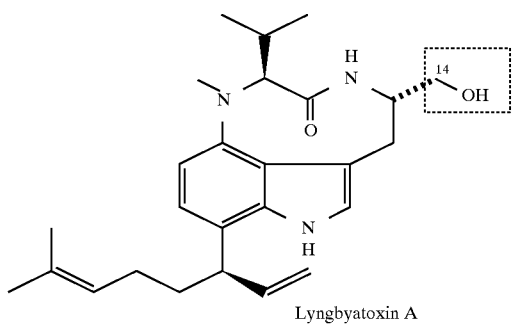
Lyngbyatoxin A
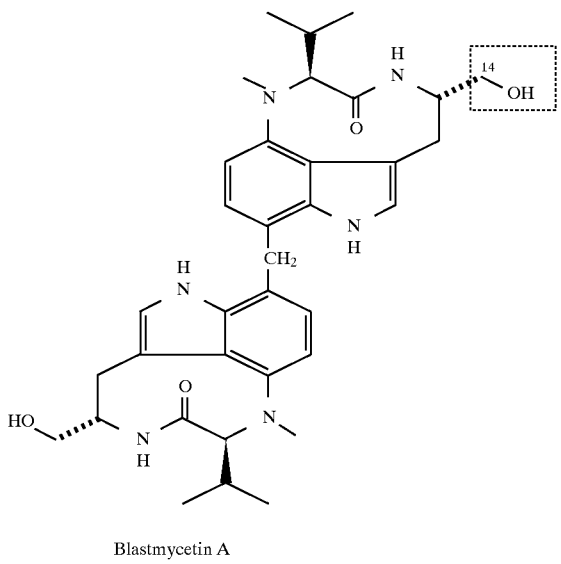
Blastmycetin A
TYPICAL DIAMINOBENZYL ALCOHOL-TYPE PHORBOID AGONISTS
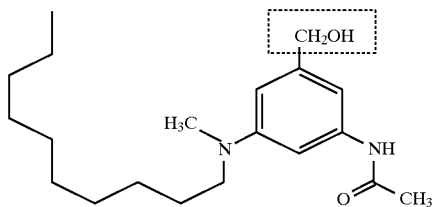
3-Acetylamino-5-(N-decyl-N-methylamino)benzyl Alcohol
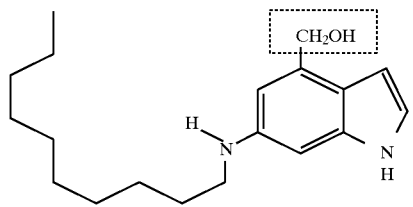
6-(N-Decylamino)-4-hydroxymethylindole
TYPICAL DIACYLGLYCEROL-TYPE PHORBOID AGONISTS
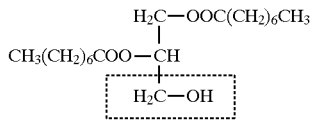
1,2-Dioctanoyl-sn-glycerol
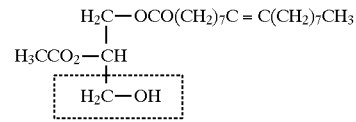
1-Oleoyl-2-acetyl-sn-glycerol
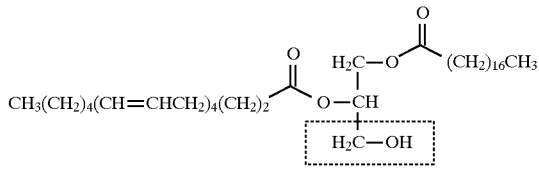
1-Stearoyl-2-arachidonyl-sn-glycerol
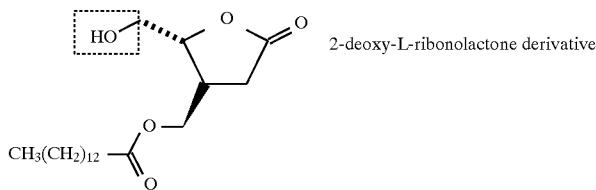
2-deoxy-L-ribonolactone derivative

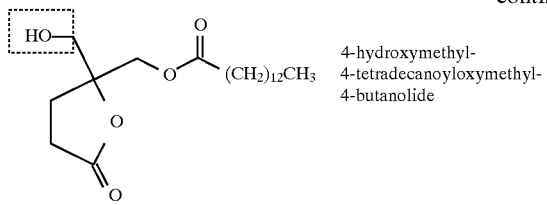
4-hydroxymethyl-4-tetradecanoyloxymethyl-4-butanolide
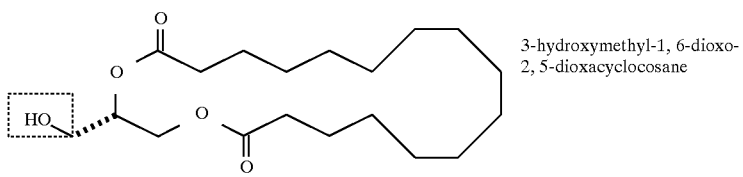
3-hydroxymethyl-1,6-dioxo-2,5-dioxacyclocosane
TYPICAL POLYACETATE-TYPE PHORBOID AGONISTS
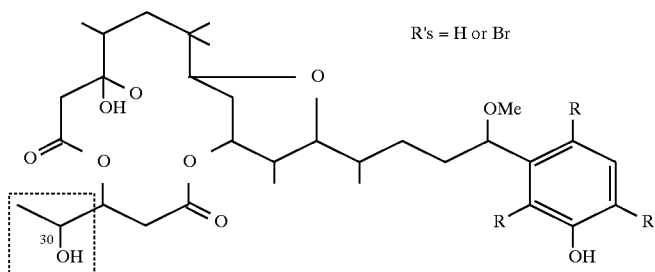
R's = H or Br
Aplysiatoxin and its debromo, bromo and dibromo derivatives
TYPICAL BRYOSTATIN-TYPE PHORBOID AGONISTS
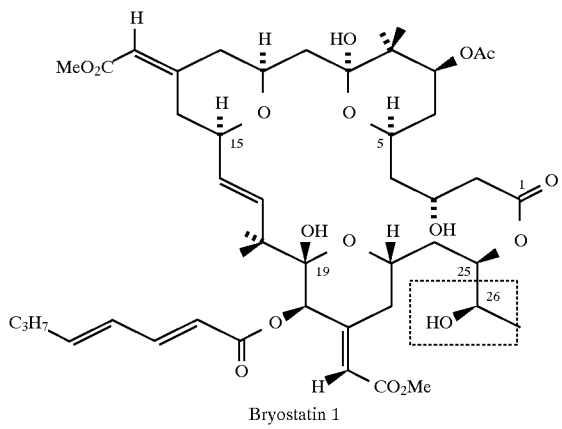
Bryostatin 1
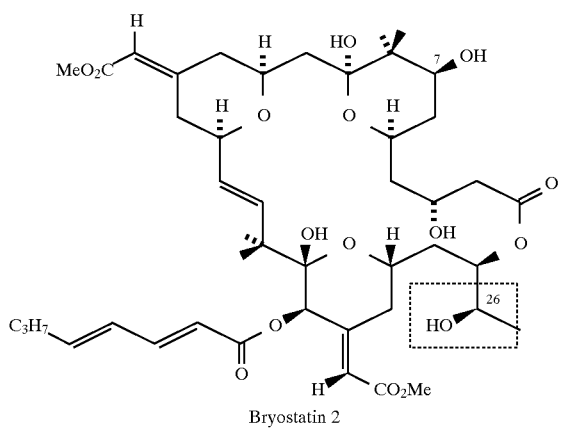
Bryostatin 2

TYPICAL BENZOLACTAM-TYPE PHORBOID AGONISTS

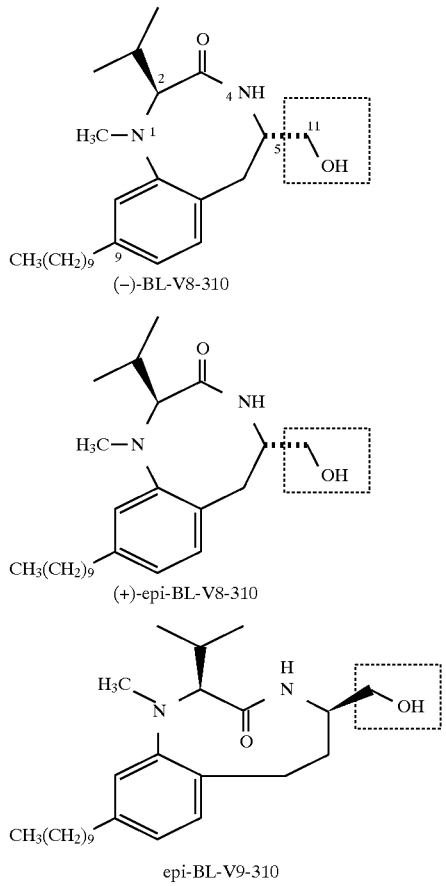

It can be seen that the phorboids depicted have diverse structural elements of both hydrophilic and hydrophobic nature, with one prominent exception, namely that each contains a hydroxymethyl or 1-hydroxyethyl group (indicated by the dashed-line boxes in each structure). In each case the phorboid depicted is among the most potent of its particular structural class, and among the seven classes the diterpenes, indolactams, polyacetates, bryostatins and benzolactams have members of especially high potency.

In addition to potent tumor promoting activity, these seven classes of compounds display a vast range of biological activities, as would be expected from the widespread distribution of their target enzyme. Some of these activities, like tumor promotion, indicate the involvement of protein kinase C in important normal or pathological processes in animals. Thus, the phorboids are potent skin inflammatory agents, cause smooth muscle contraction in several tissues, alter immune system function and can be used to cause a variety of other normal or pathological responses. Related disease states such as the development of cancer, the onset and/or maintenance of inflammatory disease, the role of vasoconstriction in hypertension, the role of bronchoconstriction in asthma, the life cycles of many pathogenic human viruses, and the role of cholinergic, adrenergic, and dopaminergic synapses in diseases of the central/peripheral nervous systems, may be mediated in vivo by the stimulation of protein kinase C or other diacylglycerol binding site-bearing entities by diacylglycerols, the latter being generated in the cell by pathological agents or conditions.

In analyzing the activity of a pharmaceutical or other bioactive compound, it is useful to consider two properties: the efficacy, defined as the capability to elicit a full or partial biological result, such as complete displacement of a ligand from its receptor site or the complete inhibition of inflammation or edema caused by a standard stimulus; and the potency, defined as that amount or concentration of drug that causes 50% of the full response (often abbreviated as the $ED_{50}$). It is frequently the case within a given class of pharmaceutical agents that individual members of the class all have equal efficacy, i.e. they each can generate a full biological effect, but they show differing potencies. Thus, the structural modifications within such a class affect only the amount necessary to achieve a given result, and the modified compounds otherwise have generally the same central biological characteristic. There may also be differences between members of such a class as regards properties other than the central biological characteristic; for example, members of the class might differ in side effects or toxicity.

Well-known pharmaceuticals that have been in extensive use for years or decades show a wide range of optimal therapeutic potencies. Aspirin, for example, is often taken in multi-gram amounts per day for treatment of inflammation or arthritis, and detailed analyses of its mechanism of action in vitro show that a concentration in the millimolar range is required. In contrast, steroid-based topical anti-inflammatory compounds such as fluocinolone acetonide are many thousand-fold more potent, and, beyond this, some oral contraceptive agents are prescribed in daily doses in the microgram range. Thus, although high potency is generally advantageous for a pharmaceutical, it is not an absolute requirement.

A thousand or more analogs of the highly skin-inflammatory and tumor-promoting phorboids have been reported in the literature, including numerous examples on which minor chemical modifications have been made [see Evans and Soper, *Lloydia* 41: 193–233 (1978) and references cited therein]. The structures of these phorboids can be compared, and their activities for inflammation and tumor promotion can be analyzed from the perspective of efficacy and potency. The structures of the different classes of phorboids vary quite markedly from one to the other class, yet widespread testing of their biological activities has shown that these classes have generally very similar biological properties. In particular, the numerous known phorboids of the highly potent diterpene, indolactam, and polyacetate classes appear to have, with very minor exceptions, virtually identical efficacies as skin irritants and tumor promoters [T. Sugimura, *Gann* 73: 499–507 (1982)]. The exceptions involve a few compounds that have a short duration of irritant activity and/or manifest diminished tumor promoting activity, perhaps due to toxicity or secondary parameters such as differing metabolic destruction rates.

In contrast to the essentially equal efficacies among the vast majority of phorboids, their relative potencies cover a wide range, as measured in inflammation and promotion tests and as measured in numerous other in vivo and in vitro systems. Example compounds can be found in the diterpene, indolactam, and polyacetate classes that have nearly equal, very high potencies. At the same time there are compounds in each of these classes which embody significant structural changes that do not diminish efficacy but do result in potency decreases of 10-fold to 100,000-fold or more [see, for example, Driedger and Blumberg, *Cancer Res.* 37: 3257–3265 (1977), *Cancer Res.* 39: 714–719 (1979)]. Thus, all these compounds appear to be capable of achieving generally the same biological results, and merely differ in the amount which must be used to obtain a given result.

In vitro measurements of biochemical properties provide an even more sensitive method for comparing the properties of the various phorboids. For example, using a radioactively labeled phorboid such as [$^3$H]phorbol 12,13-dibutyrate or [$^3$H]lyngbyatoxin, one can measure the potency of a test compound as a competitive ligand for the diacylglycerol binding site, which is also referred to herein as the "phorboid binding site" on protein kinase C or on other biological molecules which have phorboid binding sites (see below). Alternatively, one can measure the ability of a given phorboid to stimulate the protein kinase C-mediated incorporation of radioactive phosphate from [$^{32}$P]adenosine triphosphate into a standard acceptor substrate such as histone H1. Tests of this nature reveal a difference in potency between given phorbid agonists of as much as 10,000,000-fold or more [Dunn and Blumberg, *Cancer Res.* 43: 4632–4637 (1983), Table 1].

These basic data regarding the phorboid agonists are an important consideration because they underscore the concept that the structural differences among these previously known phorboids, especially the diterpenes, indolactams, polyacetates, and bryostatins, generally do not affect their efficacies as toxic agonists, and indeed a wide variety of structural changes are tolerated in this regard. Such changes generally alter potency only and do not provide agents with therapeutic utility, since the resulting compounds retain their toxicity.

Some minor changes in phorboid structure are known to result in generally inactive compounds, such as a stereochemical change from 4-β to 4-α in the phorbol series, and indeed some of the diterpene skeleton structures carry hydroxy groups that must be esterified in order for inflammatory activity to be observed. However, these inactive compounds are quite few in number among the known phorboids, and no therapeutic utility has been demonstrated for them.

The phorbol esters, indolactams, polyacetates, diaminobenzyl alcohols, and bryostatins are generally found in plants, molds, and algae, or are synthetic in origin. Although they are found in many parts of the world, normal human contact with them is thought to be low. In contrast, the diacylglycerols are part of the functioning of virtually every type of animal cell and, thus, the undesirable activation of protein kinase C by the diacylglycerols may have a very widespread role in human diseases.

Thus, compounds capable of blocking the activation of, or inhibiting, protein kinase C by acting as specific pharmacological antagonists of the diacylglycerols at the diacylglycerol binding site on protein kinase C, would be valuable agents in the prevention and treatment of a wide variety of diseases in animals and humans. For example, the need for, and potential utility of, protein kinase C inhibitors/antagonists as agents for the treatment of cancer has received much attention [D. Corda, et al., *Trends in Pharmacological Sciences* 11: 471–473 (1990), G. Powis, *Trends in Pharmacological Sciences* 12: 188–194 (1991); S. Gandy and P. Greengard, *Trends in Pharmacological Sciences* 13: 108–113 (1992); B. Henderson and S. Blake, *Trends in Pharmacological Sciences* 13: 145–152 (1992)].

Protein kinase C comprises a family of eight or more closely related protein molecules [Parker, P. J. et al., *Mol. Cell. Endocrin.* 65: 1–11 (1989)]. Because of their high degree of relatedness they are referred to as "isozymes", "isotypes" or "isoforms". Occasionally the term "subtypes" is used, but this term is usually reserved to designate, as a subdivision, two or more variants of a single isotype.

The currently known isotypes of protein kinase C are: α, β$_1$, β$_2$ and γ (the "A-group"); δ, ε, ε' [Ono, Y. et al., *J. Biol. Chem.* 263: 6927–6932 (1988)], η [also known as protein kinase C-L, Osada, S. et al., *J. Biol. Chem.* 265: 22434–22440 (1990) and Bacher, N. et al., *Mol. Cell. Biol.* 11: 126–133 (1991), respectively], and θ [Osada, S.-I. et al., *Mol. Cell. Biol.* 12: 3930–3938 (1992) (the "B-group"); ζ [Ono, Y. et al., *J. Biol. Chem.* 263: 6927–6932 (1988)]and ι [Selbie, L. A. et al., *J. Biol. Chem.* 268: 24296–24302 (1993), the latter also being known as PKCλ [Akimoto, K. et al., *J. Biol. Chem.* 269: 12677–12683 (1994)] (the "C-group"); and μ [Johannes, F.-J. et al., *J. Biol. Chem.* 269: 6140–6148 (1994)], also known as PKD [Valverde, A. M. et al., *Proc. Natl. Acad. Sci USA* 91: 8572–8576 (1994) (the "D-group"). Members of the A-group require calcium ions for maximal activation, whereas the B-, C- and D-group members are thought to be largely calcium-independent for activation. The genes for each of the isotypes above have been cloned from one or more animal and yeast species and the clones have been sequenced, the relatedness of the genes and their product polypeptides is thus well established.

It is possible that the different protein kinase C isozymes have different biological roles, and published evidence supports this idea [Homan, E., Jensen, D. and Sando, J., *J. Biol. Chem.* 266: 5676–5681 (1991), Gusovsky, F. and Gutkind, S., *Mol. Pharm.* 39: 124–129 (1991); Borner, C., "The Role of protein kinase C in Growth Control", Sixth International Symposium on Cellular Endocrinology, W. Alton Jones Cell Science Center, Lake Placid, N.Y., Aug. 12–15, 1990; Naor, Z. et al., *Proc. Natl. Acad. Sci. USA* 86: 4501–4504 (1989); Godson, C., Weiss, B. and Insel, P., *J. Biol. Chem.* 265: 8369–8372 (1990), Melloni, E. et al., *Proc. Natl. Acad. Sci. USA* 87: 4417–4420 (1990); Koretzky, G. et al., *J. Immunology* 143: 1692–1695 (1989)]. For example, the stimulation of one protein kinase C isotype or a limited subset of protein kinase C isotypes might lead to undesirable results such as the development of inflammation [Ohuchi, K. et al., *Biochim. Biophys. Acta* 925: 156–163 (1987)], the promotion of tumor formation [Slaga, T., *Envir. Health Perspec.* 50: 3–14 (1983)] or an increased rate of viral replication in cells (i.e., de novo infection of cells and/or expression, assembly and release of new viral particles) [Harada, S. et al., *Virology* 154: 249–258 (1986)].

On the other hand, other protein kinase C isozymes might be responsible for the many beneficial effects observed when protein kinase C is stimulated by known protein kinase C activators in a variety of biological settings; such beneficial effects include the cessation of division of leukemic cells [Rovera, G., O'Brien, T. and Diamond, L., *Science* 204: 868–870 (1979)], multiplication of colonies of lymphocytes [Rosenstreich, D. and Mizel, S., *J. Immunol.* 123: 1749–1754 (1979)] and leucocytes [Skinnider, L. and McAskill, J., *Exp. Hematol.* 8: 477–483 (1980)] or the secretion of useful bioregulatory factors such as interferon-c [Braude, I., U.S. Pat. No. 4,376,822] and interleukin-2 [Gillis, S., U.S. Pat. No. 4,401,756].

Recent publications indicate that diacylglycerol binding sites exist on newly-described proteins which lack the kinase domain, and thus lack the kinase activity, of protein kinase C. One such protein is n-chimaerin, found in human brain [Ahmed et al., *Biochem. J.* 272: 767–773 (1990)] and the other is the unc-13 gene product of the nematode *Caenorhabditis elegans*, [Maruyama, I. and Brenner, S., *Proc. Natl. Acad. Sci. USA* 88: 5729–5733 (1991)]. The presence of the diacylglycerol binding sites on these two proteins was demonstrated by standard binding experiments with [$^3$H] phorbol 12,13-dibutyrate. These new proteins may have other enzymatic or biological activities which can be modulated by compounds which bind to their diacylglycerol binding sites. Thus, such compounds may have utility on non-protein kinase C biological targets.

Given that there are now numerous distinct biological entities bearing diacylglycerol binding sites, it would be highly desirable to obtain chemical compounds which could specifically and selectively target one or another type of diacylglycerol binding site, thus permitting one to selectively activate or inhibit one such site without affecting the others. Such compounds would be valuable experimental tools for studying the role of individual types of proteins bearing diacylglycerol binding sites as well as providing novel means for treating diseases in which protein kinase C or other diacylglycerol binding site-bearing proteins are involved.

There are several published reports describing chemical compounds capable of selectively distinguishing several diacylglycerol/phorboid-type binding sites in mouse skin [Dunn and Blumberg, op. cit.] and in purified preparations of protein kinase C isotypes [Ryves, W. J., et al., *FEBS Letters* 288: 5–9 (1991)]. However, in these studies, even the compounds showing the clearest differences in affinity for these distinct classes, namely phorbol 12,13-dibutyrate, 12-deoxyphorbol 13-isobutyrate, 12-deoxyphorbol 13-phenylacetate and thymeleatoxin, are only selective by a factor of 10–1000 in dissociation constant among the different binding sites. Furthermore, these compounds have potent skin inflammatory activity and are not desirable in human or animal medicine because of this toxicity.

Thus, to briefly recapitulate, two kinds of new compounds relating to diacylglycerol binding sites would be highly desirable. The first type would be capable of selectively activating one or a few useful, but not other, deleterious, diacylglycerol target sites. The second type would be capable of inhibiting, or antagonizing the stimulation of, one or more deleterious diacylglycerol binding site-bearing entities without blocking the useful ones. These kinds of compounds would be valuable agents for the study of diacylglycerol binding site-bearing entities and for the prevention or treatment of a wide range of human and animal diseases thought to involve protein kinase C or other entities under the control of diacylglycerol binding sites.

Earlier efforts to use the previously known phorboids themselves or to modify the structures of these known phorboids, have generally not been successful in producing useful compounds with toxicity low enough for use in humans.

It has been known for some time that several of the toxic, inflammatory and tumor-promoting compounds such as phorbol 12-tigliate 13-decanoate, mezerein, lyngbyatoxin and aplysiatoxin have anti-leukemic activity in mouse model tests [T. Sugimura, op cit.; S. M. Kupchan and R. L. Baxter, *Science* 187: 652–653 (1975); S. M. Kupchan, et al., *Science* 191: 571–572 (1976); M. C. Territo and H. P. Koeffler, *Br. J. Haematol.* 47, 479–483 (1981)]. However, these compounds are all extremely toxic and are cancer suspect agents, thus eliminating them from consideration as human therapeutic agents.

Ganong, et al. [*Proc. Nat. Acad. Sci. USA* 83: 1184–1188 (1986)] tested a series of diacylglycerols and found no antagonistic activity in that series against the standard agonist, 1,2-dioctanoylglycerol. It is of particular note that several compounds tested in this work were modified in the hydroxymethyl portion of the diacylglycerol molecule, and these modifications produced only a loss of activity or a weakened activity that was not distinguishable from the agonist activity of 1,2-dioctanoylglycerol itself, a compound which is toxic to mouse skin [R. Smart, et al., *Carcinogenesis* 7: 1865–1870 (1986); A. Verma, *Cancer Res.* 48: 2168–2173 (1988)]. These hydroxymethyl-modified compounds were not antagonists in these tests and no utility was found. Similarly, Thielmann and Hecker [*Forsch. Krebsforsch.* Vol. VII, pp. 171–179 (1969), New York: Schattauer] found only a complete loss of biological activity in their study when the hydroxy group of the hydroxymethyl on phorbol 12,13-didecanoate was replaced with hydrogen or chlorine. Schmidt and Hecker [H. Lettre and G. Wagner (eds.), *Aktuelle Probleme aus dem Gebiet der Cancerologie*, Vol. III, 3rd Heidelberg Symposium, pp. 98–108. Berlin: Springer Verlag, 1971] also found that oxidation of the hydroxymethyl of phorbol 12,13- didecanoate to a carboxylic acid caused complete loss of activity in the assays used.

The hydroxymethyl group of the known phorboids (see structures above) has been thought to be required for biological activity, as detailed by Hecker (Hecker, E., *Carcinogenesis*, Vol. 2, eds. Slaga, Sivak and Boutwell, Raven Press, New York, 1978, pp. 11–48 and references cited therein). Indeed, it is stated therein that the replacement of the 20-hydroxyl in a phorbol ester "results in complete loss of biological activity". In another study, replacement of the hydroxy group of the hydroxymethyl (located at carbon 14) by chlorine or hydrogen in indolactam V gave rise to compounds with agonist activity weaker than but otherwise not distinguished from the agonist activity of the very toxic teleocidin class of tumor promoters [Irie et al., *Int. J. Cancer* 36: 485–488 (1985)]. Thus no utility beyond that of the toxic, hydroxymethyl-bearing parent indolactam-type compounds was found.

Schmidt and Hecker (*Carcinogenesis*, Vol. 7, ed. by E. Hecker et al., Raven Press, New York, 1982, pp. 57–63) studied the abilities of a series of diterpene phorboids to inhibit tumor promotion by the standard phorboid agonist tumor promoter phorbol 12-myristate 13-acetate (PMA). They found that, at low doses, some short-chain ester derivatives of phorbol were able to block the tumor promotion by PMA. However, all of the compounds that were active as antagonists at low doses are also very efficacious skin irritants themselves at slightly higher doses and most of them are also known to have tumor promoting activity. Thus, these short-chain esters still have toxic inflammatory and tumor promoting activity at doses only slightly different from those which would be needed to exhibit a therapeutic effect in mice.

SUMMARY OF THE INVENTION

This invention pertains to novel phorboid derivatives which variously block the toxic effects of the hydroxymethyl-containing phorboids, lack the toxic properties of previously available phorboids and show activity for applications as therapeutics. The phorboid derivatives of the present invention embody very diverse structures and have utility as anti-inflammatory agents, as cancer cell and leukemic cell inhibitory agents, anti-asthmatic and anti-hypertensive agents, as modulators of human immune cell function, as anti-viral agents, as stimulators of the production of lymphokines such as interferon and the interleukins, as central nervous system pharmaceuticals for several pathological conditions, and as xenobiotics for achieving the control of parasites.

The structural features associated with the non-toxicity and diacylglycerol binding site modulating properties of these compounds relate primarily to the hydroxymethyl or 1-hydroxyethyl group found in each of the toxic parent compounds. Specific modifications of the latter chemical groupings yields non-skin inflammatory compounds that show anti-inflammatory activity in several test systems, whereas any of a very wide variety of changes in other parts of the parent phorboid structures, including but not limited to diterpenes, indole alkaloids, polyacetates, diaminobenzyl alcohol derivatives, aplysiatoxins, bryostatinoids and benzolactams, have very markedly less effect on the overall biological properties of the derivatives, other than changes in potency. This invention also provides new compounds that discriminate between phorboid receptor-type targets, with direct or imputed relative binding activities differing by 10,000-fold or more in some cases.

The hydroxymethyl and 1-hydroxyethyl feature common to all the classes of phorboids is the primary focus of this invention, in which the variations which can be accommodated in the organic functional groups replacing the hydroxymethyl/1-hydroxyethyl groups are found to include new heteroatoms and to be larger and more complex than previously recognized. Furthermore, the parent structures of hydroxymethyl/1-hydroxyethyl-modified phorboids have now also been found to tolerate larger and more complex structural features and more kinds of heteroatoms than previously recognized.

Generally the phorboid derivatives of this invention can be represented by the formula:

$$P—G$$

wherein P represents a radical, formally derived from a parent compound, which compound:

a. binds reversibly or irreversibly to a diacylglycerol-type receptor, and/or b. activates any form of the enzyme protein kinase C; and c. contains an hydroxymethyl or 1-hydroxyethyl group bonded to a carbon atom; and wherein G is any wherein G is any group of 55 or fewer atoms selected from carbon, hydrogen, oxygen, nitrogen, halogen, sulfur, phosphorus, silicon, arsenic, boron and selenium either i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group is bound in the parent compound; and wherein the hydroxymethyl or 1-hydroxyethyl group of the parent compound is absent or has been replaced by G.

More specifically, the compounds of this invention are represented by the formula:

$$P_o—S_o—E_o$$

which depicts a phorboid "parent" compound radical $P_o$ modified by a substituent $S_oE_o$.

In general, a parent compound is a compound which:

a. binds reversibly or irreversibly to a diacylglycerol-type receptor; and/or b. activates any form of the enzyme protein kinase C, and c. contains an hydroxymethyl or 1-hydroxyethyl group bonded to a carbon atom.

For example, a parent compound can be a diterpenoid activator of protein kinase C; an aromatic heterocyclic activator of protein kinase of the indole, indene, benzofuran, or benzothiophene class, further defined here by the presence of a substituted or unsubstituted six-atom chain connecting positions 3 and 4 of the indole, indene, benzofuran or benzothiophene to form an additional 9-membered ring and by the optional presence in this class of one or two nitrogen atoms at any of positions 5, 6pk and 7 of the benzenoid ring portion of the indole, indene, benzofuran or benzothiophene skeletons, a polyacetate-derived activator of protein kinase C; an activator of protein kinase C of the diacylglycerol or diacyloxybutanol class; an activator of protein kinase C of the diaminobenzyl alcohol class; a protein kinase C activator of the bryostatin class; or, an activator of protein kinase C of the benzolactam class. The word "chain", when used in describing the compounds of this invention, means a sequence of atoms covalently bound, one to the next. These sequences of covalently bound atoms may be substituted or unsubstituted as further specified in the particulars described herein.

$S_o—E_o$ represents a modifying substituent which is either:

i) singly or doubly bonded to the carbon atom of the parent compound $P_o$ in place of the hydroxymethyl or 1-hydroxyethyl group; or ii) singly or doubly bonded to a carbon immediately adjacent to the carbon atom to which the hydroxymethyl or 1-hydroxyethyl is bonded.

In the $S_o—E_o$ substituent, $S_o$ can be a substituted or unsubstituted, saturated, unsaturated and/or aromatic, straight or branched, acyclic, ring-containing and/or ring-carrying chain of atoms which separates $P_o$ and $E_o$ by a linear count of at least two but not more than 12 atoms and contains and/or carries not more than 9 heteroatoms selected from oxygen, nitrogen, silicon, sulfur, phosphorus, arsenic, boron and selenium, and not more than 16 halogen atoms; provided that the total number of atoms does not exceed 35; and in some cases $S_o$ may be a single or double bond; and $E_o$ can be hydrogen, halogen or a saturated or singly or multiply unsaturated group containing up to 15 carbon atoms and optionally containing 1 to 12 halogen atoms and/or 1 to 6 heteroatoms selected from oxygen, nitrogen, silicon, sulfur, phosphorus, arsenic, boron and selenium. $S_oE_o$ taken together may also be a hydrogen, halogen, thionic sulfur atom or ketonic oxygen atom or a hydroxy, amino, or thiol group singly or doubly bonded to the carbon atom of the parent compound $P_o$ in place of the hydroxymethyl or 1-hydroxyethyl group.

DETAILED DESCRIPTION OF THE INVENTION

All seven classes of the known phorboids have one structural element in common. Each prototypical member of these classes has either a hydroxymethyl group or a 1-hydroxyethyl group. The design of the phorboid derivatives of this invention is based on the finding that the hydroxymethyl and 1-hydroxyethyl groups, which previously were thought to be required for biological activity of phorboids containing these groups, can be replaced by other substituents of very diverse nature, even though these new substituents are very substantially larger and of more diverse structure and heteroatom composition than the original hydroxymethyl/1-hydroxyethyl group.

For example, the hydroxymethyl group of a typical diterpene phorboid such as phorbol-12-myristate 13-acetate may even be replaced by a tetracyclic structure containing some 36 carbon atoms, to form the dimeric molecule The phorboid derivatives of this invention are generally represented by the formula:

P—G

The formula depicts a radical, P, derived from a parent compound, which compound:
a. binds reversibly or irreversibly to a diacylglycerol-type receptor; and/or
b. activates any form of the enzyme protein kinase C; and
c. contains an hydroxymethyl or 1-hydroxyethyl group bonded to a carbon atom; and wherein G is any group of 55 or fewer atoms selected from carbon, hydrogen, oxygen, nitrogen, halogen, sulfur, phosphorus, silicon, arsenic, boron and selenium either: i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group is bound in the parent compound; and wherein the hydroxymethyl or 1-hydroxyethyl group of the parent compound is absent or has been replaced by G.

More specifically, the phorboid derivatives of this invention are represented by the formula:

$P_o$—$S_o$—$E_o$

The formula depicts a radical $P_o$, formally derived from a parent hydroxymethyl-containing phorboid compound, bonded to an $S_o$—$E_o$ substituent.

$P_o$ represents a radical formally derived from a compound which contains an hydroxymethyl (or the equivalent 1-hydroxyethyl) group and which binds reversibly or irre-

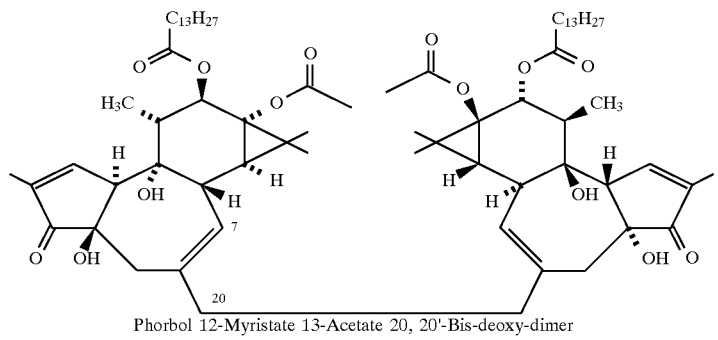

Phorbol 12-Myristate 13-Acetate 20, 20'-Bis-deoxy-dimer which still exhibits diacylglycerol site binding activity and anti-viral properties.

The compounds resulting from the hydroxymethyl changes described here variously block the toxic effects of the hydroxymethyl-containing phorboids, lack the skin-inflammatory properties associated with the previously available phorboids and show useful activity as therapeutic agents. These new compounds thus have utility as, variously, anti-inflammatory agents, anti-viral agents and anti-leukemic agents, for example.

Although the replacement of the hydroxymethyl group or 1-hydroxyethyl group is very specific and leads to an extreme and profound change in biological properties, a wide range, much wider than previously recognized, of structural alterations in the non-hydroxymethyl/1-hydroxyethyl portions of the novel compounds can be tolerated without material loss of their basic, favorable biological properties.

versibly to a diacylglycerol-type receptor and/or activates any form of the enzyme protein kinase C. $P_o$ may be formally derived from phorboids from any of the seven classes listed below:

i) a diterpenoid activator of protein kinase C;
ii) an aromatic heterocyclic activator of protein kinase of the indole, indene, benzofuran, or benzothiophene class, further defined here by the mandatory presence of a substituted or unsubstituted six-atom chain connecting positions 3 and 4 of the indole, indene, benzofuran or benzothiophene skeleton to form an additional 9-membered ring and by the optional presence in this class of one or two nitrogen atoms at any of positions 5, 6 and 7 of the benzenoid ring portion of the indole, indene, benzofuran or benzothiophene skeletons;
iii) a polyacetate-derived activator of protein kinase C,
iv) an activator of protein kinase C of the diacylglycerol or diacyloxybutanol class;

v) an activator of protein kinase C of the diaminobenzyl alcohol class;

vi) a protein kinase C activator of the bryostatin class, and vii) a protein kinase C activator of the benzolactam class.

All of these parent phorboids contain an hydroxymethyl or 1-hydroxyethyl group which is shown in the present invention to be associated with their toxic biological activity, such as skin inflammatory activity measured on the mouse ear.

$S_o$—$E_o$ represents a substituent which is either:

i) singly or doubly bonded to the carbon atom of the parent compound in place of the hydroxymethyl or 1-hydroxyethyl group, or ii) singly or doubly bonded to a carbon immediately adjacent to the carbon atom to which the hydroxymethyl or 1-hydroxyethyl group is bound in the parent compound.

In this $S_o$—$E_o$ substituent, $S_o$ can be a substituted or unsubstituted, saturated, unsaturated and/or aromatic, straight or branched, acyclic, ring-containing and/or ring-carrying chain of atoms which separates $P_o$ and $E_o$ by a linear count of at least two but not more than 12 atoms and contains and/or carries not more than 9 heteroatoms selected from oxygen, nitrogen, silicon, sulfur, phosphorus, arsenic, boron and selenium, and not more than 16 halogen atoms, provided that the total number of atoms does not exceed 35; and in some cases $S_o$ may be a single or double bond; and $E_o$ can be hydrogen, halogen or a saturated or singly or multiply unsaturated group containing up to 15 carbon atoms and optionally containing 1 to 12 halogen atoms and/or 1 to 6 heteroatoms selected from oxygen, nitrogen, silicon, sulfur, phosphorus, arsenic, boron and selenium. $S_oE_o$ taken together may also be a hydrogen, halogen, thionic sulfur atom or ketonic oxygen atom or a hydroxy, amino, or thiol group singly or doubly bonded to the carbon atom of the parent compound $P_o$ in place of the hydroxymethyl or 1-hydroxyethyl group.

In a preferred embodiment, the phorboid derivatives of this invention are represented as follows.

$$P_x—S_x—E_1$$

wherein $P_x$ can be selected from seven different classes of compounds designated $P_1$–$P_7$ and defined below, wherein $S_x$ is selected from seven different structural types as defined below and $E_1$ is as defined below.

$P_1$, $P_2$, $P_3$, $P_4$, $P_5$, $P_6$ and $P_7$ represent compounds of each of the seven classes of known phorboids and are defined by the formulae below.

$P_1$ is a radical of the formula:

in the form of an individual isomer, an isomer mixture, a racemate or optical antipode, or a pharmaceutically acceptable salt thereof, wherein $A^1$ and $A^2$ may be independently selected from hydrogen, halogen and a substituent having not more than 34 carbon atoms, not more than 24 halogen atoms and not more than 9 heteroatoms selected from oxygen, nitrogen, silicon, phosphorus and sulfur, or $A^1$ and $A^2$ taken together may complete a 5- or 6-membered saturated or unsaturated carbocyclic or heterocyclic ring, optionally substituted by 1–8 halogens and/or other groups, which halogens and groups taken together contain a total of not more than 30 carbon atoms, not more than 24 halogen atoms and not more than 9 heteroatoms selected from oxygen, nitrogen, silicon, phosphorus and sulfur; $A^3$ is a three atom chain which carries $S_xE_1$, and completes a 7-membered saturated or unsaturated carbocyclic ring optionally substituted by 1–6 halogens and/or other groups, which halogens and groups taken together, excluding $S_xE_1$, contain not more than 12 carbon atoms, not more than 8 halogen atoms, and not more than 5 heteroatoms selected from oxygen, nitrogen, silicon, phosphorus and sulfur; provided that, including $S_xE_1$, the middle carbon atom of $A^3$ is not substituted by hydroxymethyl or 1-hydroxyethyl, $A^4$ completes a 6- or 7-membered carbocyclic or heterocyclic ring which is connected in the β configuration to either carbon atom 9 or 10 and carries an 11-methyl group in the α or β configuration, wherein $A^4$ is optionally substituted further by 1–10 halogens and/or other groups, the group or groups optionally completing 1–3 additional rings through bonds among themselves and/or 1–5 additional rings when taken together with $A^1$, $A^2$, a ring formed by $A^1$ and $A^2$ together, and/or a bond to carbon atom 9, which halogens and groups taken together include not more than 40 carbon atoms, not more than 24 halogen atoms, and not more than 15 heteroatoms selected from oxygen, nitrogen, silicon, phosphorus and sulfur, carbon atom 9 may be optionally bound to a substituent by a single or double bond (some preferred substituents are hydrogen, hydroxy, acetoxy or other acyloxy, orthoesteroxy, ether or silyl ether, ketonic oxygen atom or thionic sulfur atom); $J^1$ is hydrogen, fluoro, chloro, hydroxy, amino, mono- or di(lower-alkyl)amino, methyl, ethyl, vinyl, ethynyl, propargyl, cyano, methoxy, ethoxy, trifluoromethyl, 2-hydroxyethyl, 2-hydroxypropyl, 3-hydroxypropyl, acetoxy, propanoyloxy, acetyl, propanoyl, hydroxyacetyl, 2-hydroxypropanoyloxy, 3-hydroxypropanoyl, acetamido, propanamido, hydroxyacetamido, 2-hydroxypropanamido, or 3-hydroxypropanamido (each of which must be situated in the β configuration), or $J^1$ taken together with $A^1$, $A^2$, $A^3$ or a ring formed by $A^1$ together with $A^2$ completes a 3- to 7-membered, substituted or unsubstituted, carbocyclic or heterocyclic ring, the substituents of which contain not more than 15 carbon atoms, not more than 10 halogens, and not more than 8 heteroatoms selected from oxygen, nitrogen, silicon, phosphorus and sulfur; and, $J^2$ is selected from hydrogen, methyl, ethyl, hydroxymethyl, hydroxyethyl, vinyl, ethynyl, allyl, propargyl, n-propyl and isopropyl, provided that, if $A^1$ and $A^2$ are not linked to form a ring, $A^4$ must carry a cyclopropyl at positions 13 and 14, and the total $P_1$ ring skeleton may not comprise any of the following six frameworks, which are derived from various homo-, nor- and homo-nor-steroids:

-continued

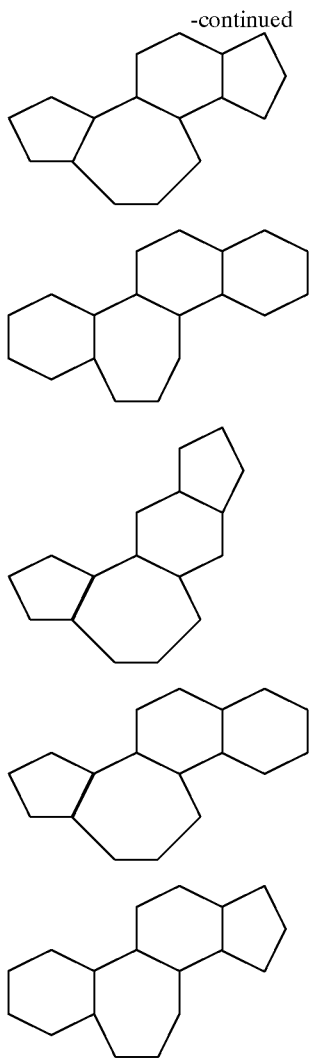

In a preferred mode of this invention the above definition of $P_1$ is maintained, provided that: for all $P_1$, when $S_xE_1$ are taken together and bonded to carbon 6, they may not comprise —$CH_3$, —CH=O, —$CH_2$O—$R_e^e$ (wherein $R_e^e$ is an acyl group, a $C_1$–$C_6$ hydrocarbon radical, a substituted or unsubstituted triphenylmethyl group, a $(C_1$–$C_6$ linear or branched alkyl)$_n$(phenyl)$_{3-n}$silyl group, wherein n is 0–3, or —C(CH$_3$)$_2$O— or —B(C$_6$H$_5$)O— linked via the oxygen atom to the β configuration of carbon 5 of $P_1$), or —CH=NNHR$_h$ wherein R$_h$ is a phenyl ring with or without substituents; $P_1S_xE_1$ may not include 12-β-13-α-diacetoxy derivatives of compounds having the exact 20-carbon tigliane or the exact 19-carbon 20-nor-tigliane skeleton; $P_1S_xE_1$ may not comprise 20-deoxy-20-chlorocrotophorbolone nor 20-deoxy-20-chlorophorbol 12,13-diesters wherein the ester groups are both selected from saturated or unsaturated alkanoyl or are both benzoyl; if $S_xE_1$ taken together is =CH$_2$ bonded to carbon 6, $P_1$ may not carry a ring formed by —OC(CH$_3$)$_2$O— bonded in the β configuration to carbons 3 and 4; and, $P_1S_xE_1$ may not comprise 6-deshydroxymethyl-6-carboxyphorbol 12,13-didecanoate or 6-deshydroxymethyl-6-carboxyphorbol 12,13-diacetate.

$P_2$ is a radical of the formula:

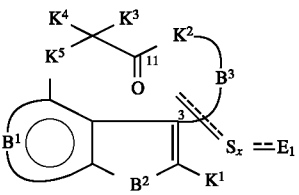

$P_2$ in the form of an individual isomer, an isomer mixture, a racemate or optical antipode, or a pharmaceutically acceptable salt thereof, wherein $B^1$ completes a 6-membered aromatic ring which may be carbocyclic or may optionally contain one or two nitrogen atoms at any of positions 5, 6 and 7 of the ring, wherein positions 5, 6 and/or 7 of $B^1$ are optionally and independently substituted on carbon by halogen(s) and/or by straight chain or branched chain, cyclic or acyclic, saturated, unsaturated and/or aromatic carbon- and/or heteroatom-containing groups, which halogen(s) and groups taken together contain not more than 40 carbon atoms, not more than 24 halogen atoms, and not more than 9 heteroatoms selected from oxygen, nitrogen, silicon, phosphorus and sulfur, the groups being optionally connected to one another and/or to $B^2$ to form 1–3 additional rings, $B^2$ is selected from oxygen, sulfur, sulfoxide, sulfone, monofluoromethylene, difluoromethylene, and a carbon or nitrogen atom optionally substituted by groups having not more than 15 carbon atoms, not more than 24 halogen atoms, and not more than 6 heteroatoms selected from oxygen, nitrogen, silicon, phosphorus and sulfur, and $B^2$ may be linked to $B^1$ or $K^1$ to form an additional carbocyclic or heterocyclic ring; $K^1$ is hydrogen, halogen or a group containing not more than 15 carbon atoms, not more than 18 halogen atoms, and not more than 6 heteroatoms selected from oxygen, nitrogen, silicon, phosphorus and sulfur, and $K^1$ may be linked to $B^2$ or $B^3$ or to both $B^2$ and $B^3$ to form one or more additional carbocyclic and/or heterocyclic rings, $B^3$ is a 2-carbon chain optionally substituted by halogen(s) and/or one or more groups which, taken together but excluding $S_xE_1$, contain not more than 12 carbon atoms, not more than 6 halogen atoms, and not more than 6 heteroatoms selected from oxygen, nitrogen, and sulfur; provided that, including $S_xE_1$, the carbon atom of $B^3$ bonded to $K^2$ as defined below does not carry —CH$_2$OH or —CHCH$_3$OH; $K^2$ is selected from oxygen, sulfur —NK$^6$— or —CK$^6$K$^7$— wherein K$^6$ is hydrogen, hydroxy, methyl, ethyl, fluoro, n-propyl, allyl, or propargyl, and K$^7$ is hydrogen, methyl, ethyl, halogen, trifluoromethyl or cyano; K$^3$ and K$^4$ may be the same or may differ and each may independently be hydrogen, halogen, a substituent group, or may complete an additional ring connecting K$^3$ and K$^4$ or connecting either K$^3$ or K$^4$ to K$^5$, such that K$^3$ and K$^4$ taken together contain not more than 18 carbon atoms, not more than 24 halogen atoms, and not more than 6 heteroatoms selected from oxygen, nitrogen, silicon, phosphorus and sulfur; and, K$^5$ is selected from oxygen, sulfur, sulfoxide, sulfone or —NK$^8$—, —NOK$^8$— or —CK$^8$K$^9$— wherein K$^8$ is hydrogen or a group containing not more than 30 carbon atoms, not more than 24 halogen atoms, and not more than 8 heteroatoms selected from oxygen, nitrogen, silicon, phosphorus and sulfur, and K$^9$ is hydrogen, methyl, ethyl, n-propyl, hydroxy, halogen, allyl, propargyl, cyano, or trifluoromethyl.

In a preferred mode of this invention the above definition of $P_2$ is maintained, provided that $P_2S_xE_1$ may not comprise (–)-1,10,14-O-trimethylindolactam V, and provided further that if $B^1$ completes an unsubstituted or substituted carbocyclic aromatic ring, and $B^2$ is —NH—, —N-($C_1$-$C_{12}$ linear or branched alkyl or alkanoyl)—, —N—COOCH$_2$C$_6$H$_5$— or —N—COOC(CH$_3$)$_3$—, and $B^3$ is —CH$_2$CH—, and $K^1$ is hydrogen, and $K^2$ is —NH—, and $K^4$ is hydrogen, and $K^5$ is —NH— or —N($C_1$-$C_3$-alkyl)—, then (i) if $S_xE_1$ is bonded to the carbon atom in $B^3$ that is adjacent to $K^2$, then $S_xE_1$ may not be —COOMe or —COOEt; and (ii) if $S_x$ is a single bond directed to the carbon atom in $B^3$ that is adjacent to $K^2$, and $E_1$ is —CH$_2$—$R_e^e$ then $R_e^e$ may not comprise any of hydrogen, chloro, bromo, $C_1$-$C_{12}$ saturated or unsaturated, linear or branched alkoxy, —OCH$_2$OCH$_3$, $C_1$-$C_{12}$ linear or branched alkanoyloxy, bromoacetoxy, benzoyloxy, azidobenzoyloxy, 3,5-(CH$_3$)$_2$C$_6$H$_3$COO—, methanesulfonyloxy, toluenesulfonyloxy, dansyloxy, (tetrahydro-2H-pyran-2-yl)oxy, or ($C_1$-$C_6$ linear or branched alkyl)$_n$(phenyl)$_{3-n}$-silyloxy, wherein n is 0–3.

$P_3$ is a radical of the formula.

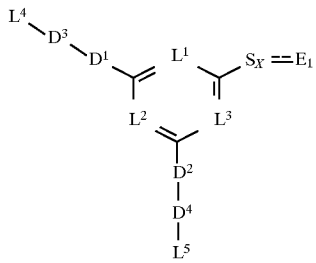

in the form of an individual isomer, an isomer mixture, a racemate or optical antipode, or a pharmaceutically acceptable salt thereof, wherein $L^1$, $L^2$ and $L^3$ are individually selected from nitrogen or substituted or unsubstituted carbon, $D^1$ and $D^2$ each may be a bond or a substituted or unsubstituted carbon atom; $D^1$ may be linked to $L^1$, $L^2$ or both $L^1$ and $L^2$ to form additional fused carbocyclic and/or heterocyclic substituted or unsubstituted rings, and $D^2$ may be linked to $L^2$, $L^3$ or both $L^2$ and $L^3$ to form additional fused carbocyclic and/or heterocyclic substituted or unsubstituted rings; $D^3$ and $D^4$ each are heteroatom-containing functional groups, the heteroatoms being selected from oxygen, nitrogen, silicon, phosphorus and sulfur; $D^3$ may be linked to $L^1$, $L^2$ or both $L^1$ and $L^2$ to form additional fused substituted or unsubstituted carbocyclic and/or heterocyclic rings; and $D^4$ may be linked to $L^2$, $L^3$ or both $L^2$ and $L^3$ to form additional fused substituted or unsubstituted carbocyclic and/or heterocyclic rings; provided that $D^1$ and $D^3$ taken together and $D^2$ and $D^4$ taken together both embody at least one oxygen, nitrogen, silicon, phosphorus or sulfur atom separated from the aromatic nucleus by zero or one intervening carbon atom; and $L^4$ and $L^5$ are groups which, taken together, contain about 2–40 carbon atoms, not more than 24 halogen atoms, and not more than 6 heteroatoms selected from oxygen, nitrogen, silicon, phosphorus and sulfur; provided that $S_xE_1$ may not be hydroxymethyl or 1-hydroxyethyl.

In a preferred mode of this invention the above definition of $P_3$ is maintained, provided that: for all $P_3$, $S_xE_1$ taken together may not comprise CO$_2$Me, CO$_2$Et, CONH$_2$, —CH$_2$—$R_e^e$ or —CH(CH$_3$)—$R_e^e$ (wherein $R_e^e$ is hydrogen, chloro, bromo, an acyloxy group, a $C_1$-$C_{12}$ saturated or unsaturated, linear or branched alkoxy, substituted or unsubstituted triphenylmethyloxy, —OCH$_2$OCH$_3$, (tetrahydro-2H-pyran-2-yl)oxy, or a ($C_1$-$C_6$ linear or branched alkyl)$_n$ (phenyl)$_{3-n}$-silyloxy, wherein n is 0–3.

$P_4$ is a radical of the formula:

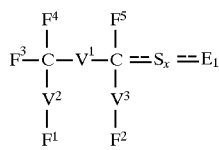

in the form of an individual isomer, an isomer mixture, a racemate or optical antipode, or a pharmaceutically acceptable salt thereof, wherein $V^1$ is a bond or is a carbon atom carrying substituents individually selected from hydrogen, methyl, and halogen; $V^2$ and $V^3$ are individually selected from oxygen, sulfur, sulfoxide, and —NV$^4$— in which $V^4$ is hydrogen or a hydrocarbon radical containing not more than 30 carbon atoms; $F^1$ and $F^2$ independently are groups which, taken together, contain 10–40 carbon atoms, not more than 24 halogen atoms, and not more than 8 heteroatoms selected from oxygen, nitrogen, silicon, phosphorus and sulfur, and wherein $F^1$ and $F^2$ may optionally be linked to form a structure comprising 1–3 rings; $F^3$ is hydrogen or a substituent selected from methyl, ethyl, trifluoromethyl, 2,2,2-trifluoroethyl, cyano, vinyl, ethynyl, allyl, and propargyl, $F^4$ and $F^5$ each may be hydrogen or may be hydrocarbon or halogenated hydrocarbon radicals which, taken together, contain not more than 40 carbon atoms, not more than 24 halogen atoms and not more than 8 heteroatoms selected from oxygen, nitrogen, silicon, phosphorus and sulfur, and wherein $F^4$ and $F^5$ may optionally be linked to form a structure comprising 1–3 rings, provided that $V^4$, $F^1$, $F^2$, $F^4$ and $F^5$ taken together contain not more than 50 carbon atoms, not more than 30 halogens and not more than 12 heteroatoms selected from oxygen, nitrogen, sulfur, silicon and phosphorus, and provided that $S_xE_1$ may not be hydrogen, methyl, chloromethyl, hydroxymethyl, mercaptomethyl, unsubstituted carboxamido, 1-hydroxyethyl or alkanoyloxymethyl.

In a preferred mode of this invention the above definition of $P_4$ is maintained, provided that: for all $P_4$, $S_xE_1$ taken together may not comprise CO$_2$Me, CO$_2$Et, CONH$_2$, —CH$_2$—$R_e^e$ or —CH(CH$_3$)—$R_e^e$, wherein $R_e^e$ is hydrogen, a halogen, an acyloxy group, a $C_1$-$C_2$ saturated or unsaturated linear or branched alkoxy, an unsubstituted or substituted triphenylmethyloxy group, —OCH$_2$OCH$_3$, (tetrahydro-2H-pyran-2-yl)oxy, or a ($C_1$-$C_6$ linear or branched alkyl)$_n$(phenyl)$_{3-n}$ silyloxy, wherein n is 0–3.

$P_5$ is a radical of the formula:

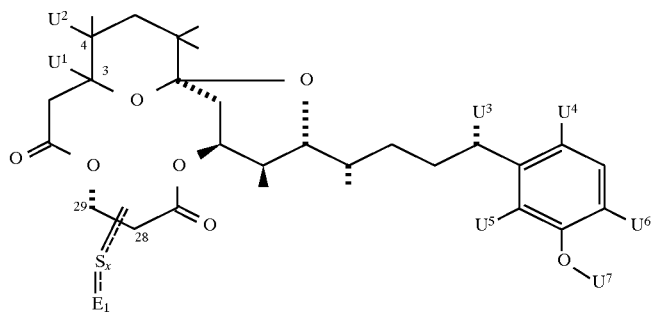

in the form of an individual isomer, an isomer mixture, a racemate or optical antipode, or a pharmaceutically acceptable salt thereof, wherein $U^1$ and $U^2$, independently, are selected from hydrogen, azide, halogen, hydroxy, $C_{1-7}$ alkoxy, $C_{1-7}$ alkenoxy, $C_{1-7}$ alkynoxy, thiol, $C_{1-7}$ alkanoyl, $C_{1-7}$ saturated or unsaturated alkyl, and cyano; or $U^1$ and $U^2$ taken together may be an oxygen atom forming an epoxy group or may be an additional bond forming an unsaturated linkage, $U^3$ is selected from hydrogen, halogen, $C_{1-12}$ alkyl $C_1$–$C_{12}$ alkenyl, $C_1$–$C_{12}$ alkynyl, $C_1$–$C_{12}$ alkoxy, $C_1$–$C_{12}$ alkenoxy, $C_1$–$C_{12}$ alkynoxy, and aryl or $C_7$–$C_{12}$ aralkyl wherein the aryl group may be substituted by nitro, halogen, cyano, and/or di(lower-alkyl)amino groups, $U^4$–$U^6$, independently, are selected from hydrogen, halogen, cyano, nitro, amino, di(lower-alkyl)amino, $C_{1-7}$ saturated or unsaturated alkyl, hydroxy, $C_{1-7}$ saturated or unsaturated alkoxy, $C_{1-7}$ carboalkoxy, $C_{1-7}$ alkanoyloxy, and azide, and $U^7$ is selected from hydrogen, $C_{1-7}$ saturated or unsaturated alkyl, and $C_{1-7}$ saturated or unsaturated alkanoyl; provided that if $S_xE_1$ is hydroxymethyl, 1-hydroxyethyl or acetoxymethyl, then $S_xE_1$ may not be bonded to carbon 29.

In a preferred mode of this invention the above definition of $P_5$ is maintained, provided that: for all $P_5$, if $S_xE_1$ is bonded to carbon 29, then $S_xE_1$ taken together may not comprise —$CH_2$—$R_e^e$ or —$CH(CH_3)$—$R_e^e$, wherein $R_e^e$ is acetoxy, benzyloxy, benzyloxymethoxy or $(C_1$–$C_6$ linear or branched alkyl$)_n$(phenyl$)_{3-n}$ silyloxy, wherein n is 0–3.

$P_6$ is a radical of the formula:

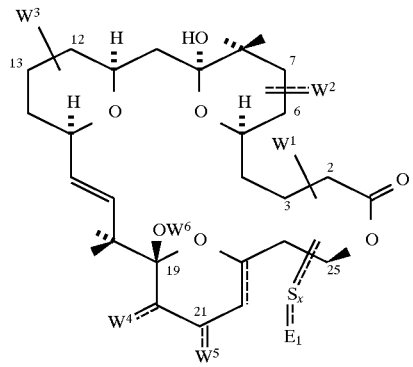

in the form of an individual isomer, an isomer mixture, a racemate or optical antipode, or a pharmaceutically acceptable salt thereof, wherein $W^1$ is selected from hydrogen, halogen, hydroxy, $C_{1-5}$ alkoxy, $C_{1-5}$ alkanoyloxy and cyano; $W^2$ is selected from oxo, hydrogen, hydroxy, cyano, $C_{1-7}$ alkyl, $C_{1-7}$ alkoxy, $C_{1-7}$ alkanoyloxy, and halogen; $W^3$–$W^5$ each may be hydrogen or a group containing not more than 30 carbon atoms, not more than 24 halogen atoms, and not more than 8 heteroatoms selected from oxygen, nitrogen, and sulfur, and $W^4$ and $W^5$ taken together may form an additional carbocyclic or heterocyclic ring; $W^6$ is hydrogen or a group containing not more than 15 carbon atoms, not more than 12 halogen atoms and not more than 5 heteroatoms selected from oxygen, nitrogen, and sulfur; and $W^6$, taken together with $W^4$ and $W^5$, may complete an additional carbocyclic or heterocyclic ring; provided that if $S_xE_1$ is hydroxymethyl or 1-hydroxyethyl then $S_xE_1$ may not be bonded to carbon 25.

In a preferred mode of this invention the above definition of $P_6$ is maintained, provided that: for all $P_6$, if $S_xE_1$ is bonded to carbon 25, then $S_xE_1$ taken together may not comprise an acetyl group or —$CH(CH_3)$—$R_e^e$, wherein $R_e^e$ is $C_1$–$C_{12}$ saturated or unsaturated, linear or branched, substituted or unsubstituted, alkanoyloxy or benzoyloxy, substituted benzoyloxy, aroyloxy or $(C_1$–$C_6$ linear or branched alkyl$)_n$(phenyl$)_{3-n}$silyloxy, wherein n is 0–3.

$P_7$ is a radical of the formula:

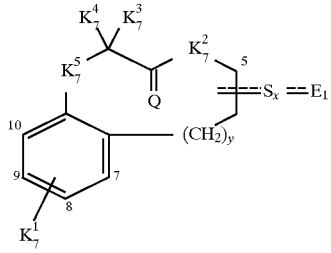

in the form of an individual isomer, an isomer mixture, a racemate or optical antipode, or a pharmaceutically acceptable salt thereof, wherein $K_7^1$ represents 1–4 identical or different substituents located independently at carbons 7, 8, 9 and/or 10, which substituents may independently be hydrogen, halogen and/or other groups which, taken together, contain not more than 9 heteroatoms selected from oxygen, nitrogen, silicon, phosphorus and sulfur, the groups being optionally connected to one another and/or to $K_7^5$ to form 1–2 additional carbocyclic or heterocyclic rings, $K_7^2$ is selected from oxygen, sulfur —$NK_7^6$— or —$CK_7^6K_7^7$— wherein $K_7^6$ is hydrogen, hydroxy, methyl, ethyl, fluoro, n-propyl, allyl, or propargyl, and $K_7^7$ is hydrogen, methyl, ethyl, halogen, trifluoromethyl or cyano; $K_7^3$ and $K_7^4$ may be the same or may differ and each may independently be hydrogen, halogen, a substituent group, or may complete an additional ring connecting $K_7^3$ and $K_7^4$ or connecting either $K_7^3$ or $K_7^4$ to $K_7^5$ such that $K_7^3$ and $K_7^4$ taken together contain not more than 18 carbon atoms, not more than 12 halogen atoms, and not more than 8 heteroatoms selected from oxygen, nitrogen, silicon, phosphorus and sulfur, $K_7^5$ is selected from oxygen, sulfur, sulfoxide, sulfone or —$NK_7^8$—, —$NOK_7^8$— or —$CK_7^8K_7^9$— wherein $K_7^8$ is hydrogen or a group containing not more than 30 carbon atoms, not more than 24 halogen atoms, and not more than 8 heteroatoms selected from oxygen, nitrogen, silicon, phosphorus and sulfur, and $K_7^9$ is hydrogen, methyl, ethyl, n-propyl, hydroxy, halogen, allyl, propargyl, cyano, or trifluoromethyl, y may either be 0 or 1; and, Q is as defined below, provided that if $S_xE_1$ is hydroxymethyl or 1-hydroxyethyl then $S_xE_1$ may not be bound to carbon 5.

In a preferred mode of this invention the above definition of $P_7$ is maintained, provided that if $K_7^3$ is isopropyl, and $K_7^4$ is hydrogen, and $K_7^2$ is —NH—, and $K_7^1$ is hydrogen and/or an unbranched alkyl group attached to carbon 9, and $K_7^5$ is —NH—, —N(CH$_3$)— or —N(CHO)—, then if $S_x$ is a single bond directed to the carbon atom that is adjacent to $K_7^2$ and $E_1$ is —CH$_2$—R$_e^e$ then R$_e^e$ is not acetoxy or (C$_1$–C$_6$ linear or branched alkyl)$_n$(phenyl)$_{3-n}$silyloxy, wherein n is 0–3.

$S_x$ may represent any of a broad range of connecting chains or groups of atoms, designated $S_B$, $S_1$, $S_2$, $S_3$, $S_4$, $S_5$ and S6. Surprisingly, these organic functional groups may be hydrophobic in nature, with few if any polar or heteroatoms present, may be extensively halogen-substituted, or may contain one or several polar atoms such as oxygen, nitrogen, silicon, phosphorus, arsenic, boron, selenium and/or sulfur in any of numerous chemical groupings. Such functional groupings may even bear positive or negative charges at physiologic pH, and the values which are permissible for $S_x$ also may include combinations of hydrophobic, halogenated, hydrophilic and/or charged functional groups. The resultant compounds in any case generally display, variously, the protein kinase C-modulatory, non-toxic agonist, and/or antagonistic properties, selectivities and utilities described in this invention.

In a preferred mode of this invention, $S_B$-$S_6$ may comprise the following values.

$S_B$ is a single or double bond.

$S_1$ is a chain of atoms of the formula:

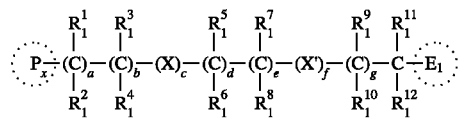

wherein a, b, d, e, and g may independently be from 0 to 3; c and f may independently be 0 or 1; the sum of (a+b+c+d+e+f+g) is at least 1 but not more than 12; and if c and f are both 1, then the sum of (d+e) must be at least 1; and X and X' are as defined below.

$S_2$ is a chain of atoms of the formula:

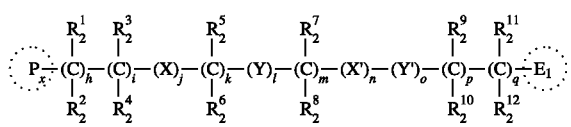

wherein h, i, k, m, p, and q may be independently be from 0 to 3; j and n may independently be 0 or 1; if j and n are both 1 and l is 0, then the sum of (k+m) must be at least 1; if n is 1 and o is 0, then the sum of (p+q) must be at least 1, the sum of (1+o) is 1–3; and the sum of (h+i+j+k+2l+m+n+2o+p+q) is at least 1 but not more than 12; and X, X', Y and Y' are as defined below.

$S_3$ is a chain of atoms of the formula:

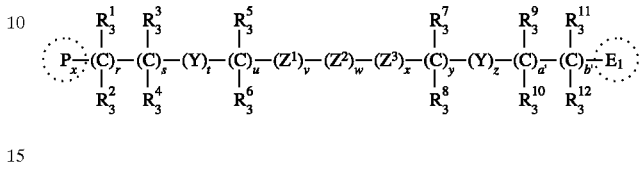

wherein r, s, u, y, a', and b' may independently be from 0 to 3; the sum of (t+z) is 0 or 1; the sum of (v+w+x) is 1; the sum of (y+z+a'+b') is at least 1; and the sum of (r+s+2t+u+2v+3w+4x+y+2z+a'+b') is at least 1 but not more than 12; and Y, Y', $Z^1$, $Z^2$, and $Z^3$ are as defined below.

$S_4$ is a chain of atoms defined by:

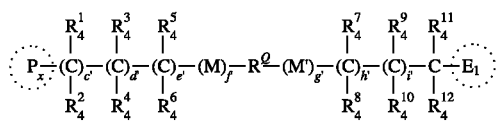

wherein c', d', e', h', and i' may independently be from 0 to 3; the sum of (f'+g') must be 1 or 2; f' and g' may independently be 0 or 1; and the sum of (c'+d'+e'+f+g'+h'+i') is at least 1 but not more than 12; and M, M', and $R^Q$ are as defined below.

$S_5$ is a chain of atoms defined by:

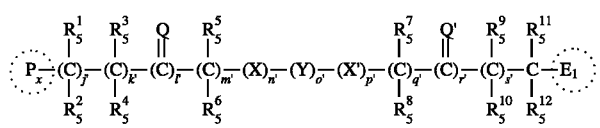

wherein j', k', m', q', and s' may independently be from 0 to 3; l' and r' may each be 0 or 1, but the sum of (l'+r') must be 1 or 2; n' and p' may each be 0 or 1, but the sum of (n'+p') must be 0 or 1; the value of o' may be 0–2; if the sum of (n'+p') is 1 and l' is 0, then q' must be at least 1; if the sum of (n'+p') is 1 and r' is 0, then m' must be at least 1; and the sum of (j'+k'+l'+m'+n'+o'+p'+q'+r'+s') is at least 1 but not more than 12; and Q, Q', X, X', and Y are as defined below.

$S_6$ is a chain of atoms defined by:

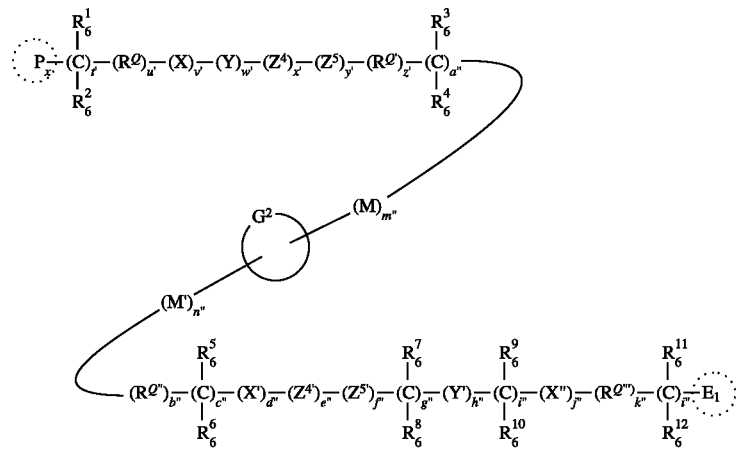

wherein u', v', w', x', y', z', and m" may each be 0 or 1; t' and a" may each independently be 0–6, the sum of (t'+u'+v'+2w'+x'+2y'+z'+a") must be 0–8; b", d", e", f", h", j", k" and n" may each independently be 0 or 1; c", g", i", and l" may each independently be 0–3; if d" and j" are both 1, then the sum of (g"+i") must be at least 1; if either j" or k" is 1, then l" must be at least 1; if b" is 1, then the sum of (c"+g"+h"+i"+l") must be at least 1; if d" is 1, then the sum of (g"+h"+i"+l") must be at least 1; and the sum of (t'+u'+v'+2w'+x'+2y'+z'+a"+b"+c"+d"+e"+2f"+g"+2h"+i"+j"+k"+l") must be 0–14; if m" is zero, $R_6^3$ or $R_6^4$ may optionally comprise an additional bond to $G^2$ as defined below, thus completing an unsaturated linkage; if n" and b" are zero, $R_6^5$ or $R_6^6$ may optionally comprise an additional bond to $G^2$, thus completing an unsaturated linkage; one of the substituents $R_6^1$–$R_6^4$ and/or one of the substituents $R_6^5$–$R_6^{12}$ may optionally comprise the same or different values of $G^1$, as defined below; and M, M', $R^Q$, $R^{Q'}$, $R^{Q''}$, $R^{Q'''}$, X, X', X", Y, Y', $Z^4$, $Z^{4'}$, $Z^5$ and $Z^{5'}$ are as defined below.

For $S_1$–$S_6$, $R_1^1$ through $R_6^{12}$ may be the same or different and each may be hydrogen, halogen or an acyclic substituent containing not more than 20 carbon atoms, not more than 16 halogen atoms, and not more than 6 heteroatoms selected from oxygen, nitrogen, sulfur, silicon, boron, arsenic, phosphorus and selenium, one substituent selected from $R_1^1$, $R_1^2$, $R_2^1$, $R_2^{22}$, $R_3^1$, $R_3^2$, $R_4^1$, $R_4^2$, $R_5^1$, $R_5^2$, $R_6^1$ and $R_6^2$ may optionally comprise an additional bond completing an unsaturated linkage to $P_x$; one or two of the substituents $R_1^1$–$R_5^{12}$ may optionally comprise the same or different values of $G^1$, as defined below; one substituent selected from $R_1^{11}$, $R_1^{12}$, $R_2^{11}$, $R_2^{12}$, $R_3^{11}$, $R_3^{12}$, $R_4^{11}$, $R_4^{12}$, $R_5^{11}$, $R_5^{12}$, $R_6^{11}$ and $R_6^{12}$ may optionally comprise an additional bond to $E_1$, thereby completing an unsaturated linkage, one of the substituents $R_1^{1-R_6^{12}}$ may be linked to either the atom in $P_x$ that carries the $S_x$ chain or to an atom in $P_x$ adjacent thereto, to form a saturated, unsaturated or aromatic, carbocyclic or heterocyclic 4–8 membered ring optionally containing 1–4 identical or different ring hetero members selected from X and =N—, the ring being optionally substituted by 1–8 identical or different substituents, preferably selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy.

The foregoing description of $S_1$–$S_6$ is subject to the restriction that, for any given $S_1$, $S_2$, $S_3$, $S_4$, $S_5$ or $S_6$, but excluding $P_x$ and $E_1$: the total of carbon atoms is 25 or less; the total of halogen atoms is 16 or less, the total of oxygen atoms is 6 or less; the total of nitrogen atoms is 4 or less; the sulfur, silicon, boron and phosphorus atoms each total 3 or less; the arsenic and selenium atoms each total 1 or less; and the total of oxygen, nitrogen, silicon, boron, arsenic, phosphorus, selenium and sulfur atoms together is 8 or less.

In a preferred mode of this invention, the oxygen, nitrogen, sulfur, silicon and/or phosphorus atoms in $R_1^1$–$R_6^{12}$ may be situated in a variety of functional groups such as hydroxy, amino, hydroxylamine, tertiary amine oxide, Schiff's base, hydrazine, thiol, nitro, nitroso, oxime, azide, ether, acetal, ketal, thioether, aldehyde, keto, hydrazone, carboxy, mercaptocarbonyl, mercaptothionocarbonyl, sulfonate, sulfonyl, sulfoxide, phosphate, phosphonate, phosphate ester, phosphonate ester, phosphine, phosphine oxide, thionophosphine, phosphite, phosphonium, phosphorothioate, thionophosphate ester, thiophosphonate, thionophosphonate ester, silane, silanol, silanediol, fluorinated silane, ester, amide, cyano, hydrazide, carbonate, carbamate, urea, isourea, carboxamidine, imidate, guanidine, thioester, thioamide, thiocarbonate, dithiocarbonate, thiocarbamate, dithiocarbamate, thiourea, isothiourea, thioimidate, nitroguanidine, cyanoguanidine and xanthate. Preferably, for any given $S_x$, the total of —OH groups is 3 or less, the total of —$NH_2$ groups is 2 or less, the total of —SH groups is 2 or less, and the total of —OH, —SH and —$NH_2$ groups is 4 or less.

X, X', X" may be the same or different and are selected from:

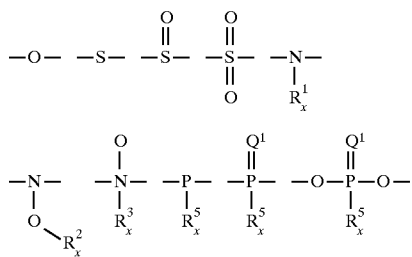

-continued

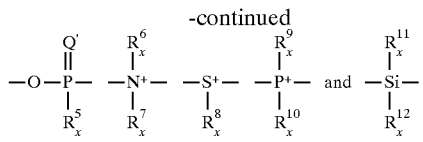

or from —Se—, —B($R_X^4$)— and —O—B($R^{X5}$)—O—; wherein $R_X^1$, $R_X^2$, $R_X^{11}$ and $R_X^{12}$ may independently be hydrogen; $R_X^1$ through $R_X^{12}$ may be the same or different and each may be an acyclic substituent containing 1–20 carbon atoms, not more than 16 halogen atoms, and not more than 6 heteroatoms selected from oxygen, nitrogen, and sulfur, such that for any substituent the oxygen atoms total 4 or less, the nitrogen atoms total 4 or less, and the sulfur atoms total 2 or less; $R_X^4$, $R_X^5$, $R_X^{11}$ and $R_X^{12}$ may independently be hydroxy; Q and Q' are as defined below; $R_X^1$ may optionally represent an additional bond to $P_x$, thus completing an unsaturated linkage; and, one to four of the substituents $R_X^1$–$R_X^{12}$ may optionally comprise the same or different values of $G^1$, as defined below.

Y and Y' may be the same or different and are selected from:

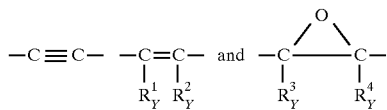

wherein $R_Y^1$ and $R_Y^2$, and $R_Y^3$ and $R_Y^4$, each pair being cis or trans relative to one another, may be the same or different and each may be hydrogen or an acyclic substituent containing not more than 20 carbon atoms, not more than 16 halogen atoms, and not more than 6 heteroatoms selected from oxygen, nitrogen, and sulfur, such that for any substituent the oxygen atoms total 4 of less, the nitrogen atoms total 4 or less, and the sulfur atoms total 2 or less, $R_Y^1$ and $R_Y^2$ may also independently be halogen; one or two of the substituents $R_Y^1$–$R_Y^4$ may optionally comprise the same or different values of $G^1$, as defined below; and one of the substituents $R_X^1$–$R_X^{12}$ and $R_Y^1$–$R_Y^4$ may be linked to either the atom in $P_x$ that carries the chain containing X, X', and/or X" or to an atom in $P_x$ adjacent thereto, to form a saturated, unsaturated or aromatic, carbocyclic or heterocyclic 4–8 membered ring defined as for the analogous $R_1^1$–$R_6^{12}$-containing ring above.

In a preferred embodiment, the substituents $R_X^1$–$R_X^{12}$ and $R_Y^1$–$R_Y^4$ are selected from hydroxy, amino, thiol, nitro, azide, ether, thioether, aldehyde, keto, carboxy, mercaptocarbonyl, mercaptothionocarbonyl, sulfonate, sulfonyl, sulfoxide, ester, amide, cyano, carbonate, carbamate, urea, isourea, carboxamidine, guanidine, thioester, thioamide, thiourea, nitroguanidine, cyanoguanidine and xanthate.

$Z^1$ is selected from:

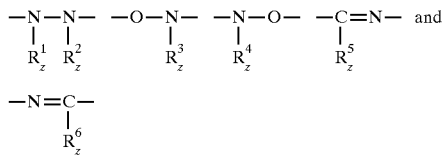

$Z^2$ is selected from:

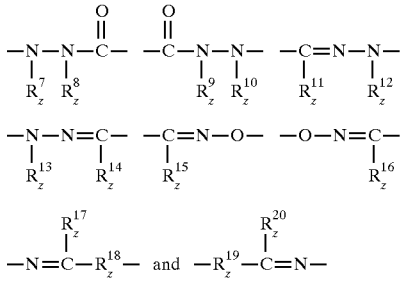

$Z^3$ is selected from:

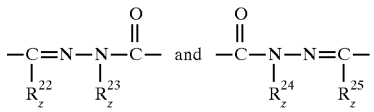

$Z^4$ and $Z^{4'}$ independently may be:

$Z^5$ and $Z^{5'}$ independently may be:

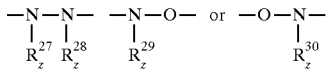

wherein the substituents $R_Z^1$–$R_Z^{30}$ are generally selected from hydrogen, halogen in cases where a chemically stable structure results, and a radical containing about 1–12 carbon atoms and optionally containing 0–12 halogens and 0–6 heteroatoms selected from oxygen, nitrogen and sulfur.

In a preferred embodiment of the invention, the substituents $R_Z^1$–$R_Z^{30}$ comprise a range of saturated or unsaturated substituents as described below, wherein the terms alkyl, halogenated alkyl and acyl are taken to include alkenyl, alkynyl, alkenoyl and alkynoyl and their halogenated forms.

Thus: $R_6^{26}$ be any of the values specified for $R_X^1$–$R_X^{12}$ above; $R_Z^{18}$ and $R_Z^{19}$ individually may be —O—, —S—, or —$NR_Z^{21}$—, wherein $R_Z^{21}$ may be hydrogen, $C_{1-4}$ alkyl, 2-hydroxyethyl, 2-hydroxy-n-propyl, 2-acetoxyethyl, or 2-acetoxy-n-propyl; $R_Z^{17}$ and $R_Z^{20}$ individually may be hydrogen or a substituent selected from $C_{1-4}$ alkyl; $C_{1-4}$ alkoxy; $C_{1-4}$ alkylthio, phenoxy or thiophenoxy optionally substituted by methyl, hydroxy, hydroxymethyl, thiol, carboxy, carboxymethyl, amino, methoxy, halogen, and/or nitro; or amino optionally mono- or disubstituted by $C_{1-4}$ alkyl or monosubstituted by cyano, nitro or phenyl optionally substituted by halogen, hydroxy, hydroxymethyl, thiol, carboxy, carboxymethyl, amino, and/or nitro; $R_Z^1$–$R_Z^{16}$, $R_Z^{22}$–$R_Z^{25}$ and $R_Z^{27}$–$R_Z^{30}$ may be hydrogen, a saturated or unsaturated substituent selected from $C_{1-6}$ alkyl, $C_{1-6}$ halogenated alkyl, and cyclohexyl, or may be phenyl or benzyl, each optionally substituted by methyl, ethyl, hydroxy, hydroxymethyl, thiol, carboxy, carboxymethyl, amino, methoxy, nitro, cyano, trifluoromethyl, and/or halogen; $R_Z^1$–$R_Z^4$, $R_Z^7$, $R_Z^{10}$, $R_Z^{12}$, $R_Z^{13}$ and $R_Z^{27}$–$R_Z^{30}$may also be independently selected from $C_{1-6}$ acyl, $C_{1-6}$ halogenated acyl, $C_{2-6}$ monohydroxyacyl, and $C_{2-6}$ hydroxyalkyl; $R_Z^5$ and $R_Z^6$ may also be independently selected from $C_{1-6}$ hydroxyalkyl, $C_{1-6}$ alkoxy, $C_{1-6}$ hydroxyalkoxy; and $R_Z^8$, $R_Z^9$, $R_Z^{23}$ and $R_Z^{24}$ may also independently be $C_{2-6}$ hydroxyalkyl; one of the substituents $R_Z^1$–$R_Z^{17}$, $R_Z^{20}$, $R_Z^{21}$, $R_Z^{22}$ and $R_Z^{25}$ may be linked to either the atom in $P_X$ that carries the chain containing $Z^1$ or to an atom in $P_X$ adjacent thereto, to form a saturated, unsaturated, or aromatic, carbocyclic or heterocyclic 4–8 membered ring optionally containing 1–4 other identical or different hetero ring members selected from O, S, =N—, and NH, the ring being optionally substituted on its carbon and/or NH members by 1–8 identical or different substituents selected from halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy; $R_Z^{26}$ may comprise $G^1$ as defined below; an optional ring may be formed between $R_Z^{26}$ and $P_X$ as described above for $R_X^1$–$R_X^{12}$; $R_Z^1$, $R_Z^4$, $R_Z^7$, $R_Z^{26}$ or $R_Z^{27}$ may comprise an additional bond to $P_X$, thus completing an unsaturated linkage; and only one of the substituents $R_Z^1$–$R_Z^{25}$ may be substituted or unsubstituted phenyl or benzyl.

M and M' independently may be:

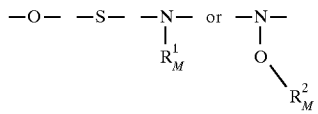

wherein $R_M^1$ and $R_M^2$ may be the same or different and each may be hydrogen or a saturated or singly or multiply unsaturated, straight or branched, acyclic substituent containing 1–20 carbon atoms, not more than 16 halogen atoms, and not more than 6 heteroatoms selected from oxygen, nitrogen, and sulfur, in which the oxygen atoms total 4 or less, the nitrogen atoms total 4 or less, and the sulfur atoms total 2 or less, the heteroatoms being preferably situated in functional groups selected from hydroxy, amino, thiol, nitro, azide, ether, thioether, aldehyde, keto, carboxy, ester, amide, cyano, nitroguanidine, and cyanoguanidine; $R_M^1$ may optionally comprise an additional bond to $P_X$ group, thus completing an unsaturated linkage; $R_M^1$ or $R_M^2$ may optionally comprise the same or different values of $G^1$, as defined below; $R_M^1$ or $R_M^2$ may be linked to either the atom in $P_X$ that carries the chain containing M and/or M' or to an atom in $P_X$ adjacent thereto, to form a saturated, unsaturated or aromatic, carbocyclic or heterocyclic 4–8 membered ring defined as for the analogous $R_1^1$–$R_6^{12}$-containing ring above.

Q-Q''' independently may be:

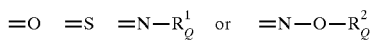

wherein $R_Q^1$ and $R_Q^2$ may be the same or different and each may have the values specified above for $R_M^1$ and $R_M^2$; $R_Q^1$ and/or $R_Q^2$ may optionally comprise the same or different values of $G^1$, as defined below; $R_Q^1$ may be linked to either the atom in $P_X$ that carries the chain containing Q and/or Q' or to an atom in $P_X$ adjacent thereto, to form a saturated, unsaturated or aromatic, carbocyclic or heterocyclic 4–8 membered ring defined as for the analogous $R_1^1$–$R_6^{12}$-containing ring above.

$R^Q$–$R^{Q'''}$ are independently selected from:

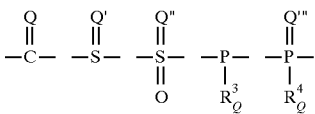

wherein $R_Q^3$ and $R_Q^4$ may be the same or different and each may be selected from halogen and the values specified above for $R_M^1$ and $R_M^2$; $R_Q^3$ and/or $R_Q^4$ may optionally comprise the same or different values of $G^1$, as defined below; Q and Q' are as defined above; one of $R_Q^3$ and $R_Q^4$ may be linked to either the atom in $P_X$ bonded to the chain that carries $R^Q$ or to an atom in $P_X$ adjacent thereto, to form a saturated, unsaturated or aromatic, carbocyclic or heterocyclic 4–8 membered ring defined as for the analogous $R_1^1$–$R_6^{12}$-containing ring above.

$G^1$ and $G^2$ independently comprise a group containing 1–3 fused or separate, saturated, unsaturated or aromatic, carbocyclic or heterocyclic 4–8 membered rings, each ring optionally containing 1–4 identical or different hetero ring members selected from X and =N—, each ring being optionally substituted on its carbon and/or NH members by 1–8 identical or different substituents, preferably selected from halogen, hydroxy, methoxy, ethoxy, methyl, ethyl, cyano, azide, nitro, hydroxymethyl, 1-hydroxyethyl, 2-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy; wherein for $G^1$ the optional second and third rings may be fused to the first ring and/or to one another or may be separate rings connected to one another and/or to the atom bearing $G^1$ by a single or double bond or by an intervening substituted or unsubstituted, linear or branched, saturated or unsaturated chain containing not more than 8 carbon atoms, not more than 8 halogens, and not more than 4 heteroatoms selected from oxygen, nitrogen, silicon, boron, arsenic, phosphorus, selenium and sulfur; and wherein for $G^2$ the first ring is singly or doubly bonded to $P_X$ or to a component atom of the $S_6$ chain connecting $P_X$ and $G^2$, and the optional second and third rings may be fused to the first ring or to one another or may be separate rings connected to one another and/or to the first ring by single or double bonds or by an intervening substituted or unsubstituted, linear or branched, saturated or unsaturated chain containing not more than 8 carbon atoms, not more than 8 halogens, and not more than 4 heteroatoms selected from oxygen, nitrogen, silicon, boron, arsenic, phosphorus, selenium and sulfur.

The capping group $E_o$ that terminates the connecting chain also may be selected from any of a surprisingly broad array of chemical groupings, and these chemical groupings can be composed of a far larger number of atoms than is found in the hydroxymethyl or 1-hydroxyethyl group. These chemical groupings may include, without limitation, hydrophobic entities such as alkyl, hydrogen, and halogenated alkyl, or may include, without limitation, quite hydrophilic organic functional groups, such as hydroxy, thiol, carboxy and carboxy esters, amines, etc. It is well-known in the art that organic functional groups spanning a wide range of properties, from ionized and very hydrophilic to very hydrophobic, can be formed from multi-atom groupings of elements selected from carbon, hydrogen, halogen, oxygen, nitrogen, silicon, phosphorus, arsenic, boron and selenium. Indeed, for this invention the single restriction appears to be that $S_oE_o$ taken together should not be hydroxymethyl or 1-hydroxyethyl bonded in the usual position in the parent compounds, since such compounds correspond to the skin-inflammatory and often tumor-promoting parent natural products.

Thus, $E_o$ may comprise $E_1$, wherein $E_1$ is selected from =O, =S, =NH, =NOR$_E^8$ wherein R$_E^8$ is hydrogen or a $C_1$-$C_8$ normal or branched alkyl radical, =N—NH$_2$, hydrogen, halogen, —OH, —SH, —NH$_2$, —NH—NH$_2$, —N$_3$, —CN, —NO, —NO$_2$, —NHOH, —ONH$_2$, or is selected from:

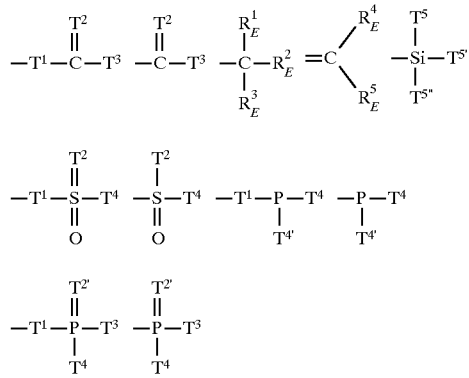

wherein T$^1$ is selected from —O—, —S—, and —NH—, T$^2$ is selected from =O, =S, and =N—R$_E^6$ in which R$_E^6$ may be hydrogen, hydroxy, cyano, or nitro; T$^{2'}$ is selected from =O and =S; T$^3$, T$^4$ and T$^{4'}$ are independently selected from —OH, —NH$_2$, —SH, —N$_3$, —NH—NH$_2$, and —NH—OR$_E^7$ in which R$_E^7$ may be hydrogen, $C_{1-3}$ alkyl or $C_{1-3}$ acyl, T$^3$ may also be hydrogen or halogen; T$^5$–T$^{5''}$ are independently selected from hydrogen and hydroxy; T$^5$ may also be halogen; R$_E^1$ is selected from hydrogen, halogen, hydroxy, nitro, nitroso, cyano, azide, —NH$_2$, —NH—OH, —SH, —O—NH$_2$, —NH—NH$_2$, —T$^1$—C(=T$^2$)—T$^3$, —C(=T$^2$)—T$^3$, —SiT$^5$T$^{5'}$T$^{5''}$, —T$^1$—S(=O)(=T$^2$)—T$^4$, —S(=O)(=T$^2$)—T$^4$, —T$^1$—P(—T$^4$)—T$^{4'}$, —P(—T$^4$)—T$^{4'}$, —T$^1$—P(=T$^{2'}$)(—T$^3$)—T$^4$, and —P(=T$^{2'}$)(—T$^3$)—T$^4$; R$_E^2$ and R$_E^3$ are individually selected from hydrogen, —C(=T$^2$)—T$^3$, cyano, nitro, azide, halogen and a $C_1$-$C_{15}$ straight or branched chain, saturated, unsaturated and/or aromatic substituent optionally containing not more than 10 halogen atoms and not more than 4 heteroatoms selected from oxygen, nitrogen and sulfur.

Finally, if R$_E^1$ is cyano or —C(=T$^2$)—T$^3$, then R$_E^2$ or R$_E^3$ may optionally be selected from —SiT$^5$T$^{5'}$T$^{5''}$, —T$^1$—P(=T$^{2'}$)(—T$^3$)—T$^4$, and —P(=T$^{2'}$)(—T$^3$)—T$^4$; and R$_E^4$ and R$_E^5$ are individually selected from hydrogen, halogen, cyano, nitro, —C(=T$^2$)—T$^3$, —T$^1$—C(=T$^2$)—T$^3$, —CR$_E^1$R$_E^2$R$_E^3$, —SiT$^5$T$^{5'}$T$^{5''}$, —S(=O)(=T$^2$)—T$^4$, and —P(=T$^{2'}$)(—T$^3$)—T$^4$.

In this invention, novel phorboids of the $P_1$ diterpene class are further illustrated by the general structure $P_{1R}$,

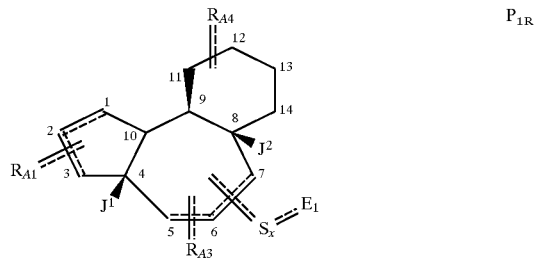

wherein carbons (1 and 2) or (2 and 3) may be joined by a double bond; carbons (5 and 6) or (6 and 7) may be joined by a double bond; $S_xE_1$ may be bonded to carbon 5, 6 or 7; R$_{A1}$ represents not more than 6 identical or different substituents bonded independently via single and/or double bonds to carbons 1, 2 and/or 3, which substituents may independently be halogen(s) and/or other groups, which halogens and groups taken together contain a total of not more than 30 carbon atoms, not more than 24 halogen atoms and not more than 9 heteroatoms selected from oxygen, nitrogen, silicon, phosphorus and sulfur; R$_{A3}$ represents not more than 6 identical or different substituents bonded independently via single and/or double bonds to carbons 5, 6 and/or 7, which substituents may independently be halogen (s) and/or other groups, which halogens and groups taken together contain not more than 12 carbon atoms, not more than 8 halogen atoms, and not more than 5 heteroatoms selected from oxygen, nitrogen, silicon, phosphorus and sulfur; and R$_{A4}$ represents not more than 10 identical or different substituents bonded independently via single or double bonds to carbons 9, 11, 12, 13 and/or 14, which substituents may independently be halogen(s) and/or other groups, the group or groups optionally completing 1–3 additional rings through bonds among themselves and/or 1–5 additional rings when taken together with the 5-membered ring and its substituent(s) R$_{A1}$, which halogen and groups taken together, include not more than 50 carbon atoms, not more than 24 halogen atoms, and not more than 15 heteroatoms selected from oxygen, nitrogen, silicon, phosphorus and sulfur.

Preferred embodiments of $P_{1R}$ are illustrated by, but not limited to, structures carrying a substituted or unsubstituted cyclopropyl ring, forming $P_{1P}$

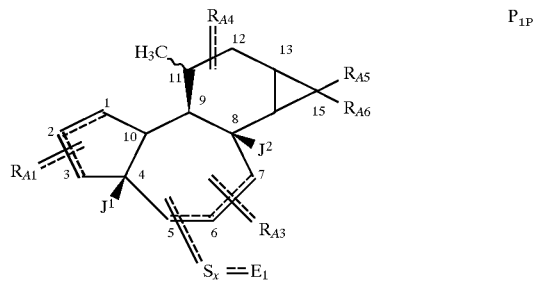

wherein the R$_{A5}$ and R$_{A6}$ radicals may independently be hydrogen, halogen and/or other groups, which halogens and groups taken together contain a total of not more than 30 carbon atoms, not more than 24 halogen atoms and not more than 9 heteroatoms selected from oxygen, nitrogen, silicon, phosphorus and sulfur.

In compounds further illustrating $P_{1P}$, carbon 2 carries a methyl group, J$^1$ is hydroxy, carbon 9 carries a hydroxy group in the α configuration, carbons 10 and 14 carry hydrogens in the α configuration, carbon 11 carries a methyl group in the α configuration and R$_{A5}$ and R$_{A6}$ are both methyl, forming a preferred parent structure for use in the present invention, $P_{1PP}$:

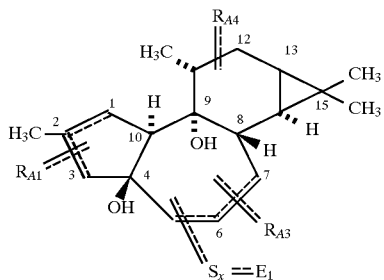

In another embodiment of $P_{1R}$, an orthoester structure is bonded to the 6-membered ring via one orthoester oxygen atom in the α configuration to carbon 9 and via two orthoester oxygen atoms in the α configuration to any two of carbons 12-14, forming $P_{1RR}$:

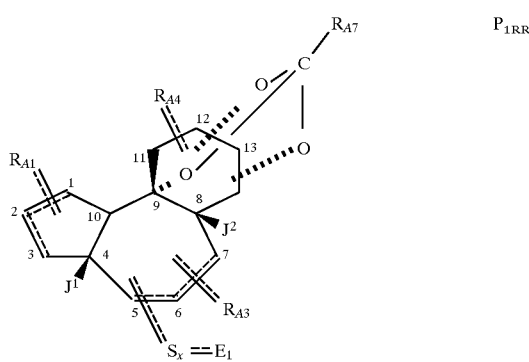

wherein $R_{A7}$ represents hydrogen, halogen or other group, the group optionally completing 1 additional ring to carbon 1, which group includes not more than 30 carbon atoms, not more than 16 halogen atoms, and not more than 9 heteroatoms selected from oxygen, nitrogen, silicon, phosphorus and sulfur.

In a preferred embodiment of $P_{1RR}$, carbon 2 carries a methyl group, $J^1$ is hydroxy, carbon 10 carries a hydrogen atom in the α configuration, carbon 11 carries a methyl group in the α configuration and carbon 13 carries an isopropenyl group, forming $P_{1RRR}$:

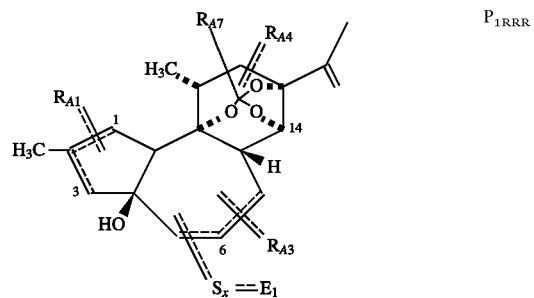

Novel phorboids of the $P_1$ diterpene class may also advantageously embody the general structure illustrated by formula $P_{1I}$:

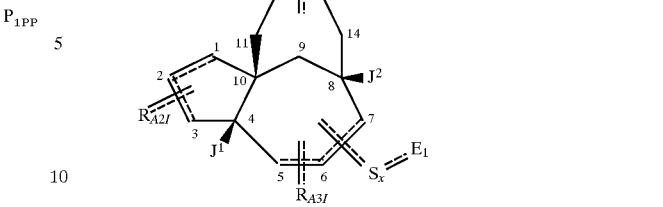

wherein $R_{A2I}$ represents not more than 8 identical or different substituents bonded independently via single and/or double bonds to carbons 1, 2 and/or 3, which substituents may independently be halogen(s) and/or other groups, which halogens and groups taken together contain a total of not more than 30 carbon atoms, not more than 24 halogen atoms and not more than 9 heteroatoms selected from oxygen, nitrogen, silicon, phosphorus and sulfur; $R_{A3I}$ represents not more than 6 identical or different substituents bonded independently via single and/or double bonds to carbons 5, 6 and/or 7, which substituents may independently be halogen (s) and/or other groups, which halogens and groups taken together contain not more than 12 carbon atoms, not more than 8 halogen atoms, and not more than 5 heteroatoms selected from oxygen, nitrogen, silicon, phosphorus and sulfur; $R_{A4I}$ represents not more than 10 identical or different substituents bonded independently via single or double bonds to carbons 11, 12, 13 and/or 14, which substituents may independently be halogen(s) and/or other groups, the group or groups optionally completing 1–3 additional rings through bonds among themselves and/or 1–5 additional rings when taken together with the 5-membered ring and its substituent(s) $R_{A2I}$, which halogen and groups taken together, include not more than 50 carbon atoms, not more than 24 halogen atoms, and not more than 15 heteroatoms selected from oxygen, nitrogen, silicon, phosphorus and sulfur, and carbon atom 9 may be unsubstituted or may carry a substituent defined as for $R_{A4I}$ above.

In compounds further illustrating $P_{1I}$, carbons 13 and 14 carry a substituted or unsubstituted cyclopropyl ring, thus forming $P_{1IN}$:

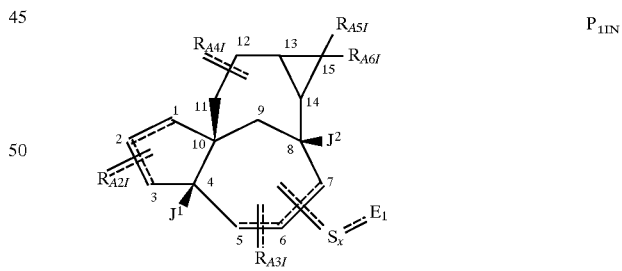

wherein the $R_{A5I}$ and $R_{A6I}$ radicals may independently be hydrogen, halogen and/or other groups, which halogens and groups taken together contain a total of not more than 30 carbon atoms, not more than 24 halogen atoms and not more than 9 heteroatoms selected from oxygen, nitrogen, silicon, phosphorus and sulfur.

In preferred embodiments of $P_{1IN}$ as a parent structure for the practice of the present invention, carbon 2 carries a methyl group, $J^1$ is hydroxy, carbon 11 carries a methyl group in the α configuration, carbon 14 carries a hydrogen in the α configuration and $R_{A5I}$ and $R_{A6I}$ are both methyl, forming $P_{1INL}$:

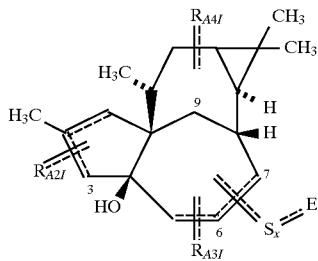

P_{1INL}

Among very diverse parent phorboids of the $P_2$ class of indole/indene/benzofuran/benzothiophene derivatives, the novel compounds of this invention may advantageously embody the general structure $P_{2NN}$,

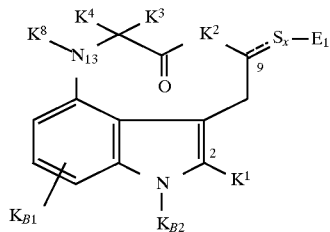

P_{2NN} wherein $K_{B1}$ represents 1–3 identical or different substituents located independently at carbons 5, 6, and/or 7, which substituents may independently be hydrogen, halogen(s) and/or other groups which, taken together, contain not more than 40 carbon atoms, not more than 24 halogen atoms, and not more than 9 heteroatoms selected from oxygen, nitrogen, silicon, phosphorus, and sulfur, the groups being optionally connected to one another, to $K^8$ and/or to $K_{B2}$ to form 1–3 additional carbocyclic or heterocyclic rings; and wherein $K_{B2}$ is hydrogen or a group which contains not more than 20 carbon atoms, not more than 24 halogen atoms, and not more than 6 heteroatoms selected from oxygen, nitrogen, silicon, phosphorus and sulfur, this group being optionally connected to $K_{B1}$ or $K^1$ to form an additional carbocyclic or heterocyclic ring.

In compounds further illustrating $P_{2NN}$, $K^1$ and $K^3$ are hydrogen and $K^2$ is —NH—, forming $P_{2NNN}$

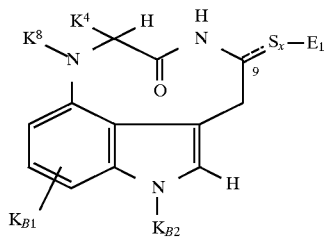

P_{2NNN} and $K^4$ is hydrogen or a group containing not more than 20 carbon atoms, not more than 24 halogen atoms, and not more than 9 heteroatoms selected from oxygen, nitrogen, silicon, phosphorus and sulfur, the group being optionally connected to $K^8$ to form an additional ring.

Two particularly preferred embodiments of $P_{2NNN}$ comprise $P_{2L}$ and $P_{2T}$, wherein $P_{2L}$ is

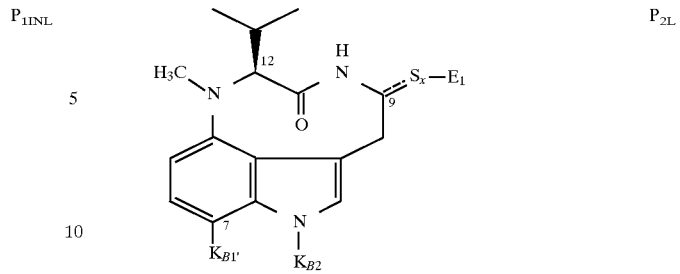

P_{2L} wherein $K_{B1'}$ is hydrogen, halogen or other group which contains not more than 40 carbon atoms, not more than 24 halogen atoms, and not more than 9 heteroatoms selected from oxygen, nitrogen, silicon, phosphorus and sulfur, this group being optionally connected to $K_{B2}$ to form an additional ring, and wherein $P_{2T}$ is:

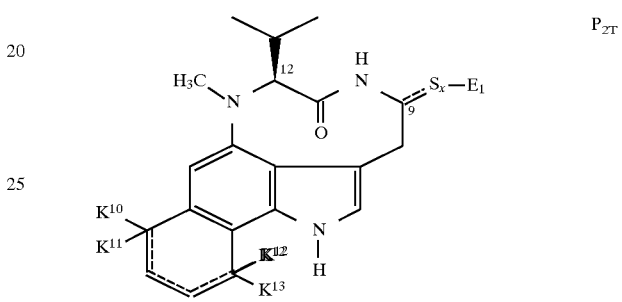

P_{2T} wherein a four-carbon saturated, unsaturated or aromatic ring connects positions 6 and 7 and substituents $K^{10}$–$K^{13}$ may independently be absent in favor of unsaturated linkages or may be hydrogen, halogen and/or other groups which, taken together, contain not more than 36 carbon atoms, not more than 24 halogen atoms, and not more than 9 heteroatoms selected from oxygen, nitrogen, silicon, phosphorus and sulfur.

Among the parent phorboids of the $P_7$ class of benzolactams, the novel compounds of this invention may advantageously embody the general structure $P_{7B}$,

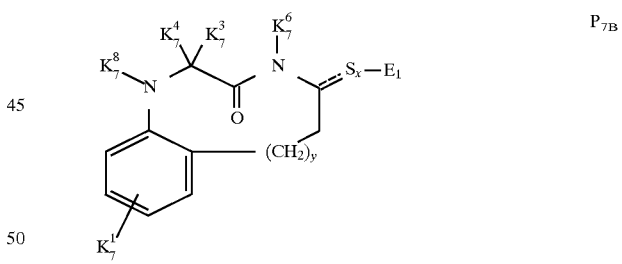

P_{7B}

In compounds further illustrating $P_{7B}$, $K_7^4$ is hydrogen, $K_7^8$ is methyl and y is 0, forming $P_{7BL}$,

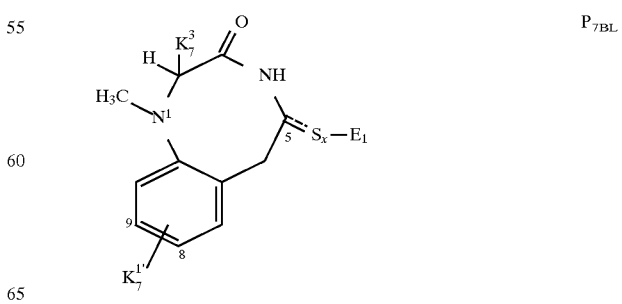

P_{7BL} wherein $K_7^{1'}$ represents 1–2 identical or different substituents attached independently to carbons 8 and/or 9, which substituents may independently be hydrogen, halogen(s) and/or other groups which taken together, contain not more than 40 carbon atoms, not more than 24 halogen atoms and not more than 9 heteroatoms selected from oxygen, nitrogen, silicon, phosphorus and sulfur, the groups being optionally connected to one another to form 1–2 additional carbocyclic or heterocyclic rings. In a preferred embodiment $K_7^{1'}$ is a $C_1$–$C_{14}$ saturated or unsaturated alkyl group.

It will be appreciated that the many different permissible changes to the hydroxymethyl or 1-hydroxyethyl groups of the parent phorboids lead to diverse compounds with diverse biological properties, and different embodiments will be preferred for different utilities. If different protein kinase C isotypes and other proteins bearing phorboid-type binding sites have different biological functions, as has been extensively hypothesized and to some extent demonstrated in biological experiments, then the novel compounds of this invention with differing activity on different protein kinase C isotypes will obviously display a wide range of differing utilities.

For example, a preferred set of compounds for anti-viral activity, including anti-retroviral and anti-Human Immunodeficiency Virus (HIV) activities, in human cells is generated by replacing the hydroxymethyl or 1-hydroxyethyl groups of parent phorboids with the following organic functional groups: (i) dihalomethyl, trihalomethyl, —$N_3$, —$NH_2$, —CN, —CH=NOH, —CH=NOCH$_3$, —CH=N(→O)CH$_3$, —C(CH$_3$)=NOH, —CH=CHR$_a^a$, —C≡C—R$_a^a$, —CH$_2$C≡C—R$_a^a$, —Si(CH$_3$)$_2$OH, —Si(OH)$_2$CH$_3$, —Si(CH$_3$)$_2$F, —Si(CH$_3$)$_2$R$_a^a$, —CH$_2$Si(CH$_3$)$_2$R$_a^a$, or =CHR$_a^a$, in which R$_a^a$ is hydrogen or $C_{1-12}$ linear or branched, saturated, unsaturated and/or aromatic hydrocarbon optionally substituted by not more than 16 halogens, or (ii) —CH$_2$— or —CH(CH$_3$)—, to either of which is bonded —R$_a^a$, —F, —$N_3$, —$NH_2$, —CN, —Si(CH$_3$)$_2$OH, —Si(OH)$_2$CH$_3$, —Si(CH$_3$)$_2$F, the o-, m- or p-isomer of —M—C$_6$H$_4$CH$_2$—T$^3$, the o-, m- or p-isomer of —C$_6$H$_4$CH$_2$—T$^3$, —SR$_a^a$, —SCH$_2$CH$_2$OH, —S(=O)—CH$_2$CH$_2$OH, —S(CH$_2$)$_3$OH, —S(CH$_2$)$_4$OH, —SCH$_2$CH$_2$SH, —M—C(=T$^2$)—M'—R$_a^a$ (except —OC(=O)NH$_2$), —OCH$_2$C(=O)CH$_3$, —OCH$_2$C(=NOH)CH$_3$, the o-, m- or p-isomer of —M—C(=T$^2$)—M'—C$_6$H$_4$—T$^3$, the o-, m- or p-isomer of —M—C(=T$^2$)—M'—C$_6$H$_4$CH$_2$—T$^3$, or -imidazol-2-yl.

Preferred compounds for anti-viral use, for example, incorporate parent radicals selected from $P_{1PP}$, $P_{1RRR}$, $P_{1INL}$, $P_{2L}$, $P_{2T}$ and $P_{7BL}$ bearing functionally diverse $S_xE_1$ groups selected from (i) dihalomethyl, trihalomethyl, —$N_3$, —$NH_2$, —CN, —CH=NOH, —Si(CH$_3$)$_2$OH, —Si(OH)$_2$CH$_3$, or (ii) —CH$_2$— or —CH(CH$_3$)—, to either of which is bonded —R$_a^a$, —F, —$N_3$, —$NH_2$, —CN, —Si(CH$_3$)$_2$OH, —Si(OH)$_2$CH$_3$, the o-, m- or p-isomer of —M—C$_6$H$_4$CH$_2$—T$^3$, the o-, m- or p-isomer of —C$_6$H$_4$CH$_2$—T$^3$, —SR$_a^a$, —SCH$_2$CH$_2$OH, —S(=O)—CH$_2$CH$_2$OH, —S(CH$_2$)$_3$OH, —S(CH$_2$)$_4$OH, —SCH$_2$CH$_2$SH, the o-, m- or p-isomer of —M—C(=T$^2$)—M'—C$_6$H$_4$—T$^3$, or the o-, m- or p-isomer of —M—C(=T$^2$)—M'—C$_6$H$_4$CH$_2$—T$^3$, in which R$_a^a$ is hydrogen or $C_{1-12}$ linear or branched, saturated, unsaturated and/or aromatic hydrocarbon optionally substituted by not more than 16 halogens.

The compounds of this invention have been found to possess valuable pharmacological properties for human and veterinary medicine. For therapeutic use in humans or animals the compounds of this invention are dispensed in unit dosage form comprising 0.001 to 1000 mg per unit dosage in a pharmaceutically acceptable carrier. In particular, unit dosages in the range of 0.1 to 100 mg are preferred. The compounds of this invention may also be incorporated in topical formulations in concentrations of about 0.001 to 10 weight percent, with concentrations of 0.01 to 10 weight percent being preferred.

It will be appreciated that the actual preferred amounts of active compound in a specific case will vary according to the specific compound being utilized, the particular compositions formulated, the mode of application, and the particular sites and organism being treated. Compounds of this invention having higher potencies should be used in generally smaller amounts, and compounds with lower potencies should be used in generally larger amounts. Dosages for a given host, whether a small animal such as a cat or a human patient, can be determined using conventional considerations, e.g., the host's weight or body surface area. In general, the compounds of the present invention are administered in quantities of about 0.0001 to about 1000 mg/kg of body weight, and quantities of about 0.01 to about 100 mg/kg of body weight are preferred.

As specific examples, representative compounds of this invention variously block inflammation, show cytostatic and/or cytotoxic activity against very diverse types of human cancer cells representative of several human cancers such as leukemia, carcinoma and melanoma; inhibit the infection of human lymphoid cells by HIV; and induce production of thrombolytic activity. These effects are demonstrated by (i) inhibition in standard topical in vivo mouse ear inflammation tests wherein inflammation by established agonists such as PMA and the ionophore A23187 are blocked; (ii) by the inhibition of proliferation of human leukemic cells in culture via induction of differentiation; (iii) by assays of cytotoxicity against human carcinoma cancer cells; (iv) by assays of inhibition of growth of human melanoma cells; (v) by assays of inhibitory activity against acute and chronic HIV viral replication in human lymphocyte cells; and (vi) by measurement of stimulation of fibrinolytic activity in cultured cells. These demonstrations of efficacy are achieved at doses per ear, per kg of body weight or per kg of bodily fluid equivalent, using numerous representative compounds of the present invention, as follows: (i) about 0.01–1000 nanogram/ear, corresponding to about 0.0001–10 mg per square meter of body surface being treated; (ii) about 0.1–100 mg/kg fluids; (iii) about 0.1–100 mg/kg fluids; (iv) about 1–100 mg per kg of fluids, (v) about 0.1–100 mg/kg fluids; and (vi) about 0.1–100 mg/kg fluids, respectively.

The activities of representative compounds of this invention against the three diverse types of human cancer cells described above are particularly noteworthy. Cancer is in fact a broad classification containing at least 110 clinically different types of tumorous diseases. The activities of compounds of this invention against three very different types of cancer cells demonstrate not only those utilities against specific human cancer cells but also significant breadth for the anti-cancer effects of this invention beyond a single class of cancer disease, indicative of additional anti-cancer utilities.

The anti-viral activities of numerous compounds of this invention are also of great importance. For example, the tests demonstrating the anti-HIV properties of these compounds [see Examples 111–114] were carried out in widely validated and accepted cellular assays of HIV infectivity in human cells that are indicative of in vivo activity. Thus the anti-HIV properties of the compounds of this invention relate directly to the in vivo activities of standard anti-HIV reverse transcription inhibitors such as azidothymidine, dideoxyinosine, dideoxycytidine and non-nucleoside reverse transcription inhibitors, HIV-protease inhibitors and inhibitors of tat-gene function, which are fully active in the assay by which the compounds of this invention were tested. This is in contrast to many in vitro HIV-related assays that are unable to provide predictive information about the anti-HIV effects of test compounds in living cells, such as assays of inhibition against isolated HIV enzymes. For example, the inadequacy of isolated enzyme assays was indicated by the finding that, of two compounds able to inhibit the HIV protease when assayed on the purified protease enzyme, only one of the compounds was able to inhibit HIV infectivity in the whole-cell assay in human lymphocytes [T. K. Antonucci et al., "Characterizations of HIV-1 protease inhibitors" in *Innovations in therapy of human viral diseases; a Wellcome Symposium*, Dec. 6–9, 1992, Book of Abstracts, Page 2.]

The compounds of this invention also show selective effects as antagonists for protein kinase C in some cases, as noninflammatory agonists for protein kinase C in other cases, and as selective ligands for protein kinase C and/or for phorboid receptors.

Thus, these compounds can be used as agents for the abrogation of pathophysiological conditions and disease states in applications such as anti-inflammatory, anti-psoriatic, anti-cancer, anti-ulcer, anti-hypertensive, anti-asthma, anti-arthritic, anti-autoimmune, anti-nociceptive, anti-secretory, anti-parasitic, anti-amoebic, anti-viral including anti-HIV replication, in prophylaxis against infection by any HIV form, and any other application in which pathological involvement of protein kinase C is found.

For example, evidence for involvement of protein kinase C in the physiology of many human and animal pathogenic viruses has long been known, particularly from experiments in which a standard protein kinase C activator such as a phorbol ester greatly stimulates viral production for many different kinds of viruses [see, for example: H. zur Hausen et al., "Persisting oncogenic herpesvirus induced by the tumour promoter TPA", *Nature* 272: 373–375 (1978); H. zur Hausen et al., "Tumor initiators and promoters in the induction of Epstein-Barr virus", *Proc. Natl. Acad. Sci. USA* 76: 782–785 (1979); D. V. Ablashi et al., "Increased infectivity of oncogenic Herpes viruses of primates with tumor promoter 12-O-tetradecanoylphorbol-13-acetate", *Proc. Soc. Exp. Biol. Med.* 164: 485–490 (1980), G. Colletta et al., "Enhancement of viral gene expression in Friend erythroleukemia cells by 12-O-tetradecanoylphorbol-13-acetate", *Cancer Research* 40: 3369–3373 (1980); S. K. Arya, "Phorbol ester-mediated stimulation of the synthesis of mouse mammary tumour virus", *Nature* 284: 71–72 (1980), K. B. Hellman and A. Hellman, "Induction of type-C retrovirus by the tumor promoter TPA", *Int. J. Cancer* 27: 95–99 (1981); E. Amtmann and G. Sauer, "Activation of non-expressed bovine papilloma virus genomes by tumour promoters", *Nature* 296: 675–677 (1982); L. S. Kucera, et al., "12-O-Tetradecanoyl-phorbol-13-acetate enhancement of the tumorigenic potential of Herpes Simplex virus type 2 Transformed cells", *Oncology* 40: 357–362 (1983); and V. Wunderlich, et al., "Enhancement of primate retrovirus synthesis of tumor promoters", *Symposium on role of cocarcinogens and promoters in human and experimental carcinogenesis,* 16–18 May, 1983, Budapest, Hungary, *Book of Abstracts,* p. 88].

Similar experiments indicate involvement of protein kinase C in the life cycle of HIV, and initial molecular genetics studies helped illuminate the mechanisms by which cellular protein kinase C can influence HIV [see, for example: S. Harada, et al., "Tumor promoter, TPA, enhances replication of HTLV-III/LAV", *Virology* 154: 249–258 (1986); H. Dinter, et al., "In Vitro activation of the HIV-1 enhancer in extracts from cells treated with a phorbol ester tumor promoter", *EMBO Journal* 6: 4067–4071 (1987); J. D. Kaufman, et al., "Phorbol ester enhances human immunodeficiency virus-promoted gene expression and acts on a repeated 10-base-pair functional enhancer element", *Mol. Cell. Biol.* 7: 3759–3766 (1987); and M. Siekevitz, et al., "Activation of the HIV-1 LTR by T cell mitogens and the transactivator protein of HTLV-I", *Science* 238: 1575–1578 (1987)].

These and later molecular genetics-based virological investigations provided clear mechanistic explanations for the effects, observed much earlier, of protein kinase C modulators on the life cycles of numerous human and animal viruses. Such studies showed that many viruses contain genetic control elements, called enhancers, whose functions in controlling viral expression involve the protein kinase C of the host cell. Of particular importance for the role of protein kinase C in virus-cell interactions are the enhancers known as AP-1 and NF-κB [see, for example: J. E. Marich et al., "The phylogenetic relationship and complete nucleotide sequence of human papillomavirus Type 35", *Virology* 186: 770–776 (1992), R. L. Smith et al., "Activation of second-messenger pathways reactivates latent Herpes Simplex virus in neuronal cultures", *Virology* 188: 311–318 (1992); S. L. Gdovin and J. E. Clements, "Molecular mechanisms of visna virus tat: identification of the targets for transcriptional activation and evidence for a post-transcriptional effect", *Virology* 188: 438–450 (1992), D. S. Shih et al., "Involvement of FOS and JUN in the activation of visna virus gene expression in macrophages through an AP-1 site in the viral LTR", *Virology* 190: 84–91 (1992), A. Mirza, "Stimulation of adenovirus early gene expression by phorbol ester: its possible mechanism", *Virology* 190: 645–653 (1992); E. J. Wade et al., "An AP-1 binding site is the predominant cis-acting regulatory element in the 1.2-kilobase early RNA promoter of human cytomegalovirus", *J. Virology* 66: 2407–2417 (1992); F. Stubenrauch et al., "Late promoter of human papillomavirus Type 8 and its regulation", *J. Virology* 66: 3485–3493 (1992); F. Thierry et al., "Two AP-1 sites binding JunB are essential for human papillomavirus Type 18 transcription in keratinocytes", *J. Virology* 66: 3740–3748 (1992); J. Liu et al., "Specific NF-κB subunits act in concert with tat to stimulate human immunodeficiency virus Type 1 transcription", *J. Virology* 66: 3883–3887 (1992); W. A. Jensen et al., "Inhibition of protein kinase C results in decreased expression of bovine leukemia virus", *J. Virology* 66: 4427–4433 (1992); K. Shiroki et al., "Adenovirus E1A proteins stimulate inositol phospholipid metabolism in PC12 cells", *J. Virology* 66: 6093–6098 (1992), J. C. Cross et al., "Transactivation by hepatitis B virus X protein is promiscuous and dependent on mitogen-activated cellular serine-threonine kinases", *Proc. Natl. Acad. Sci. USA* 90: 8078–8082 (1993); and A. S. Kekule et al, "Hepatitis B virus transactivator HBx uses a tumour promoter signalling pathway", *Nature* 361: 742–745 (1993)].

The compounds of this invention can also be used in combination with other therapeutic agents, for example for use in the treatment of viral infections. Thus, a compound of this invention can be used in combination with a nucleoside analog such as azidothymidine or dideoxyinosine, a tetrahydroimidazo[4,5,1-jk][1,4]-benzodiazepin-2(1H)-one derivative, other HIV reverse transcriptase inhibitors, HIV protease inhibitors, or HIV tat-gene function inhibitors for the prophylaxis against or treatment of HIV infections. A method for treating a mammal infected with a virus comprises administering to a mammal in need of such treatment an antivirally effective quantity of a composition comprising an acceptable pharmaceutical carrier and an antivirally active compound or compounds or a pharmaceutically acceptable salt thereof.

Furthermore, the non-inflammatory agonists among the compounds of this invention may be used to achieve desired physiological results such as interferon release, interleukin induction, tumor necrosis factor production, immune system stimulation and/or reconstitution, insulin secretion, insulinomimetic activity, acceleration of wound healing, improvement in central nervous system functions such as memory and learning and abrogation of the symptoms or progress of Alzheimer's disease, and any other application for which desirable actions of protein kinase C are found.

As phorboid receptor subtype- and/or protein kinase C subtype-selective ligands, the compounds of this invention also have very valuable application as experimental agents for research into the role of protein kinase C and/or phorboid receptors in important biological processes and in human and veterinary diseases. Thus, their value extends to their use as pharmacological tools for in vitro and in vivo research, in a manner similar to the important roles that selective agonists and antagonists have played in the studies of the mechanism of action of adrenergic, dopaminergic, opiate, benzodiazepine, cholinergic, and serotoninergic receptor systems, among others.

In addition, the compounds can be used in in vitro diagnostics (e.g., in an assay for protein kinase C). They are also useful as intermediates in the production of other drugs, e.g., as described in the present invention.

The compounds of this invention are generally administered to animals, including but not limited to fish, avians, and mammals including humans.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients and carriers, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcoholics, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., enzyme inhibitors, to reduce metabolic degradation. Such carriers do not include the following solvents when used alone: dimethylsulfoxide, acetone, or methanol or ethanol of greater than 80% concentration in water.

When compounds of the present invention are provided as part of a pharmaceutical composition, many of the specifically stated exceptions enumerated in the previous detailed description of the compounds, themselves, are no longer needed. This occurs because the enumerated exceptions were known to be in the prior art as synthetic intermediates or as compounds believed to have no pharmacological activities. In the present invention, these compounds, as part of pharmaceutical compositions, have antiviral activities or anti-inflammatory activities, etc. That is, the pharmaceutical composition formulation confers an inventive significance to these compounds.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

A preferred method of administration comprises oral dosing, with tablets, dragees, liquids, drops, or capsules. For the oral route of administration, either compounds of this invention lacking functional groups destroyed by acid, or tablets or capsules which protect the active compound from upper gastrointestinal acidity, are preferred.

Sustained or directed release compositions can be formulated, e.g., in liposomes or in compositions wherein the active compound is protected with differentially degradable coatings, e.g., by microencapsulation, multiple coatings, absorption onto charcoal, entrapment in human serum albumin microspheres, etc. It is also possible to freeze-dry the new compounds and use the lyophilizates obtained, for example, for the preparation of products for injection.

Another preferred route of administration comprises topical application, for which are employed nonsprayable forms, viscous to semi-solid or solid forms comprising a carrier compatible with topical application and having a dynamic viscosity compatible with topical application, preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The compounds of this invention, admixed with appropriate carriers, may also be delivered to subjects by means of an externally connected or internally implanted pumping device to give a controlled and/or sustained release of the therapeutic mixture, or by means of a patch of natural or synthetic fabric and/or polymer impregnated with the compounds in a suitable carrier and affixed to the skin to achieve transdermal release and absorption of the active compounds.

The compounds of this invention may also be modified by covalent attachment of metabolically modifiable groups, to form "prodrugs" which are released by cleavage in vivo of the metabolically removable groups. For example, amine, hydroxy and/or thiol groups present in many compounds of this invention may be converted to prodrugs by covalent attachment of acyl or aminoacyl organic functional groups. Likewise, compounds of this invention containing carboxylic, sulfonic, phosphoric, phosphonic or related free acids, including those in which one or more oxygen atoms are replaced by sulfur, may be converted to prodrugs by formation of their esters or amides by covalent attachment of alcohols, amines, amino acids and the like. Compounds of this invention may also incorporate N-alkyldihydropyridine functional groups, which become localized to the central nervous system after administration to the subject and subsequent metabolic modification of the N-alkyldihydropyridine group in the central nervous system.

It will be recognized by persons with ordinary skill in medicinal chemistry that conversion of alcohol-, amine-, thiol- or acid-containing compounds of this invention to prodrugs is preferably done by derivatization of such groups located in regions of the molecule having minimal steric hindrance, to permit access of metabolizing enzymes, other bioreactants or water. Such alcohol-, amine-, thiol- or acid-containing groups may be located in any of the parent, side-chain or capping-group organic functional groups described above. A prodrug-type group such as the N-alkyldihydropyridine group, however, is preferably added to the parent structures $P_1$–$P_7$, etc., unless it is found for a given compound that the N-alkyldihydropyridine group and/or its metabolic pyridinium oxidation product has desirable bioactivity when located in the side chain ($S_o$ or $S_x$) or capping group ($E_o$ or $E_1$) of a compound of this invention.

It will be appreciated that starting materials for obtaining compounds of this invention from natural sources or from total or partial synthesis may be altered in very diverse ways, consistent with this invention, to obtain compounds with novel and diverse primary biological/medicinal activities resulting from, and controlled by, the specific new $S_oE_o$ or $S_xE_1$ group created, such properties include, for example, loss of skin inflammatory activity and appearance or retention of anti-inflammatory, anti-HIV, anti-leukemic and cytokine-induction activities. It is also possible to introduce an extremely wide variety of changes into either (i) the groups replacing the hydroxymethyl/1-hydroxyethyl group or (ii) the previously-described parent phorboid structures, to obtain new entities with improved secondary properties, such as, variously, hydrophobicity, water solubility, potency, oral availability, metabolic and chemical stability, reduced therapeutic side effects, and so on, using strategies and techniques widely recognized in the art of medicinal chemistry and pharmacology.

Starting materials for the synthesis of the compounds of this invention may be obtained from any of a wide variety of natural sources, and the diterpene, indole alkaloid, diacylglycerol, diaminobenzyl alcohol and polyacetate compounds are available by total synthesis.

The diversity of phorboids modified in the parent portion and in the hydroxymethyl/1-hydroxyethyl-modified phorboids are illustrated in the Examples, and are also discussed below, separately for each phorboid parent class.

Routine synthetic routes, transformations and procedures common in the art of synthetic organic chemistry are sufficient for highly varied and extensive practice of this invention in great breadth. Indeed, a particularly remarkable aspect of this invention is the ease with which hydroxymethyl/1-hydroxyethyl-modified phorboids with highly novel protein kinase C-modulatory, anti-inflammatory and anti-viral properties, but lacking skin inflammatory activity, may be obtained from well-known starting materials through simple organic chemical transformation. This is illustrated by the diversity of Examples found below and by a general discussion, as follows. Although somewhat different kinds of hydroxymethyl/1-hydroxyethyl modifications are discussed immediately below for the different parent classes of phorboids, it should be noted that procedures for modification of the hydroxymethyl/1-hydroxyethyl group of one parent class of phorboid are generally applicable to the hydroxymethyl/1-hydroxyethyl groups of other parent classes of phorboids.

Compounds of this invention from the diterpenoid ($P_1$) class of phorboids may be obtained by semisynthetic procedures, starting from any of a variety of compounds from naturally occurring sources as described in the literature [see *Naturally Occurring Phorbol Esters*, ed. F. J. Evans, CRC Press, Boca Raton (1986), chapters 7, 8 and 9 and references cited therein].

Furthermore, these diterpene phorboids are available by total synthesis from common organic chemical starting materials. These syntheses provide a variety of approaches and associated flexibility in arriving at diverse functionalities on the parent nucleus and on the final $S_oE_o$ or $S_xE_1$ side chain [see Paquette, L. et al., *J. Am. Chem. Soc.* 106: 1446–1454 (1984); Rigby, J. and Moore, T., *J. Org. Chem.* 55: 2959–2962 (1990), Wender, P. et al., *J. Am. Chem. Soc.* 111: 8954–8957 (1989); Wender, P. et al., *J. Am. Chem. Soc.* 111: 8957–8958 (1989); and Wender, P. and McDonald, F., *J. Am. Chem. Soc.* 112: 4956–4958 (1990)].

The means for modifying the hydroxymethyl group of diterpenoid phorboids to produce the compounds of this invention will be obvious to workers with ordinary skill in synthetic organic chemistry.

In many diterpenoid phorboids the hydroxymethyl group may be modified without the necessity of protecting other functional groups in the molecule. In other cases, especially when strong nucleophiles or bases are used, other regions of the molecule must be suitably protected using methodologies widely practiced in synthetic organic chemistry. Frequently one or more oxygen atoms must be blocked before some types of chemical modifications may be accomplished on the hydroxymethyl group or on other portions of the diterpene parent. Many widely used and thoroughly characterized protecting groups for the oxygen atoms present as hydroxy groups are acyl, benzyl, trialkylsilane, benzyloxycarbonyl, 4'-methoxyphenyldiphenylmethyl and trimethylsilylyethoxycarbonyl, which are variously stable to or removed under acidic, basic or reducing conditions or with fluoride ion reagents. The use of such groups is obvious to any worker with modest skill in the art of synthetic organic chemistry. Carbonyl functions may be protected by conversion to acetals or ketals, or by reduction to the alcohol level followed by protection with standard protecting groups for the hydroxy group. With or without such protection of non-hydroxymethyl portions of the parent diterpene the hydroxymethyl may, for example, be conveniently capped under very mild conditions by treatment with a substituted or unsubstituted alkyl, aryl, or aralkyl isocyanate, optionally containing silicon or phosphorus atoms in a variety of functional groups, in the presence of a catalyst such as dibutyltin dilaurate. The resulting compounds lack the toxic inflammatory activity of the phorboid from which they were derived and have, themselves, anti-inflammatory utility. Illustrations are provided in the Examples below.

Conversion of the hydroxy group to a halogen or pseudohalogen not only in itself provides active and useful compounds, but also permits the displacement of the resultant electrophile from the protected or in some cases, unprotected, parent nucleus by a very wide range of nucleophiles. Persons with ordinary skill in the art of organic synthesis will recognize that such nucleophiles may include, without limitation, reagents having carbon, hydrogen, oxygen, nitrogen, sulfur, phosphorus, silicon, arsenic, boron, and/or selenium atoms in their structures. Particular examples would be reaction with ammonia, methylamine, the sodium salt of dimethylphosphine, trimethylphosphite, triphenylphosphine, potassium sulfite, trimethylsilylmethyl-metal salts, lithium trimethylsilylacetylide, sodium cyanide, N-methyl-2-hydroxyethyl amine, 1[H]-tetrazole, or with the sodium salt of 2-mercaptoethanol, 3-mercaptoethanol, or of hydroxymethylphenol. Many variations may be executed as described for nucleophilic displacement of electrophilic groups in organic molecules by standard textbooks of synthetic organic chemistry, such as J. March, *Advanced Organic Chemistry*, Third Edition, Wiley-Interscience, New York, 1985. As an illustration, 20-deoxy-20-chlorophorbol 12,13-bis-diphenylphosphate yields 20-deoxy-20-(pentadecafluoro-[1H,1H]-octylthio)phorbol 12-butyrate 13-diphenylphosphate upon treatment with sodiopentadecafluoro-[1H,1H]-octylthiol. As another example, the 20-phosphonic acid derivative of 20-deoxyresiniferonol 9,13,14-orthophenylacetate may be made by reacting the sodium salt of dibenzylphosphonate with 20-deoxy-20-bromoresiniferonol 9,13,14-orthophenylacetate to form 20-deoxy-20-dibenzylphosphonyl resiniferonol 9,13,14-orthophenylacetate dibenzylphosphonyl followed by catalytic hydrogenolysis of the benzyl ester groups to yield the free phosphonic acid derivative.

By use of protecting groups or modifications of the diterpenoid parent using methods well-known in the art of synthetic chemistry, the hydroxy group of the hydroxymethyl group may be replaced by a metal and then reacted with an electrophile, effectively replacing the hydroxy with a group derived from the electrophile. The techniques for this replacement are obvious to workers with ordinary skill in organic synthesis, in that replacement of the hydroxymethyl hydroxy group by halogen in a suitably protected or modified diterpene permits strong and/or hard nucleophiles to be generated by the use of metals or strong bases, and persons with ordinary skill in the art of organic chemistry will recognize that such nucleophiles can be contacted with a very diverse range of electrophilic reagents having carbon, hydrogen, oxygen, nitrogen, sulfur, phosphorus, silicon, arsenic, boron and/or selenium atoms in their structures to obtain hydroxymethyl-modified diterpenes of widely varying structures. As one approach among many, the hydroxymethyl group of an appropriately protected diterpene may be converted to the 20-bromo derivative with methanesulfonyl bromide in dimethylformamide/pyridine. The resulting bromide may be modified by halogen-metal exchange using appropriately active metals or metal-containing reagents such as magnesium, zinc, alkali metals, metal alkyl reagents and so on, to obtain carbanionic character at the carbon atom previously bearing the hydroxy group, as shown in the following structures, which also illustrate typical protection of oxygen functions elsewhere in the molecule:

-continued wherein Met is the metal ion, $PG_1$–$PG_3$ are typically selected from the list above and $PG_4$ is typically 2',2'-propylidene or dialkyl- or diarylsilyl. $PG_3$ may be unnecessary in some cases (i.e. may be hydrogen or an anionic charge). The simultaneous presence or subsequent addition to the metal/anion-containing reaction of an electrophile such as, without limitation, an aldehyde, ketone, epoxide or oxetane then provides, after reaction and workup, compounds having one or more methylenes inserted between the original hydroxy group and the methylene to which it was attached. This methodology is particularly advantageous for replacement of the hydroxy with a group containing silicon, phosphorus or other atoms by contacting the anionic metal derivative of the parent nucleus with electrophilic reagents having halogen or pseudohalogen groups, in addition to other functions chosen for biological specificity, bonded directly to the silicon or phosphorus atoms, affording compounds with useful biological activity.

For those diterpene-type phorboids wherein the hydroxy of the hydroxymethyl group is allylic, such as phorbol, ingenol, and resiniferonol esters, the replacement of the hydroxy by chloro or preferably by bromo or iodo yields compounds that can be conveniently reacted with activated zinc, barium or many other metals in the presence of electrophiles such as, without limitation, aldehydes, ketones, epoxides, or oxetane; the resultant compounds have one or more methylenes inserted between the original hydroxy group and the methylene to which it was attached, or, after an allylic rearrangement, a new functional group results at position 7 of the diterpene skeleton. An illustration of this would be the reaction of 20-deoxy-20-chlorophorbol 12-myristate 13-acetate with an excess of formaldehyde and an excess of zinc in the presence of tetrahydrofuran and saturated ammonium chloride solution with vigorous stirring for 24 hours. The resultant compound has the 6,7-double bond rearranged to the 6,20-position and bears a new hydroxymethyl group attached to position 7 instead of to position 6 as in the parent diterpene, and this compound, 12-β-myristoyloxy-13-acetoxy-4,9-dihydroxy-7-hydroxymethyl-1,6(20)-tigliadien-3-one, has good anti-inflammatory activity.

Alternatively, the hydroxy group on the hydroxymethyl of appropriately protected or modified diterpenoids may be oxidized to an aldehyde and then reacted via condensation or addition chemistries to provide a very wide variety of modified indolactams. Examples, without limitation, would be reactions with Wittig reagents; hydroxylamines; hydrazines; semicarbazides; ammonia, primary amines or secondary amines followed by sodium cyanoborohydride reduction to primary amines, secondary amines or tertiary amines, respectively; or Grignard reagents. Many variations may be executed as described in standard textbooks of synthetic organic chemistry, such as J. March, op cit. After completion of reactions in the hydroxymethyl region, an acetonide group protecting the 3-OH and 4-OH groups is removed with mild acid followed by reoxidation of the 3-OH to keto with sulfur trioxide-pyridine-dimethylsulfoxide. Trialkylsilane protecting groups $PG_1$ and $PG_2$ may then be removed with fluoride ion, preferably followed by derivatization of the now-free 12- and 13-OH's with acylating agents, isocyanates, alkyl- or aryl chloroformates or alkylating agents to establish hydrophobic groups in this region of the diterpene.

Even a relatively base-sensitive compound such as a phorbol 12,13-diester may be oxidized to the 20-aldehyde with manganese dioxide and reacted directly, as is obvious to workers with ordinary skill in synthetic organic chemistry, with stabilized Wittig reagents such as methyl triphenylphosphoranylideneacetate, to yield a 20-deoxy-20-methoxycarbonylmethylidenephorbol 12,13-diester.

Alternatively, a phorbol 12,13-diester may be selectively protected at the 4 and 9 hydroxy groups using trimethylsilyl trifluoromethanesulfonate, followed by reaction with manganese dioxide to obtain a protected aldehyde. The latter compound may be successfully treated with strong Wittig reagents such as the lithium salt of 2-hydroxyethylidenetriphenylphosphorane, followed by deprotection with tetrabutylammonium fluoride to obtain the corresponding chain-extended, 20,21-didehydro-21,22-dihomophorbol diester.

The hydroxymethyl group of suitable diterpene phorboids may be oxidized to the carboxylic acid level by methods well-known in the art or these carboxylic acids may be prepared by modifications of the total syntheses described in the literature cited above. Besides being useful examples of this invention themselves these acids permit the preparation of further modified diterpene phorboids. For example, this carboxylic group may be activated for condensation reactions by any of a number of well-known methods, e.g. by conversion to an acyl halide or to an active ester such as the N-succinimidyl ester. The resultant activated carboxyl may then be easily converted to simple or multifunctional ester, amide, or thioester derivatives by reaction with alcohols, amines, or thiols respectively, alone or in the presence of condensation catalysts.

The use of the methods of total synthesis as described in the literature cited above permits specific modifications of the parent structures of the diterpenoids. By established techniques in the art of organic synthesis modified parent structures may be obtained which embody alterations at the hydroxymethyl group as well, and which have useful biological activity. This wide variety of modified diterpenoid structures may result from the use of modified starting materials, from modifications of one or more synthetic steps or from a combination of both.

Starting materials for the synthesis of the compounds of this invention from the indolactam ($P_2$) class of phorboids may be obtained from any of a variety of natural sources as described in the literature [T. Sugimura, Gann 73: 499–507 (1982), H. Fujiki and T. Sugimura, *Advances in Cancer Research* 49: 223–264 (1987), K. Irie and K. Koshimizu, *Mem. Coll. Agric., Kyoto Univ.* 132: 1–59 (1988) and references cited therein]. Furthermore, these indolactam phorboids are available by total synthesis from common organic chemical starting materials. These syntheses provide a considerable variety of approaches and associated flexibility in arriving at highly diverse functionalities on the parent nucleus and on the final $S_oE_o$ or $S_xE_1$ side chain, and include, but are not limited to, the procedures described by Y. Endo et al., *Tetrahedron* 42: 5905–5924 (1986), S. de Laszlo et al., *J. Chem. Soc., Chem. Comm.* 344–346 (1986), S. Nakatsuka et al., *Tetrahedron Letters* 27: 5735–5738 (1986) and *Tetrahedron Letters* 28: 3671–3674 (1987), H. Muratake and M. Natsume, *Tetrahedron Letters* 28: 2265–2268 (1987), M. Mascal and C. Moody, *J. Chem. Soc., Chem. Comm.* 589–590 (1988), A. Kozikowski et al., *J. Am. Chem. Soc.* 111: 6228–6234 (1989), and T. Kogan et al., *Tetrahedron* 46: 6623–6632 (1990) and references therein.

Given indolactams containing hydroxymethyl groups, the means for modifying the hydroxymethyl group to produce the compounds of this invention will be obvious to workers with ordinary skill in synthetic organic chemistry.

In some cases, the hydroxymethyl group may be modified once other regions of the molecule have been suitably protected using simple, obvious and widely-precedented methodologies practiced extensively in synthetic organic chemistry. In some specific cases the indole nitrogen must be blocked before some types of chemical modifications may be accomplished on the hydroxymethyl group or on other portions of the indolactam parent. Many protecting groups for the indole nitrogen have been used in the organic chemical literature, and their use here is obvious. Among these are t-butoxycarbonyl, acetyl, benzyl, trimethylsilylethoxymethylene, benzyloxycarbonyl and benzenesulfonyl, which are variously stable to or removed under acidic, basic or reducing conditions or with fluoride ion reagents. With or without such protection the hydroxymethyl may, for example, be conveniently capped under very mild conditions by the treatment with a substituted or unsubstituted alkyl, aryl, or aralkyl isocyanate, optionally containing silicon or phosphorus atoms in a variety of functional groups, in the presence of a catalyst such as dibutyltin dilaurate. The resulting compounds lack the toxic inflammatory activity of the phorboid from which they were derived, and have themselves anti-inflammatory utility. As an illustration, treatment of (−)-7-octylindolactam V with methylisocyanate in the presence of dibutyltin dilaurate and 4-dimethylaminopyridine in tetrahydrofuran affords 14-O-(N-methyl)carbamoyl-7-octyl-(9S,12S)-indolactam V.

Conversion of the hydroxy group to a halogen or pseudohalogen not only in itself provides active and useful compounds, but also permits the displacement of the resultant electrophile from the protected or in some cases, unprotected, parent nucleus by a very wide range of nucleophiles. Persons with ordinary skill in the art of organic synthesis will recognize that such nucleophiles may include, without limitation, reagents having carbon, hydrogen, oxygen, nitrogen, sulfur, phosphorus, silicon, arsenic, boron, and/or selenium atoms in their structures. Particular examples would be reaction with ammonia, methylamine, the sodium salt of dimethylphosphine, trimethylphosphite, triphenylphosphine, potassium sulfite, trimethylsilylmethylmetal salts, lithium trimethylsilylacetylide, sodium cyanide, N-methyl-2-hydroxyethyl amine, 1[H]-tetrazole, or with the sodium salt of 2-mercaptoethanol, 3-mercaptoethanol, or of hydroxymethylphenol. Many variations may be executed as described in standard textbooks of synthetic organic chemistry, such as J. March, *Advanced Organic Chemistry*, Third Edition, Wiley-Interscience, New York, 1985. As an illustration, 14-O-methanesulfonyl-1-trimethylsilylmethylindolactam V yields 14-deoxy-14-(pentadecafluoro-[1H,1H]-octylthio)-1-trimethylsilylmethylindolactam V upon treatment with sodiopentadecafluoro-[1H,1H]-octylthiol. In a similar manner 14-deoxy-14-(pentadecafluoro-[1H,1H]-octylthio)-6,7-tetramethyleneindolactam V is prepared. See Y. Endo et al., *Tetrahedron* 42: 5905–5924 (1986) for a synthesis of 6,7-tetramethyleneindolactam V. As a further illustration, treatment of 14-O-methanesulfonyl-7-[2'-(2"-diphenylphosphonylethyl)aminoethyl]indolactam V with the sodium salt of 4-t-butyldimethylsilyloxy-2-phenylphenol followed by treatment of the product with tetrabutylammonium fluoride in tetrahydrofuran affords 14-O-(4'-hydroxy-2'-phenyl)phenyl-7-[2'-(2"-diphenylphosphonylethyl)aminoethyl]indolactam V. In a similar manner 14-O-(5'-hydroxy-1'-naphthyl)-7-[1',1'-dimethyl-3'-(hexyldimethylsilyl)propyl]indolactam V, 14-O-(3'-hydroxy-5'-benzyloxy)phenyl-7-octylindolactam V, 14-O-(4'-hydroxy-2'-phenyl)phenyl-6,7-tetramethyleneindolactam V, 14-O-(5'-hydroxy-1'-naphthyl)-6,7-tetramethyleneindolactam V, 14-O-(3'-hydroxy-5'-benzyloxy)phenyl-6,7-tetramethyleneindolactam V are prepared. As a further illustration, treatment of 14-O-methanesulfonyl-7-octylindolactam V with sodium sulfite in methanol provides 14-deoxy-7-octylindolactam V 14-sulfonic acid. In a similar manner 14-deoxy-6,7-tetramethyleneindolactam V 14-sulfonic acid is prepared. As another example, the 14-phosphonic acid derivative of 14-deoxy-6,7-tetramethyleneindolactam V may be made by reacting the sodium salt of dibenzylphosphonate with 14-O-methanesulfonyl-7-octylindolactam V to form 14-deoxy-14-dibenzylphosphonyl-6,7-tetramethyleneindolactam V followed by catalytic hydrogenolysis of the benzyl ester groups to yield the free phosphonic acid.

By use of protecting groups or modifications of the indolactam parent by methods well-known in the art of synthetic chemistry, the hydroxy group of the hydroxymethyl may be replaced by a metal and then reacted with an electrophile, effectively replacing the hydroxy with a group derived from the electrophile. The techniques for this replacement are obvious to workers with ordinary skill in organic synthesis, in that replacement of the hydroxymethyl hydroxy group by halogen in a suitably protected or modified indolactam permits strong and/or hard nucleophiles to be generated by the use of metals or strong bases, and persons with ordinary skill in the art of organic chemistry will recognize that such nucleophiles can be contacted with a very diverse range of electrophilic reagents having carbon, hydrogen, oxygen, nitrogen, sulfur, phosphorus, silicon, arsenic, boron and/or selenium atoms in their structures to obtain hydroxymethyl-modified indolactams of widely varying structures. As one approach among many, the 14-O-methanesulfonyl derivative of an appropriate indolactam may be converted to an iodo compound with sodium iodide in acetone. The resulting iodide may be modified by halogen-metal exchange using appropriately active metals or metal-containing reagents such as magnesium, zinc, alkali metals, metal alkyl reagents and so on, to obtain carbanionic character at the carbon atom previously bearing the hydroxy group, as shown:

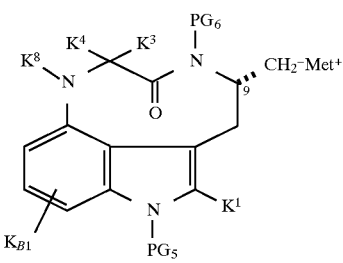

wherein Met is the metal ion, $PG_5$ may be one of the indole nitrogen protecting groups listed above, and $PG_6$ may be unnecessary (i.e. may be hydrogen or an anionic charge), may be benzyl (removable by hydrogenolysis) or may be a stable group, such as methyl or ethyl, intended to remain in the final bioactive synthetic product. The simultaneous presence or subsequent addition to the reaction of an electrophile such as, without limitation, an aldehyde, ketone, epoxide or oxetane then provides, after reaction and workup, compounds having one or more methylenes inserted between the original hydroxy group and the methylene to which it was attached. This methodology is particularly advantageous for replacement of the hydroxy with a group containing silicon, phosphorus or other atoms by contacting the anionic metal derivative of the parent nucleus with electrophilic reagents having halogen or pseudohalogen groups, in addition to other functions chosen for biological specificity, bonded directly to the silicon or phosphorus atoms, affording compounds with useful biological activity.

Alternatively, the hydroxy group on the hydroxymethyl of appropriately protected or modified indolactams may be oxidized to an aldehyde and then reacted via condensation or addition chemistries to provide a very wide variety of modified indolactams. Examples, without limitation, would be reactions with Wittig reagents, hydroxylamines, or Grignard reagents. Many variations may be executed as described in standard textbooks of synthetic organic chemistry, such as J. March, op cit. As an illustration, the aldehyde, 14-deoxy-14-oxo-7-octylindolactam V, may be prepared by oxidation of the parent hydroxymethyl compound with periodinane among other oxidizing agents. This aldehyde may be treated with O-(4-mercaptophenyl)hydroxylamine hydrochloride in ethanol to afford the O-(4-mercaptophenyl)oxime. This aldehyde may also be treated with $N^1$-(3-methoxyphenyl)semicarbazide to afford the corresponding $N^1$-(3-methoxyphenyl)semicarbazone. The O-(4-mercaptophenyl)hydroxylamine hydrochloride may be prepared from O-(4-nitrophenyl)hydroxylamine hydrochloride [A. Hirsch et al., *J. Med. Chem.* 20: 1546–1551 (1977)] in ways obvious to one with ordinary skill in the art of organic synthesis.

These aldehydes may also be obtained by reduction of appropriate carboxylic acid derivatives by application of well-known techniques. As an illustration, 9-deshydroxymethyl-9-methoxycarbonyl-6,7-tetramethyleneindolactam V (prepared as described below) may be reduced to the aldehyde, 14-deoxy-14-oxo-6,7-tetramethyleneindolactam V, by any of several reagents widely known in the art of organic chemistry, for example diisobutylaluminum hydride. This aldehyde may be further modified to afford the O-(4-mercaptophenyl)oxime and the $N^1$-(3-methoxyphenyl)semicarbazone in the manner described above.

The hydroxymethyl group of suitable indolactam phorboids may be oxidized to the carboxylic acid level by methods well-known in the art or these carboxylic acids may be prepared by modifications of the total syntheses described in the literature cited above. Besides being useful examples of this invention themselves these acids permit the preparation of further modified indolactams. For example, this carboxylic group may be activated for condensation reactions by any of a number of ordinary and well-known methods, e.g. by conversion to an acyl halide or to an active ester such as the N-succinimidyl ester. The resultant activated carboxyl may then be easily converted to simple or multifunctional ester, amide, or thioester derivatives by reaction with alcohols, amines, or thiols respectively, alone or in the presence of condensation catalysts. As an illustration, rac-9-deshydroxymethyl-9-carboxyindolactam V (obtained as described below) may be treated with N-hydroxysuccinimide and dicyclohexylcarbodiimide in acetonitrile. After purification, the resulting N-succinimidyl ester may be treated with 3-amino-1,2-propandiol and 4-dimethylaminopyridine in methylene chloride/tetrahydrofuran to afford rac-9-deshydroxymethyl-9-[N-(2', 3'-dihydroxy)propyl]carboxamidoindolactam V. The stereoisomers may be obtained separately either by using optically active starting materials or by separation from the mixture by chromatography on an enantioselective column packing [D. Armstrong, *Analytical Chem.* 59: 84–91A (1987)].

The total syntheses described in the literature cited above are also amenable to extensive adaptations so as to provide a wide variety of modifications in the parent structures of the indolactam group. By established techniques in the art of organic synthesis modified parent structures may be obtained which embody alterations at the hydroxymethyl group and which have useful biological activity. This extremely wide variety of modified indolactam structures may result from the use of modified starting materials, from modifications of one or more synthetic steps or from a combination of both. As an illustration, 9-deshydroxymethyl-9-carboxy-6,7-tetramethyleneindolactam V may be prepared from 4-nitro-6,7-tetramethylenegramine (Y. Endo et al., op cit.) by the application of several routes obvious to workers with ordinary skill in organic synthesis. For example, methyl α-nitro-4-amino-6,7-tetramethyleneindole-3 acetate is prepared from 4-nitro-6,7-tetramethylenegramine in the manner described by T. Masuda et al., *Agric. Biol. Chem.* 53: 2257–2260 (1989). Alkylation of the amino group of this compound with benzyl D-α-trifluoromethylsulfonyloxyisovalerate in the manner described by T. Kogan et al., op cit., affords an optically active intermediate which, after removal of the benzyl ester and reduction of the nitro group, is lactamized in the manner of T. Masuda et al., op cit., and methylated by treatment with formaldehyde/sodium cyanoborohydride to afford 9-deshydroxymethyl-9-methoxycarbonyl-6,7-tetramethylene-(9S,12S)-indolactam V. Hydrolysis with methanolic sodium hydroxide affords 9-deshydroxymethyl-9-carboxy-6,7-tetramethylene-(9S,12S)-indolactam V.

To further illustrate the synthesis of the compounds of this invention, the modified indolactam, 1,2,4,5,6,8-hexahydro-5-methyl-2-(1-methylethyl)-3H-pyrrolo(4,3,2-gh)-1,4-benzodiazonin-3-one, may be prepared from N-BOC-4-nitrotryptophanol [Y. Endo et al., *Tetrahedron* 42: 5905–5924 (1986)] by the application of several routes obvious to workers with ordinary skill in synthetic chemistry. For example, preparation of N-BOC-4-nitrodeoxytryptophanol may be accomplished by reduction of the phenylselenium derivative with triphenyltin hydride [D. Clive et al., *Chemical Communications* 41–42 (1978)] or by reduction of the mesylate derivative with lithium triethylborohydride [R. W. Holder and M. G. Matturro, *J. Org. Chem.* 42: 2166–2168 (1977)] or by several other routes. From the deoxy derivative the synthesis could proceed in the manner described by Y. Endo et al., loc cit., for the hydroxy derivative. Specifically, the resulting substituted indolylvaline methyl ester is hydrolyzed and the resulting acid is converted to the N-succinimidyl ester. Upon cleavage of the BOC group under acidic conditions cyclization to the lactam occurs directly to provide all four stereoisomers, i.e., 2R,5R-, 2R,5S-, 2S,5S-, and 2S,5R-1,2,4,5,6,8-hexahydro-5-methyl-2-(1-methylethyl)-3H-pyrrolo (4,3,2-gh)-1,4-benzodiazonin-3-one. These stereoisomers may be obtained separately either by beginning the synthesis with optically active N-BOC-4-nitrotrytophanol or by separation from the mixture by chromatography on an enantioselective column packing [D. Armstrong, *Analytical Chem.* 59: 84–91A (1987)]. Similarly, the further modified indolactam, 1-(1-oxobutyl)-1,2,4,5,6,8-hexahydro-5-methyl-3H-pyrrolo(4,3, 2-gh)-1,4-benzodiazonin-3-one, may be prepared. Specifically, hydrogenation of N-BOC-4-nitrodeoxytrytophanol over palladium on carbon will provide N(2')-BOC-4-aminodeoxytrytophanol. Alkylation of this compound with methyl bromoacetate affords N-[3-(N-BOC-2'-aminopropyl)-4-indolyl]glycine methyl ester [Y. Endo, et al., *Chem. Pharm. Bull.* 30: 3457–3460 (1982)]. Acylation of this material with butanoyl chloride in the presence of potassium carbonate or pyridine will provide N-butanoyl-N-[3-(N-BOC-2-aminopropyl)-4-indolyl] glycine methyl ester. This latter material may be converted to 1-(1-oxobutyl)-1,2,4,5,6,8-hexahydro-5-methyl-3H-pyrrolo(4,3,2-gh)-1,4-benzodiazonin-3-one by application of the methods of Y. Endo, et al., loc cit. (1986). The enantiomers, 5R- and 5S-, may be obtained separately by beginning with optically active materials as described above or by separation at the final stage by chromatography also as described above.

Derivatives of the indole, indene, benzofuran and benzothiophene classes in which the benzenoid ring contains one or two nitrogen atoms in positions 5, 6 and/or 7 may be obtained by modifying the known synthetic sequences for indolactams cited above. For example, a 5-, 6- and/or 7-monoaza- or diaza-indolactam derivatives may be obtained by replacing 4-aminoindole starting material in an appropriate synthetic sequence with a 5-, 6- and/or 7-monoaza- or diazaindole.

Beyond the extensive changes in the hydroxymethyl group of indolactam and related $P_2$-type parent phorboids described above, the present invention also discloses broad and diverse alterations which are accommodated in the non-hydroxymethyl regions of the parent $P_2$-type phorboids. Such modifications of the indolactam parents can be carried out before, after or in alternating fashion with respect to construction of the hydroxymethyl modifications, depending on obvious considerations of chemical stability of the various functional groups in intermediates being subjected to chemical modifications.

It is obvious to one skilled in the art that many modified indolactam parents may be obtained by carrying a modification through the de novo synthesis as described in the literature cited above. As an illustration, 7-alkylindolactam Vs containing a wide variety of alkyl groups may be prepared by application of the method of A. Kozikowski et al., op cit., to a variety of alkyl substituted isoxazolines. As a further illustration, the modified indolactam, 1-(1'-octyl)-1,2,4,5,6,8-hexahydro-5-hydroxymethyl-3H-pyrrolo[4,3,2-gh]-1,4-benzodiazonin-3-one (13-N-octylindolactam G), may be prepared. Alkylation of 4-aminoindole with methyl bromoacetate followed by acylation with octanoyl chloride in the presence of pyridine affords N-octanoyl-N-(4-indolyl) glycine methyl ester. This is converted to 13-N-octylindolactam G by the method described by A. Kozikowski et al., op cit. The enantiomers are obtained separately by silica gel chromatography of the 14-O-[N-(S)-(1'-naphthyl)ethyl]carbamates followed by reduction with trichlorosilane-triethylamine. Further modifications of this material to produce hydroxymethyl modified embodiments of this invention are carried out by the preparation of 1-N-(t-butyloxycarbonyl)-13-N-octylindolactam G, according to the method of Y. Endo et al., *Tetrahedron* 43: 2241–2247 (1987). Then, 14-O-methanesulfonyl-1-N-(t-butyloxycarbonyl)-13-N-octylindolactam G may be prepared by treatment of the above indolactam with methanesulfonyl chloride. Treatment of this material with a variety of nucleophiles as described above followed by removal of the t-butyloxycarbonyl group by treatment with acid, for example trifluoroacetic acid in methylene chloride, affords a very wide variety of hydroxymethyl-modified derivatives. 14-Deoxy-14-(2'-hydroxyethylthio)-13-N-octylindolactam G and 14-deoxy-14-(pentadecafluoro-[1H,1H]-octylthio)-13-N-octylindolactam G are specific illustrations of the types of useful compounds which may be prepared by application of these approaches.

As a further illustration, 1,2-tetramethyleneindolactam V may be prepared. One of the many preparations of this parent uses 2-carbethoxy-4-nitroindole, which is a side-product from the preparation of 4-nitroindole, as the starting material for transformation to 4-amino-1,2-tetramethyleneindole. Alkylation of the amino group of this compound with benzyl D-α-trifluoromethylsulfonyloxyisovalerate in the manner described by T. Kogan et al, op cit., affords N-(1,2-tetramethyleneindol-4-yl)valine benzyl ester as a single enantiomer. This material may then be converted to 1,2-tetramethyleneindolactam V by the methods described by A. Kozikowski et al., op cit. Further modifications of this material to produce hydroxymethyl modified embodiments of this invention may be carried out by the techniques discussed above. As specific examples, 14-deoxy-14-(2'-hydroxyethylthio)-1,2-tetramethyleneindolactam V and 14-deoxy-14-(pentadecafluoro-[1H,1H]-octylthio)-1,2-tetramethyleneindolactam V are prepared from 14-O-methanesulfonyl-1,2-tetramethyleneindolactam V.

Further synthetic elaborations may be effected at the end or near the end of the preparation of the modified indolactam-parent or of the hydroxymethyl-modified indolactam. As one of many possible illustrations, 7-(2'-methylbut-3'-en-2'-yl)indolactam V (pendolmycin), which may be prepared by the method of Kozikowski et al., op cit., or by the method of Okabe et al., *Tetrahedron* 46: 5113–5120 (1990), or a derivative of pendolmycin, may be hydroborated. The resulting trialkylborane, or haloborane, may be converted into other functional groups including but not limited to hydroxy, carbonyl, alkyl, amino and halo, all by well-known methods such as those referenced by A. Pelter et al., *Borane Reagents*, Academic Press, London, 1988. In a specific illustration, t-butyldimethylsilyl ether of pendolmycin may be prepared by treatment of a dimethylformamide solution of pendolmycin and imidazole (1:10 molar ratio) with t-butyldimethylchlorosilane. Treatment of this ether with 9-borabicyclo[3.3.1]nonane (9-BBN) affords the trialkylborane at the terminal carbon of the former terminal olefin, the oxidation of which with hydrogen peroxide in sodium hydroxide affords the primary alcohol. Acetylation of this alcohol with acetic anhydride in pyridine and removal of the silyl ether with tetrabutylammonium fluoride in tetrahydrofuran provides 7-(2'-methyl-4'-acetoxybutan-2'-yl) indolactam V. This may then be converted to 14-deoxy-14-(2''-hydroxyethylthio)-7-(2'-methyl-4'-hydroxybutan-2'-yl) indolactam V or many other hydroxymethyl modified derivatives by the methods discussed above followed by treatment with sodium hydroxide in methanol to hydrolyze the acetate, yielding a hydroxy group amenable to a wide range of further transformations, preferably to establish a hydrophobic substituent in that position of the molecule.

Similarly, compounds containing silicon and phosphorus may be obtained by adding reagents having Si—H or P—H bonds across the double bond of pendolmycin, for example, under the influence of chloroplatinic acid or light/peroxide catalysis, respectively. Such means for introducing silicon or phosphorus-containing groups may also be applied to structures having vinyl groups elsewhere in the molecule. For example, diethylphosphine may be added across the double bond of (−)-9-deshydroxymethyl-9-vinyl-7-octylindolactam V in a reaction promoted by light and peroxide catalysis to obtain 14-deoxy-14-diethylphosphinylmethyl-7-octylindolactam V.

An illustration of the modification of the parent group after the introduction of appropriate hydroxymethyl modifications is the preparation of 14-deoxy-14-(pentadecafluoro-[1H,1H]-octylthio)-7-[2'-methyl-4'-(N-octanoyl-N-ethyl)aminobutan-2'-yl]indolactam V. Hydroboration of 14-deoxy-14-(pentadecafluoro-[1H,1H]-octylthio)pendolmycin, prepared in the manner discussed above from 14-methanesulfonylpendolmycin, with dichloroborane-dimethylsulfide in the presence of boron trifluoride provides 14-deoxy-14-(pentadecafluoro-[1H,1H]-octylthio)-7-(2'-methyl-4'-dichloroboranylbutan-2'-yl) indolactam V which upon treatment with ethylazide affords 14-deoxy-14-(pentadecafluoro-[1H,1H]-octylthio)-7-(2'-methyl-4'-ethylaminobutan-2'-yl)indolactam V, itself amenable to further reactions, for example acylation with octanoyl chloride to yield the more hydrophobic 14-deoxy-14-(pentadecafluoro-[1H,1H]-octylthio)-7-[2'-methyl-4'-N-octanoyl-N-ethyl)aminobutan-2'-yl]indolactam V.

The application of established techniques in the art of synthetic chemistry to naturally derived or to synthetically derived parents of the indolactam group also permits the obtainment of specifically modified parents of that class. These modified parents may then be further modified at the hydroxymethyl group by the methods discussed above. To illustrate this, 14-O-t-butlydimethylsilylindolactam V [Y. Endo et al., *Tetrahedron* 43: 2241–2247 (1987)] may be treated with sodium hydride in dimethylformamide followed by phosgene. The reactive chloroformamide so formed is quenched with perfluoroheptylmethanol to afford, after removal of the silyl ether, 1-N-(pentadecafluoro-[1H,1H]-octyloxy)carbonylindolactam V. By application of methods discussed above a variety of hydroxymethyl modified derivatives may be prepared as specifically illustrated by 14-deoxy-14-(2'-hydroxyethylthio)-1-N-(pentadecafluoro-[1H,1H]-octyloxy)carbonylindolactam V and by 14-deoxy-14-(pentadecafluoro-[1H,1H]-octylthio)-1-N-(pentadecafluoro-[1H,1H]-octyloxy)carbonylindolactam V. As a further illustration, 14-O-acetylindolactam V [K. Irie and K. Koshimizu, *Mem. Coll. Agric., Kyoto Univ.* 132: 1–59 (1988)] may be alkylated with ethyl acrylate in the presence of sodium hydride to afford 14-O-acetoxy-1-N-(2'-ethoxycarbonyl)indolactam V. Treatment of this material with aluminum chloride in nitrobenzene followed by reduction of the purified product with lithium aluminum hydride-aluminum chloride in tetrahydrofuran provides 1,7-trimethyleneindolactam V. By application of methods discussed above a variety of hydroxymethyl modified derivatives may be prepared as specifically illustrated by 14-deoxy-14-(2'-hydroxyethylthio)-1,7-trimethyleneindolactam V and by 14-deoxy-14-(pentadecafluoro-[1H,1H]-octylthio)-1,7-trimethyleneindolactam V.

Such specifically modified parents of the indolactam class may also be further modified at positions other than the hydroxymethyl group either before or after the modifications of hydroxymethyl group to produce embodiments of this invention. The means for accomplishing these modifications are obvious to workers with ordinary skill in organic synthesis. As an illustration, 7-(2'-aminoethyl)indolactam V may be prepared from indolactam V by methods similar to those described by K. Irie and K. Koshimizu, op cit. N-Derivatization of this compound with pentadecafluoro-[1H,1H]-octyl isocyanate, 3-trimethylsilylpropanoyl chloride or 3-diphenyloxophosphinylpropanoyl chloride yields 7-[2'-(N'-pentadecafluoro-[1H,1H]-octylureido)ethyl]indolactam V, 7-[2'-(N-(3"-trimethylsilylpropanoyl)amino)ethyl]indolactam V or 7-[2'-(N-(3"-diphenyloxophosphinylpropanoyl)amino)ethyl]indolactam V respectively. By application of methods discussed above a variety of hydroxymethyl modified derivatives may be prepared as specifically illustrated by 14-deoxy-14-azido-7-[2'-(N'-pentadecafluoro-[1H,1H]-octylureido)ethyl] indolactam V, 14-deoxy-14-(2'-hydroxyethoxy)-7-[2'-(N-(3"-trimethylsilylpropanoyl)amino)ethyl]indolactam V, 14-O-[1'(5'-hydroxynaphthyl)]-7-[2'-(N-(3"-diphenyloxophosphinylpropanoyl)amino)ethyl]indolactam V, 14-deoxy-14-mercapto-7-[2'-(N'-pentadecafluoro-[1H,1H]-octylureido)ethyl]indolactam V, 14-deoxy-14-(pentadecafluoro-[1H,1H]-octylthio)-7-[2'-(N-(3"-trimethylsilylpropanoyl)amino)ethyl]indolactam V, and 14-deoxy-7-[2'-(N-(3"-diphenyloxophosphinylpropanoyl) amino)ethyl]indolactam V 14-sulfonic acid.

As a further illustration, 14-O-acetyl-2-formyl-7-ethylindolactam V may be prepared by the treatment of 14-O-acetyl-7-ethylindolactam V with dichloromethyl methyl ether-titanium tetrachloride [K. Irie et al., *Int. J. Cancer* 43: 513–519 (1989)]. Condensation with nitromethane followed by reduction of the nitrovinyl derivative with lithium aluminum hydride-aluminum chloride affords 2-(2'-aminoethyl)-7-ethylindolactam V. Derivatization of this compound with pentadecafluoro-[1H,1H]-octyl isocyanate, trimethylsilylpropanoyl chloride or 3-diphenyloxophosphinylpropanoyl chloride yields 7-ethyl-2-[2'-(N'-pentadecafluoro-[1H,1H]-octylureido)ethyl] indolactam V, 7-ethyl-2-[2'-(N-(3"-trimethylsilylpropanoyl) amino)ethyl]indolactam V or 7-ethyl-2-[2'-(N-(3"-diphenyloxophosphinylpropanoyl)amino)ethyl]indolactam V respectively. By application of methods discussed above a variety of hydroxymethyl modified derivatives may be prepared.

Many parent phorboids of the diaminobenzyl alcohol ($P_3$) class are available via total synthesis [see, for example, Wender, P. et al., *Proc. Nat. Acad. Sci. USA* 83: 4214–4218, (1986)]. Given the ready availability of a wide variety of precursors for phorboids of this class and for hydroxymethyl-modified members of that class, the means for producing the $P_3$-based compounds of this invention will be obvious to workers with ordinary skill in synthetic organic chemistry.

For example, 4-carboxy-6-(N-decanoylamino)indole may be converted to its N-hydroxysuccinimide ester by reaction with one equivalent of dicyclohexylcarbodiimide and one equivalent of N-hydroxysuccinimide in acetonitrile/tetrahydrofuran/methylene chloride suspension. The product N-hydroxysuccinimide ester is purified and then reacted with 3-amino-1,2-propanediol in tetrahydrofuran to obtain 4-(N-2',3'-dihydroxypropylcarboxamido)-6-(N-decanoylamino)indole.

Given the ready availability of a wide variety of precursors for phorboids of the diacylglycerol ($P_4$) class and for hydroxymethyl-modified members of that class, the means for producing compounds of this invention based on the $P_4$ parent phorboid class will be obvious to workers with ordinary skill in synthetic organic chemistry. In some cases these precursors will be available with suitable blocking groups in place or they may be put in place using well understood techniques or blocking groups are not needed. An illustration of the preparation of compounds of this invention is the preparation of 3R-3-carboxy-1,6-dioxo-2,5-dioxacyclotetracosane. Diesterification of readily available D-glyceric acid with 9-decynoyl chloride in the presence of pyridine affords 2,3-O,O-didecynoyl-D-glyceric acid. Treatment of this material with cupric acetate/pyridine affords the material coupled at the acetylenic termini, the catalytic hydrogenation of which affords 3R-3-carboxy-1,6-dioxo-2,5-dioxacyclotetracosane. In similar and related manner 2R-2,3-octanoyloxypropionic acid and 4R-4-carboxy-2,7-dioxo-3,6-dioxa-1,8-diazacyclocosane may be prepared. Furthermore, the same acylation with terminal acetylenic carboxylic acids followed by cyclization and reduction may be applied to 1-chloro-2,3-dihydroxypropane, preceded or followed by displacement of the chloro leaving group with any of the nucleophilic type of reagents described above, to yield, after an appropriate sequence of protection-deprotection of chemically sensitive functional groups in the intermediates, novel and useful hydroxymethyl-modified phorboids of the diacylglycerol class.

Compounds of the polyacetate ($P_5$) class of phorboids may be obtained by semisynthetic modification of starting compounds purified from natural sources [see Mynderse, J. et al., *Science* 196: 538–540 (1977) and references cited therein] or by adaptations and modifications of the intermediates or final products of total syntheses of the polyacetates [see Park, P. et al., *J. Am. Chem. Soc.* 109: 6205–6207 (1987); Ireland, R. et al., *J. Am. Chem. Soc.* 110: 5768–5779 (1988); and Nakamura, H. et al., *Proc. Nat. Acad. Sci. USA* 86: 9672–9676 (1989)].

Given the availability of compounds of the bryostatin ($P_6$) phorboid class by purification from natural sources, e.g., *Bugula neritina* [see Pettit, G. R. et al., "Isolation and structure of bryostatin 1," *J. Am. Chem. Soc.* 104: 6846–6848 (1982)] or by total or partial synthesis [see Kageyama, M. et al., "Synthesis of bryostatin 7," *J. Am. Chem. Soc.* 112: 7407–7408 (1990) and references cited therein] the means for producing compounds of this invention based upon the $P_6$ parent phorboid class will be obvious to workers with ordinary skill in synthetic organic chemistry. Where necessary reactive functional groups in the parent structure may be selectively blocked with protecting groups such as esters, ethers or silyl ethers which are commonly used in the ordinary practice of organic chemistry. The 1-hydroxyethyl group of the natural bryostatins may be "capped" using condensation or addition reactions as discussed in detail above for other phorboid parents. Also as discussed previously the hydroxy group may be activated towards nucleophilic displacement which may take place with inversion or retention of stereochemistry. Oxidation of the 1-hydroxyethyl groups in the parent or modified parent compounds affords ketones which may then be readily derivatized and modified in ways obvious to workers with ordinary skill in synthetic organic chemistry to afford compounds of this invention. The above ketones or their derivatives may be further oxidized to afford the carboxylic acid with one less carbon than the parent. These carboxylic acids may be further derivatized to produce other compounds of this invention or reduced to the hydroxymethyl-containing compounds which may be modified to afford compounds of this invention as discussed previously in detail.

Compounds of this invention from the benzolactam ($P_7$) class of phorboids are readily available by total synthesis from common organic chemical starting materials. These syntheses provide flexibility in arriving at diverse functionalities on the parent nucleus and on the $S_oE_o$ or $S_xE_1$ side chain. Modifications of the parent structure may also be made by the application of well known organic synthetic procedures to the benzolactam as well as on precursor molecules. [See A. P. Kozikowski et al. "Synthesis, molecular modeling, 2-D NMR, and biological evaluation of ILV mimics as potential modulators of protein kinase C", *J. Am. Chem. Soc.* 115: 3957–3965 (1993) and M. Ohno et al. "Designed molecules Reproducing the two conformations of teleocidins", *Tetrahedron Lett.* 34: 8119–8122 (1993).]

The means for modifying the hydroxymethyl group of benzolactam phorboids to produce the compounds of this invention will be obvious to workers with ordinary skill in synthetic organic chemistry.

The limited reactivity of the other portions of the simplest benzolactam parents enhances the ability to achieve selective modification of the hydroxymethyl group with or without the need for protecting groups. For example, the hydroxymethyl group may be conveniently capped under very mild conditions by the treatment with a substituted or unsubstituted alkyl, aryl, or aralkyl isocyanate, optionally containing silicon or phosphorus atoms in a variety of functional groups, in the presence of a catalyst such as dibutyltin dilaurate or activated and displaced with a wide variety of nucleophiles. The resulting compounds lack the toxic inflammatory activity of the phorboid from which they were derived, and have themselves anti-inflammatory utility. As an illustration, treatment of (–)-BL-V8-310 with methylisocyanate in the presence of dibutyltin dilaurate and 4-dimethylaminopyridine in tetrahydrofuran affords 11-O-(N-methyl)carbamoyl-(2S,5S)-BL-V8-310.

Conversion of the hydroxy group to a halogen or pseudohalogen not only in itself provides active and useful compounds, but also permits the displacement of the resultant electrophile from the protected or in some cases, unprotected, parent nucleus by a very wide range of nucleophiles. Persons with ordinary skill in the art of organic synthesis will recognize that such nucleophiles may include, without limitation, reagents having carbon, hydrogen, oxygen, nitrogen, sulfur, phosphorus, silicon, arsenic, boron, and/or selenium atoms in their structures. Particular examples would be reaction with ammonia, methylamine, the sodium salt of dimethylphosphine, trimethylphosphite, triphenylphosphine, potassium sulfite, trimethylsilylmethyl-metal salts, lithium trimethylsilylacetylide, sodium cyanide, N-methyl-2-hydroxyethyl amine, 1[H]-tetrazole, or with the sodium salt of 2-mercaptoethanol, 3-mercaptoethanol, or of hydroxymethylphenol. Many variations may be executed as described in standard textbooks of synthetic organic chemistry, such as J. March, op cit. As an illustration, 11-O-methanesulfonyl-(2S,5S)-BL-V8-310 yields 11-deoxy-(2S,5S)-BL-V8-310 11-sulfonic acid upon treatment with sodium sulfite. As a further illustration, treatment of 11-O-methansulfonyl-(2R,5S)-BL-V8-310 with the sodium salt of 4-t-butyldimethylsilyloxyphenol followed by treatment of the product with tetrabutylammonium fluoride in tetrahydrofuran affords 11-O-(4'-hydroxyphenyl)-(2R,2S)-BL-V8-310.

The hydroxy group of the hydroxymethyl of benzolactams may be replaced by a metal and then reacted with an electrophile, effectively replacing the hydroxy with a group derived from the electrophile. The techniques for this replacement are obvious to workers with ordinary skill in organic synthesis, in that replacement of the hydroxymethyl hydroxy group by halogen in a suitably protected or modified benzolactam permits strong and/or hard nucleophiles to be generated by the use of metals or strong bases, and persons with ordinary skill in the art of organic chemistry will recognize that such nucleophiles can be contacted with a very diverse range of electrophilic reagents having carbon, hydrogen, oxygen, nitrogen, sulfur, phosphorus, silicon, arsenic, boron and/or selenium atoms in their structures to obtain hydroxymethyl-modified benzolactams. As one approach among many, the 14-O-methanesulfonyl derivative of an appropriate benzolactam may be converted to an iodo compound with sodium iodide in acetone. The resulting iodide may be modified by halogen-metal exchange using appropriately active metals or metal-containing reagents such as magnesium, zinc, alkali metals, metal alkyl reagents and so on, to obtain carbanionic character at the carbon atom previously bearing the hydroxy group, as shown:

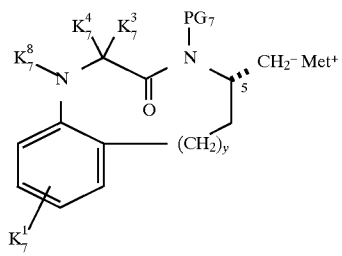

wherein Met is the metal ion, and $PG_7$ may be unnecessary (i.e. may be hydrogen or an anionic charge), may be benzyl (removable by hydrogenolysis) or may be a stable group, such as methyl or ethyl, intended to remain in the final bioactive synthetic product. The simultaneous presence or subsequent addition to the reaction of an electrophile such as, without limitation, an aldehyde, ketone, epoxide or oxetane then provides, after reaction and workup, compounds having one or more methylenes inserted between the original hydroxy group and the methylene to which it was attached. This methodology is particularly advantageous for replacement of the hydroxy with a group containing silicon, phosphorus or other atoms by contacting the anionic metal derivative of the parent nucleus with electrophilic reagents having halogen or pseudohalogen groups, in addition to other functions chosen for biological specificity, bonded directly to the silicon or phosphorus atoms, affording compounds with useful biological activity.

Alternatively, the hydroxy group on the hydroxymethyl of benzolactams may be oxidized to an aldehyde and then reacted via condensation or addition chemistries to provide a very wide variety of modified benzolactams. Examples, without limitation, would be reactions with Wittig reagents, hydroxylamines, or Grignard reagents. Many variations may be executed as described in standard textbooks of synthetic organic chemistry, such as J. March, op cit. As an illustration, the aldehyde, 11-deoxy-11-oxo-epi-BL-V9-310, may be prepared by oxidation of the parent hydroxymethyl compound with periodinane among other oxidizing agents. This aldehyde may be treated with methyl triphenylphosphoranylideneacetate in toluene to afford 5-deshydroxymethyl-5-[2'-(methoxycarbonyl)-(E)-vinyl]-epi-BL-V9-310.

These aldehydes may also be obtained by reduction of appropriate carboxylic acid derivatives by application of well-known techniques. These carboxylic acid derivatives may be prepared by modification of the published synthetic routes, which modifications are well understood by those with skill in the art of organic synthesis. The carboxylic acid derivatives of the benzolactam phorboids may also be prepared by oxidation of the hydroxymethyl group of suitable benzolactam phorboids or of aldehydic derivatives of benzolactams by methods well-known in the art.

Besides being useful examples of this invention themselves, these acids permit the preparation of further modified benzolactams. For example, this carboxylic group may be activated for condensation reactions by any of a number of ordinary and well-known methods, e.g. by conversion to an acyl halide or to an active ester such as the N-succinimidyl ester. The resultant activated carboxyl may then be easily converted to simple or multifunctional ester, amide, or thioester derivatives by reaction with alcohols, amines, or thiols respectively, alone or in the presence of condensation catalysts.

The total syntheses described in the literature cited above are also amenable to extensive adaptations so as to provide a wide variety of modifications in the parent structures of the benzolactam group. By established techniques in the art of organic synthesis modified parent structures may be obtained which embody alterations at the hydroxymethyl group and which have useful biological activity. This extremely wide variety of modified benzolactam structures may result from the use of modified starting materials, from modifications of one or more synthetic steps or from a combination of both.

Beyond the extensive changes in the hydroxymethyl group of benzolactam and related $P_7$-type parent phorboids described above, the present invention also discloses broad and diverse alterations which are accommodated in the non-hydroxymethyl regions of the parent $P_7$-type phorboids. Such modifications of the benzolactam parents can be carried out before, after or in alternating fashion with respect to construction of the hydroxymethyl modifications, depending on obvious considerations of chemical stability of the various functional groups in intermediates being subjected to chemical modifications.

It is obvious to one skilled in the art that many modified benzolactam parents may be obtained by carrying a modification through the de novo synthesis as described in the literature cited above. Specifically modified parents of the benzolactam class may also be further modified at positions other than the hydroxymethyl group either before or after the modifications of hydroxymethyl group to produce embodiments of this invention. The means for accomplishing these modifications are obvious to workers with ordinary skill in organic synthesis.

This invention is illustrated further by the following examples.

EXAMPLE 1

20-Deoxy-20-(2'-hydroxyethylthio)phorbol 12,13-Dibutyrate

One gram of sodium metal was dissolved in 50 mL methanol, and 44 $\mu$L of this solution was placed in a test tube. Then 2.63 grams distilled 2-mercaptoethanol was dissolved in 50 mL acetonitrile, and 44 $\mu$L of this solution was added to the test tube. Then 20 mg 20-deoxy-20-chlorophorbol 12,13-dibutyrate were dissolved in 0.25 mL acetonitrile in a capped, nitrogen-flushed test tube. This latter solution was then rapidly treated with the methoxide/mercaptoethanol solution. An immediate precipitate formed. After 7 minutes, the reaction was freed of solvent and treated with 1 mL water and 1 drop acetic acid. This residue was partitioned between water and ethyl acetate, followed by drying of the organic phase over sodium sulfate. Silica gel preparative liquid chromatography using hexane/ethyl acetate mixtures yielded 9.5 mg of 20-deoxy-20-(2'-hydroxyethylthio)phorbol 12,13-dibutyrate, which could not be crystallized.

EXAMPLE 2

20-Deoxy-20-(2'-hydroxyethylthio)phorbol 12-Butyrate

Further preparative liquid chromatography of the reaction mixture from Example 1 using hexane/ethyl acetate on silica gel yielded 5.7 mg 20-deoxy-20-(2'-hydroxyethylthio) phorbol 12-butyrate, the latter being the more polar compound. This compound could not be crystallized.

EXAMPLE 3

20-Deoxy-20-(2'-hydroxyethylthio)phorbol 12-Myristate 13-Acetate

To 0.1 gram 20-deoxy-20-chlorophorbol 12-myristate 13-acetate in 1 mL acetonitrile was added 0.5 mL of a solution of 246 mg 2-mercaptoethanol and 436 mg 2,4,6-collidine in 10 mL acetonitrile, followed by 50 mg diisopropylethylamine in 0.2 mL acetonitrile and 0.1 mL t-butyl methyl ether. Ten minutes later the reaction was treated with 0.107 mmoles sodium methoxide and 0.225 mmoles 2-mercaptoethanol in 0.25 mL methanol. Five minutes later the proportion of sodium methoxide/mercaptoethanol was doubled. After 10 minutes the reaction was stopped by addition of 2 drops acetic acid and 0.5 mL water. The organics were extracted into ethyl acetate, washed once with water, and dried over sodium sulfate. After solvent removal, the crude residue was purified by preparative liquid chromatography on silica gel using hexane/ethyl acetate (60:40). The product was 87 mg 20-deoxy-20-(2'-hydroxyethylthio) phorbol 12-myristate 13-acetate in high purity. The compound did not crystallize.

EXAMPLE 4

20-Deoxy-20-(2'-hydroxyethylthio)phorbol 12-Myristate

Twenty-five mg of 20-deoxy-20-chlorophorbol 12-myristate 13-acetate was dissolved in 0.2 mL ethylene glycol and 0.2 mL acetonitrile. This solution was treated with 0.13 mL of a solution of 200 mg sodium metal in 20 mL ethylene glycol over a period of 40 minutes. The reaction was partitioned between water and ethyl acetate, and the separated organics were dried over sodium sulfate. After removal of the ethyl acetate, the crude 20-deoxy-20-chlorophorbol 12-myristate was dissolved in 0.8 mL acetonitrile and treated with 0.18 mL of a solution of 0.31 mL 2-mercaptoethanol, 0.5 mL acetonitrile, and 0.5 mL of 1% sodium in methanol. After 40 minutes, an additional 0.04 mL of 1% sodium in methanol was added. Ten minute later the reaction was stopped with 1 drop of acetic acid. After removal of the solvents in a stream of nitrogen, the residue was partitioned between ethyl acetate and pH 8 potassium phosphate. The organics were dried over sodium sulfate and freed of solvent prior to preparative liquid chromatographic purification using silica gel and hexane/ethyl acetate (45:55). The product, 37 mg of 20-deoxy-20-(2'-hydroxyethylthio)phorbol 12-myristate, could not be crystallized.

EXAMPLE 5

20-Deoxy-20-[(2'-hydroxyethyl)methylamino] phorbol 12-Myristate 13-Acetate 25 mg 20-deoxy-20-chlorophorbol 12-myristate 13-acetate was dissolved in 0.4 mL acetonitrile. To this was added 0.1 mL of a solution of 29.6 mg 2-(methylamino) ethanol in 1 mL acetonitrile. After 70 minutes and additional 0.1 mL of the same amine solution was added. After an additional 70 minutes, 0.2 mL more amine solution was added. After 6.6 hours of total reaction time, the reaction was diluted with 4 mL methylene chloride and subjected to preparative liquid chromatography on silica gel using methylene chloride/methanol (92:8) followed by repurification on silica gel using methylene chloride/methanol (96:4). The product, 20-deoxy-20-[(2'-hydroxyethyl)methylamino] phorbol 12-myristate 13-acetate, 14 mg, could not be crystallized.

EXAMPLES 6, 7, and 8

20-Deoxy-20-fluorophorbol 12,13-Bis[(2',4'-difluorophenyl)acetate], 12-β, 13-Bis[(2',4'-difluorophenyl)acetoxy]-7-fluoro-9-hydroxy-1,4,6 (20)-tigliadien-3-one and 12-β,13-Bis[(2',4'-difluorophenyl)acetoxy]-4,9-dihydroxy-7-fluoro-1,6 (20)-tigliadien-3-one One-hundred mg of phorbol 12,13-bis[(2',4'-difluorophenyl)acetate] were dissolved in 1.5 mL methylene chloride and the solution was set at 0° C. Then 26.2 mg diethylaminosulfur trifluoride in 0.5 mL methylene chloride were added drop wise during 1 minute. After 40 minutes, 0.2 mL more diethylaminosulfur trifluoride was added. After 10 more minutes, the reaction was shaken with 2 mL pH 8 potassium phosphate buffer, after which the organics were separated and dried over sodium sulfate. The reaction was repeated twice more, and the combined reaction products were freed of solvent, taken up in 10 mL ethyl acetate, and sucked through a funnel containing a layer of silica at the bottom, a layer of sodium sulfate in the middle and sodium chloride at the top. After washing the funnel contents with 50 mL ethyl acetate the combined eluants were freed of solvent and repeatedly chromatographed on silica preparative liquid chromatography columns using hexane/ethyl acetate (85:15) solvent mixtures. The products were 20-deoxy-20-fluorophorbol 12,13-bis[(2',4'-difluorophenyl) acetate], 40 mg; 12-β, 13-bis[(2',4'-difluorophenyl)acetoxy]-7-fluoro-9-hydroxy-1,4,6(20)-tigliadien-3-one 25 mg; and 12-β,13-bis[(2',4'-difluorophenyl)acetoxy]-4,9-dihydroxy-7-fluoro-1,6(20)-tigliadien-3-one, 40 mg, none of which could be crystallized.

EXAMPLE 9

4-Carboxy-6-(N-decanoylamino)indole

Five hundred-fifteen mg of 4-carbomethoxy-6-(N-decanoylamino)indole [prepared by the method of Wender et al., *PNAS*, 83: 4214–4218 (1986)] was dissolved in 60 mL of tetrahydrofuran. This solution was treated with 3 mL of a 1N KOH solution in water and also with 5 mL of methanol. The mixture was heated at 80° C. for 32 h. During this period another 2.5 mL of 1N KOH was added in two portions. After cooling the mixture was concentrated in vacuo. The mixture was then diluted with water and acidified with concentrated hydrochloric acid. The mixture was then extracted with methylene chloride. The organic layers were dried over sodium sulfate and concentrated to afford 300 mg of 4-carboxy-6-(N-decanoylamino)indole (60% yield), mp 248°–50° C.

EXAMPLE 10

4-Carboxy-6-(N-decanoylamino)indole N-Succinimidyl Ester

A suspension of 470 mg of 4-carboxy-6-(N-decanoylamino)indole and 427 mg of N-hydroxysuccinimide in 100 mL of acetonitrile, 10 mL of methylene chloride and 10 mL of tetrahydrofuran was prepared. This suspension was stirred vigorously by a magnetic stirring bar as a solution of 540 mg of dicyclohexylcarbodiimide in 20 mL of acetonitrile was slowly added over a period of 1 h. The mixture was stirred vigorously for 72 h. It was then concentrated in vacuo and diluted with ethyl acetate. The resulting mixture was filtered to remove the copious precipitate. The filtrate was washed with water, dried over sodium sulfate and concentrated. Treatment of the resulting mixture with hexane/ethyl acetate (50:50) followed by filtration afforded 600 mg of 4-carboxy-6-(N-decanoylamino)indole N-succinimidyl ester, mp 154°–5° C.

EXAMPLE 11

4-(N-2',3'-Dihydroxypropylcarboxamido)-6-(N-decanoylamino)indole

To a solution of 89 mg of 3-amino-1,2-propanediol in 20 mL of tetrahydrofuran was added 136 mg of 4-carboxy-6-(N-decanoylamino)indole N-succinimidyl ester. The solution was stirred for 48 h. After concentration in vacuo the mixture was purified by preparative liquid chromatography using silica gel and methylene chloride/methanol (92:8). The product, 135 mg of 4-(N-2',3'-dihydroxypropylcarboxamido)-6-(N-decanoylamino) indole, was recrystallized from methanol/methylene chloride, mp 139°–41° C.

EXAMPLE 12

4-(N-2'-Mercaptoethylcarboxamido)-6-(N-decanoylamino)indole and 4-(S-2'-Aminoethylthiolcarbonyl)-6-(N-decanoylamino) indole To a solution of 113 mg of triethylamine in 20 mL of tetrahydrofuran was added, first, 86 mg of 2-aminoethanethiol hydrochloride and, then, 139 mg of 4-carboxy-6-(N-decanoylamino)indole N-succinimidyl ester. The solution was stirred for 48 h and then concentrated in vacuo. Purification by liquid chromatography using silica gel and methylene chloride/methanol (96:4) afforded two products. The earlier eluting product, 23 mg of 4-(N-2'-mercaptoethylcarboxamido)-6-(N-decanoylamino)indole, decomposed at 200°–5° C. The later eluting product, 22 mg of 4-(S-2'-aminoethylthiolcarbonyl)-6-(N-decanoylamino) indole, was recrystallized from methanol, mp 192°–3° C.

EXAMPLE 13

4-(2'-Hydroxymethylpiperidinocarbonyl)-6-(N-decanoylamino)indole

To a solution of 145 mg of 4-carboxy-6-(N-decanoylamino)indole N-hydroxysuccinimidyl ester in 20 mL of tetrahydrofuran was added 103 mg or piperidinemethanol. The solution was heated at reflux for 5 days, at which time another 100 mg of piperidinemethanol was added and heating continued for another day. The solution was then concentrated in vacuo and purified by liquid chromatography using silica gel and methylene chloride/isopropyl alcohol (93:7). In this manner 21 mg of 4-(2'-hydroxymethylpiperidinocarbonyl)-6-(N-decanoylamino)indole was obtained, mp 126°–129° C.

EXAMPLE 14

Phorbol 12-Myristate 13-Acetate 20-Methylcarbamate

One hundred milligrams of phorbol 12-myristate 13-acetate was dissolved in 1 mL tetrahydrofuran. To this solution was added 11.5 µL of methyl isocyanate, followed immediately by 20 µL of a 10% by weight solution of dibutyltin dilaurate in tetrahydrofuran. After three hours an additional 11.5 µL of methylisocyanate was added. Sixteen hours later 30 µL of the reaction solution was applied to a silica gel TLC plate and developed with hexanes/ethyl acetate (46:54). The band at $R_f$=0.4 was scraped off and the product was eluted from the silica with acetone. Removal of the solvent in a stream of nitrogen gave 2.8 mg of phorbol 12-myristate 13-acetate 20-methylcarbamate as a glassy solid for spectroscopic analysis and bioassay.

EXAMPLE 15

12-β-Myristoyloxy-13-acetoxy-4,9-dihydroxy-7-hydroxymethyl-1,6(20)-tigliadien-3-one Ninety-eight mg of 20-deoxy-20-chlorophorbol 12-myristate 13-acetate was dissolved in 0.5 mL tetrahydrofuran. To this was added 0.15 mL saturated aqueous ammonium chloride, 0.15 mL 37% formalin solution, and 50 mg zinc dust (less than 325 mesh). The reaction was capped and shaken vigorously for 24 hours. At the end of this time the reaction was partitioned between pH 8 phosphate buffer and ethyl acetate. The ethyl acetate phase was reduced to a volume of 2 mL under a stream of nitrogen and 0.125 mL was applied to a silica gel TLC plate and developed with hexanes/ethyl acetate (46:54). The band at $R_f$=0.45 was scraped off and the product was eluted from the silica powder with acetone. Removal of the acetone yielded 3.0 mg of 12-β-myristoyloxy-13-acetoxy-4,9-dihydroxy-7-hydroxymethyl-1,6(20)-tigliadien-3-one as a glassy solid for spectroscopic analysis and bioassay.

EXAMPLE 16

Method: A stock solution of 300 pmoles of the standard inflammatory compound phorbol 12-myristate 13-acetate per 5 µL acetone was prepared. This solution was used to prepare four-fold dilutions of 20-deoxy-20-(2'-hydroxyethylthio)phorbol 12-myristate 13-acetate, prepared as in Example 3, covering concentrations of the latter ranging from 4 to 64,000 pmoles per 5 µL. These solutions were used to demonstrate the anti-inflammatory activity of the latter compound by application of 5 µL to the insides of the right ears of mice, followed by the observation of ear inflammation/erythema at intervals from 1 to 48 hours after application. Inhibition of the phorbol 12-myristate 13-acetate induced inflammation was observed at the medium and higher concentrations of the inhibitor.

In a like manner, the anti-inflammatory activities of the following compounds are demonstrated; lower doses produce shorter periods of inflammation/erythema and higher doses produce longer periods of, and in most cases complete, inhibition during the entire assay period.

A. Diterpenoid-type phorboids
(i) 20-deoxy-20-chlorophorbol 12-myristate 13-acetate;
(ii) 20-deoxy-20-(2'-hydroxyethylthio)phorbol 12,13-dibutyrate;
(iii) 20-deoxy-20-(2'-hydroxyethylthio)phorbol 12-myristate 13-acetate;
(iv) 20-deoxy-20-[(2'-hydroxyethyl)methylamino]phorbol 12-myristate 13-acetate,
(v) 20-deoxy-20-fluorophorbol 12,13-bis[(2',4'-difluorophenyl)acetate];
(vi) 12-β,13-bis[(2',4'-difluorophenyl)acetoxy]-7-fluoro-9-hydroxy-1,4,6(20)-tigliatren-3-one;
(vii) 12-β,13-bis[(2',4'-difluorophenyl)acetoxy]-4,9-dihydroxy-7-fluoro-1,6(20)-tigliadien-3-one;
(viii) 12-β-myristoyloxy 13-acetoxy-4,9-dihydroxy-7-hydroxymethyl-1,6(20)-tigliadien-3-one;
(ix) phorbol 12-myristate 13-acetate 20-methylcarbamate;
(x) 6-deshydroxy-6-carboxyphorbol 12,13-didecanoate;
(xi) 6-deshydroxy-6-carboxyphorbol 12-octyldimethylsilylacetate 13-(2',4'-difluorophenyl) acetate;
(xii) 6-deshydroxy-6-carboxyresiniferonol 9,13,14-orthophenylacetate;
(xiii) 20-deshydroxy-20-carboxyingenol 3-benzoate;
(xiv) 20-deshydroxy-20-carboxymethylidenephorbol 12,13-bis[(2',4'-difluorophenyl)acetate];
(xv) 20-deoxy-20-dimethylphosphinylphorbol 12-myristate 13-acetate;
(xvi) 20-deoxy-20-dimethylphosphonylphorbol 12-myristate 13-acetate;
(xvii) 20-deoxy-20-cyanophorbol 12-myristate 13-acetate;
(xviii) 20-deoxy-20-azidophorbol 12,13-bis[(2',4'-difluorophenyl)acetate];
(xix) 20-deoxy-20-mercaptophorbol 12,13-bis[(2',4'-difluorophenyl)acetate];
(xx) 20-deoxy-20-hydroximinophorbol 12,13-bis[(2',4'-difluorophenyl)acetate];
(xxi) 6-deshydroxymethyl-6-carboxyphorbol 12,13-bis[(2',4'-difluorophenyl)acetate];
(xxii) 20-deoxy-20-(2'-hydroxyethylthio)phorbol 12,13-bis[(2',4'-difluorophenyl)acetate];
(xxiii) 20-deoxyphorbol 12,13-bis[(2',4'-difluorophenyl) acetate] 20-sulfonic acid; and
(xxiv) 20-deoxy-20-azidophorbol 12,13-bis[(2',4'-difluorophenyl)acetate].

B. Indolactam-type phorboids
(i) rac-14-O-(N-methyl)carbamoyl-1-N-(2'-triphenylphosphonium)ethylindolactam V, methanesulfonate salt;
(ii) 14-O-(N-methyl)carbamoyl-7-octyl-(9S,12S)-indolactam V;
(iii) 9-deshydroxymethyl-9-[N-(2',3'-dihydroxypropyl)] carboxamidoindolactam V;
(iv) 9-deshydroxy-9-(2'-hydroxyethylthio)indolactam V;
(v) 9-deshydroxy-9-(3'-hydroxypropylthio)-7-octyl-(9S, 12S)-indolactam V;
(vi) 9-deshydroxymethyl-9-carboxyindolactam V, triethylamine salt;

(vii) 9-deshydroxy-9-(2'-hydroxyethylthio)-7-octyl-(9S, 12S)-indolactam V;
(viii) 7-octyl-(9S,12S)-indolactam V 14-O-(N'-methylcarbamate);
(ix) 1-(2'-triphenylphosphonium)ethyl-7-octyl-(9S,12S)-indolactam V 14-O-(N'-methylcarbamate);
(x) 9-deshydroxymethyl-9-carboxyindolactam V; and
(xi) 14-deoxy-14-(3'-hydroxypropylthio)-7-octyl-(9S,12S)-indolactam V.

C. Benzolactam-type Phorboids
(i) 5-deshydroxymethyl-5-carboxy-BL-V8-310.

EXAMPLE 17

9-Deshydroxymethyl-9-carboxyindolactam V

A solution of 60 g of 4-nitrogramine [J. B. Hester, *J. Org. Chem.*, 29: 1158 (1964)] and 54 g of ethyl nitroacetate in 1.2 L of chlorobenzene was heated at 100° C. for 1.5 h. After cooling the mixture was filtered, washed with cold methylene chloride and dried in vacuo to afford 58.9 g of ethyl 3-(4'-nitroindol-2'-yl)-2-nitropropionate as a yellow solid: mp 159°–160.5° C. Another 11 g may be recovered from the filtrate by dilution with hexane, preparative liquid chromatography [silica; methylene chloride/ethyl acetate (90:10)] and recrystallization from methanol. The structure was confirmed by NMR.

To a solution of 7.29 g of ethyl 3-(4'-nitroindol-2'-yl)-2-nitropropionate in 100 mL of tetrahydrofuran and 100 mL of ethanol was added 721 mg of 10% Pd on carbon. The resulting mixture was shaken in a Parr apparatus under about 50 psi hydrogen. After 70 min the mixture was filtered through celite and washed with ethanol. The filtrate was concentrated in vacuo. After purification by preparative liquid chromatography [silica; hexane/tetrahydrofuran (60:40)] 5.5 g of ethyl 3-(4'-aminoindol-2'-yl)-2-nitropropionate was obtained as an off-white solid, mp 110°–112° C. The structure was confirmed by NMR.

To a mixture prepared by treatment of 8.6 g of the sodium salt of 3-methyl-2-oxobutanoic acid in 40 mL of dimethylformamide with 63 mmole of hydrogen chloride in 17 mL of dimethylformamide was added 10 g of ethyl 3-(4'-aminoindol-2'-yl)-2-nitropropionate in 45 mL of N,N-dimethylformamide. After the resulting mixture had been cooled in an ice water bath, a solution of 6 g of sodium cyanoborohydride in 45 mL of N,N-dimethylformamide was added over 15 min. After the addition was complete, the mixture was allowed to warm to room temperature over a period of 30 min, at which time 200 mL of water was added and the mixture acidified with 2N hydrochloric acid. This solution was extracted with ethyl acetate. The organic layers were combined, washed with brine, dried over sodium sulfate and concentrated in vacuo and at a temperature only slightly above ambient to afford a crude mixture containing N-[4-[3-(2'-nitro-2'-ethoxycarbonyl)ethyl]indolyl]valine.

To a cooled solution of this crude residue and 7.2 g of N-hydroxysuccinimide in 250 mL of acetonitrile was added 15.5 g of dicyclohexylcarbodiimide in 35 mL of acetonitrile. After 40 min, 2.7 mL of glacial acetic acid was added. After another 20 min the mixture was filtered and washed with ethyl acetate. The filtrates were washed with water and brine, dried over sodium sulfate and concentrated in vacuo to afford crude N-[4-[3-(2'-nitro-2'-ethoxycarbonyl)ethyl]indolyl]valine N-succinimidyl ester. After combination with another batch and purification by preparative liquid chromatography [silica; hexane/tetrahydrofuran (57:43)], 24.4 g (91% yield) of the ester was obtained as a gum. The structure was confirmed by NMR and mass spectral analysis.

To a solution of 3.75 g of N-[4-[3-(2'-nitro-2'-ethoxycarbonyl)ethyl]indolyl]valine N-succinimidyl ester in 200 mL of methanol was added 11.5 mL of a slurry of Raney nickel. This mixture was shaken on a Parr apparatus under about 50 psi of hydrogen for 35 min. The supernatant was removed by decantation and concentrated in vacuo. Several such crude mixtures were combined and purified by preparative liquid chromatography [silica; hexane/tetrahydrofuran (60:40)] to afford 3.23 g (31% yield) of N-desmethyl-9-deshydroxymethyl-9-ethoxycarbonylindolactam V, mp 195°–5° C. (dec), and 2.13 g (20.5% yield) of N-desmethyl-9-deshydroxymethyl-9-ethoxycarbonyl-epi-indolactam V, mp 206°–8° C. (dec). The structures of these compounds were confirmed by NMR and mass spectral analysis and by conversion to the known indolactam V and epi-indolactam V respectively.

To a solution of 204 mg of N-desmethyl-9-deshydroxymethyl-9-ethoxycarbonylindolactam V in 20 mL of acetonitrile containing 1.5 mL of water was added 400 μL of 37% aqueous formaldehyde. After 20 min, 182 mg of sodium cyanoborohydride was added. After the mixture had stirred at room temperature for 3 hours, phosphate buffer (pH 2) was added. The mixture was then concentrated in vacuo before rediluting with water and extracting with ethyl acetate. The organic layer was dried over sodium sulfate, filtered and concentrated in vacuo. The resulting solid was purified by preparative liquid chromatography [silica, hexane/tetrahydrofuran (60:40)] to afford 167 mg of 9-deshydroxymethyl-9-ethoxycarbonylindolactam V. The structure was confirmed by NMR and mass spectral analysis.

To a solution of 160 mg of 9-deshydroxymethyl-9-ethoxycarbonylindolactam V in 23 mL of methanol was added 2.3 mL of 2N sodium hydroxide. After one hour 2N hydrochloric acid was added until the mixture was acidic whereupon it was concentrated to a small volume in vacuo. The residue was then diluted with water and extracted with ethyl acetate. The organic layer was dried over sodium sulfate, filtered and concentrated in vacuo to afford 137 mg of 9-deshydroxymethyl-9-carboxyindolactam V as a white solid.

EXAMPLE 18

9-Deshydroxymethyl-9-carboxy-epi-indolactam V

A solution of 10 mg of N-desmethyl-9-deshydroxymethyl-9-ethoxycarbonyl-epi-indolactam V in 1 mL of acetonitrile containing 90 μL of water was added 20 μL of 37% aqueous formaldehyde. After 15 min 9 mg of sodium cyanoborohydride was added. After the mixture had stirred at room temperature for 3.5 hours, phosphate buffer (pH 2) was added and the mixture further diluted with water and extracted with ethyl acetate. The organic layer was dried over sodium sulfate, filtered and concentrated in vacuo to afford crude 9-deshydroxymethyl-9-ethoxycarbonyl-epi-indolactam V.

To a solution of 9-deshydroxymethyl-9-ethoxycarbonyl-epi-indolactam V in 2 mL of methanol was added 150 μL of 2N sodium hydroxide. After 50 min 2N hydrochloric acid was added until the mixture was acidic whereupon it was then diluted with water and extracted with ethyl acetate. The organic layer was dried over sodium sulfate, filtered and concentrated in vacuo to afford a residue of 9-deshydroxymethyl-9-carboxy-epi-indolactam V. The structure was confirmed by conversion to 9-deshydroxymethyl-9-methoxycarbonyl-epi-indolactam V by treatment with a solution of diazomethane in ether.

EXAMPLE 19

9-Deshydroxymethyl-9-carboxyindolactam V N-Succinimidyl Ester

To a solution of 137 mg of 9-deshydroxymethyl-9-carboxyindolactam V and 66 mg of N-hydroxysuccinimide in 7 mL of acetonitrile was added 119 mg of dicyclohexylcarbodiimide in 3 mL of acetonitrile. After about one hour the reaction mixture was filtered and then concentrated in vacuo. Purification by preparative liquid chromatography [silica, hexane/tetrahydrofuran (70:30)] afforded 136 mg of 9-deshydroxymethyl-9-carboxyindolactam V N-succinimidyl ester.

EXAMPLE 20

9-Deshydroxymethyl-9-[N-(2',3'-dihydroxy)propyl] carboxamidoindolactam V

To 11 mg of 3-amino-1,2-propandiol and 1 mg of 4-dimethylaminopyridine was added 25 mg of 9-deshydroxymethyl-9-carboxyindolactam V N-succinimidyl ester in 250 μL of methylene chloride and 0.4 mL tetrahydrofuran. After 5 h the mixture was concentrated in vacuo. After preparative liquid chromatography [silica, methylene chloride/isopropyl alcohol (85:15); followed by ODS silica; acetonitrile/water (33:67)], 10.5 mg of 9-deshydroxymethyl-9-[N-(2',3'-dihydroxy)propyl] carboxamidoindolactam V and 3.4 mg of 9-deshydroxymethyl-9-[N-(2',3'-dihydroxy)propyl] carboxamido-epi-indolactam V were obtained. The structures of these compounds were confirmed by mass spectral analysis.

EXAMPLE 21

9-Deshydroxymethyl-9-(2',3'-dihydroxy) propyloxycarbonyl indolactam V

To 30 mg of glycerol and 1 mg of 4-dimethylaminopyridine was added 25 mg of 9-deshydroxymethyl-9-carboxyindolactam V N-succinimidyl ester in 250 μL of methylene chloride and 0.4 mL tetrahydrofuran. After 20 h the mixture was concentrated in vacuo. After preparative liquid chromatography [silica; methylene chloride/isopropyl alcohol (91:9); followed by ODS silica; acetonitrile/water (36:64)] 13.3 mg of 9-deshydroxymethyl-9-(2',3'-dihydroxy) propyloxycarbonylindolactam V and 1.2 mg of 9-deshydroxymethyl-9-(2',3'-dihydroxy) propyloxycarbonyl-epi-indolactam V were obtained. The structures of these compounds were confirmed by mass spectral analysis.

EXAMPLE 22

9-Deshydroxymethyl-9-[N-(2'glucosyl)] carboxamidoindolactam V

To 29 mg of 2-glucosamine hydrochloride, 19 mg of triethylamine and 1 mg of 4-dimethylaminopyridine was added 25 mg of 9-deshydroxymethyl-9-carboxyindolactam V N-succinimidyl ester in 250 μL of methylene chloride and 0.4 mL tetrahydrofuran. After 7.5 h the mixture was concentrated in vacuo. After preparative liquid chromatography [silica, methylene chloride/methanol (80:20); followed by ODS silica; acetonitrile/water (1.2% triethylamine) (21:79)], 12.4 mg of 9-deshydroxymethyl-9-[N-(2'-glucosyl)] carboxamidoindolactam V and 2.4 mg of 9-deshydroxymethyl-9-[N-(2'-glucosyl)]carboxamido-epi-indolactam V were obtained.

EXAMPLE 23

In a similar manner the following compounds are prepared:
(i) 9-deshydroxymethyl-9-[N-(2'-carboxy)ethyl] carboxamidoindolactam V;
(ii) 9-deshydroxymethyl-9-[N-(2'-hydroxy)ethyl] carboxamidoindolactam V;
(iii) 9-deshydroxymethyl-9-(2'-hydroxy) ethylthiocarbonylindolactam V;
(iv) 9-deshydroxymethyl-9-(2'-hydroxy) ethoxycarbonylindolactam V;
(v) 9-deshydroxymethyl-9-[N-(2',3'-dihydroxy)propyl] carboxamido-7-octylindolactam V;
(vi) 9-deshydroxymethyl-9-[N-(2'-carboxy)ethyl] carboxamido-7-octylindolactam V;
(vii) 9-deshydroxymethyl-9-[N-(2'-hydroxy)ethyl] carboxamido-7 -octylindolactam V;
viii) 9-deshydroxymethyl-9-(2'-hydroxy)ethylthiocarbonyl-7-octylindolactam V;
(ix) 9-deshydroxymethyl-9-(2'-hydroxy)ethoxycarbonyl-7-octylindolactam V;
(x) 9-deshydroxymethyl-9-[N-(2',3'-dihydroxy)propyl] carboxamido-7-octyl-epi-indolactam V;
(xi) 9-deshydroxymethyl-9-[N-(2'-carboxy)ethyl] carboxamido-7-octyl-epi-indolactam V;
(xii) 9-deshydroxymethyl-9-[N-(2'-hydroxy)ethyl] carboxamido-7-octyl-epi-indolactam V;
(xiii) 9-deshydroxymethyl-9-(2'-hydroxy) ethylthiocarbonyl-7-octyl-epi-indolactam V;
(xiv) 9-deshydroxymethyl-9-(2'-hydroxy)ethoxycarbonyl-7-octyl-epi-indolactam V;
(xv) 9-deshydroxymethyl-9-[N-(2',3'-dihydroxy)propyl] carboxamido-6,7-tetramethyleneindolactam V;
(xvi) 9-deshydroxymethyl-9-[N-(2'-carboxy)ethyl] carboxamido-6,7-tetramethyleneindolactam V;
(xvii) 9-deshydroxymethyl-9-[N-(2'-hydroxy)ethyl] carboxamido-6,7-tetramethyleneindolactam V;
(xviii) 9-deshydroxymethyl-9-(2'-hydroxy) ethylthiocarbonyl-6,7-tetramethyleneindolactam V;
(xix) 9-deshydroxymethyl-9-(2'-hydroxy)ethoxycarbonyl-6,7-tetramethyleneindolactam V;
(xx) 9-deshydroxymethyl-9-[N-(2',3'-dihydroxy)propyl] carboxamido-7-octyl-12-des-iso-propyl-12-benzylindolactam V;
(xxi) 9-deshydroxymethyl-9-[N-(2'-carboxy)ethyl] carboxamido-7-octyl-12-des-iso-propyl-12-benzylindolactam V;
(xxii) 9-deshydroxymethyl-9-[N-(2'-hydroxy)ethyl] carboxamido-7-octyl-12-des-iso-propyl-12-benzylindolactam V;
(xxiii) 9-deshydroxymethyl-9-(2'-hydroxy) ethylthiocarbonyl-7-octyl-12-des-iso-propyl-12-benzylindolactam V; and
(xxiv) 9-deshydroxymethyl-9-(2'-hydroxy)ethoxycarbonyl-7-octyl-12-des-iso-propyl-12-benzylindolactam V.

EXAMPLE 24

14-O-[N-(S)-(1'-Naphthyl)ethyl]carbamoyl-7-octyl-(9S,12S)-indolactam V and 14-O-[N-(S)-(1'-Naphthyl)ethyl]carbamoyl-7-octyl-(9R,12R)-indolactam V To a solution of 139 mg of racemic 7-octylindolactam V [prepared as in K. Irie et al., *Agric. Biol. Chem.* 50: 2679

(1986)] in 15 mL of anhydrous tetrahydrofuran was added 56 mg of dibutyltin dilaurate and 48 mg of 4-dimethylaminopyridine in 3 mL of tetrahydrofuran. To this solution was added 445 mg of(S)-1-(1-napthyl)ethyl isocyanate in two portions over a two day period. The mixture was then concentrated in vacuo and the residue partitioned between water and ethyl acetate. The organic layer was dried over sodium sulfate and concentrated in vacuo. After preparative liquid chromatography [silica, hexane/tetrahydrofuran (75:25)], 200 mg of a mixture of diastereomers was obtained. Repetitive chromatography of this mixture [wet silica; hexane/wet ethyl acetate (65:35)] afforded 87 mg of pure 14-O-[N-(S)-(1'-naphthyl)ethyl] carbamoyl-7-octyl-(9S,12S)-indolactam V and 96 mg of pure 14-O-[N-(S)-(1'-naphthyl)ethyl]carbamoyl-7-octyl-(9R,12R)-indolactam V. The structures of these compounds were confirmed by reduction to the known (–)-7-octylindolactam V and (+)-7-octylindolactam V respectively.

EXAMPLE 25

14-O-[N-(R)-(1'-Naphthyl)ethyl]carbamoyl-(9S,12S)-indolactam V and 14-O-[N-(R)-(1'-Naphthyl)ethyl]carbamoyl-(9R,12R)-indolactam V To a solution of 2.3 g of racemic indolactam V in 80 mL of anhydrous tetrahydrofuran with 569 mg of dibutyltin dilaurate and 560 mg of 4-dimethylaminopyridine was added 2.4 g of(R)-1-(1-napthyl)ethylisocyanate. After stirring at room temperature for 24 h, the mixture was concentrated in vacuo and the residue partitioned between water and ethyl acetate. The organic layer was dried over sodium sulfate and concentrated in vacuo. After preparative liquid chromatography [silica; hexane/tetrahydrofuran (55:45)], 3.65 g of a mixture of diastereomers was obtained. Repetitive chromatography of this mixture [wet silica; hexane/wet ethyl acetate (65:35)] afforded 1.92 g of 14-O-[N-(R)-(1'-naphthyl)ethyl]carbamoyl-(9R,12R)-indolactam V and 1.77 g of 14-O-[N-(R)-(1'-naphthyl)ethyl]carbamoyl-(9S,12S)-indolactam V. The structures of these compounds were confirmed by NMR, by comparison with a sample of 14-O-[N-(R)-(1'-naphthyl)ethyl]carbamoyl-(9S,12S)-indolactam V prepared from authentic (–)-indolactam V, and by reduction to the known (+)-indolactam V and (–)-indolactam V respectively.

EXAMPLE 26

14-O-(N-Methyl)carbamoyl-7-octyl-(9S,12S)-indolactam V

A solution of 3 mg of dibutyltin dilaurate and 2 mg of 4-dimethylaminopyridine in 0.5 mL of anhydrous tetrahydrofuran was added to 5 mg of (–)-7-octylindolactam V. Then 5 µL of methylisocyanate was added. After four hours at room temperature the mixture was concentrated under nitrogen and purified by preparative liquid chromatography [silica; hexane/tetrahydrofuran (70:30)] to afford 5 mg of 14-O-(N-methyl)carbamoyl-7-octyl-(9S,12S)-indolactam V.

EXAMPLE 27 rac-14-O-(N-Methyl)carbamoylindolactam V

To a solution of 105 mg of racemic indolactam V, 41 mg of 4-dimethylaminopyridine, and 57 mg of dibutyltin dilaurate in 18 mL of anhydrous tetrahydrofuran was added 150 µL of methylisocyanate in two portions over 1.5 h. One hour after the final addition the mixture was concentrated in vacuo and the residue purified by recrystallization from tetrahydrofuran with hexane to afford 100 mg of rac-14-O-(N-methyl)carbamoylindolactam V, mp 184°–185° C.

EXAMPLE 28

In a similar manner the following compounds are prepared:
(i) 14-O-(N-ethyl)carbamoylindolactam V;
(ii) 14-O-(N-methyl)thiocarbamoylindolactam V;
(iii) 14-O-(N-benzyl)carbamoylindolactam V;
(iv) 14-O-(N-ethyl)carbamoyl-7-octylindolactam V;
(v) 14-O-(N-methyl)thiocarbamoyl-7-octylindolactam V;
(vi) 14-O-(N-benzyl)carbamoyl-7-octylindolactam V;
(vii) 14-O-(N-methyl)carbamoyl-7-octyl-epi-indolactam V;
(viii) 14-O-(N-ethyl)carbamoyl-7-octyl-epi-indolactam V;
(ix) 14-O-(N-methyl)thiocarbamoyl-7-octyl-epi-indolactam V;
(x) 14-O-(N-benzyl)carbamoyl-7-octyl-epi-indolactam V;
(xi) 14-O-(N-methyl)carbamoyl-6,7-tetramethyleneindolactam V;
(xii) 14-O-(N-ethyl)carbamoyl-6,7-tetramethyleneindolactam V;
(xiii) 14-O-(N-methyl)thiocarbamoyl-6,7-tetramethyleneindolactam V;
(xiv) 14-O-(N-benzyl)carbamoyl-6,7-tetramethyleneindolactam V;
(xv) 14-O-(N-methyl)carbamoyl-7-octyl-12-des-iso-propyl-12-benzylindolactam V;
(xvi) 14-O-(N-ethyl)carbamoyl-7-octyl-12-des-iso-propyl-12-benzylindolactam V;
(xvii) 14-O-(N-methyl)thiocarbamoyl-7-octyl-12-des-iso-propyl-12-benzylindolactam V;
(xviii) 14-O-(N-benzyl)carbamoyl-7-octyl-12-des-iso-propyl-12-benzylindolactam V;
(xix) 14-O-(N-ethyl)carbamoylteleocidin B;
(xx) 14-O-(N-methyl)thiocarbamoylteleocidin B; and
(xxi) 14-O-(N-benzyl)carbamoylteleocidin B.

EXAMPLE 29 rac-14-O-(N-Methyl)carbamoyl-1-N-diphenylphosphorylindolactam V

To 12 mg of rac-14-O-(N-methyl)carbamoylindolactam V in 500 µL of anhydrous tetrahydrofuran was added approximately 2 mg of sodium hydride (50% dispersion in oil) followed by 30 µL of diphenylchlorophosphate in two portions. After 2–3 hours, thin layer chromatographic analysis [silica, methylene chloride/methanol (95:5)] showed that the starting rac-14-O-(N-methyl)carbamoylindolactam V ($R_f$=0.36) had been converted to rac-14-O-(N-methyl)carbamoyl-1-N-diphenylphosphorylindolactam V with $R_f$=0.43.

EXAMPLE 30 rac-14-O-(N-Methyl)carbamoyl-1-N-(2'-triphenylphosphonium)ethylindolactam V, Methanesulfonate salt To 16 mg of rac-14-O-(N-methyl)carbamoylindolactam V in 0.75 mL of N,N-dimethylformamide in an ice-water bath was added 8 mg of sodium hydride (60% dispersion in oil). After about 10 min this solution was added to 20 mg of 2-methanesulfonyloxyethyltriphenylphosphonium bromide (prepared from 2-hydroxyethyltriphenylphosphonium bromide). After 1 h this mixture was concentrated in vacuo.

The residue was partitioned between ethyl acetate and phosphate buffer (pH 2). The organic layer was dried over sodium sulfate and concentrated in vacuo. The crude mixture was taken up in methanol, treated with a small amount of methanesulfonic acid in methanol and reconcentrated. Thin layer chromatographic analysis [silica; methylene chloride/methanol (90:10)] showed that the starting rac-14-O-(N-methyl)carbamoylindolactam V ($R_f$=0.63) had been converted to rac-14-O-(N-methyl)carbamoyl-1-N-(2'-triphenylphosphonium)ethylindolactam V, methanesulfonate salt, with $R_f$=0.57.

EXAMPLE 31

In a similar manner the following compounds are prepared;
(i) 14-O-(N-methyl)thiocarbamoyl-1-N-(2'-triphenylphosphonium)ethylindolactam V, methanesulfonate salt;
(ii) 14-O-(N-benzyl)carbamoyl-1-N-(2'-triphenylphosphonium)ethylindolactam V, methanesulfonate salt;
(iii) 14-O-(N-methyl)thiocarbamoyl-1-N-(2'-triphenylphosphonium)ethyl-epi-indolactam V, methanesulfonate salt;
(iv) 14-O-(N-benzyl)carbamoyl-1-N-(2'-triphenylphosphonium)ethyl-epi-indolactam V, methanesulfonate salt;
(v) 14-O-(N-methyl)carbamoyl-1-N-(2'-triphenylphosphonium)ethyl-epi-indolactam V, methanesulfonate salt;
(vi) 14-O-(N-methyl)carbamoyl-1-N-(2'-triphenylphosphonium)ethyl-12-des-iso-propyl-12-benzylindolactam V, methanesulfonate salt;
(vii) 14-O-(N-methyl)thiocarbamoyl-1-N-(2'-triphenylphosphonium)ethyl-12-des-iso-propyl-12-benzylindolactam V, methanesulfonate salt; and
(viii) 14-O-(N-benzyl)carbamoyl-1-N-(2'-triphenylphosphonium)ethyl-12-des-iso-propyl-12-benzylindolactam V, methanesulfonate salt.

EXAMPLE 32 rac-14-O-(N-Methyl)carbamoyl-1-N-trimethylsilylmethylindolactam V

To 16 mg of rac-14-O-(N-methyl)carbamoylindolactam V in 0.75 mL of N,N-dimethylformamide in an ice-water bath was added 8 mg of sodium hydride (60% dispersion in oil). After about 10 min, 20 µL of bromomethyltrimethylsilane was added. After 1 h this mixture was concentrated in vacuo and the residue partitioned between ethyl acetate and phosphate buffer (pH 8). The organic layer was dried over sodium sulfate and concentrated in vacuo. Thin layer chromatographic analysis [silica, methylene chloride/methanol (95:5)] showed that the starting rac-14-O-(N-methyl)carbamoylindolactam V ($R_f$=0.36) had been converted to rac-14-O-(N-methyl)carbamoyl-1-N-trimethylsilylmethylindolactam V with $R_f$=0.59.

EXAMPLE 33

In a similar manner the following compounds are prepared:
(i) 14-O-(N-methyl)thiocarbamoyl-1-N-trimethylsilylmethylindolactam V;
(ii) 14-O-(N-benzyl)carbamoyl-1-N-trimethylsilylmethylindolactam V;
(iii) 14-O-(N-methyl)carbamoyl-1-N-trimethylsilylmethyl-epi-indolactam V;
(iv) 14-O-(N-methyl)thiocarbamoyl-1-N-trimethylsilylmethyl-epi-indolactam V;
(v) 14-O-(N-benzyl)carbamoyl-1-N-trimethylsilylmethyl-epi-indolactam V;
(vi) 14-O-(N-methyl)carbamoyl-1-N-trimethylsilylmethyl-12-des-iso-propyl-12-benzylindolactam V;
(vii) 14-O-(N-methyl)thiocarbamoyl-1-N-trimethylsilylmethyl-12-des-iso-propyl-12-benzylindolactam V; and
(viii) 14-O-(N-benzyl)carbamoyl-1-N-trimethylsilylmethyl-12-des-iso-propyl-12-benzylindolactam V.

EXAMPLE 34

14-O-[(Diisopropylamino)methoxy]phosphinyl-7-octyl-(9S,12S)-indolactam V

To 5 mg of (−)-7-octylindolactam V in 180 µL of anhydrous methylene chloride was added 15 µL of diisopropylethylamine followed by 7 µL of N,N-diisopropylmethylphosphoramidic chloride. After 0.5 h, thin layer chromatographic analysis [silica, hexane/ethyl acetate (45:55)] showed that the starting (−)-7-octylindolactam V ($R_f$=0.17) had been converted to 14-O-[(diisopropylamino) methoxy]phosphinyl-7-octyl-(9S,12S)-indolactam V with $R_f$=0.72.

EXAMPLE 35

14-O-(Dimethyl)thiophosphoryl-7-octyl-(9S,12S)-indolactam V

To 5 mg of (−)-7-octylindolactam V in 200 µL of anhydrous methylene chloride and containing 5 µL of pyridine was added 14 µL of dimethyl chlorothiophosphate and approximately 10 mg of 4-dimethylaminopyridine. After 2 h, thin layer chromatographic analysis [silica; methylene chloride/methanol (95:5)] showed that the starting (−)-7-octylindolactam V ($R_f$=0.32) had been converted to 14-O-(dimethyl)thiophosphoryl-7-octyl-(9S,12S)-indolactam V with $R_f$=0.36.

EXAMPLE 36

In a similar manner the following compounds are prepared:
(i) 14-O-(dimethyl)phosphorylindolactam V;
(ii) 14-O-(tetramethyl)phosphorodiamidylindolactam V;
(iii) 14-O-(diethyl)phosphonylindolactam V;
(iv) 14-O-[bis(2',2',2'-trichloroethyl)]phosphorylindolactam V;
(v) 14-O-(dimethyl)thiophosphorylindolactam V;
(vi) 14-O-(dimethyl)phosphoryl-7-octylindolactam V;
(vii) 14-O-(tetramethyl)phosphorodiamidyl-7-octylindolactam V;
(viii) 14-O-(diethyl)phosphonyl-7-octylindolactam V;
(ix) 14-O-[bis(2',2',2'-trichloroethyl)]phosphoryl-7-octylindolactam V;
(x) 14-O-(dimethyl)thiophosphoryl-7-octyl-epi-indolactam V;
(xi) 14-O-(dimethyl)phosphoryl-7-octyl-epi-indolactam V;
(xii) 14-O-(tetramethyl)phosphorodiamidyl-7-octyl-epi-indolactam V;
(xiii) 14-O-(diethyl)phosphonyl-7-octyl-epi-indolactam V;
(xiv) 14-O-[bis(2',2',2'-trichloroethyl)]phosphoryl-7-octyl-epi-indolactam V;
(xv) 14-O-(dimethyl)phosphoryl-6,7-tetramethyleneindolactam V;
(xvi) 14-O-(tetramethyl)phosphorodiamidyl-6,7-tetramethyleneindolactam V;

(xvii) 14-O-(diethyl)phosphonyl-6,7-tetramethyleneindolactam V;
(xviii) 14-O-[bis(2',2',2'-trichloroethyl)]phosphoryl-6,7-tetramethyleneindolactam V;
(xix) 14-O-(dimethyl)thiophosphoryl-6,7-tetramethyleneindolactam V;
(xx) 14-O-(dimethyl)thiophosphoryl-7-octyl-12-des-iso-propyl-12-benzylindolactam V;
(xxi) 14-O-(dimethyl)phosphoryl-7-octyl-12-des-iso-propyl-12-benzyl-indolactam V;
(xxii) 14-O-(tetramethyl)phosphorodiamidyl-7-octylindolactam V;
(xxiii) 14-O-(diethyl)phosphonyl-7-octyl-12-des-iso-propyl-12-benzylindolactam V;
(xxiv) 14-O-[bis(2',2',2'-trichloroethyl)]phosphoryl-7-octyl-12-des-iso-propyl-12-benzylindolactam V;
(xxv) 14-O-(dimethyl)phosphorylteleocidin B;
(xxvi) 14-O-(tetramethyl)phosphorodiamidylteleocidin B;
(xvii) 14-O-(diethyl)phosphonylteleocidin B;
(xxviii) 14-O-[bis(2'2',2'-trichloroethyl)]phosphorylteleocidin B; and
(xxix) 14-O-(dimethyl)thiophosphorylteleocidin B.

EXAMPLE 37

14-Deoxy-14-(3'-hydroxy)propylthio-7-octyl-(9S,12S)-indolactam V

To a solution of 6 mg of 3-mercapto-1-propanol in 150 μL of methanol containing 1.3 mg of sodium methoxide was added approximately 6 mg of 14-O-methanesulfonyl-7-octyl-(9S,12S)-indolactam V (prepared from (-)-7-octylindolactam V) in 300 μL of acetonitrile. After 20 h this mixture was diluted with ethyl acetate and washed twice with phosphate buffers (pH 2 and pH 8). After drying over sodium sulfate, the organic layer was concentrated under a nitrogen stream. Thin layer chromatographic analysis [silica; methylene chloride/methanol (96:4)] showed that the starting 14-O-methanesulfonyl-7-octyl-(9S,12S)-indolactam V ($R_f$=0.67) had been converted to 14-deoxy-14-(3'-hydroxy)propylthio-7-octyl-(9S,12S)-indolactam V with $R_f$=0.22.

EXAMPLE 38

In a similar manner the following compounds are prepared:
(i) 14-deoxy-14-butylthio-7-octylindolactam V;
(ii) 14-deoxy-14-(2'-hydroxy-1'-methyl)ethylthio-7-octylindolactam V;
(iii) 14-deoxy-14-(2'-carboxy)ethylthio-7-octylindolactam V;
(iv) 14-deoxy-14-(2'-amino)ethylthio-7-octylindolactam V;
(v) 14-deoxy-14-(3'-hydroxymethyl)phenylthio-7-octylindolactam V;
(vi) 14-deoxy-14-propylthio-7-octyl-epi-indolactam V;
(vii) 14-deoxy-14-(2'-hydroxy-'-methyl)ethylthio-7-octyl-epi-indolactam V;
(viii) 14-deoxy-14-(2'-carboxy)ethylthio-7-octyl-epi-indolactam V;
(ix) 14-deoxy-14-(2'-amino)ethylthio-7-octyl-epi-indolactam V;
(x) 14-deoxy-14-(3'-hydroxymethyl)phenylthio-7-octyl-epi-indolactam V;
(xi) 14-deoxy-14-(2'-hydroxy)ethylthio-7-octyl-epi-indolactam V;
(xii) 14-deoxy-14-propylthio-6,7-tetramethyleneindolactam V;
(xiii) 14-deoxy-14-(2'-hydroxy-1'-methyl)ethylthio-6,7-tetramethyleneindolactam V;
(xiv) 14-deoxy-14-(2'-carboxy)ethylthio-6,7-tetramethyleneindolactam V;
(xv) 14-deoxy-14-(2'-amino)ethylthio-6,7-tetramethyleneindolactam V;
(xvi) 14-deoxy-14-(3'-hydroxymethyl)phenylthio-6,7-tetramethyleneindolactam V;
(xvii) 14-deoxy-14-(2'-hydroxy)ethylthio-6,7-tetramethyleneindolactam V;
(xviii) 14-deoxy-14-propylthio-7-octyl-12-des-iso-propyl-12-benzylindolactam V;
(xix) 14-deoxy-14-(2'-hydroxy-1'-methyl)ethylthio-7-octyl-12-des-iso-propyl-12-benzylindolactam V;
(xx) 14-deoxy-14-(2'-carboxy)ethylthio-7-octyl-12-des-iso-propyl-12-benzylindolactam V;
(xxi) 14-deoxy-14-(2'-amino)ethylthio-7-octyl-12-des-iso-propyl-12-benzylindolactam V;
(xxii) 14-deoxy-14-(3'-hydroxymethyl)phenylthio-7-octyl-12-des-iso-propyl-12-benzylindolactam V;
(xxiii) 14-deoxy-14-(2'-hydroxy)ethylthio-7-octyl-12-des-iso-propyl-12-benzylindolactam V;
(xxiv) 14-deoxy-14-propylthioteleocidin B;
(xxv) 14-deoxy-14-(2'-hydroxy-1'-methyl)ethylthioteleocidin B;
(xxvi) 14-deoxy-14-(2'-carboxy)ethylthioteleocidin B;
(xxvii) 14-deoxy-14-(2'-amino)ethylthioteleocidin B;
(xxviii) 14-deoxy-14-(3'-hydroxymethyl)phenylthioteleocidin B; and
(xxix) 14-deoxy-14-(2'-hydroxy)ethylthioteleocidin B.

EXAMPLE 39

14-Deoxy-14-(N-methanesulfonyl)amino-7-octyl-(9S,12S)-indolactam V

To a solution of 4 mg of methanesulfonamide in 150 μL of methanol containing 1.3 mg of sodium methoxide was added approximately 6 mg of 14-O-methanesulfonyl-7-octyl-(9S,12S)-indolactam V (prepared from (-)-7-octylindolactam V) in 300 μL of acetonitrile. After 26 h this mixture was diluted with ethyl acetate and washed twice with phosphate buffers (pH 2 and pH 8). After drying over sodium sulfate, the organic layer was concentrated under a nitrogen stream. Thin layer chromatographic analysis [silica, hexane/ethyl acetate (45:55)] showed that the starting 14-O-methanesulfonyl-7-octyl-(9S,12S)-indolactam V ($R_f$=0.47) had been converted to 14-deoxy-14-N-(methanesulfonyl)amino-7-octyl-(9S,12S)-indolactam V with $R_f$=0.38.

EXAMPLE 40

14-Deoxy-14-trimethylphosphonium-7-octyl-(9S,12S)-indolactam V, Methanesulfonate salt To a solution of approximately 6 mg of 14-O-methanesulfonyl-7-octyl-(9S,12S)-indolactam V (prepared from (-)-7-octylindolactam V) in 300 μL of acetonitrile was added 30 μL of 1M trimethylphosphine in toluene. After 26 h this mixture was concentrated under a nitrogen stream. Thin layer chromatographic analysis [silica; methylene chloride/methanol (95:5)] showed that the starting 14-O-methanesulfonyl-7-octyl-(9S,12S)-indolactam V ($R_f$=0.63) had been converted to 14-deoxy-14-trimethylphosphonium-7-octyl-(9S,12S)-indolactam V, methanesulfonate salt, with $R_f$=0.07.

EXAMPLE 41

14-Deoxy-14-triphenylphosphonium-7-octyl-(9S,12S)-indolactam V, Iodide salt

To a solution of approximately 5 mg of 14-deoxy-14-iodo-7-octyl-(9S,12S)-indolactam V (prepared from 14-O- methanesulfonyl-7-octyl-(9S,12S)-indolactam V) in 1 mL of tetrahydrofuran was added 6 mg of triphenyphosphine. After 2.5 h this mixture was concentrated under a nitrogen stream. Thin layer chromatographic analysis [silica, hexane/ethyl acetate (45:55)] showed that the starting 14-deoxy-14-iodo-7-octyl-(9S,12S)-indolactam V ($R_f$=0.37) had been converted to 14-deoxy-14-triphenylphosphonium-7-octyl-(9S,12S)-indolactam V, iodide salt, with $R_f$=0.88.

EXAMPLE 42

In a similar manner the following compounds are prepared:
(i) 14-deoxy-14-tributylphosphonium-7-octylindolactam V, iodide salt;
(ii) 14-deoxy-14-triethylphosphonium-7-octylindolactam V, iodide salt;
(iii) 14-deoxy-14-methyldiphenylphosphonium-7-octylindolactam V, iodide salt;
(iv) 14-deoxy-14-trimethylphosphonium-7-octyl-epi-indolactam V, iodide salt;
(v) 14-deoxy-14-tributylphosphonium-7-octyl-epi-indolactam V, iodide salt;
(vi) 14-deoxy-14-triethylphosphonium-7-octyl-epi-indolactam V, iodide salt;
(vii) 14-deoxy-14-methyldiphenylphosphonium-7-octyl-epi-indolactam V, iodide salt;
(viii) 14-deoxy-14-trimethylphosphonium-6,7-tetramethyleneindolactam V, iodide salt;
(ix) 14-deoxy-14-tributylphosphonium-6,7-tetramethyleneindolactam V, iodide salt;
(x) 14-deoxy-14-triethylphosphonium-6,7-tetramethyleneindolactam V, iodide salt;
(xi) 14-deoxy-14-methyldiphenylphosphonium-6,7-tetramethyleneindolactam V, iodide salt;
(xii) 14-deoxy-14-tributylphosphonium-7-octyl-12-des-iso-propyl-12-benzylindolactam V, iodide salt;
(xiii) 14-deoxy-14-triethylphosphonium-7-octyl-12-des-iso-propyl-12-benzylindolactam V, iodide salt;
(xiv) 14-deoxy-14-methyldiphenylphosphonium-7-octyl-12-des-iso-propyl-12-benzylindolactam V, iodide salt;
(xv) 14-deoxy-14-trimethylphosphonium-7-octyl-12-des-iso-propyl-12-benzylindolactam V, iodide salt;
(xvi) 14-deoxy-14-tributylphosphoniumteleocidin B, iodide salt;
(xvii) 14-deoxy-14-triethylphosphoniumteleocidin B, iodide salt;
(xviii) 14-deoxy-14-methyldiphenylphosphoniumteleocidin B, iodide salt; and
(xix) 14-deoxy-14-trimethylphosphoniumteleocidin B, iodide salt.

EXAMPLE 43

14-Deoxy-14-trimethylsilyl-7-octyl-(9S,12S)-indolactam V

To a mixture of 10 mg of powdered zinc and 10 μL of trimethylchlorosilane in 300 μL of anhydrous tetrahydrofuran was added approximately 5 mg of 14-deoxy-14-iodo-7-octyl-(9S,12S)-indolactam V (prepared from 14-O-methanesulfonyl-7-octyl-(9S,12S)-indolactam V) in 500 μL of tetrahydrofuran. After 2.5 h, thin layer chromatographic analysis [silica, hexane/ethyl acetate (45:55)] showed that the starting 14-deoxy-14-iodo-7-octyl-(9S,12S)-indolactam V ($R_f$=0.37) had been largely converted to 14-deoxy-14-trimethylsilyl-7-octyl-(9S,12S)-indolactam V with $R_f$=0.49.

EXAMPLE 44

In a similar manner the following compounds are prepared:
(i) 14-deoxy-14-trimethylsilyl-7-octyl-epi-indolactam V;
(ii) 14-deoxy-14-trimethylsilyl-7-octyl-12-des-iso-propyl-12-benzylindolactam V;
(iii) 14-deoxy-14-trimethylsilyl-6,7-tetramethyleneindolactam V; and (iv) 14-deoxy-14-trimethylsilylteleocidin B.

EXAMPLE 45

20-Deoxy-20-hydroximinophorbol 12,13-Bis[(2',4'-difluorophenyl)acetate] and 20-Deoxy-3-deoxo-3,20-bis(hydroximino)phorbol 12,13-Bis[(2',4'-difluorophenyl)acetate]

To a solution of 250 mg of 20-deoxy-20-oxophorbol 12,13-bis[(2',4'-difluorophenyl)acetate] [G. Kreibich and E. Hecker, Z. Krebsforsch., 74: 448–456 (1970)] in 6 mL of methanol was added 4 mL of a solution prepared by adding 40 mL of 0.375M sodium methoxide in methanol to 2.5 g of hydroxylamine hydrochloride. After 2.5 h the mixture was concentrated in vacuo and the residue was partitioned between water and ethyl acetate. The organic layer was filtered through a funnel containing layers of sodium chloride, sodium sulfate and silica gel (N/N/S) and concentrated in vacuo. After purification of the residue by preparative liquid chromatography [silica; methylene chloride/ethyl acetate (85:15)], 211 mg of 20-deoxy-20-hydroximinophorbol 12,13-bis[(2',4'-difluorophenyl)acetate] and 27 mg of 20-deoxy-3-deoxo-3,20-bis(hydroximino)phorbol 12,13-bis[(2',4'-difluorophenyl)acetate] were obtained. The structures were confirmed by NMR and mass spectral analysis.

EXAMPLE 46

In a similar manner the following compounds are prepared:
(i) 20-deoxy-20-hydroximinophorbol 12,13-didecanoate;
(ii) 20-deoxy-20-hydroximinophorbol 12,13-dibutyrate;
(iii) 12,20-dideoxy-20-hydroximinophorbol 13-decanoate;
(iv) 12,20-dideoxy-20-hydroximinophorbol 13-(2',4'-difluorophenyl)acetate;
(v) 20-deoxy-20-hydroximinophorbol 12-myristate 13-acetate; and
(vi) 20-deoxy-3-deoxo-3,20-bis(hydroximino)phorbol 12-myristate 13-acetate.

EXAMPLE 47

20-Deoxy-20-methoximinophorbol 12,13-Bis[(2',4'-difluorophenyl)acetate] and 20-Deoxy-3-deoxo-3,20-bis(methoximino)phorbol 12,13-Bis[(2',4'-difluorophenyl)acetate]

To a solution of 100 mg of 20-deoxy-20-oxophorbol 12,13-Bis[(2',4'-difluorophenyl)acetate] in 1 mL of pyridine was added 35 mg of methoxylamine hydrochloride. After 2.5 h the mixture was partitioned between ethyl acetate and phosphate buffer (pH 2). The organic layer was washed with phosphate buffer (pH 8), filtered through N/N/S and concentrated in vacuo. After preparative liquid chromatography [silica; hexane/ethyl acetate (80:20)] of the residue, 96 mg of 20-deoxy-20-methoximinophorbol 12,13-bis[(2',4'-difluorophenyl)acetate] and 4 mg of 20-deoxy-3-deoxo-3,20-bis(methoximino)phorbol 12,13-bis[(2',4'-difluorophenyl)acetate] were obtained. The structures were confirmed by NMR and high resolution mass spectral analysis.

EXAMPLE 48

In a similar manner the following compounds are prepared:
(i) 20-deoxy-20-hydroximinophorbol 12-(3'-phenoxy) benzoate 13-butyrate;
(ii) 20-deoxy-20-hydroximinophorbol 12-(3',5'-difluorophenyl)acetate 13-(3',4'-difluorobenzoate);
(iii) 20-deoxy-20-hydroximinophorbol 12-(3',5'-difluorocinnamate) 13-[3'-(2",4"-difluorophenyl) propionate];
(iv) 20-deoxy-20-hydroximinophorbol 12,13-bis[(2',4'-dichlorophenyl)acetate];
(v) 20-deoxy-20-methoximinophorbol 12,13-didecanoate;
(vi) 12,20-dideoxy-20-methoximinophorbol 13-decanoate;
(vii) 20-deoxy-20-t-butoximinophorbol 12-myristate 13-acetate;
(viii) 20-deoxy-20-carboxymethoximinophorbol 12,13-bis[(2',4'-difluorophenyl)acetate];
(ix) 20-deoxy-20-(4-nitrobenzoximino)phorbol 12,13-bis[(2',4'-difluorophenyl)acetate];
(x) 20-deoxy-20-alloximinophorbol 12-myristate 13-acetate; and
(xi) 20-deoxy-20-oxophorbol 12,13-bis[(2',4'-difluorophenyl)acetate] 20-semicarbazone.

EXAMPLE 49

6-Deshydroxymethyl-6-cyanophorbol 12,13-Bis[(2',4'-difluorophenyl)acetate]

A solution of 100 mg of 20-deoxy-20-hydroximinophorbol 12,13-bis[(2',4'-difluorophenyl) acetate] in 0.5 mL pyridine was added to a mixture of 9 mg cupric sulfate and 35 mg of triethylamine in 1.5 mL of methylene chloride. After 1 h 47 mg of dicyclohexylcarbodiimide was added to the green solution. After 3 h at room temperature the reaction mixture was heated at 40°–45° C. for 3 h. During this period another 50 mg of dicyclohexylcarbodiimide was added. After cooling the mixture to room temperature, 0.5 mL of formic acid was added followed by partitioning between ethyl acetate and phosphate buffer (pH 2). The organic layer was washed with phosphate buffer (pH 8), filtered through N/N/S and concentrated in vacuo. Preparative liquid chromatography [silica, hexane/ethyl acetate (75:25)] afforded 43 mg of 6-deshydroxymethyl-6-cyanophorbol 12,13-bis[(2',4'-difluorophenyl)acetate]. The structure was confirmed by NMR and high resolution mass spectral analysis.

EXAMPLE 50

In a similar manner the following compounds are prepared:
(i) 6-deshydroxymethyl-6-cyanophorbol 12-(3',5'-difluorophenyl)acetate 13-(3',4'-difluorobenzoate);
(ii) 6-deshydroxymethyl-6-cyanophorbol 12,13-didecanoate; and
(iii) 12-deoxy-6-deshydroxymethyl-6-cyanophorbol 13-decanoate.

EXAMPLE 51

6-Deshydroxymethyl-6-carboxyphorbol 12,13-Bis[(2',4'-difluorophenyl)acetate]

To a solution of 1.51 g of 20-deoxy-2-oxo-phorbol 12,13-bis[(2',4'-difluorophenyl)acetate] in 55 mL of methylene chloride, 150 mL of t-butyl alcohol and 10 mL of 2-methyl-2-butene was added 18.75 mL of a solution prepared by dissolving 1.99 g of sodium chlorite and 2 g of potassium dihydrogen phosphate in 20 mL of deionized water. After 1.25 h about 10 mL of 20% aq. sodium thiosulfate was added and the mixture was partially concentrated in vacuo. The residue was partitioned between ethyl acetate and phosphate buffer (pH 8). The organic layer was washed sequentially with pH 2 and pH 8 phosphate buffers and dried over sodium sulfate. After concentration in vacuo, 1.53 g of 6-deshydroxymethyl-6-carboxyphorbol 12,13-bis[(2',4'-difluorophenyl)acetate] was obtained. An analytical sample was obtained by preparative liquid chromatography [silica; methylene chloride/methanol (95:5)] and the structure confirmed by NMR and mass spectral analysis.

EXAMPLE 52

In a similar manner the following compounds are prepared:
(i) 6-deshydroxymethyl-6-carboxyphorbol 12,13-dibutyrate;
(ii) 6-deshydroxymethyl-6-carboxyphorbol 12,13-didecanoate;
(iii) 6-deshydroxymethyl-6-carboxy-3-deoxo-3-benzoyloxyphorbol 12-butyrate 13-(2',4'-difluorobenzoate);
(iv) 6-deshydroxymethyl-6-carboxy-3-deoxo-3-(2',4'-difluorophenylacetoxy)phorbol 12-(2',4'-difluorophenyl)acetate 13-(4'-biphenyl)acetate;
(v) 12-deoxy-6-deshydroxymethyl-6-carboxyphorbol 13-decanoate;
(vi) 12-deoxy-6-deshydroxymethyl-6-carboxyphorbol 13-(2',4'-difluorophenyl)acetate;
(vii) 6-deshydroxymethyl-6-carboxyphorbol 12-myristate 13-acetate;
(viii) 6-deshydroxymethyl-6-carboxyphorbol 12-(3'-phenoxy)benzoate 13-butyrate;
(ix) 6-deshydroxymethyl-6-carboxyphorbol 12-(3',5'-difluorophenyl)acetate 13-(3',4'-difluorobenzoate);
(x) 6-deshydroxymethyl-6-carboxyphorbol 12-(3',5'-difluorocinnamate) 13-[3'-(2",4"-difluorophenyl) propionate];
(xi) 6-deshydroxymethyl-6-carboxyphorbol 12,13-bis[(2',4'-dichlorophenyl)acetate];
(xii) 6-deshydroxymethyl-6-carboxyresiniferonol 9,13,14-orthophenylacetate,
(xiii) 5-O-trimethylsilyl-6-deshydroxymethyl-6-carboxyingenol 3,4-acetonide;
(xiv) 6-deshydroxymethyl-6-carboxyphorbol 12-octyldimethylsilylacetate 13-(2',4'-difluorophenyl) acetate; and
(xv) 6-deshydroxymethyl-6-carboxy-12-deoxyphorbol 13-(2',4'-difluorophenyl)acetate.

EXAMPLE 53

6-Deshydroxymethyl-6-methoxycarbonylphorbol 12,13-Bis[(2',4'-difluorophenyl)acetate]

To a solution of approximately 100 mg of 6-deshydroxymethyl-6-carboxyphorbol 12,13-bis[(2',4'-difluorophenyl)acetate] in 10 mL of tetrahydrofuran was added an excess of diazomethane in ether. After about one hour the solution was concentrated in vacuo and the residue subjected to preparative liquid chromatography [silica; hexane/ethyl acetate (70:30)] to afford 96 mg of 6-deshydroxymethyl-6-methoxycarbonylphorbol 12,13-bis[(2',4'-difluorophenyl)acetate]. The structure was confirmed by NMR and mass spectral analysis.

EXAMPLE 54

In a similar manner the following compounds are prepared:
(i) 6-deshydroxymethyl-6-methoxycarbonylphorbol 12,13-didecanoate; and
(ii) 12-deoxy-6-deshydroxymethyl-6-methoxycarbonylphorbol 13-decanoate.

EXAMPLE 55

6-Deshydroxymethyl-6-(N-succinimidyloxy) carbonylphorbol 12,13-Bis[ (2',4'-difluorophenyl)acetate]

A solution of 580 mg of dicyclohexylcarbodiimide in 20 mL of tetrahydrofuran was added to an ice cooled mixture of 256 mg of N-hydroxysuccinimide and 1.38 g of 6-deshydroxymethyl-6-carboxyphorbol 12,13-bis[(2',4'-difluorophenyl)acetate] in acetonitrile (85 mL)/tetrahydrofuran (50 mL). After 10 min the mixture was allowed to warm to room temperature under positive nitrogen pressure. After 7 h the mixture was filtered and then concentrated in vacuo. Preparative liquid chromatography [silica; hexane/ethyl acetate (50:50)] afforded 1.53 g of 6-deshydroxymethyl-6-(N-succinimidyloxy)carbonylphorbol 12,13-bis[(2',4'-difluorophenyl)acetate], the structure of which was confirmed by NMR spectral analysis.

EXAMPLE 56

In a similar manner the following compounds are prepared:
(i) 12-deoxy-6-deshydroxymethyl-6-(N-succinimidyloxy) carbonylphorbol 13-decanoate;
(ii) 6-deshydroxymethyl-6-(N-succinimidyloxy) carbonylphorbol 12-myristate 13-acetate; and
(iii) 6-deshydroxymethyl-6-(N-succinimidyloxy) carbonylphorbol 12-(3'-phenoxy)benzoate 13-butyrate.

EXAMPLE 57

6-Deshydroxymethyl-6-[N-(2',3'-dihydroxypropyl) carboxamido]phorbol 12,13-Bis[(2',4'-difluorophenyl)acetate]

Over 2.5 h a total of about 50 mg of (±)-3-amino-1,2-propandiol was added to a solution of 100 mg of 6-deshydroxymethyl-6-(N-succinimidyloxy)carbonylphorbol 12,13-bis[(2',4'-difluorophenyl)acetate] in tetrahydrofuran (1 mL)/acetonitrile (0.5 mL). After another 0.75 h the mixture was partitioned between phosphate buffer (pH 2) and ethyl acetate. The organic layer was washed with phosphate buffer (pH 8), dried over sodium sulfate and concentrated in vacuo. The resulting residue was subjected to preparative liquid chromatography [silica; methylene chloride/methanol (94:6) to afford 78 mg of 6-deshydroxymethyl-6-[N-(2',3'-dihydroxypropyl)carboxamido]phorbol 12,13-bis[(2',4'-difluorophenyl)acetate]. The structure was confirmed by NMR and mass spectral analysis.

EXAMPLE 58

In a similar manner the following compounds are prepared:
(i) 12-deoxy-6-deshydroxymethyl-6-[N-(2'-hydroxyethyl) carboxamido]phorbol 13-decanoate;
(ii) 6-deshydroxymethyl-6-[N-(2'S)-1'-hydroxyprop-2'-yl) carboxamido]phorbol 12-myristate 13-acetate;
(iii) 6-deshydroxymethyl-6-(2'-hydroxymethylpiperidin-1'-yl)carbonylphorbol 12-(3'-phenoxy)benzoate 13-butyrate; and
(iv) 6-deshydroxymethyl-6-carboxamidophorbol 12,13-bis[(2',4'-difluorophenyl)acetate].

EXAMPLE 59

6-Deshydroxymethyl-6-(2'-hydroxy) ethoxycarbonylphorbol 12,13-Bis[(2',4'-difluorophenyl)acetate]

A solution consisting of 100 mg of 6-deshydroxymethyl-6-(N-succinimidyloxy)carbonylphorbol 12,13-bis[(2',4'-difluorophenyl)acetate], a few mg of 4-dimethylaminopyridine and a large excess of ethylene glycol in 1 mL of tetrahydrofuran was allowed to stand for 6 days at room temperature. The solution was then partitioned between water and ethyl acetate, the organic layer dried over sodium sulfate and concentrated in vacuo. After purification by preparative liquid chromatography [silica; hexane/ethyl acetate], 32 mg of 6-deshydroxymethyl-6-(2'-hydroxy)ethoxycarbonylphorbol 12,13-bis[(2',4'-difluorophenyl)acetate] was obtained. The structure was confirmed by NMR and mass spectral analysis.

EXAMPLE 60

In a similar manner the following compounds are prepared:
(i) 12-deoxy-6-deshydroxymethyl-6-(2'-hydroxy) ethoxycarbonylphorbol 13-decanoate; and
(ii) 6-deshydroxymethyl-6-(3'-hydroxy) propyloxycarbonylphorbol 12-myristate 13-acetate.

EXAMPLE 61

20-Deoxy-20-(3'-hydroxypropylthio)phorbol 12,13-Bis[(2',4'-difluorophenyl)acetate]

To a solution of 100 mg of 20-deoxy-20-chlorophorbol 12,13-bis[(2',4'-difluorophenyl)acetate] in 1 mL of acetonitrile was added a solution of 37 μL of 3-mercaptopropanol in 383 μL of 0.43M methanolic sodium methoxide. After about 15 min the reaction mixture was partitioned between ethyl acetate and phosphate buffer (pH 8). The organic layer was dried over sodium sulfate and concentrated under a stream of nitrogen. The residue was chromatographed [silica, hexane/ethyl acetate (65:35)] to afford 77 mg of 20-deoxy-20-(3'-hydroxypropylthio)phorbol 12,13-bis[(2', 4'-difluorophenyl)acetate].

EXAMPLE 62

In a similar manner the following compounds are prepared:
(i) 20-deoxy-20-(2'-hydroxyethylthio)phorbol 12,13-bis[(2', 4'-difluorophenyl)acetate];
(ii) 20-deoxy-20-(2',3'-dihydroxypropylthio)phorbol 12,13-bis[(2',4'-difluorophenyl)acetate];
(iii) 20-deoxy-20-(4'-hydroxy-n-butylthio)phorbol 12,13-bis [(2',4'-difluorophenyl)acetate];
(iv) 20-deoxy-20-(2'-hydroxypropylthio)phorbol 12,13-bis[ (2',4'-difluorophenyl)acetate];
(v) 20-deoxy-20-(2'-aminoethylthio)phorbol 12,13-bis[(2', 4'-difluorophenyl)acetate];
(vi) 20-deoxy-20-[2'-(formylamino)ethylthio]phorbol 12-myristate 13-acetate;
(vii) 20-deoxy-20-[2'-(acetylamino)ethylthio]phorbol 12-myristate 13-acetate;

(viii) 20-deoxy-20-[2'-(methylsulfonylamino)ethylthio] phorbol 12-myristate 13-acetate;

(ix) 20-deoxy-20-propylthiophorbol 12,13-bis[(2',4'-difluorophenyl)acetate];

(x) 20-deoxy-20-(2'-mercaptoethylthio)phorbol 12,13-bis[(2',4'-difluorophenyl)acetate];

(xi) 20-deoxy-20-[2'-(hydroxymethyl)phenylthio]phorbol 12-myristate 13-acetate;

(xii) 20-deoxy-20-(2'-hydroxyethylthio)phorbol 12,13-dibenzoate;

(xiii) 20-deoxy-20-(2'-hydroxyethylthio)phorbol 12,13-bis(phenylacetate);

(xiv) 20-deoxy-20-(2'-hydroxyethylthio)phorbol 12,13-bis[(pentafluorophenyl)acetate];

(xv) 20-deoxy-20-(2'-hydroxyethylthio)phorbol 12,13-bis[(2',4'-dichlorophenyl)acetate];

(xvi) 20-deoxy-20-(2',3'-dihydroxypropylthio)phorbol 12-4'-(9",10"-dihydrophenanthrene-2")butyrate] 13-(2',4'-difluorobenzoate);

(xvii) 20-deoxy-20-(3'-hydroxypropylthio)phorbol 12-(2',4'-difluorocinnamate) 13-(2',4'-difluorophenyl)acetate;

(xviii) 20-deoxy-20-(2'-hydroxyethylthio)phorbol 12-(4'-biphenylacetate) 13-[3'-(31",5"-difluorophenyl)propionate];

(xix) 20-deoxy-20-(2'-carboxamidoethylthio)phorbol 12,13-bis[(2',4'-dichlorophenyl)acetate], (xx) 20-deoxy-20-(2'-hydroxyethylthio)-12-O-, 13-O-bis(isopropyldimethylsilyl)phorbol;

(xxi) 20-deoxy-20-(4'-hydroxy-2'-butenylthio)phorbol 12,13-bis[(2',4'-difluorophenyl)acetate];

(xxii) 12,20-dideoxy-20-(2'-hydroxyethylthio)phorbol 13-(2',4'-difluorophenyl)acetate;

(xxiii) 20-deoxy-20-(2'-hydroxyethylthio)resiniferonol 9,13,14-orthophenylacetate;

(xxiv) 20-deoxy-20-phenylselenophorbol 12,13-bis[(2',4'-difluorophenyl)acetate]; and (xxv) 20-deoxy-20-methylselenophorbol 12,13-bis[(2',4'-difluorophenyl)acetate] (sodium methylselenide is prepared by treatment of dimethyldiselenide with sodium borohydride).

EXAMPLE 63

20-Deoxy-20-[2'-(t-butyldiphenylsilyloxy)ethylthio] phorbol

A solution containing 12 g of 2-hydroxyethyldisulfide and 12.2 g of imidazole in 150 mL of dried N,N-dimethylformamide was treated with 41.65 g of t-butyldiphenylchlorosilane. After 2 h, another 25 g of the silane and 5 g of imidazole were added along with 10 mL of pyridine. After another 3.5 h the mixture was partitioned between ethyl acetate and water. The organic layer was then washed with phosphate buffer (pH 2 and pH 8, sequentially), filtered through N/N/S and concentrated in vacuo. Preparative liquid chromatography [silica, hexane/methylene chloride (90:10)] afforded about 46 g of 2-t-butyldiphenylsilyloxyethyldisulfide.

To a solution of 46 g of 2-t-butyldiphenylsilyloxyethyldisulfide in 650 mL of tetrahydrofuran was added a mixture of 40 g of zinc dust and 10 mL of acetic acid in 50 mL of tetrahydrofuran. After 2 h the supernatant was decanted into 2 L of water and the residue washed twice with 500 mL of ethyl acetate each. The aqueous solution was extracted with ethyl acetate and the combined organic layers washed with brine, filtered through N/N/S and concentrated in vacuo. The residue was dissolved in hexane/methylene chloride (85:15) and filtered through silica. Concentration in vacuo afforded 37.5 g of 2-t-butyldiphenylsilyloxyethylthiol.

A solution prepared from 1 g of sodium and 17 g of 2-t-butyldiphenylsilyloxyethylthiol in 100 mL of methanol was added to approximately 4 g of crude 20-deoxy-20-chlorophorbol in 500 mL of ethyl acetate. After 35 min, a dilute phosphate buffer (pH 2) was added and then the organic layer was washed with phosphate buffer (pH 8), filtered through N/N/S and concentrated in vacuo. Preparative liquid chromatography [silica; hexane/ethyl acetate (25:75)] of the residue afforded 6.0 g of 20-deoxy-20-[2'-(t-butyldiphenylsilyloxy)ethylthio]phorbol.

EXAMPLE 64

20-Deoxy-20-(2'-hydroxyethylthio)phorbol 12,13-Bis[3-(pentafluorophenyl)propionate]

To an ice-cold solution of 300 mg of 1,1'-carbonyldiimidazole in 3 mL nitromethane was added 420 μL of methyl triflate followed by 441 mg of 3-(pentafluorophenyl)propionic acid in 5 mL of nitromethane. After 5 min a solution of 245 mg of 20-deoxy-20-[2'-(t-butyldiphenylsilyloxy)ethylthio]phorbol and 30 mg of 4-dimethylaminopyridine in 1.5 mL of anhydrous tetrahydrofuran was added. This mixture was allowed to stand at room temperature for 17 h then it was partitioned between ethyl acetate and phosphate buffer (pH 8). After drying (over sodium sulfate) the organic layer was concentrated in vacuo. By analysis of the thin layer chromatogram this residue was found to consist of a mixture of the mono and diesters. The residue was again subjected to the above conditions for 2 h and then treated as before. Preparative liquid chromatography [silica; hexane/ethyl acetate (85:15)] afforded 320 mg of 20-deoxy-20-[2'-(t-butyldiphenylsilyloxy)ethylthio]phorbol 12,13-bis[3'-(pentafluorophenyl)propionate].

Three hundred μL of 1M tetrabutylammonium fluoride in tetrahydrofuran was added to a solution of 250 mg of 20-deoxy-20-[2'-(t-butyldiphenylsilyloxy)ethylthio]phorbol 12,13-bis[3'-(pentafluorophenyl)propionate] in 4 mL of tetrahydrofuran. After 2 h the solution was partitioned between phosphate buffer (pH 8) and ethyl acetate. The organic layer was filtered through N/N/S and concentrated in vacuo. Preparative liquid chromatography [silica, hexane/ethyl acetate (60:40)] afforded 66 mg of 20-deoxy-20-(2'-hydroxyethylthio)phorbol 12,13-bis[3'-(pentafluorophenyl)propionate]. This structure was confirmed by NMR and mass spectral analysis.

EXAMPLE 65

In a similar manner the following compounds are prepared:

(i) 20-deoxy-20-(2'-hydroxyethylthio)phorbol 12,13-bis(2',4'-difluorobenzoate);

(ii) 20-deoxy-20-(2'-hydroxyethylthio)phorbol 12,13-bis[(3',4'-dimethoxyphenyl)acetate];

(iii) 20-deoxy-20-(2'-hydroxyethylthio)phorbol 12,13-didecanoate (decanoyl anhydride is used as the acylating agent in the presence of pyridine and 4-dimethylaminopyridine);

(iv) 20-deoxy-20-(2'-hydroxyethylthio)phorbol 12,13-bis(diphenylphosphate) (diphenylchlorophosphate is used as the acylating agent in the presence of triethylamine and 4-dimethylaminopyridine);

(v) 20-deoxy-20-(2'-hydroxyethylthio)phorbol 12,13-bis(diethylphosphate) (diethylchlorophosphate is used as the acylating agent in the presence of triethylamine and 4-dimethylaminopyridine); and (vi) 20-deoxy-20-(2'-hydroxyethylthio)phorbol 12,13-bis[(2',4'-difluorophenyl)carbamate] (2,4-difluorophenyl isocyanate is used as the carbamoylating agent in the presence of dibutyltin dilaurate and 4-dimethylaminopyridine).

EXAMPLE 66

20-Deoxy-20-(2'-carboxyethylthio)phorbol 12,13-Bis[(2',4'-difluorophenyl)acetate]

Fifty µL of 3-mercaptopropionic acid was added to 1.6 mL of 0.435M methanolic sodium methoxide. This solution was then added to 100 mg of 20-deoxy-20-chlorophorbol 12,13-bis[(2',4'-difluorophenyl)acetate] in 2 mL of dried acetonitrile. After 0.5 h the mixture was partitioned between ethyl acetate and phosphate buffer (pH 2). The organic layer was then washed with phosphate buffer (pH 8), filtered through N/N/S and concentrated in vacuo. Purification by preparative liquid chromatography [silica, methylene chloride/methanol (97:3)] afforded 54 mg of 20-deoxy-20-(2'-carboxyethylthio)phorbol 12,13-bis(2',4'-difluorophenylacetate). This structure was confirmed by NMR and mass spectral analysis.

EXAMPLE 67

In a similar manner the following compounds are prepared:
(i) 20-deoxy-20-(2'-carboxyethylthio)phorbol 12-(4'-biphenyl)acetate 13-[3'-(3",5"-difluorophenyl)propionate];
(ii) 20-deoxy-20-(2'-carboxyethylthio)phorbol 12-myristate 13-acetate;
(iii) 12,20-deoxy-20-(2'-carboxyethylthio)phorbol 13-(2',4'-difluorophenyl)acetate;
(iv) 20-deoxy-20-(2'-carboxyethylthio)phorbol 12-(4'-biphenyl)acetate 13-[3'-(3",5"-difluorophenyl)propionate];
(v) 20-deoxy-20-(2'-carboxyethylthio)phorbol 12-myristate 13-acetate;
(vi) 12,20-dideoxy-20-(2'-carboxyethylthio)phorbol 13-(2',4'-difluorophenyl)acetate;
(vii) 20-deoxy-20-(2'-carboxyethylthio)resiniferonol 9,13,14-orthophenylacetate; and
(viii) 20-deoxy-20-[(3'-hydroxylamino-3'-oxopropyl)thio]phorbol 12-myristate 13-acetate.

EXAMPLE 68

20-Deoxy-20-mercaptophorbol 12,13-Bis[(2',4'-difluorophenyl)acetate]

A solution of 72 mg of hydrated sodium hydrogensulfide in 1 mL of methanol and 2 µL of acetic acid was prepared. Two hundred and fifty µL of this solution was added to a solution of 100 mg of 20-deoxy-20-chlorophorbol 12,13-bis[(2',4'-difluorophenyl)acetate] in 1 mL of acetonitrile. After 35 min another 100 µL of the solution was added. After 25 min phosphate buffer (pH 6) was added and the mixture was extracted with ethyl acetate. The organic layer was filtered through N/N/S and concentrated in vacuo. The residue was subjected to preparative liquid chromatography [silica; hexane/ethyl acetate mixtures] to afford 32 mg of 20-deoxy-20-mercaptophorbol 12,13-bis[(2',4'-difluorophenyl)acetate]. The structure was confirmed by NMR and mass spectral analysis.

EXAMPLE 69

In a similar manner the following compounds are prepared:
(i) 20-deoxy-20-mercaptophorbol 12-(4'-biphenyl)acetate 13-[3'-(3",5"-difluorophenyl)propionate];
(ii) 20-deoxy-20-mercaptophorbol 12-myristate 13-acetate;
(iii) 12,20-dideoxy-20-mercaptophorbol 13-(2',4'-difluorophenyl)acetate; and
(iv) 20-deoxy-20-mercaptoresiniferonol 9,13,14-orthophenylacetate.

EXAMPLE 70

20-Deoxy-20-acetonylthiophorbol 12,13-Bis[(2',4'-difluorophenyl)acetate]

To a mixture of chloroacetone and potassium iodide in acetonitrile is added 20-deoxy-20-mercaptophorbol 12,13-bis[(2',4'-difluorophenyl)acetate]. After a period of time the mixture is partitioned between ethyl acetate and phosphate buffer (pH 8) and the organic layer is filtered through N/N/S and concentrated in vacuo. Purification by liquid chromatography affords 20-deoxy-20-acetonylthiophorbol 12,13-bis[(2',4'-difluorophenyl)acetate].

EXAMPLE 71

20-Deoxy-20-(2'-hydroxyethylsulfinyl)phorbol 12-Myristate 13-Acetate and 20-Deoxy-20-(2'-hydroxyethylsulfonyl)phorbol 12-Myristate 13-Acetate To a solution of 100 mg of 20-deoxy-20-(2'-hydroxyethylthio)phorbol 12-myristate 13-acetate in 2 mL of t-butyl alcohol was added 100 µL of 30% hydrogen peroxide. After 30 min, 2 mL of 20% aq. sodium thiosulfate was added and the mixture partitioned between water and ethyl acetate. The organic layer was dried over sodium sulfate and concentrated in vacuo. After preparative liquid chromatography [silica, methylene chloride/isopropyl alcohol] on the residue, 67 mg of 20-deoxy-20-(2'-hydroxyethylsulfinyl)phorbol 12-myristate 13-acetate and 14 mg of 20-deoxy-20-(2'-hydroxyethylsulfonyl)phorbol 12-myristate 13-acetate were obtained. The structures were confirmed by NMR and mass spectral analysis.

EXAMPLE 72

In a similar manner the following compounds are prepared:
(i) 20-deoxy-20-(2'-hydroxyethylsulfinyl)phorbol 12,13-bis[(2',4'-difluorophenyl)acetate];
(ii) 20-deoxy-20-(2'-hydroxyethylsulfinyl)phorbol 12,13-bis[(pentafluorophenyl)acetate];
(iii) 20-deoxy-20-(propylsulfinyl)phorbol 12,13-bis[(2',4'-difluorophenyl)acetate];
(iv) 20-deoxy-20-(2'-hydroxyethylsulfinyl)phorbol 12,13-bis[3'-(pentafluorophenyl)propionate];
(v) 20-deoxy-20-(2'-hydroxyethylsulfinyl)-3-deoxo-3-hyroximinophorbol 12,13-bis[3'-(pentafluorophenyl)propionate];
(vi) 20-deoxy-20-(2'-carboxyethylsulfinyl)phorbol 12,13-bis[(2',4'-difluorophenyl)acetate]; and
(vii) 20-deoxy-20-(3'-hydroxypropylsulfinyl)phorbol 12,13-bis[(2',4'-difluorophenyl)acetate].

EXAMPLE 73

20-Deoxy-20-(2'-hydroxyethylsulfonyl)phorbol 12,13-Bis[(2',4'-difluorophenyl)acetate]

To a solution of 100 mg of 20-deoxy-20-(2'-hydroxyethylthio)phorbol 12,13-bis[(2',4'-difluorophenyl)

acetate] in 1 mL of methylene chloride was added, drop wise, 49 mg of m-chloroperbenzoic acid in 1 mL of methylene chloride. After about one hour another 28 mg of peracid was added. A few minutes later the reaction mixture was partitioned between aq. sodium thiosulfate (approximately 5%) and ethyl acetate. The organic layer was dried over sodium sulfate and concentrated in vacuo. Preparative liquid chromatography [silica; hexane/ethyl acetate (40:60)] of the residue afforded 69 mg of 20-deoxy-20-(2'-hydroxyethylsulfonyl)phorbol 12,13-bis[(2',4'-difluorophenyl)acetate]. The structure was confirmed by NMR and mass spectral analysis.

EXAMPLE 74

In a similar manner the following compounds are prepared:
(i) 20-deoxy-20-(2'-hydroxyethylsulfonyl)phorbol 12,13-bis[(pentafluorophenyl)acetate];
(ii) 20-deoxy-20-(propylsulfonyl)phorbol 12,13-bis[(2',4'-difluorophenyl)acetate];
(iii) 20-deoxy-20-(2'-hydroxyethylsulfonyl)phorbol 12,13-bis[3'-(pentafluorophenyl)propionate];
(iv) 20-deoxy-20-(2'-hydroxyethylsulfonyl)-3-deoxo-3-hyroximinophorbol 12,13-bis[3'-(pentafluorophenyl)propionate];
(v) 20-deoxy-20-(2'-carboxyethylsulfonyl)phorbol 12,13-bis[(2',4'-difluorophenyl)acetate];
(vi) 20-deoxy-20-(3'-hydroxypropylsulfonyl)phorbol 12,13-bis[(2',4'-difluorophenyl)acetate]; and
(vii) 20-deoxy-20-(2'-hydroxyethylsulfonyl)phorbol 12-myristate 13-acetate.

EXAMPLE 75

20-Deoxy-20-cyanophorbol 12-Myristate 13-Acetate

A mixture consisting of 500 mg of 20-deoxy-20-chlorophorbol 12-myristate 13-acetate, 80 mg of potassium cyanide, 150 mg of tetrabutylammonium chloride, 75 mg of 18-crown-6, 3 mL of chloroform and 2.8 mL of water was stirred for 22 h at room temperature. The mixture was then partitioned between ethyl acetate and phosphate buffer (pH 8) and the organic layer was filtered through N/N/S and concentrated in vacuo. Preparative liquid chromatography [silica; hexane/isopropyl alcohol (92:8)] afforded 20-deoxy-20-cyanophorbol 12-myristate 13-acetate.

EXAMPLE 76

In a similar manner the following compounds are prepared:
(i) 20-deoxy-20-cyanophorbol 12,13-bis(phenylacetate);
(ii) 20-deoxy-20-cyanophorbol 12,13-bis[(pentafluorophenyl)acetate];
(iii) 20-deoxy-20-cyanophorbol 12,13-bis[(2',4'-dichlorophenyl)acetate];
(iv) 20-deoxy-20-cyanophorbol 12-4'-(9",10"-dihydrophenanthrene-2")-butyrate] 13-(2',4'-difluorobenzoate);
(v) 20-deoxy-20-cyanophorbol 12-(2',4'-difluorocinnamate) 13-(2',4'-difluorophenylacetate);
(vi) 20-deoxy-20-cyanophorbol 12-(4'-biphenyl)acetate 13-[3'-(3",5"-difluorophenyl)propionate];
(vii) 12,20-dideoxy-20-cyanophorbol 13-(2',4'-difluorophenyl)acetate; and
(viii) 20-deoxy-20-cyanoresiniferonol 9,13,14-orthophenylacetate.

EXAMPLE 77

20-Deoxy-20-azidophorbol 12,13-Bis[(2',4'-difluorophenyl)acetate]

To a solution of 100 mg of 20-deoxy-20-chlorophorbol 12,13-bis[(2',4'-difluorophenyl)acetate] in 1 mL of anhydrous methanol was added 88 mg of sodium azide. After 3 h the mixture was partitioned between water and ethyl acetate. The organic layer was filtered through N/N/S and concentrated in vacuo. Upon further purification by chromatography [silica; hexane/ethyl acetate (80:20)], 88 mg of 20-deoxy-20-azidophorbol 12,13-bis[(2',4'-difluorophenyl)acetate] was obtained. The structure was confirmed by NMR and mass spectral analysis.

EXAMPLE 78

In a similar manner the following compounds are prepared:
(i) 20-deoxy-20-azidophorbol 12,13-bis(phenylacetate);
(ii) 20-deoxy-20-azidophorbol 12,13-bis[(pentafluorophenyl)acetate];
(iii) 20-deoxy-20-azidophorbol 12,13-bis[(2',4'-dichlorophenyl)acetate];
(iv) 20-deoxy-20-azidophorbol 12-4'-(9",10"-dihydrophenanthrene-2")-butyrate]13-(2',4'-difluorobenzoate);
(v) 20-deoxy-20-azidophorbol 12-(2',4'-difluorocinnamate) 13-(2',4'-difluorophenylacetate);
(vi) 20-deoxy-20-azidophorbol 12-(4'-biphenyl)acetate 13-[3'-(3",5"-difluorophenyl)propionate];
(vii) 12,20-dideoxy-20-azidophorbol 13-(2',4'-difluorophenyl)acetate;
(viii) 12,20-dideoxy-20-azidophorbol 13-decanoate,
(ix) 20-deoxy-20-azidoresiniferonol 9,13,14-orthophenylacetate;
(x) 20-deoxy-20-azidophorbol 12-myristate 13-acetate;
(xi) 20-deoxy-20-azidophorbol 12,13-dibenzoate;
(xii) 20-deoxy-20-azido-12-O-, 13-O-bis(isopropyldimethylsilyl)phorbol;
(xiii) 20-deoxy-20-azidophorbol 12,13-bis(2',4'-difluorobenzoate);
(xiv) 20-deoxy-20-azidophorbol 12,13-bis[(3',4'-dimethoxyphenyl)acetate];
(xv) 20-deoxy-20-azidophorbol 12,13-didecanoate;
(xvi) 5-O-trimethylsilyl-20-deoxy-20-azidoingenol 3,4-acetonide;
(xvii) 20-deoxy-20-azidophorbol 12-octyldimethylsilylacetate 13-(2',4'-difluorophenylacetate); and
(xviii) 20-deoxy-20-azidophorbol 12-(2',4'-difluorophenylacetate) 13-diphenylphosphate.

EXAMPLE 79

20-Deoxy-20-aminophorbol 12,13-Bis[(2',4'-difluorophenyl)acetate]

A solution of 47.5 mg of 20-deoxy-20-azidophorbol 12,13-bis[(2',4'-difluorophenyl)acetate] and 27 mg of triphenylphosphine in 1 mL of tetrahydrofuran was stirred for 4.5 h at room temperature. At this time 10 mg of triphenylphosphine was added followed 1.5 h later by 100 μL of water and 1.5 h after that with a few mg of silica. After another 1.5 h the mixture was filtered through silica gel and concentrated by a stream of nitrogen. Preparative liquid chromatography afforded 18 mg of 20-deoxy-20-aminophorbol 12,13-bis[(2',4'-difluorophenyl)acetate].

EXAMPLE 80

In a similar manner the following compounds are prepared:
(i) 20-deoxy-20-aminophorbol 12,13-bis(phenylacetate);
(ii) 20-deoxy-20-aminophorbol 12,13-bis[(pentafluorophenyl)acetate];
(iii) 20-deoxy-20-aminophorbol 12,13-bis[(2',4'-dichlorophenyl)acetate];
(iv) 20-deoxy-20-aminophorbol 12-4'-(9",10"-dihydrophenanthrene-2")-butyrate]13-(2',4'-difluorobenzoate);
(v) 20-deoxy-20-aminophorbol 12-(4'-biphenyl)acetate 13-[3'-(3",5"-difluorophenyl)propionate];
(vi) 12,20-dideoxy-20-aminophorbol 13-(2',4'-difluorophenyl)acetate;
(vii) 20-deoxy-20-aminoresiniferonol 9,13,14-orthophenylacetate;
(viii) 20-deoxy-20-aminophorbol 12-myristate 13-acetate;
(ix) 20-deoxy-20-aminophorbol 12,13-dibenzoate;
(x) 20-deoxy-20-aminophorbol 12,13-bis(2',4'-difluorobenzoate); and
(xi) 20-deoxy-20-aminophorbol 12,13-bis[(3',4'-dimethoxyphenyl)acetate].

EXAMPLE 81

20-Deoxy-20-(N'-methylureido)phorbol 12,13-Bis[(2',4'-difluorophenyl)acetate]

To a solution of 50 mg of 20-deoxy-20-aminophorbol 12,13-bis[(2',4'-difluorophenyl)acetate] in 1 mL of tetrahydrofuran is added 20 µL of methyl isocyanate. After several hours some methanol is added to the reaction mixture to consume excess isocyanate and the mixture is concentrated. Purification by liquid chromatography affords 20-deoxy-20-(N'-ureido)phorbol 12,13-bis[(2',4'-difluorophenyl)acetate].

EXAMPLE 82

In a similar manner the following compounds are prepared:
(i) 20-deoxy-20-(N'-ethylureido)phorbol 12-myristate 13-acetate;
(ii) 20-deoxy-20-(N'-propylureido)phorbol 12,13-dibenzoate;
(iii) 20-deoxy-20-(N'-methylthioureido)phorbol 12,13-bis(2',4'-difluorobenzoate);
(iv) 12,20-dideoxy-20-(N'-butylureido)phorbol 13-(2',4'-difluorophenyl)acetate;
(v) 20-deoxy-20-[N'-(3'-methoxyphenyl)ureido]phorbol 12,13-bis[(2',4'-difluorophenyl)acetate];
(vi) 20-deoxy-20-[N'-(3'-trifluoromethylphenyl)ureido]phorbol 12,13-bis[(2',4'-difluorophenyl)acetate];
(vii) 20-deoxy-20-(N'-allylthioureido)phorbol 12,13-bis[(2',4'-difluorophenyl)acetate];
(viii) 20-deoxy-20-(N'-phenethylthioureido)phorbol 12,13-bis[(2',4'-difluorophenyl)acetate]; and
(ix) 20-deoxy-20-(N'-methylureido)resiniferonol 9,13,14-orthophenylacetate.

EXAMPLE 83

20-Deoxy-20-bromophorbol 12,13-Bis[(2',4'-difluorophenyl)acetate]

To a solution of 1.0 g of phorbol 12,13-bis[(2',4'-difluorophenyl)acetate] and 1.58 g of 2,6-lutidine in 20 mL of dry acetonitrile was added 3.21 g of dibromotriphenylphosphorane. After 0.5 h approximately 10 mL of water was added and the mixture was extracted with ethyl acetate. The combined organic layers were washed with phosphate buffers, pH 2 and pH 8 sequentially, and then brine before being filtered through N/N/S and concentrated in vacuo. Preparative liquid chromatography [silica; hexane/ethyl acetate (75:25)] afforded 665 mg of 20-deoxy-20-bromophorbol 12,13-bis[(2',4'-difluorophenyl)acetate]. The structure was confirmed by NMR and mass spectral analysis.

EXAMPLE 84

In a similar manner the following compounds are prepared:
(i) 20-deoxy-20-bromophorbol 12-myristate 13-acetate;
(ii) 20-deoxy-20-bromophorbol 12-(4'-biphenyl)acetate 13-acetate; and
(iii) 20-deoxy-20-bromophorbol 12-[(2',2'-dimethyl)(2",4"-difluorophenyl)-acetate 13-butyrate.

EXAMPLE 85

20-Deoxy-20-[N,N-bis(2'-hydroxyethyl)amino]phorbol 12,13-Bis[(2',4'-difluorophenyl)acetate]

To a solution of 100 mg of 20-deoxy-20-bromophorbol 12,13-bis[(2',4'-difluorophenyl)acetate] and 11 µL of pyridine in 1 mL of acetonitrile was added, over a 5 h period, 50 mg of diethanolamine in 1 mL of acetonitrile. The reaction was then partitioned between ethyl acetate and phosphate buffer (pH 2). The organic layer was washed with phosphate buffer (pH 8), dried over sodium sulfate and concentrated in vacuo. After preparative liquid chromatography [silica; methylene chloride/tetrahydrofuran (75:25)], 51 mg of 20-deoxy-20-[N,N-bis(2'-hydroxyethyl)amino]phorbol 12,13-bis[(2',4'-difluorophenyl)acetate] was obtained. The structure was confirmed by NMR and mass spectral analysis.

EXAMPLE 86

In a similar manner the following compounds are prepared:
(i) 20-deoxy-20-(2'-hydroxyethylamino)phorbol 12,13-bis[(2',4'-difluorophenyl)acetate];
(ii) 20-deoxy-20-[(2'S)-1-hydroxyprop-2'-yl)amino]phorbol 12-myristate 13-acetate;
(iii) 20-deoxy-20-(2'-hydroxymethylpiperidin-1-yl)phorbol 12-(4'-biphenyl)acetate 13-acetate; and
(iv) 20-deoxy-20-[(2'-carboxyethyl)amino]phorbol 12-[(2',2'-dimethyl)(2",4"-difluorophenyl)acetate 13-butyrate.

EXAMPLE 87

20-Deoxy-20-(imidazol-1'-yl)phorbol 12,13-Bis[(2',4'-difluorophenyl)acetate] and 20-Deoxy-20-(imidazol-2'-yl)phorbol 12,13-Bis[(2',4'-difluorophenyl)acetate]

Twelve mg of imidazole was added to 100 mg of 20-deoxy-20-bromophorbol 12,13-bis[(2',4'-difluorophenyl)acetate] in 1.5 mL of acetonitrile followed by 11 µL of pyridine 10 min later. After 2 h another 10 mg of imidazole was added. Three hours later a drop of pyrollidinyl pyridine was added. After 1.5 h the mixture was partitioned between ethyl acetate and phosphate buffer (pH 2). The organic layer was washed with phosphate buffer (pH 8), dried over sodium sulfate and concentrated in vacuo. The residue was chromatographed [silica; methylene chloride/tetrahydrofuran (65:35)] to afford 33 mg of 20-deoxy-20-(imidazol-1'-yl)

phorbol 12,13-bis[(2',4'-difluorophenyl)acetate] and 13 mg of 20-deoxy-20-(imidazol-2'-yl)phorbol 12,13-bis[(2',4'-difluorophenyl)acetate]. The structures were confirmed by NMR and mass spectral analysis.

EXAMPLE 88

20-Deoxy-20-(4'-dimethylaminopyridine-1'-yl) phorbol 12-Myristate 13-Acetate, Bromide (Iodide) salt A solution of 75 mg of 20-deoxy-20-bromophorbol 12-myristate 13-acetate and 1 mL of ethylene glycol in 1 mL of acetone was treated with 15 mg of potassium iodide and 30 mg of 4-dimethylaminopyridine at room temperature. After 30 min the mixture was partitioned between ethyl acetate and phosphate buffer (pH 2). The organic layer was washed with phosphate buffer (pH 8), dried over sodium sulfate and concentrated in vacuo. After purification by preparative liquid chromatography [silica; methylene chloride/methanol (50:50)] 20-deoxy-20-(4'-dimethylaminopyridinium-1'-yl)phorbol 12-myristate 13-acetate, bromide (iodide) salt, was obtained. It did not crystallize.

EXAMPLE 89

20-Deoxy-20-[(3'-hydroxymethylphenyl) aminophorbol 12,13-Bis[(2',4'-difluorophenyl) acetate]

A total of 99 mg of 3-aminobenzyl alcohol was added over 1.5 h to 95 mg of 20-deoxy-20-oxophorbol 12,13-bis [(2',4'-difluorophenyl)acetate] in 3 mL of acetonitrile/10% aq. acetic acid (9:1). To this mixture was then added 23 mg of sodium cyanoborohydride, and, after 25 min, phosphate buffer (pH 2) was added. This solution was extracted with ethyl acetate and the organic layer washed with phosphate buffer (pH 8), filtered through N/N/S and concentrated in vacuo. Chromatographic purification [silica; hexane/ethyl acetate (55:45)] afforded 70 mg of 20-deoxy-20-[(3'-hydroxymethylphenyl)amino]phorbol 12,13-bis[(2',4'-difluorophenyl)acetate]. The structure was confirmed by NMR and mass spectral analysis.

EXAMPLE 90

In a similar manner the following compounds are prepared:
(i) 20-deoxy-20-[(4'-(2'-hydroxyethyl)phenyl)amino] phorbol 12,13-didecanoate;
(ii) 20-deoxy-20-[(3'-methoxycarbonylmethylphenyl) amino]phorbol 12-myristate 13-acetate;
(iii) 20-deoxy-20-[(3'-cyanophenyl)amino]phorbol 12-(3'-phenoxy)benzoate 13-butyrate;
(iv) 20-deoxy-20-[(4'-carboxamidophenyl)amino]phorbol 12-(3',5'-difluorophenyl)acetate 13-(3',4'-difluorobenzoate);
(v) 20-deoxy-20-[(3'-acetylphenyl)amino]phorbol 12,13-bis [(2',4'-dichlorophenyl)acetate];
(vi) 20-deoxy-20-[(3'-dihydroxyboranylphenyl)amino] phorbol 12,13-bis[(2',4'-difluorophenyl)acetate];
(vii) 20-deoxy-20-[(4'-oxoarsinylphenyl)amino]phorbol 12,13-bis[(2',4'-difluorophenyl)acetate];
(viii) 20-deoxy-20-[(4'-dihydroxyphosphonylphenyl)amino] phorbol 12,13-bis[(2',4'-difluorophenyl)acetate]; and
(ix) 12,20-dideoxy-20-[(3'-hydroxymethylphenyl)amino] phorbol 13-(2',4'-difluorophenyl)acetate.

EXAMPLE 91

20-O-(2'-Hydroxyethyl)phorbol 12-Myristate 13-Acetate

A solution of 75 mg of 20-deoxy-20-bromophorbol 12-myristate 13-acetate and 1 mL of ethylene glycol in 1 mL of acetone was treated with 15 mg of potassium iodide and 30 mg of 2,6-di-t-butyl-4-methylpyridine at room temperature in the dark and under a nitrogen atmosphere for 12 days. It was then partitioned between ethyl acetate and phosphate buffer (pH 2). The organic layer was washed with phosphate buffer (pH 8), filtered through N/N/S and concentrated in vacuo. After purification by preparative liquid chromatography [silica; hexane/ethyl acetate (50:50)] 28.5 mg of 20-O-(2'-hydroxyethyl)phorbol 12-myristate 13-acetate was obtained. The structure was confirmed by NMR and high resolution mass spectral analysis.

EXAMPLE 92

In a similar manner the following compounds are prepared:
(i) 20-O-(4'-hydroxy-2'-butynyl)phorbol 12,13 bis[(2',4'-difluorophenyl)acetate];
(ii) 20-O-(4'-hydroxy-2'-butenyl)phorbol 12-(4'-biphenyl) acetate 13 -acetate;
(iii) 20-O-acetonylphorbol 12-[(2',2'-dimethyl)(2'',4''-difluorophenyl)acetate] 13-butyrate,
(iv) 20-O-(2'-propyl)phorbol 12-myristate 13-acetate; and
(v) 20-O-(3'-hydroxyprop-1'-yl)phorbol 12-myristate 13-acetate.

EXAMPLE 93

20-O-(4'-Hydroxyphenoxy)carbonylphorbol 12,13-Bis[(2',4'-difluorophenyl)acetate]

To a solution of 8.26 g of hydroquinone and 6.3 g of imidazole in 80 mL of pyridine was added 20.6 g of t-butyldiphenylchlorosilane in 20 mL of pyridine. After 1.5 h the mixture was partitioned between water and ethyl acetate. The organic layer was washed twice with phosphate buffer (pH 2) and once each with phosphate buffer (pH 8) and brine before being filtered through N/N/S and concentrated in vacuo. Preparative liquid chromatography [silica; hexane/ethyl acetate (85:15)] afforded 14.4 g of 4-(t-butyldiphenylsilyloxy)phenol. The structure was confirmed by its NMR spectrum.

To a solution of 46 mg of 1,1'-carbonyldiimidazole in 0.5 mL nitromethane was added 65 μL of methyl triflate followed by 100 mg of 4-(t-butyldiphenylsilyloxy)phenol in 1.4 mL of nitromethane. A total of 1.9 mL of this solution was added to a mixture of 100 mg of phorbol 12,13-bis[(2',4'-difluorophenyl)acetate] and approximately 10 mg of 4-dimethylaminopyridine in 500 μL of anhydrous tetrahydrofuran. After 4.5 h this mixture was partitioned between ethyl acetate and water. The organic layer was filtered through N/N/S, concentrated in vacuo and subjected to preparative liquid chromatography [silica; hexane/ethyl acetate (80:20)] to afford 142 mg of 20-O-[4'-(t-butyldiphenylsilyloxy)phenoxy]carbonylphorbol 12,13-bis[(2',4'-difluorophenyl)acetate]. A solution of this material in 1 mL tetrahydrofuran was treated with 160 μL of 1.0M tetrabutylammonium fluoride in tetrahydrofuran. After 14 min the mixture was partitioned between ethyl acetate and phosphate buffer (pH 8). The organic layer was filtered through N/N/S and concentrated in vacuo. After preparative liquid chromatography [silica, hexane/ethyl acetate (65:35)] 108 mg of 20-O-(4'-hydroxyphenoxy)carbonylphorbol 12,13-bis[(2',4'-difluorophenyl)acetate] was obtained. The structure was confirmed by NMR and mass spectral analysis.

EXAMPLE 94

In a similar manner the following compounds are prepared:
(i) 20-O-(4'-hydroxyphenoxy)carbonylphorbol 12,13-didecanoate;
(ii) 20-O-(4'-hydroxyphenoxy)carbonyl-12-deoxyphorbol 13-decanoate;
(iii) 20-O-(4'-hydroxyphenoxy)carbonyl-12-deoxyphorbol 13-(2',4'-difluorophenyl)acetate;
(iv) 20-O-(3'-hydroxyphenoxy)carbonylphorbol 12-myristate 13-acetate;
(v) 20-O-(3'-hydroxyphenoxy)carbonylphorbol 12-(3'-phenoxy)benzoate 13-butyrate;
(vi) 20-O-(4'-hydroxyphenoxy)carbonylphorbol 12-(3',5'-difluorophenyl)acetate 13-(3',4'-difluorobenzoate);
(vii) 20-O-(2'-hydroxyphenoxy)carbonylphorbol 12-(3',5'-difluorocinnamate) 13-[3'-(2",4"-difluorophenyl)propionate];
(viii) 20-O-phenoxycarbonylphorbol 12,13-bis[(2',4'-dichlorophenyl)acetate];
(ix) 20-O-(2'-hydroxyphenoxy)carbonylingenol 3-benzoate;
(x) 20-O-(3'-hydroxyphenoxy)carbonylresiniferonol 9,13,14-orthophenylacetate;
(xi) 3-[(4'-hydroxy)phenoxycarbonyloxymethyl]-1,6-dioxo-2,5-dioxacyclotetracosane;
(xii) 30-O-(4'-hydroxyphenoxy)carbonyldebromoaplysiatoxin 20-acetate; and
(xiii) 26-O-(4'-hydroxyphenoxy)carbonylbryostatin 1.

EXAMPLE 95

Phorbol 12-Myristate 13-Acetate 20-(4'-Fluoro-3'-nitrophenyl)carbamate

To a solution of 100 mg of phorbol 12-myristate 13-acetate in 1 mL of tetrahydrofuran was added, 73 mg of 4-fluoro-3-nitrophenyl isocyanate, 5 mg of dibutyltin dilaurate and 25 mg of 4-dimethylaminopyridine. After 3 h 100 μL of methanol was added to the reaction mixture. After removal of the solvents under a nitrogen stream, the mixture was subjected to preparative liquid chromatography [silica; hexane/iso-propyl alcohol (86:14)] to afford 71 mg of phorbol 12-myristate 13-acetate 20-(4'-fluoro-3'-nitrophenyl)carbamate.

EXAMPLE 96

In a similar manner the following compounds are prepared:
(i) phorbol 12-myristate 13-acetate 20-ethylcarbamate;
(ii) phorbol 12-myristate 13-acetate 20-n-propylcarbamate;
(iii) phorbol 12-myristate 13-acetate 20-n-butylcarbamate;
(iv) phorbol 12,13-didecanoate 20-(3'-trifluoromethyl)phenylcarbamate;
(v) phorbol 12,13-bis[(2',4'-difluorophenyl)acetate] 20-methylcarbamate;
(vi) 12-deoxyphorbol 13-decanoate 20-(3'-methoxy)phenylcarbamate;
(vii) 12-deoxyphorbol 13-(2',4'-difluorophenyl)acetate 20-n-propylcarbamate;
(viii) phorbol 12-(3'-phenoxy)benzoate 13-butyrate 20-(4'-ethoxycarbonyl)phenylcarbamate;
(ix) phorbol 12-(3',5'-difluorophenyl)acetate 13-(3',4'-difluorobenzoate) 20-ethoxycarbonylmethylcarbamate;
(x) ingenol 3-benzoate 20-methylcarbamate;
(xi) resiniferonol 9,13,14-orthophenylacetate 20-ethylcarbamate;
(xii) mezerein 20-methylcarbamate;
(xiii) 3-[(N-methylamino)carbonyloxymethyl]-1,6-dioxo-2,5-dioxacyclotetracosane;
(xiv) debromoaplysiatoxin 20-acetate 30-methylcarbamate; and
(xv) bryostatin 1 26-methylcarbamate.

EXAMPLE 97

Phorbol 12-Myristate 13-Acetate 20-Methylthiocarbamate

To a solution of 100 mg of phorbol 12-myristate 13-acetate in 1 mL of tetrahydrofuran was added, over a six hour period, a total of 180 mg of methyl isothiocyanate, 105 mg of dibutyltin dilaurate and 125 mg of 4-dimethylaminopyridine. After 4 days the reaction mixture was subjected to preparative liquid chromatography [silica; hexane/acetate mixtures] to afford 4 mg of phorbol 12-myristate 13-acetate 20-methylthiocarbamate.

EXAMPLE 98

In a similar manner the following compounds are prepared:
(i) phorbol 12,13-didecanoate 20-allylthiocarbamate;
(ii) phorbol 12,13-bis[(2',4'-difluorophenyl)acetate] 20-(tetrahydrofuran-2'-yl)methylthiocarbamate;
(iii) 12-deoxyphorbol 13-(2',4'-difluorophenyl)acetate 20-(3'-methoxy)propylthiocarbamate; and
(iv) phorbol 12-(3'-phenoxy)benzoate 13-butyrate 20-phenethylthiocarbamate.

EXAMPLE 99

Phorbol 12-Myristate 13-Acetate 20-Carbamate

To a solution of 100 mg of phorbol 12-myristate 13-acetate in 2 mL of methylene chloride was added 25 mg of chlorosulfonyl isocyanate in 200 μL of methylene chloride. After 3 h a few hundred μL of phosphate buffer (pH 2) was added. After 20 min pH 8 buffer was added and the mixture extracted with ethyl acetate. The organic layer was filtered through N/N/S and concentrated in vacuo. After preparative liquid chromatography [silica; hexane/tetrahydrofuran (65/35)], 57 mg of phorbol 12-myristate 13-acetate 20-carbamate was obtained.

EXAMPLE 100

In a similar manner the following compounds are prepared:
(i) phorbol 12,13-bis[(2',4'-difluorophenyl)acetate] 20-carbamate;
(ii) phorbol 12,13-didecanoate 20-carbamate;
(iii) phorbol 12-(3'-phenoxy)benzoate 13-butyrate 20-carbamate; and
(iv) 12-deoxyphorbol 13-(2',4'-difluorophenyl)acetate 20-carbamate.

EXAMPLE 101

20-Deoxy-20-(2'-hydroxyethylsulfonyl)-3-deoxo-3-hydroximinophorbol 12,13-Bis[(2',4'-difluorophenyl)acetate]

To a solution of 100 mg of 20-deoxy-20-(2'-hydroxyethylthio)phorbol 12,13-bis[(2',4'-difluorophenyl)acetate] in 1 mL of pyridine was added 214 mg of hydroxylamine hydrochloride. After heating at 53° C. for 8 h the mixture was cooled and partitioned between phosphate buffer (pH 2) and ethyl acetate. The organic layer was washed with phosphate buffer (pH 8), dried over sodium sulfate and concentrated in vacuo. Preparative liquid chromatography of the residue [silica; methylene chloride/tetrahydrofuran (92.5:7.5)] afforded 62 mg of 20-deoxy-20-(2'-hydroxyethylsulfonyl)-3-deoxo-3-hydroximinophorbol 12,13-bis[(2',4'-difluorophenyl)acetate]. The structure was confirmed by NMR and mass spectral analysis.

EXAMPLE 102

In a similar manner the following compounds are prepared:
(i) 6-deshydroxymethyl-6-carboxy-3-deoxo-3-hydroximinophorbol 12,13-bis[(2',4'-difluorophenyl)acetate]; and
(ii) 20-deoxy-20-(2'-hydroxyethylthio)-3-deoxo-3-hydroximinophorbol 12,13-bis[3'-(pentafluorophenyl)propionate].

EXAMPLE 103

20-Deoxy-20-(2'-hydroxyethylthio)-3-deoxo-3-β-hydroxyphorbol 12,13-Bis[(2',4'-difluorophenyl)acetate]

To a mixture of 25 mg of 20-deoxy-20-(2'-hydroxyethylthio)phorbol 12,13-bis[(2',4'-difluorophenyl)acetate] and 15 mg of cerium (III) chloride in 0.5 mL of methanol was added approximately 3 mg of sodium borohydride. After 8 min the mixture was partitioned between phosphate buffer (pH 2) and ethyl acetate. The organic layer was washed with phosphate buffer (pH 8), dried over sodium sulfate and concentrated by a stream of nitrogen. Purification by preparative liquid chromatography [silica; hexane/ethyl acetate (50:50)] afforded 13 mg of 20-deoxy-20-(2'-hydroxyethylthio)-3-deoxo-3-β-hydroxyphorbol 12,13-bis[(2',4'-difluorophenyl)acetate]. The structure was confirmed by NMR and high resolution mass spectral analysis.

EXAMPLE 104

In a similar manner the following compounds are prepared:
(i) 3-deoxo-3-β-hydroxyphorbol 12-[4'-(9",10"-dihydrophenanthren-2")butyrate]; and
(ii) 6-deshydroxymethyl-6-carboxy-3-deoxo-3-β-hydroxyphorbol 12,13-bis[(2',4'-difluorophenyl)acetate].

EXAMPLE 105

20-Deoxyphorbol 12-Myristate 13-Acetate and 12-β-Myristoyloxy-13-acetoxy-4,9-dihydroxy-1,6(20)-tigladien-3-one and 20-Deoxy-20-[20'-deoxyphorbol-20'-yl-(12'-myristate 13'-acetate)] phorbol 12-Myristate 13-Acetate Extensive further purification of the crude residue from Example 15 by preparative liquid chromatography afforded 20-deoxyphorbol 12-myristate 13-acetate, 12-β-myristoyloxy-13-acetoxy-4,9-dihydroxy-1,6(20)-tigladien-3-one and 20-deoxy-20-[20'-deoxyphorbol-20'-yl (12'-myristate 13'-acetate)]phorbol 12-myristate 13-acetate. These structures were confirmed by NMR and high resolution mass spectral analysis.

EXAMPLE 106

6-Deshydroxymethyl-6-[2'-(methoxcyarbonyl)-(E)-vinyl]phorbol 12-Myristate 13-Acetate A solution of 100 mg of 20-deoxy-20-oxophorbol 12-myristate 13-acetate and 90 mg of methyl triphenylphosphoranylideneacetate in 4 mL of toluene was allowed to stir for 18 hours at room temperature. After concentration in vacuo, the residue was purified by preparative liquid chromatography [silica, methylene chloride/tetrahydrofuran (96:4)] to yield 116 mg of 6-deshydroxymethyl-6-[2'-(methoxycarbonyl)-(E)-vinyl]phorbol 12-myristate 13-acetate as an oil.

EXAMPLE 107

20-Deoxyphorbol 12-Myristate 13-Acetate 20-Sulfonic Acid, Triethylamine Salt

A mixture containing 100 mg of 20-deoxy-20-chlorophorbol 12-myristate 13-acetate, 22 mg of sodium sulfite, 20 mg of sodium iodide and 0.6 mmoles of acetic acid in about 11 mL of ethanol/water (approximately 1:1) was stirred for a total of 4 hours alternating between ambient and 60° C. After that time the mixture was concentrated in vacuo and partitioned between ethyl acetate and brine to afford a residue which was purified by liquid chromatography [silica, methylene chloride/methanol (90:10)] to yield 82 mg of 20-deoxyphorbol-20-sulfonic acid 12-myristate 13-acetate. This acid was converted to its triethylamine salt by the addition of 24 μL of triethylamine in t-butyl methyl ether followed by concentration in vacuo.

EXAMPLE 108

20-Deoxy-20-trimethylphosphoniumphorbol 12,13-Bis[(2',4'-difluorophenyl)acetate]Bromide To solution of approximately 50 mg of 20-deoxy-20-bromophorbol 12,13-bis[(2',4'-difluorophenyl)acetate] in 1 mL of dry acetonitrile is added 100 μL of 1M trimethylphosphine in toluene. After a period of time this mixture is concentrated under a nitrogen stream and the residue is subjected to chromatographic purification to afford 20-deoxy-20-trimethylphosphoniumphorbol 12,13-bis[(2',4'-difluorophenyl)acetate]bromide.

EXAMPLE 109

20-Deoxy-20-trimethylsilylphorbol 12,13-Bis[(2',4'-difluorophenyl)acetate]

To a suspension of 50 mg of 20-deoxy-20-bromophorbol 12,13-bis[(2',4'-difluorophenyl)acetate] and 40 mg of powdered zinc (less than 325 mesh) in 500 μL of anhydrous tetrahydrofuran was added 15 μL trimethylchlorosilane. After stirring overnight at room temperature the reaction mixture was treated with another 50 μL of silane and sonicated for 5 h. The mixture is then partitioned between ethyl acetate and phosphate buffer (pH 8) and chromatographed in the usual way to obtain 20-deoxy-20-trimethylsilylphorbol 12,13-bis[(2',4'-difluorophenyl)acetate].

EXAMPLE 110

In a similar manner the following compounds are prepared:
(i) 20-deoxy-20-diphenyloxophosphinylphorbol 12,13-bis[(2',4'-difluorophenyl)acetate];
(ii) 20-deoxy-20-trimethylsilylphorbol 12-myristate 13-acetate; and
(iii) 20-deoxy-20-diphenyloxophosphinylphorbol 12-myristate 13-acetate.

EXAMPLE 111

Demonstration of Anti-HIV Activity of 20-Deoxy-20-chlorophorbol 12,13-bis[(2',4'-difluorophenyl) acetate]

Human peripheral blood lymphocytes were isolated from the buffy coat fractions of blood donations. The lymphocytes were then stimulated with 5 µg/ml of phytohemagglutinin for 48 hours. Prior to infection with HIV, the lymphocytes were washed and resuspended in mitogen-free medium. On day 0 the cells were infected with HIV and were cultured for four days in the presence or absence of graded concentrations of 20-deoxy-20-chlorophorbol 12,13-bis[(2',4'-difluorophenyl)acetate]. On days 3 and 4 the supernatant levels of total viral RNA and viral core protein p24 were determined at each drug concentration and dose-response curves were used to determine the concentration of drug giving 50% inhibition of production of viral RNA and of p24 core protein. At four days these $ED_{50}$ values were less than 100 pM for both RNA and p24.

EXAMPLE 112

Demonstration of Anti-HIV Activity of Diterpenoid Phorboids

In a manner similar to Example 111, the anti-HIV $ED_{50}$ values for RNA [drug concentration is in brackets] for the following diterpenoid compounds were determined from dose-response curves or by estimation from one or more experimental drug concentrations:

(i) 20-deoxy-20-bromophorbol 12,13-bis[(2',4'-difluorophenyl)acetate] [less than 1 nM];
(ii) 20-deoxy-20-chlorophorbol 12,13-bis[(pentafluorophenyl)acetate] [less than 1 nM];
(iii) 20-deoxy-20-cyanophorbol 12-myristate 13-acetate [1.5 µM];
(iv) phorbol 12-myristate 13-acetate 20-(4'-fluoro-3'-nitrophenyl)carbamate [4 µM];
(v) 20-deoxy-20-(2'-hydroxyethylthio)phorbol 12,13-bis[(2',4'-difluorophenyl)acetate] [1.0 µM];
(vi) 20-deoxy-20-(2',3'-dihydroxypropylthio)phorbol 12,13-bis[(2',4'-difluorophenyl)acetate] [3 µM];
(vii) 20-deoxy-20-hydroximinophorbol 12,13-bis[(2',4'-difluorophenyl)acetate] [5.5 µM];
(viii) 20-deoxy-3-deoxo-3,20-bis(hydroximino)phorbol 12,13-bis[(2',4'-difluorophenyl)acetate] [45 nM];
(x) 6-deshydroxymethyl-6-methoxycarbonylphorbol 12,13-bis[(2',4'-difluorophenyl)acetate] [1.6 µM];
(xi) 20-deoxy-20-(2'-carboxyethylthio)phorbol 12,13-bis(2',4'-difluorophenylacetate) [4.5 µM];
(xii) 20-deoxy-20-(2'-hydroxyethylsulfinyl)phorbol 12,13-bis[(2',4'-difluorophenyl)acetate] [1.6 µM];
(xiii) 20-deoxy-20-(2'-hydroxyethylsulfonyl)phorbol 12,13-bis[(2',4'-difluorophenyl)acetate] [5.0 µM];
(xiv) 20-deoxy-20-(2'-hydroxyethylsulfinyl)phorbol 12-myristate 13-acetate [1.1 µM];
(xv) 20-deoxy-20-(2'-hydroxyethylsulfonyl)phorbol 12-myristate 13-acetate [500 nM];
(xvi) 20-deoxy-20-[(3'-hydroxymethylphenyl)amino]phorbol 12,13-bis[(2',4'-difluorophenyl)acetate] [180 nM];
(xvii) 20-deoxy-20-azidophorbol 12,13-bis[(2',4'-difluorophenyl)acetate] [65 nM];
(xviii) 20-deoxy-20-aminophorbol 12,13-bis[(2',4'-difluorophenyl)acetate] [100 nM];
(xix) 20-O-(4'-hydroxyphenoxy)carbonylphorbol 12,13-bis[(2',4'-difluorophenyl)acetate] [less than 10 nM];
(xx) 20-deoxy-20-propylthiophorbol 12,13-bis[(2',4'-difluorophenyl)acetate] [10 nM];
(xxi) 20-deoxy-20-propylsulfinylphorbol 12,13-bis[(2',4'-difluorophenyl)acetate] [500 nM];
(xxii) 20-deoxy-20-(2'-mercaptoethylthio)phorbol 12,13-bis[(2',4'-difluorophenyl)acetate] [50 nM];
(xxiii) 6-deshydroxymethyl-6-cyanophorbol 12,13-bis[(2',4'-difluorophenyl)acetate] [less than 100 nM]; and
(xxiv) 20-deoxy-20-fluorophorbol 12,13-bis[(pentafluorophenyl)acetate] [1 nM].

EXAMPLE 113

Demonstration of Anti-HIV Activity of Indolactam-Type Phorboids

In a manner similar to Example 111, the anti-HIV $ED_{50}$ values for RNA [drug concentration is in brackets] for the following indolactam-type compounds were determined from dose-response curves or by estimation from one or more experimental drug concentrations; data giving percent inhibition of viral RNA production at selected concentrations appear in parentheses:

(i) rac-14-O-(N-methyl)carbamoylindolactam V (52% inhibition at 10 µM);
(ii) rac-14-O-(N-methyl)carbamoyl-1-N-(2'-triphenylphosphonium)ethylindolactam V, methanesulfonate salt (82% inhibition at 10 µM);
(iii) 14-O-(N-methyl)carbamoyl-7-octyl-(9S,12S)-indolactam V (87% inhibition at 10 µM);
(iv) 9-deshydroxymethyl-9-[N-(2'-glucosyl)]carboxamidoindolactam V (35% inhibition at 10 µM);
(v) 9-deshydroxymethyl-9-[N-(2',3'dihydroxypropyl)]carboxamidoindolactam V (22% inhibition at 10 µM);
(vi) 9-deshydroxymethyl-9-ethoxycarbonylindolactam V (47% inhibition at 10 µM);
(vii) -N-hydroxymethyl-9-deshydroxymethyl-9-ethoxycarbonylindolactam V (31% inhibition at 10 µM);
(viii) 9-deshydroxymethyl-9-(2',3'-dihydroxy)propyloxycarbonylindolactam V (20% inhibition at 10 µM);
(ix) 14-deoxy-14-(2'-hydroxyethylthio)indolactam V [ 1 MM], and
(x) 14-deoxy-14-(2'-hydroxyethylthio)-7-octyl-(9S,12S)-indolactam V [100 nM].

EXAMPLE 114

Demonstration of Anti-HIV Activity of Diacylglycerol-Type Phorboids

In a manner similar to Example 111, the anti-HIV $ED_{50}$ values for RNA [drug concentration is in brackets] for the following diacylglycerol-type compounds were determined from dose-response curves or by estimation from one or more experimental drug concentrations; data giving percent inhibition of viral RNA production at selected concentrations appear in parentheses:

(i) 3-[(2'-hydroxyethylthio)methyl]-1,6-dioxo-2,5-dioxacyclotetracosane [10 nM].

EXAMPLE 115

Demonstration of Anti-melanoma Activity

Human RPMI-7272 melanoma cells were grown in the standard culture medium under normal incubation conditions. On day 1 the cells were cultured in the absence (control) or presence of graded concentrations (3–100 µg/ml) of 20-deoxy-20-(2'-hydroxyethylthio)phorbol 12-myristate 13-acetate in separate tubes. On day 4 after 72 h of exposure the number of cells in each tube was measured and the number of cell doublings determined. The drug treated tubes were compared to the control tube. The $ID_{50}$ (the concentration of drug required to inhibit cell doublings by 50%) was 42 µM.

EXAMPLE 116

Demonstration of Anti-leukemic Activity

HL-60 promyelocytic leukemia cells were cultured in RPMI 1640 medium supplemented with 10% fetal bovine serum. Cells (7,500) were seeded into 96-well microtiter plates and incubated overnight. Serial dilutions of 20-deoxy-20-(2'-hydroxyethylthio)phorbol 12-myristate 13-acetate (dissolved in DMSO and then diluted with culture medium) were added to the wells on day 1. The plates were incubated for 8 days to allow the control cultures to undergo at least 3 cell divisions. The cell growth was monitored by using the calorimetric MTT (tetrazolium) assay [Mosmann, T., *J. Immunol. Meth.* 65: 55–63 (1983)]. After the incubation period, the cells were washed with phosphate-buffered saline in the microtiter plate. DMSO was then added to each well and the dish was put on a shaker for 20 min. The optical density was measured at 540 nm and compared using the formula: (OD Test-OD Start)/(OD Control-OD Start)×100. The $IC_{50}$ (the drug concentration which leads to 50% of cells per well compared to control cultures (100%) at the end of the incubation period) is 5.4 $\mu$M.

In a like manner, the anti-leukemic activities of the following other compounds were demonstrated:
(i) phorbol 12-myristate 13-acetate 20-methylcarbamate ($IC_{50}$=2.6 $\mu$M);
(ii) 20-deoxy-20-cyanophorbol 12-myristate 13-acetate ($IC_{50}$=5 $\mu$M); and
(iii) 12-β-myristoyloxy-13-acetoxy-4,9-dihydroxy-7-hydroxymethyl-1,6(20)-tigiadien-3-one ($IC_{50}$=5.2 $\mu$M).

EXAMPLE 117

Demonstration of Anti-cancer Activity

T-24 human bladder carcinoma cells were cultured in Eagle's minimal essential medium supplemented with 5% fetal bovine serum. Cells (1,000) were seeded into 96-well microtiter plates and incubated overnight. Serial dilutions of 20-deoxy-20-(2'-hydroxyethylthio)phorbol 12-myristate 13-acetate (dissolved in DMSO and then diluted with culture medium) were added to the wells on day 1. The plates were incubated for 5–6 days to allow the control cultures to undergo at least 3 cell divisions. After the incubation period, the cells were fixed with glutaraldehyde, washed with water and stained with 0.05% methylene blue. After washing the dye was eluted with 3% HCl. The optical density per well was measured at 665 nm and compared using the formula: (OD Test-OD Start)/(OD Control-OD Start)×100. The $IC_{50}$ (the drug concentration which leads to 50% of cells per well compared to control cultures (100%) at the end of the incubation period) is 13 $\mu$M.

In a like manner, the anti-cancer activities of the following other compounds were demonstrated:
(i) phorbol 12-myristate 13-acetate 20-methylcarbamate ($IC_{50}$=6.3 $\mu$M);
(ii) 20-deoxy-20-cyanophorbol 12-myristate 13-acetate ($IC_{50}$=2 $\mu$M); and
(iii) 12-β-myristoyloxy-13-acetoxy-4,9-dihydroxy-7-hydroxymethyl-1,6(20)-tigliadien-3-one ($IC_{50}$=5.5 $\mu$M).

EXAMPLE 118

Gelatin Capsules

Gelatin capsules containing the following ingredients are prepared:

| | |
|---|---|
| rac-14-O-(N-methyl)carbamoyl-1-N-(2'-triphenylphosphonium)ethyl-indolactam V, methanesulfonate salt | 125 mg |
| lactose | 300 mg |
| talc | 15 mg |

The finely powdered ingredients are blended together. The mixture is used to fill hard shell two-piece gelatin capsules of a suitable size at a net fill weight of 440 mg.

EXAMPLE 119

Injectable Solution

A suspension (1.0 mL) suitable for intramuscular injection is prepared from the following ingredients:

| | |
|---|---|
| 14-deoxy-14-(3'-hydroxypropylthio)indolactam V | 20 mg |
| polyethylene glycol 3350 | 29 mg |
| polysorbate 80 | 2 mg |
| monobasic sodium phosphate | 6.8 mg |
| dibasic sodium phosphate | 1.4 mg |
| benzyl alcohol | 9 mg |
| water for injection to make | 1.0 ml |

The materials are mixed, homogenized and filled into 1 ml ampuls which are sealed.

EXAMPLE 120

Topical Gel

An illustrative composition for a topical gel is the following:

| | |
|---|---|
| 20-deoxy-20-cyanophorbol 12-myristate 13-acetate | 20 mg |
| hydroxypropylcellulose | 60 mg |
| ethyl alcohol | 920 mg |

The materials are mixed, homogenized and filled into containers each holding 1 gram of gel.

EXAMPLE 121

Topical Solution

An illustrative composition for a topical solution is the following:

| | |
|---|---|
| 14-deoxy-14-[(2',3'-hydroxy)propylthio]-teleocidin B-1 | 20 mg |
| propylene glycol | 300 mg |
| citric acid | 20 mg |
| SD alcohol 40-2 to make | 1.0 mL |

The materials are mixed, homogenized and filled into squeezable plastic containers each holding 1 milliliter of solution.

EXAMPLE 126

11-O-(N-Methyl)carbamoyl-(2S,5S)-BL-V8-310

To a solution of the benzolactam (−)-BL-V8-310 [obtained by the method of Y. Endo et al., *Bioorg. Med. Chem. Lett.* 4: 491–494 (1994)], 4-dimethylaminopyridne and dibutyltin dilaurate in anhydrous tetrahydrofuran is added methylisocyanate over a peroid of time. The mixture is concentrated in vacuo and purified by liquid chromatography affording 11-O-(N-methyl)carbamoyl-(2S,5S)-BL-V8-310.

EXAMPLE 127

11-Deoxy-(2S,5S)-BL-V8-310 11-Sulfonic Acid

A solution of (–)-BL-V8-310 and pyridine in anhydrous methylene chloride is cooled in a cold bath under a nitrogen atmosphere and is treated with methanesulfonyl chloride. After a period of time the mixture is warmed to room temperature and washed with brine, pH 2 phosphate buffer and brine sequentially. The organic layer is then dried and concentrated in vacuo to afford 11-O-methanesulfonyl-(2S, 5S)-BL-V8-310.

A mixture of 11-O-methanesulfonyl-(2S,5S)-BL-V8-310, sodium sulfite and sodium iodide in a 1:1 mixture of ethanol/water containing a small amount of acetic acid is stirred for a period of time at an elevated temperature. After that time the mixture is concentrated in vacuo and partitioned between ethyl acetate and brine to afford a residue which is purified by liquid chromatography to yield 11-deoxy-(2S,5S)-BL-V8-310 11-sulfonic acid.

EXAMPLE 128

In a similar manner the following compounds are prepared:
(i) 11-O-(4'-hydroxyphenyl)-(2R,2S)-BL-V8-310;
(ii) 11-deoxy-11-(2'-hydroxyethylthio)-(2R,2S)-BL-V9-310;
(iii) 11-deoxy-11-cyano-(2S,5S)-BL-V8-310; and
(iv) 11-deoxy-11-azido-(2S,5S)-BL-V8-310.

EXAMPLE 129

11-Deoxy-11-oxo-BL-V8-310

To a solution of BL-V8-310 in methylene chloride is added periodinane reagent [Dess, D. B. and Martin, J. C., *J. Org. Chem.* 48: 4155–4156 (1983)]. After a period of time the mixture is diluted with ethyl acetate and washed sequentially with phosphate buffer (pH 8), aqueous sodium thiosulfate (20%), phosphate buffer (pH 2) and phosphate buffer (pH 8). The organic layer is then filtered through N/N/S and concentrated to afford 11-deoxy-11-oxo-BL-V8-310.

EXAMPLE 130

5-Des(hydroxymethyl)-5-carboxy-BL-V8-310

To a solution of 11-deoxy-11-oxo-BL-V8-310 in a mixture of methylene chloride, t-butyl alcohol and 2-methyl-2-butene is added a 10% (wt/vol) of sodium chlorite in a dihydrogen phosphate buffered solution. After a period of time 20% aqueous sodium thiosulfate is added and the mixture is partially concentrated in vacuo. The residue is partitioned between ethyl acetate and phosphate buffer (pH 8). The organic layer is washed sequentially with pH 2 and pH 8 phosphate buffers and dried over sodium sulfate. After concentration in vacuo and purification by preparative liquid chromatography, 5-des(hydroxymethyl)-5-carboxy-BL-V8-310 is obtained.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound, in the form of an individual isomer, an isomer mixture, a racemate or optical antipode, or a pharmaceutically acceptable salt thereof, of the formula:

$$P—G$$

wherein
P represents a moiety, formally derived from a parent compound of the benzolactam phorboid class, which parent compound:
  a. binds reversibly or irreversibly to a diacylglycerol-type receptor; and/or
  b. activates any form of the enzyme protein kinase C; and
  c. contains an hydroxymethyl or 1-hydroxyethyl group bonded to a carbon atom; and
P is derived by the formal removal of the hydroxymethyl or 1-hydroxyethyl group from the parent compound; and
wherein
G is any group of 55 or fewer atoms selected from the group consisting of carbon, hydrogen, oxygen, nitrogen, halogen, sulfur, phosphorus, silicon, arsenic, boron and selenium either: i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group was bound in the parent compound; and wherein the hydroxymethyl or 1-hydroxyethyl group of the parent compound is absent or has been replaced by G;
provided that, for all derived P, if G is bonded to the equivalent of carbon 5 in benzolactam, then G may not comprise —$CH_2$—$R_e^e$ wherein $R_e^e$ is selected from the group consisting of acetoxy, t-butoxy and ($C_1$–$C_6$ linear or branched alkyl)$_n$(phenyl)$_{3-n}$ silyloxy wherein n is 0–3; and provided further that, P—G may not be selected from the group consisting of (3S)-1,2,3,4,5,7-hexahydro-3-(1-methylethyl)-2-(p-toluenesulphonyl)-4-oxo-6H-2,5-benzodiazonine-6,6-dicarboxylic acid, its diethyl ester and {3S,6S(or R)}-1,2,3,4,5,7-hexahydro-3-(1-methylethyl)-2-(p-toluenesulphonyl)-4-oxo-6H-2,5-benzodiazonine-6-carboxylic acid.

2. A compound, in the form of an individual isomer, an isomer mixture, a racemate or optical antipode, or a pharmaceutically acceptable salt thereof, of the formula:

$$P_o—S_o—E_o$$

wherein
$P_o$ represents a moiety, formally derived from a parent compound of the benzolactam phorboid class, which parent compound:
  a. binds reversibly or irreversibly to a diacylglycerol-type receptor; and/or
  b. activates any form of the enzyme protein kinase C; and
  c. contains an hydroxymethyl or 1-hydroxyethyl group bonded to a carbon atom; and
$P_o$ is derived by the formal removal of the hydroxymethyl or 1-hydroxyethyl group from the parent compound; and
wherein
$S_o$—$E_o$ represents a substituent which is either i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group was bound in the parent compound; and wherein $S_o$ is an organic, substituted or unsubstituted, saturated or unsaturated or aromatic, straight or branched, acyclic or ring-containing and/or ring-carrying chain of atoms which separates $P_o$ and $E_o$ by a linear count of at least two but not more than 12 atoms and contains and/or carries not more than 9 heteroatoms selected from the group consisting of oxygen, nitrogen, silicon, sulfur, phosphorus, arsenic, boron and selenium, and carries not more than 16 halogen atoms; provided that the total number of atoms does not exceed 35; and wherein $E_o$ is selected from the group consisting of hydrogen, halogen and a saturated or singly or multiply unsaturated group containing up to 15 carbon atoms and optionally containing 1 to 12 halogen atoms and/or optionally containing 1 to 6 heteroatoms selected from the group consisting of oxygen, nitrogen, silicon, sulfur, phosphorus, arsenic, boron and selenium; or wherein $S_oE_o$ taken together is selected from the group consisting of hydrogen, halogen, thionic sulfur atom, ketonic oxygen atom, hydroxy, amine and thiol, singly or doubly bonded to the carbon atom of the parent compound $P_o$ in place of the hydroxymethyl or 1-hydroxyethyl group;

provided that, for all derived $P_o$, if $S_oE_o$ is bonded to the equivalent of carbon 5 in benzolactam, then $S_oE_o$, taken together, may not comprise —CH$_2$—R$_e^e$ wherein R$_e^e$ is selected from the group consisting of acetoxy, t-butoxy and (C$_1$–C$_6$ linear or branched alkyl)$_n$(phenyl)$_{3-n}$silyloxy wherein n is 0–3; and provided further that, $P_o$—S$_o$—E$_o$ may not be selected from the group consisting of (3,S)-1,2,3,4,5,7-hexahydro-3-(1-methylethyl)-2-(p-toluenesulphonyl)-4-oxo-6H-2,5-benzodiazonine-6,6-dicarboxylic acid, its diethyl ester and {3S,6S(or R)}-1,2,3,4,5,7-hexahydro-3-(1-methylethyl)-2-(p-toluenesulphonyl)-4-oxo-6H-2,5-benzodiazonine-6-carboxylic acid.

3. A compound of the formula:

wherein $P_7$ is a radical of the formula:

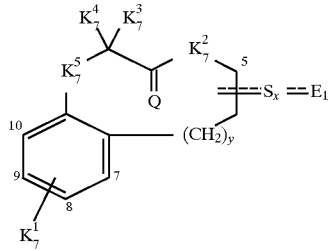

in the form of an individual isomer, an isomer mixture, a racemate or optical antipode, or a pharmaceutically acceptable salt thereof, wherein $K_7^1$ represents 1–4 identical or different substituents located at carbons 7, 8, 9 and/or 10, which substituents are independently selected from the group consisting of hydrogen, halogen and a straight chain or branched chain, cyclic or acyclic, saturated or unsaturated or aromatic carbon- and/or heteroatom-containing moiety which, taken together, contain not more than 40 carbon atoms, not more than 24 halogen atoms and not more than 9 heteroatoms selected from the group consisting of oxygen, nitrogen, silicon, phosphorus and sulfur, the moieties being optionally connected to one another and/or to $K_7^5$ to form 1–2 additional carbocyclic or heterocyclic rings;

$K_7^2$ is selected from the group consisting of oxygen, sulfur, —NK$_7^6$— and —CK$_7^6$K$_7^7$—, wherein K$_7^6$ is selected from the group consisting of hydrogen, hydroxy, methyl, ethyl, fluoro, n-propyl, allyl and propargyl and wherein K$_7^7$ is selected from the group consisting of hydrogen, methyl, ethyl, halogen, trifluoromethyl and cyano;

$K_7^3$ and $K_7^4$ are independently selected from the group consisting of hydrogen, halogen, a straight chain or branched chain, cyclic or acyclic, saturated or unsaturated or aromatic carbon- and/or heteroatom-containing moiety, an additional ring formed by connections between themselves and an additional ring formed by connection of one of $K_7^3$ or $K_7^4$ to $K_7^5$, such that $K_7^3$ and $K_7^4$, taken together, contain not more than 18 carbon atoms, not more than 12 halogen atoms, and not more than 8 heteroatoms selected from the group consisting of oxygen, nitrogen, silicon, phosphorus and sulfur;

$K_7^5$ is selected from the group consisting of oxygen, sulfur, sulfoxide, sulfone, —NK$_7^8$—, —NOK$_7^8$— and —CK$_7^8$K$_7^9$—, wherein K$_7^8$ is hydrogen or a straight chain or branched chain, cyclic or acyclic, saturated or unsaturated or aromatic carbon- and/or heteroatom-containing group containing not more than 30 carbon atoms, not more than 24 halogen atoms and not more than 8 heteroatoms selected from the group consisting of oxygen, nitrogen, silicon, phosphorus and sulfur, wherein K$_7^8$ may form an additional ring by a connection to one of $K_7^1$, $K_7^3$ or $K_4^4$, and wherein K$_7^9$ is selected from the group consisting of hydrogen, methyl, ethyl, n-propyl, hydroxy, halogen, allyl, propargyl, cyano and trifluoromethyl;

y may either be 0 or 1;

$S_xE_1$ may be bound to either carbon 5 or the carbon immediately adjacent to it; provided that: if $S_xE_1$ is hydroxymethyl or 1-hydroxyethyl, then $S_xE_1$ may not be bound to carbon 5;

wherein $S_x$ is selected from the group consisting of $S_B$, $S_1$, $S_2$, $S_3$, $S_4$, $S_5$ and $S_6$;

wherein $S_B$ is a single or double bond;

wherein $S_1$ is a chain of atoms of the formula:

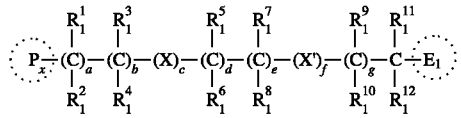

wherein a, b, d, e, and g may independently be from 0 to 3;

c and f may independently be 0 or 1;

the sum of (a+b+c+d+e+f+g) is at least 1 but not more than 12; and if c and f are both 1, then the sum of (d+e) must be at least 1;

wherein $S_2$ is a chain of atoms of the formula:

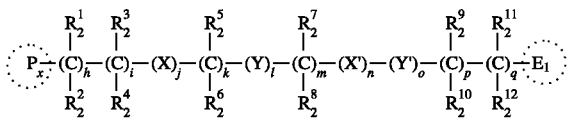

wherein h, i, k, m, p, and q may be independently be from 0 to 3;

j and n may independently be 0 or 1;

if j and n are both 1 and 1 is 0, then the sum of (k+m) must be at least 1;

if n is 1 and o is 0, then the sum of (p+q) must be at least 1;

the sum of (1+o) is 1–3;

and the sum of (h+i+j+k+2l+m+n+2o+p+q) is at least 1 but not more than 12;

wherein $S_3$ is a chain of atoms of the formula:

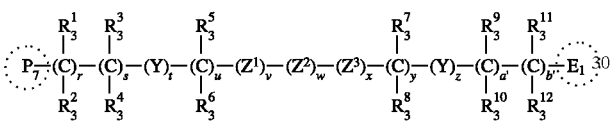

wherein r, s, u, y, a', and b' may independently be from 0 to 3;

the sum of (t+z) is 0 or 1;

the sum of (v+w+x) is 1;

the sum of (y+z+a'+b') is at least 1;

the sum of (r+s+2t+u+2v+3w+4x+y+2z+a'+b') is at least 1 but not more than 12;

wherein $S_4$ is a chain of atoms defined by:

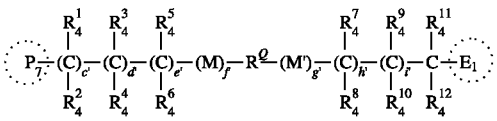

wherein c', d', e', h', and i' may independently be from 0 to 3;

the sum of (f'+g') must be 1 or 2;

f' and g' may independently be 0 or 1;

the sum of (c'+d'+e'+f'+g'+h'+i') is at least 1 but not more than 12;

wherein $S_5$ is a chain of atoms defined by:

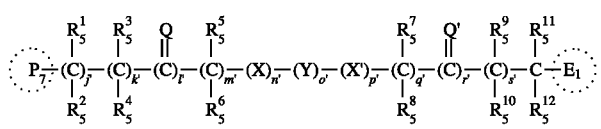

wherein j', K', m', q', and s' may independently be from 0 to 3;

l' and r' may each be 0 or 1, but the sum of (l'+r') must be 1 or 2;

n' and p' may each be 0 or 1, but the sum of (n'+p') must be 0 or 1;

the value of o' may be 0–2;

if the sum of (n'+p') is 1 and l' is 0, then q' must be at least 1;

if the sum of (n'+p') is l and r' is 0, then m' must be at least 1;

the sum of (j'+k'+l'+m'+n'+o'+p'+q'+r'+s') is at least 1 but not more than 12;

wherein $S_6$ is a chain of atoms defined by:

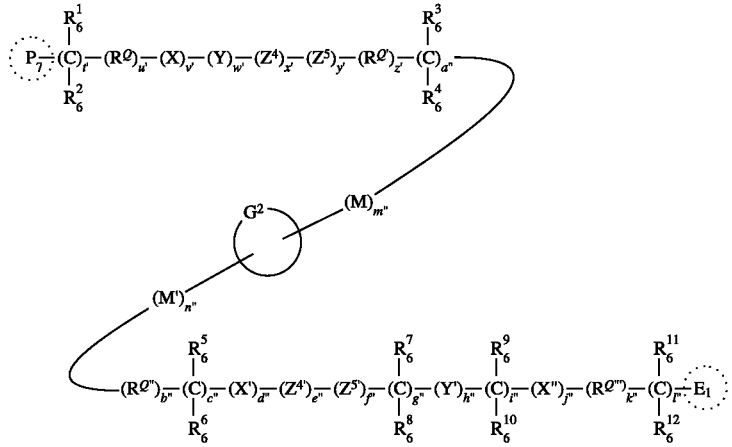

wherein u', v', w', x', y', z', and m" may each be 0 or 1;

t' and a" may each independently be 0–6;

the sum of(t'+u'+v'+2w'+x'+2y'+z'+a") must be 0–8;

b", d", e", f", h", j", k" and n" may each independently be 0 or 1;

c", g", i", and l" may each independently be 0–3;

if d" and j" are both 1, then the sum of (g"+i") must be at least 1;

if either j" or k" is 1, then l" must be at least 1;

if b" is 1, then the sum of (c"+g"+h"+i"+l") must be at least 1;

if d" is 1, then the sum of (g"+h"+i"+l") must be at least 1;

the sum of (t'+u'+v'+2w'+x'+2y'+z'+a"+b"+c"+d"+e"+2f"+g"+2h"+i"+j"+k"+l") must be 0–14;

if m" is zero, $R_6^3$ or $R_6^4$ may optionally comprise an additional bond, thereby completing an unsaturated linkage to $G^2$;

if n" and b" are zero, $R_6^5$ or $R_6^6$ may optionally comprise an additional bond, thereby completing an unsaturated linkage to $G^2$;

one of the substituents $R_6^1$–$R_6^4$ and/or one of the substituents $R_6^5$–$R_6^{12}$ may optionally comprise the same or different values of $G^1$, as defined below;

wherein, for $S_1$–$S_6$, $R_1^1$ through $R_6^{12}$ may independently be selected from the group consisting of hydrogen, halogen and a saturated or singly or multiply unsaturated, straight or branched acyclic substituent containing not more than 20 carbon atoms, not more than 16 halogen atoms, and not more than 6 heteroatoms selected from the group consisting of oxygen, nitrogen, sulfur, silicon, boron, selenium, arsenic and phosphorus, such that for any substituent the oxygen, nitrogen, sulfur, silicon and/or phosphorus atoms must be situated in functional groups selected from the group consisting of hydroxy, amino, hydroxylamine, tertiary amine oxide, Schiff's base, hydrazine, thiol, nitro, oxime, azide, ether, acetal, ketal, thioether, aldehyde, keto, hydrazone, carboxy, mercaptocarbonyl, mercaptothionocarbonyl, sulfonate, sulfonyl, sulfoxide, phosphate, phosphonate, phosphate ester, phosphonate ester, phosphine, phosphine oxide, thionophosphine, phosphite, phosphonium, phosphorothioate, thionophosphate ester, thiophosphonate, thionophosphonate ester, silane, silanol, silanediol, fluorinated silane, ester, amide, cyano, hydrazide, carbonate, carbamate, urea, isourea, carboxamidine, imidate, guanidine, thioester, thioamide, thiocarbonate, thiocarbamate, thiourea, nitroguanidine, cyanoguanidine and xanthate;

one substituent selected from the group consisting of $R_1^1$, $R_1^2$, $R_2^1$, $R_2^2$, $R_3^1$, $R_3^2$, $R_4^1$, $R_4^2$, $R_5^1$, $R_5^2$, $R_6^1$ and $R_6^2$ may optionally comprise an additional bond, thereby completing an unsaturated linkage to $P_7$;

one or two of the substituents $R_1^1$–$R_5^{12}$ may optionally comprise the same or different values of $G^1$, as defined below;

one substituent selected from the group consisting of $R_1^{11}$, $R_1^{12}$, $R_2^{11}$, $R_2^{12}$, $R_3^{11}$, $R_3^{12}$, $R_4^{11}$, $R_4^{12}$, $R_5^{11}$, $R_5^{12}$, $R_6^{11}$, and $R_6^{12}$ may optionally comprise an additional bond, thereby completing an unsaturated linkage to $E_1$;

one of the substituents $R_1^1$–$R_6^{12}$ may be linked to either the atom in $P_7$ that carries the $S_x$ chain or to an atom in $P_7$ adjacent thereto, to form a saturated or unsaturated or aromatic, carbocyclic or heterocyclic 4–8 membered ring containing 0–4 identical or different hetero ring members selected from the group consisting of —O—, —S—, —S(O)—, —S(O)$_2$—, —C(O)—, —NH— and =N—, the ring being optionally substituted by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxy-2-propyl, CF$_3$, OCF$_3$, SH, SCH$_3$, SOCH$_3$, SCF$_3$, COOH, COOCH$_3$, COCH$_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

provided that, for any given $S_1$, $S_2$, $S_3$, $S_4$, $S_5$ or $S_6$, but excluding $P_7$ and $E_1$: the total of carbon atoms is 25 or less; the total of halogen atoms is 16 or less; the total of oxygen atoms is 6 or less; the total of nitrogen atoms is 4 or less; the sulfur, silicon, boron and phosphorus atoms each total 3 or less; the arsenic and selenium atoms each total 1 or less; and the total of oxygen, nitrogen, silicon, boron, arsenic, phosphorus, selenium and sulfur atoms together is 8 or less; the total of OH groups is 3 or less; the total of NH$_2$ groups is 2 or less; the total of SH groups is 2 or less; the total of OH, SH and NH$_2$ groups, together, is 4 or less;

X, X' and X" are independently selected from the group consisting of:

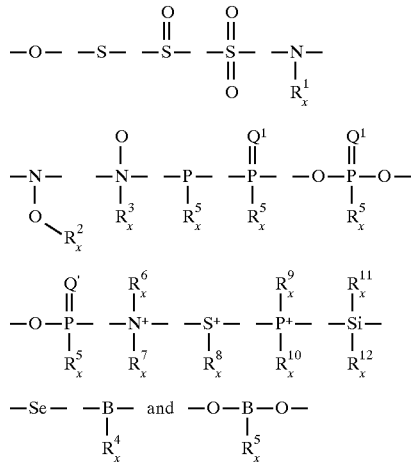

wherein $R_X^1$, $R_X^2$, $R_X^{11}$ and $R_X^{12}$ may independently be hydrogen;

$R_X^1$ through $R_X^{12}$ may independently be a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, such that for any substituent the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, mercaptocarbonyl, mercaptothionocarbonyl, sulfonate, sulfonyl, sulfoxide, ester, amide, cyano, carbonate, carbamate, urea, isourea, carboxamidine, guanidine, thioester, thioamide, thiocarbamate, thiourea, nitroguanidine, cyanoguanidine and xanthate; wherein said functional groups are separated from the atom to which $R_X^1$–$R_X^{12}$ is attached by at least two carbon atoms;

$R_X^4$, $R_X^5$, $R_X^{11}$ and $R_X^{12}$ may independently be hydroxy;

$R_X^1$ may optionally represent an additional bond, thereby completing an unsaturated linkage to $P_7$;

one or two of the substituents $R_X^1-R_X^{12}$ may optionally comprise the same or different values of $G^1$, as defined below;

wherein

Y and Y' are selected from the group consisting of:

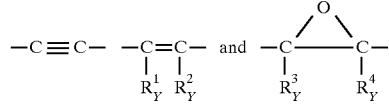

wherein $R_Y^1$ and $R_Y^2$, and $R_Y^3$ and $R_y^4$, each pair being cis or trans relative to one another, may independently be hydrogen or a saturated or singly or multiply unsaturated, straight or branched acyclic substituent containing not more than 20 carbon atoms, not more than 16 halogen atoms, and not more than 6 heteroatoms selected from the group consisting of oxygen, nitrogen and sulfur, such that for any substituent the oxygen atoms total 4 of less, the nitrogen atoms total 4 or less, and the sulfur atoms total 2 or less, the heteroatoms being situated in functional groups as defined for $R_X^1-R_X^{12}$;

$R_Y^1$ and $R_Y^2$ may also independently be a halogen;

one or two of the substituents $R_Y^1-R_Y^4$ may optionally comprise the same or different values of $G^1$, as defined below;

one of the substituents selected from the group consisting of $R_X^1-R_X^{12}$ and $R_Y^1-R_Y^4$ may be linked to either the atom in $P_7$ that carries the chain containing X, X', X", Y and/or Y' or to an atom in $P_7$ adjacent thereto, to form a 4–8 membered ring defined as for the analogous $R_1^1-R_6^{12}$-containing ring above;

wherein $Z^1$ is selected from the group consisting of:

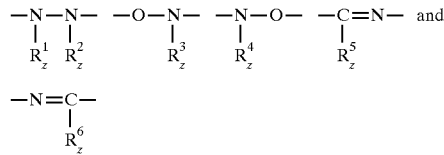

$Z^2$ is selected from the group consisting of:

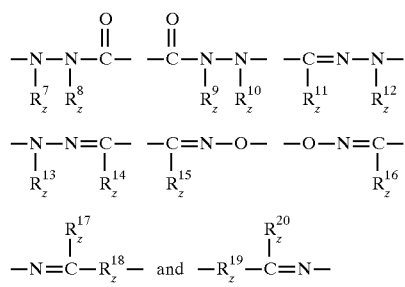

$Z^3$ is selected from the group consisting of:

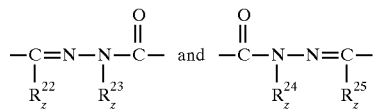

$Z^4$ and $Z^{4'}$ independently are:

and $Z^5$ and $Z^{5'}$ independently are selected from the group consisting of

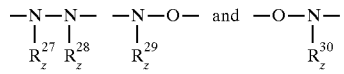

wherein $R_Z^{26}$ may be any of the values specified for $R_X^1-R_X^{12}$ above;

$R_Z^{18}$ and $R_Z^{19}$ may independently be selected from the group consisting of —O—, —S— and —$NR_Z^{21}$— wherein $R_Z^{21}$ may be selected from the group consisting of hydrogen, $C_{1-4}$ alkyl, 2-hydroxyethyl, 2-hydroxy-n-propyl, 2-acetoxyethyl and 2-acetoxy-n-propyl;

$R_Z^{17}$ and $R_Z^{20}$ may independently be hydrogen or a substituent selected from the group consisting of $C_{1-4}$ alkyl, $C_{1-4}$ alkoxy, $C_{1-4}$ alkylthio, phenoxy or thiophenoxy wherein each phenyl group may optionally be substituted by moieties selected from the group consisting of methyl, hydroxy, hydroxymethyl, thiol, carboxy, carboxymethyl, amino, methoxy, halogen and nitro, and amino optionally mono- or disubstituted by $C_{1-4}$ alkyl or monosubstituted by a substituent selected from the group consisting of cyano, nitro and phenyl (optionally substituted by moieties selected from the group consisting of halogen, hydroxy, hydroxymethyl, thiol, carboxy, carboxymethyl, amino and nitro);

$R_Z^1-R_Z^{16}$, $R_Z^{22}-R_Z^{25}$ and $R_Z^{27}-R_Z^{30}$ may independently be hydrogen or a saturated or unsaturated substituent selected from the group consisting of $C_{1-6}$ alkyl, $C_{1-6}$ halogenated alkyl, cyclohexyl and phenyl or benzyl wherein each phenyl group may optionally be substituted by moieties selected from the group consisting of methyl, ethyl, hydroxy, hydroxymethyl, thiol, carboxy, carboxymethyl, amino, methoxy, nitro, cyano, trifluoromethyl and halogen;

$R_Z^1-R_Z^4$, $R_Z^7$, $R_Z^{10}$, $R_Z^{12}$, $R_Z^{13}$ and $R_Z^{27}-R_Z^{30}$ may also be independently selected from the group consisting of $C_{1-6}$ acyl, $C_{1-6}$ halogenated acyl, $C_{2-6}$ monohydroxyacyl and $C_{2-6}$ hydroxyalkyl;

$R_Z^5$ and $R_Z^6$ may also be independently selected from the group consisting of $C_{1-6}$ hydroxyalkyl, $C_{1-6}$ alkoxy and $C_{1-6}$ hydroxyalkoxy;

$R_Z^8$, $R_Z^9$, $R_Z^{23}$ and $R_Z^{24}$ may also independently be $C_{2-6}$ hydroxyalkyl;

one of the substituents $R_Z^1-R_Z^{17}$, $R_Z^{20}$, $R_Z^{21}$, $R_Z^{22}$ and $R_Z^{25}$ may be linked to either the atom in $P_7$ that carries the chain containing $Z^1$, $Z^2$ or $Z^3$ or to an atom in $P_7$ adjacent thereto, to form a saturated or unsaturated or aromatic, carbocyclic or heterocyclic 4–8 membered ring containing 0–4 identical or different hetero ring members selected from the group consisting of O, S, =N— and NH, the ring being optionally substituted on its carbon and/or NH members by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy; p1 $R_Z^{26}$ may comprise $G^1$ as defined below, and/or an optional ring may be formed between $R_Z^{26}$ and $P_7$ as described above for $R_1^1$–$R_6^{12}$;

$R_Z^1$, $R_Z^4$, $R_Z^7$, $R_Z^{26}$ or $R_Z^{27}$ may comprise an additional bond, thereby completing an unsaturated linkage to $P_7$;

only one of the substituents $R_Z^1$–$R_Z^{25}$ may be substituted or unsubstituted phenyl or benzyl;

wherein

M and M' are independently selected from the group consisting of:

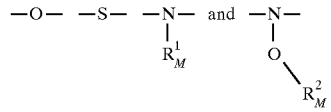

wherein $R_M^1$ and $R_M^2$ may independently be hydrogen or a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, in which the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, ester, amide, cyano, nitroguanidine and cyanoguanidine;

$R_M^1$ may optionally comprise an additional bond, thereby completing an unsaturated linkage to $P_7$;

$R_M^1$ or $R_M^2$ may optionally comprise the same or different values of $G^1$, as defined below;

$R_M^1$ or $R_M^2$ may be linked to either the atom in $P_7$ that carries the chain containing M and/or M' or to an atom in $P_7$ adjacent thereto, to form a 4–8 membered ring defined as for the analogous $R_1^1$–$R_6^{12}$-containing ring above;

wherein

Q, Q' and Q''' are independently selected from the group consisting of:

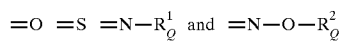

and wherein Q'' is selected from the group consisting of:

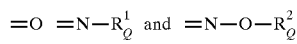

wherein $R_Q^1$ and $R_Q^2$ may independently be hydrogen or a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, in which the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, ester, amide, cyano, nitroguanidine and cyanoguanidine;

$R_Q^1$ and/or $R_Q^2$ may optionally comprise the same or different values of $G^1$, as defined below;

$R_Q^1$ may be linked to either the atom in $P_7$ that carries the chain containing Q and/or Q' or to an atom in $P_7$ adjacent thereto, to form a 4–8 membered ring defined as for $R_1^1$–$R_6^{12}$-containing ring above;

wherein $R^Q$–$R^{Q'''}$ are independently selected from the group consisting of:

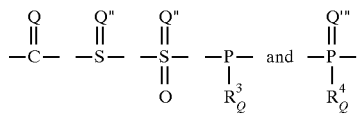

wherein $R_Q^3$ and $R_Q^4$ may independently be selected from the group consisting of halogen, hydrogen and a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, in which the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, ester, amide, cyano, nitroguanidine and cyanoguanidine;

$R_Q^3$ and/or $R_Q^4$ may optionally comprise the same or different values of $G^1$, as defined below;

one of $R_Q^3$ and $R_Q^4$ may be linked to either the atom in $P_7$ bonded to the chain that carries $R^Q$ or to an atom in $P_7$ adjacent thereto, to form a 4–8 membered ring defined as for $R_1^1$–$R_6^{12}$-containing ring above;

wherein $G^1$ and $G^2$ independently comprise a group containing 1–3 fused or separate, saturated or unsaturated or aromatic, carbocyclic or heterocyclic 4–8 membered rings, each ring containing 0–4 identical or different hetero ring members selected from the group consisting of —O—, —S—, —S(O)—, —S(O)$_2$—, —C(O)—, —NH— and =N—, each ring being optionally substituted on its carbon and/or NH members by 1–8 identical or different substituents, selected from the group consisting of halogen, hydroxy, methoxy, ethoxy, methyl, ethyl, cyano, azide, nitro, hydroxymethyl, 1-hydroxyethyl, 2-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

wherein for $G^1$ the optional second and third rings may be fused to the first ring and/or to one another or may be separate rings connected to one another and/or to the atom bearing $G^1$ by a single or double bond or by an intervening substituted or unsubstituted, linear or branched, saturated or unsaturated chain containing not more than 8 carbon atoms, not more than 8 halogens, and not more than 4 heteroatoms selected from the group consisting of oxygen, nitrogen, silicon, boron, arsenic, phosphorus, selenium and sulfur;

and wherein for $G^2$ the first ring is singly or doubly bonded to $P_7$ or to a component atom of the $S_6$ chain connecting $P_7$ and $G^2$, and the optional second and third rings may be fused to the first ring or to one another or may be separate rings connected to one another and/or to the first ring by single or double bonds or by an intervening substituted or unsubstituted, linear or branched, saturated or unsaturated chain containing not more than 8 carbon atoms, not more than 8 halogens, and not more than 4 heteroatoms selected from the group consisting of oxygen, nitrogen, silicon, boron, arsenic, phosphorus, selenium and sulfur;

wherein $E_1$ is selected from the group consisting of =O, =S, =NH, =NOR$_E^8$ wherein R$_E^8$ is hydrogen or a $C_1$–$C_8$ normal or branched alkyl radical, =N—NH$_2$, hydrogen, halogen, —OH, —SH, —NH$_2$, —NH—NH$_2$, —N$_3$, —CN, —NO, —NO$_2$, —NHOH, —ONH$_2$,

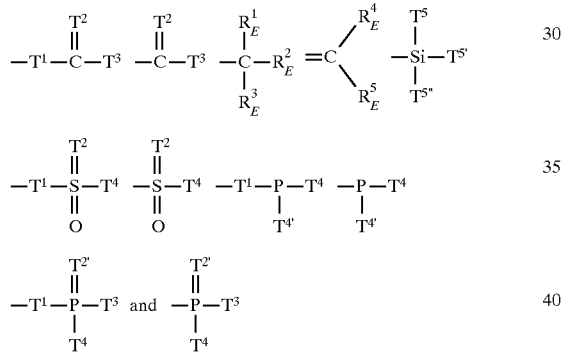

wherein $T^1$ is selected from the group consisting of —O—, —S— and —NH—;

$T^2$ is selected from the group consisting of =O, =S and =N—R$_E^6$ wherein R$_E^6$ is selected from the group consisting of hydrogen, hydroxy, cyano and nitro;

$T^{2'}$ is selected from the group consisting of =O and =S;

$T^3$, $T^4$ and $T^{4'}$ may independently be selected from the group consisting of —OH, —NH$_2$, —SH, —N$_3$, —NH—NH$_2$ and —NH—OR$_E^7$ wherein R$_E^7$ is selected from the group consisting of hydrogen, $C_{1-3}$ alkyl and $C_{1-3}$ acyl;

$T^3$ may also be hydrogen or halogen;

$T^5$ is selected from the group consisting of hydrogen, halogen and hydroxy;

$T^{5'}$ and $T^{5''}$ are independently hydrogen or hydroxy;

R$_E^1$ is selected from the group consisting of hydrogen, halogen, hydroxy, nitro, nitroso, cyano, azide, —NH$_2$, —NH—OH, —SH, —O—NH$_2$, —NH—NH$_2$, —T$^1$—C(=T$^2$)—T$^3$, —C(=T$^2$)—T$^3$, —SiT$^5$T$^{5'}$T$^{5''}$, —T$^1$—S(=O)(=T$^2$)—T$^4$, —S(=O)(=T$^2$)—T$^4$, —T$^1$—P(=T$^4$)—T$^{4'}$, —P(—T$^4$)—T$^{4'}$, —T$^1$13 P(=T$^2$)(—T$^3$)—T$^4$ and —P(=T$^2$)(—T$^3$)—T$^4$;

R$_E^2$ and R$_E^3$ may individually be selected from the group consisting of hydrogen, —C(=T$^2$)—T$^3$, cyano, nitro, azide, halogen and a $C_1$–$C_{15}$ straight or branched chain, saturated or unsaturated or aromatic-containing alkyl moiety optionally containing not more than 10 halogen atoms and not more than 4 heteroatoms selected from the group consisting of oxygen, nitrogen and sulfur;

if R$_E^1$ is cyano or —C(=T$^2$)—T$^3$, then R$_E^2$ or R$_E^3$ may optionally be selected from the group consisting of —SiT$^5$T$^{5'}$T$^{5''}$, —T$^1$—P(=T$^{2'}$)(—T$^3$)—T$^4$ and —P(=T$^{2'}$)(—T$^3$)—T$^4$; and R$_E^4$ and R$_E^5$ are individually selected from the group consisting of hydrogen, halogen, cyano, nitro, —C(=T$^2$)—T$^3$, —T$^1$—C(=T$^2$)—T$^3$, —CR$_E^1$R$_E^2$R$_E^3$, —SiT$^5$T$^{5'}$T$^{5''}$, —S(=O)(=T$^2$)—T$^4$ and —P(=T$^{2'}$)(—T$^3$)—T$^4$; and provided that: for all $P_7$, if $S_xE_1$ is bonded to the equivalent of carbon 5 in benzolactam, then $S_xE_1$, taken together, may not comprise —CH$_2$—R$_e^e$ wherein R$_e^e$ is selected from the group consisting of acetoxy, t-butoxy and ($C_1$–$C_6$ linear or branched alkyl)$_n$(phenyl)$_{3-n}$silyloxy wherein n is 0–3.

4. A compound of claim 3 wherein $S_xE_1$, taken together, is selected from the group consisting of (i) a moiety selected from the group consisting of dihalomethyl, trihalomethyl, —N$_3$, —NH$_2$, —CN, —COOH, —CH=CHCOOH, —C≡CCOOH, —CSSH, —COSH, —SO$_2$H, —SO$_3$H, —PO$_3$H$_2$, —P(=O)(R$_a^a$)OH, —P(=S)(R$_a^a$)OH, —P(=O)(OR$_a^a$)OH, —P(=S)(OR$_a^a$)OH, —CH=NOH, —CH=NOCH$_3$, —CH=N(→O)CH$_3$, —C(CH$_3$)=NOH, —CH=CHR$_a^a$, —C≡C—R$_a^a$, —CH$_2$C≡C—R$_a^a$, —Si(CH$_3$)$_2$OH, —Si(OH)$_2$CH$_3$, —Si(CH$_3$)$_2$F, —Si(CH$_3$)$_2$R$_a^a$, —CH$_2$Si(CH$_3$)$_2$R$_a^a$ and =CHR$_a^a$; and (ii) —CH$_2$— or —CH(CH$_3$)—, to either of which is bonded a moiety selected from the group consisting of —R$_a^a$, —F, —N$_3$, —NH$_2$, —CN, —COOH, —COSH, —CSSH, —Si(CH$_3$)$_2$OH, —Si(OH)$_2$CH$_3$, —Si(CH$_3$)$_2$F, —SO$_2$H, —SO$_3$H, —PO$_3$H$_2$, —P(=O)(R$_a^a$)OH, —P(=S)(R$_a^a$)OH, —P(=O)(OR$_a^a$)OH, —P(=S)(OR$_a^a$)OH, the o-, m- or p-isomer of —M—C$_6$H$_4$CH$_2$—T$^3$, the o-, m- or p-isomer of —C$_6$H$_4$CH$_2$—T$^3$, —SR$_a^a$, —SCH$_2$CH$_2$OH, —S(=O)CH$_2$CH$_2$OH, —S(CH$_2$)$_3$OH, —S(CH$_2$)$_4$OH, —SCH$_2$CH$_2$SH, —M—C(=T$^2$)—M'—R$_a^a$, —OCH$_2$C(=O)CH$_3$, —OCH$_2$C(=NOH)CH$_3$, the o-, m- or p-isomer of —M—C(=T$^2$)—M'—C$_6$H$_4$—T$^3$, the o-, m- or p-isomer of —M—C(=T$^2$)—M'—C$_6$H$_4$CH$_2$—T$^3$ and -imidazol-2-yl;

wherein R$_a^a$ is hydrogen or $C_{1-12}$ linear or branched, saturated or unsaturated or aromatic hydrocarbon optionally substituted by not more than 16 halogens.

5. A compound of claim 3 wherein $K_7^2$ is NK$_7^6$, $K_7^5$ is NK$_7^8$ and $S_xE_1$ is bonded to carbon 5 forming $P_{7B}$:

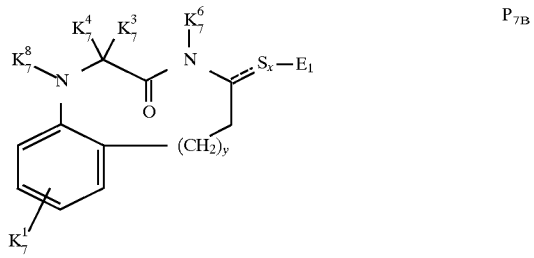

6. A compound of claim 5 wherein $K_7^4$ and $K_7^6$ are hydrogen, $K_7^8$ is methyl and y is 0 forming $P_{7BL}$

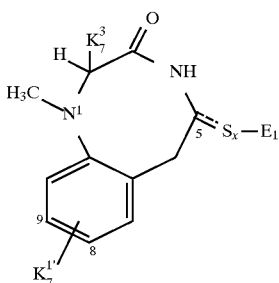

wherein
$K_7^1$ represents 1–2 identical or different substituents attached to carbons 8 and/or 9, which substituents are independently selected from the group consisting of hydrogen, halogen and a straight chain or branched chain, cyclic or acyclic, saturated or unsaturated or aromatic carbon- and/or heteroatom-containing moiety which, taken together, contain not more than 40 carbon atoms, not more than 24 halogen atoms and not more than 9 heteroatoms selected from the group consisting of oxygen, nitrogen, silicon, phosphorus and sulfur, the moieties being optionally connected to one another to form 1–2 additional carbocyclic or heterocyclic rings.

7. A compound of claim 6 selected from the group consisting of:
(i) 11-O-(4'-hydroxyphenyl)-(2R,2S)-BL-V8-310;
(ii) 11-deoxy-11-(2'-hydroxyethylthio)-(2R,2S)-BL-V9-310;
(iii) 11-deoxy-11-cyano-(2S,5S)-BL-V8-310;
(iv) 11-deoxy-11-azido-(2S,5S)-BL-V8-310;
(v) 11-O-(N-methyl)carbamoyl-(2S,5S)-BL-V8-310;
(vi) 11-O-methanesulfonyl-(2S,5S)-BL-V8-310;
(vii) 11-deoxy-(2S,5S)-BL-V8-310 11-sulfonic acid;
(viii) 11-deoxy-11-oxo-BL-V8-310;
(ix) 5-des(hydroxymethyl)-5-carboxy-BL-V8-310;
(x) 11-deoxy-11-oxo-epi-BL-V9-310; and
(xi) 5-des(hydroxymethyl)-5-[2'-methoxycarbonyl)-(E)-vinyl]-epi-BL-V9-310.

8. A compound comprising a phorboid-type pharmacological antagonist of the diacylglycerol binding site of protein kinase C, a phorboid-type noninflammatory agonist of the diacylglycerol binding site of protein kinase C, a phorboid-type pharmacological antagonist of a diacylglycerol binding site or a noninflammatory phorboid-type agonist of a diacylglycerol binding site, excluding compounds of the:
a) diterpene phorboid class;
b) indole, indene, benzofuran and benzothiophene phorboid class, further here defined by the mandatory presence of a substituted or unsubstituted six-atom chain connecting positions 3 and 4 of the indole, indene, benzofuran or benzothiophene skeleton to form an additional 9-membered ring and by the optional presence in this class of one or two nitrogen atoms at any of positions 5, 6 and 7 of the benzenoid ring portion of the skeleton;
c) bryostatin phorboid class;
d) polyacetate-derived phorboid class;
e) diaminobenzyl alcohol phorboid class;
f) diacylglycerol and diacyloxybutanol phorboid class;
g) benzolactam phorboid class wherein the group attached to carbon 5 is hydroxymethyl, acetoxymethyl, t-butoxymethyl or $(C_1–C_6$ linear or branched alkyl)$_n$ (phenyl)$_{3-n}$silyloxy wherein n is 0–3 or wherein the compound is (3S)-1,2,3,4,5,7-hexahydro-3-(1-methylethyl)-2-(p-toluenesulphonyl)-4-oxo-6H-2,5-benzodiazonine-6,6-dicarboxylic acid, its diethyl ester or {3S,6S(or R)}-1,2,3,4,5,7-hexahydro-3-(1-methylethyl)-2-(p-toluenesulphonyl)-4-oxo-6H-2,5-benzodiazonine-6-carboxylic acid;
h) perylenequinone class; and,
i) naphthodianthrone class.

9. A compound of claim 8 wherein the compound is selected from the benzolactam phorboid class.

10. A composition comprising:
a physiologically acceptable pharmaceutical carrier; and
a compound, in a quantity of between about 0.001–1000 mg per unit dosage, in the form of an individual isomer, an isomer mixture, a racemate or optical antipode, or a pharmaceutically acceptable salt thereof, of the formula:

$$P\text{—}G$$

wherein
P represents a moiety, formally derived from a parent compound of the benzolactam phorboid class, which parent compound:
a. binds reversibly or irreversibly to a diacylglycerol-type receptor; and/or
b. activates any form of the enzyme protein kinase C; and
c. contains an hydroxymethyl or 1-hydroxyethyl group bonded to a carbon atom; and P is derived by the formal removal of the hydroxymethyl or 1-hydroxyethyl group from the parent compound; and wherein
G is any group of 55 or fewer atoms selected from the group consisting of carbon, hydrogen, oxygen, nitrogen, halogen, sulfur, phosphorus, silicon, arsenic, boron and selenium either: i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group was bound in the parent compound; and wherein the hydroxymethyl or 1-hydroxyethyl group of the parent compound is absent or has been replaced by G.

11. A composition comprising:
a physiologically acceptable pharmaceutical carrier; and
a compound, in a quantity of between about 0.000–1000 mg per unit dosage, in the form of an individual isomer, an isomer mixture, a racemate or optical antipode, or a pharmaceutically acceptable salt thereof, of the formula:

$$P_o\text{—}S_o\text{—}E_o$$

wherein
$P_o$ represents a moiety, formally derived from a parent compound of the benzolactam phorboid class, which parent compound:
a. binds reversibly or irreversibly to a diacylglycerol-type receptor; and/or
b. activates any form of the enzyme protein kinase C; and c. contains an hydroxymethyl or 1-hydroxyethyl group bonded to a carbon atom; and $P_o$ is derived by the formal removal of the hydroxymethyl or 1-hydroxyethyl group from the parent compound; and wherein $S_o$—$E_o$ represents a substituent which is either i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group was bound in the parent compound; and wherein $S_o$ is an organic, substituted or unsubstituted, saturated or unsaturated or aromatic, straight or branched, acyclic or ring-containing and/or ring-carrying chain of atoms which separates $P_o$ and $E_o$ by a linear count of at least two but not more than 12 atoms and contains and/or carries not more than 9 heteroatoms selected from the group consisting of oxygen, nitrogen, silicon, sulfur, phosphorus, arsenic, boron and selenium, and carries not more than 16 halogen atoms; provided that the total number of atoms does not exceed 35; and wherein $E_o$ is selected from the group consisting of hydrogen, halogen and a saturated or singly or multiply unsaturated group containing up to 15 carbon atoms and optionally containing 1 to 12 halogen atoms and/or optionally containing 1 to 6 heteroatoms selected from the group consisting of oxygen, nitrogen, silicon, sulfur, phosphorus, arsenic, boron and selenium; or wherein $S_oE_o$ taken together is selected from the group consisting of hydrogen, halogen, thionic sulfur atom, ketonic oxygen atom, hydroxy, amine and thiol, singly or doubly bonded to the carbon atom of the parent compound $P_o$ in place of the hydroxymethyl or 1-hydroxyethyl group.

12. A composition comprising:

a physiologically acceptable pharmaceutical carrier; and a compound, in a quantity of between about 0.001–1000 mg per unit dosage, of the formula:

wherein $P_7$ is a radical of the formula:

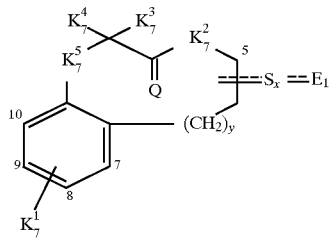

in the form of an individual isomer, an isomer mixture, a racemate or optical antipode, or a pharmaceutically acceptable salt thereof, wherein $K_7^1$ represents 1–4 identical or different substituents located at carbons, 7, 8, 9, and/or 10, which substituents are independently selected from the group consisting of hydrogen, halogen and a straight chain or branched chain, cyclic or acyclic saturated or unsaturated or aromatic carbon- and/or heteroatom-containing moiety which, taken together, contain not more than 40 carbon atoms, not more than 24 halogen atoms and not more than 9 heteroatoms selected from the group consisting of oxygen, nitrogen, silicon, phosphorus and sulfur, the moieties being optionally connected to one another and/or to $K_7^5$ to form 1–2 additional carbocyclic or heterocyclic rings;

$K_7^2$ is selected from the group consisting of oxygen, sulfur, —$NK_7^6$— and —$CK_7^6K_7^7$—wherein $K_7^6$ is selected from the group consisting of hydrogen, hydroxy, methyl, ethyl, fluoro, n-propyl, allyl and propargyl and wherein $K_7^7$ is selected from the group consisting of hydrogen, methyl, ethyl, halogen, trifluoromethyl and cyano;

$K_7^3$ and $K_7^4$ are independently selected from the group consisting of hydrogen, halogen, a straight chain or branched chain, cyclic or acyclic saturated or unsaturated or aromatic carbon- and/or heteroatom-containing moiety, an additional ring formed by connection between themselves and an additional ring formed by connections of one of $K_7^3$ or $K_7^4$ to $K_7^5$, such that $K_7^3$ and $K_7^4$, taken together, contain not more than 18 carbon atoms, not more than 12 halogen atoms, and not more than 8 heteroatoms selected from the group consisting of oxygen, nitrogen, silicon, phosphorus and sulfur;

$K_7^5$ is selected from the group consisting of oxygen, sulfur, sulfoxide, sulfone, —$NK_7^8$—, —$NOK_7^8$— and —$CK_7^8K_7^9$—, wherein $K_7^8$ is hydrogen or a straight chain or branched chain, cyclic or acyclic, saturated or unsaturated or aromatic carbon- and/or heteroatom-containing group containing not more than 30 carbon atoms, not more than 24 halogen atoms and not more than 8 heteroatoms selected from the group consisting of oxygen, nitrogen, silicon, phosphorus and sulfur, wherein $K_7^8$ may form an additional ring by a connection to one of $K_7^1$, $K_7^3$ or $K_7^4$, and wherein $K_7^9$ is selected from the group consisting of hydrogen, methyl, ethyl, n-propyl, hydroxy, halogen, allyl, propargyl, cyano and trifluoromethyl;

y may either be 0 or 1;

$S_xE_1$ may be bound to either carbon 5 or the carbon immediately adjacent to it; provided that: if $S_xE_1$ is hydroxymethyl or 1-hydroxyethyl, then $S_xE_1$ may not be bound to carbon 5;

wherein $S_x$ is selected from the group consisting of $S_B$, $S_1$, $S_2$, $S_3$, $S_4$, $S_5$ and $S_6$;

wherein $S_B$ is a single or double bond;

wherein wherein $S_1$ is a chain of atoms of the formula:

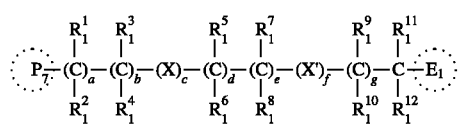

wherein a, b, d, e, and g may independently be from 0 to 3;

c and f may independently be 0 or 1;

the sum of (a+b+c+d+e+f+g) is at least 1 but not more than 12; and if c and f are both 1, then the sum of (d+e) must be at least 1;

wherein $S_2$ chain of atoms of the formula:

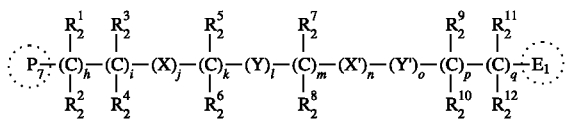

wherein h, i, k, m, p, and q may be independently be from 0 to 3;

j and n may independently be 0 or 1;

if j and n are both 1 and l is 0, then the sum of (k+m) must be at least 1;

if n is 1 and o is 0, then the sum of (p+q) must be at least 1;

the sum of (l+o) is 1–3;

and the sum of (h+i+j+k+2l+m+n+2o+p+q) is at least 1 but not more than 12;

wherein $S_3$ is a chain of atoms of the formula:

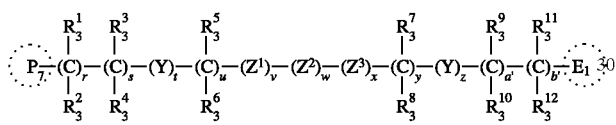

wherein r, s, u, y, a', and b' may independently be from 0 to 3;

the sum of (t+z) is 0 or 1;

the sum of (v+w+x) is 1;

the sum of (y+z+a'+b') is at least 1;

the sum of (r+s+2t+u+2v+3w+4x+y+2z+a'+b') is at least 1 but not more than 12;

wherein $S_4$ is a chain of atoms defined by:

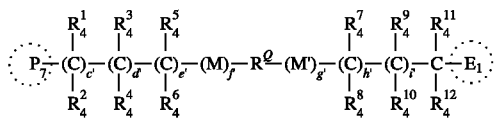

wherein c', d', e', h', and i' may independently be from 0 to 3;

the sum of (f'+g') must be 1 or 2;

f' and g' may independently be 0 or 1;

the sum of (c'+d'+e'+f'+g'+h'+i') is at least 1 but not more than 12;

wherein $S_5$ is a chain of atoms defined by:

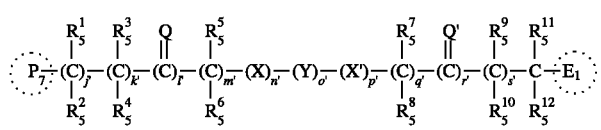

wherein j', k', m', q', and s' may independently be from 0 to 3;

l' and r' may each be 0 or 1, but the sum of (l'+r') must be 1 or 2;

n' and p' may each be 0 or 1, but the sum of (n'+p') must be 0 or 1;

the value of o' may be 0–2;

if the sum of (n'+p') is 1 and l' is 0, then q' must be at least 1;

if the sum of (n'+p') is 1 and r' is 0, then m' must be at least 1;

the sum of (j'+k'+l'+m'+n'+o'+p'+q'+r'+s') is at least 1 but not more than 12;

wherein $S_6$ is a chain of atoms defined by:

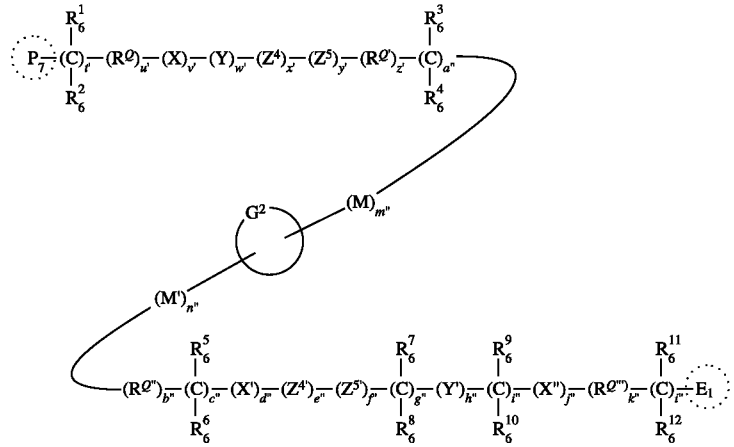

wherein u', v', w', x', y', z', and m" may each be 0 or 1;

t' and a" may each independently be 0–6;

the sum of(t'+u'+v'+2w'+x'+2y'+z'+a") must be 0–8;

b", d", e", f", h", j", k" and n" may each independently be 0 or 1;

c", g", i", and l" may each independently be 0–3;

if d" and j" are both 1, then the sum of (g"+i") must be at least 1;

if either j" or k" is 1, then l" must be at least 1;

if b" is 1, then the sum of (c"+g"+h"+i"+l") must be at least 1;

if d" is 1, then the sum of (g"+h"+i"+l") must be at least 1;

the sum of (t'+u'+v'+2w'+x'+2y'+z'+a"+b"+c"+d"+e"+2f"+g"+2h"+i"+j"+k"+l") must be 0–14;

if m" is zero, $R_6^3$ or $R_6^4$ may optionally comprise an additional bond, thereby completing an unsaturated linkage to $G^2$;

if n"and b"are zero, $R_6^5$ or $R_6^6$ may optionally comprise an additional bond, thereby completing an unsaturated linkage to $G^2$;

one of the substituents $R_6^1$–$R_6^4$ and/or one of the substituents $R_6^5$–$R_6^{12}$ may optionally comprise the same or different values of $G^1$, as defined below;

wherein, for $S_1$–$S_6$, $R_1^1$ through $R_6^{12}$ may independently be selected from the group consisting of hydrogen, halogen and a saturated or singly or multiply unsaturated, straight or branched acyclic substituent containing not more than 20 carbon atoms, not more than 16 halogen atoms, and not more than 6 heteroatoms selected from the group consisting of oxygen, nitrogen, sulfur, silicon, boron, selenium, arsenic and phosphorus such that for any substituent the oxygen, nitrogen, sulfur, silicon and/or phosphorus atoms must be situated in functional groups selected from the group consisting of hydroxy, amino hydroxylamine, tertiary amine oxide, Schiff's base, hydrazine, thiol, nitro, oxime, azide, ether, acetal, ketal, thioether, aldehyde, keto, hydrazone, carboxy, mercaptocarbonyl, mercaptothionocarbonyl, sulfonate, sulfonyl, sulfoxide, phosphate, phosphonate, phosphate ester, phosphonate ester, phosphine, phosphine oxide, thionophosphine, phosphite, phosphonium, phosphorothioate, thionophosphate ester, thiophosphonate, thionophosphonate ester, silane, silanol, silanediol, fluorinated silane, ester, amide, cyano, hydrazide, carbonate, carbamate, urea, isourea, carboxamidine, imidate, guanidine, thioester, thioamide, thiocarbonate, thiocarbamate, thiourea, nitroguanidine, cyanoguanidine and xanthate;

one substituent selected from the group consisting of $R_1^1$, $R_1^2$, $R_2^1$, $R_2^2$, $R_3^1$, $R_3^2$, $R_4^1$, $R_4^2$, $R_5^1$, $R_5^2$, $R_6^1$ and $R_6^2$ may optionally comprise an additional bond, thereby completing an unsaturated linkage to $P_7$;

one or two of the substituents $R_1^1$–$R_5^{12}$ may optionally comprise the same or different values of $G^1$, as defined below;

one substituent selected from the group consisting of $R_1^{11}$, $R_1^{12}$, $R_2^{11}$, $R_2^{12}$, $R_3^{11}$, $R_3^{12}$, $R_4^{11}$, $R_4^{12}$, $R_4^{11}$, $R_4^{12}$, $R_5^{11}$, $R_5^{12}$, $R_6^{11}$ and $R_6^{12}$ may optionally comprise an additional bond, thereby completing an unsaturated linkage to $E_1$;

one of the substituents $R_1^1$–$R_6^{12}$ may be linked to either the atom in $P_7$ that carries the $S_x$ chain or to an atom in $P_7$ adjacent thereto, to form a saturated or unsaturated or aromatic, carbocyclic or heterocyclic 4–8 membered ring containing 0–4 identical or different hetero ring members selected from the group consisting of —O—, —S—, —S(O)—, —S(O)$_2$—, —C(O)—, —NH— and =N—, the ring being optionally substituted by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxy-2-propyl, CF$_3$, OCF$_3$, SH, SCH$_3$, SOCH$_3$, SCF$_3$, COOH, COOCH$_3$, COCH$_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

provided that, for any given $S_1$, $S_2$, $S_3$, $S_4$, $S_5$ or $S_6$, but excluding $P_7$ and $E_1$: the total of carbon atoms is 25 or less; the total of halogen atoms is 16 or less; the total of oxygen atoms is 6 or less; the total of nitrogen atoms is 4 or less; the sulfur, silicon, boron and phosphorus atoms each total 3 or less; the arsenic and selenium atoms each total 1 or less; and the total of oxygen, nitrogen, silicon, boron, arsenic, phosphorus, selenium and sulfur atoms together is 8 or less; the total of OH groups is 3 or less; the total of NH$_2$ groups is 2 or less; the total of SH groups is 2 or less; the total of OH, SH and NH$_2$ groups, together, is 4 or less;

X, X' and X" are independently selected from the group consisting of:

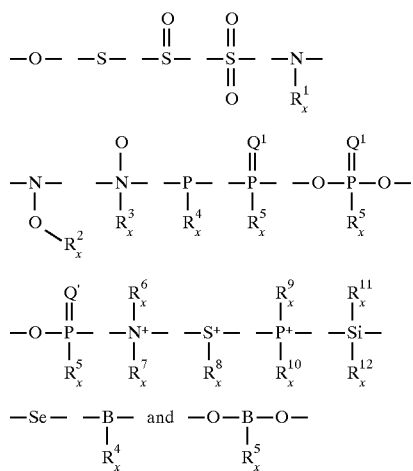

wherein $R_X^1$, $R_X^2$, $R_X^{11}$ and $R_X^{12}$ may independently be hydrogen;

$R_X^1$ through $R_X^{12}$ may independently be a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, such that for any substituent the oxygen atoms total 4 or less, the nitrogen atoms total 4 or less, and the sulfur atoms total 2 or less, the heteroatoms being situated in functional groups selected from the group consisting of hydroxy, amino, thiol nitro, azide, ether, thioether, aldehyde, keto, carboxy, mercaptocarbonyl, mercaptothionocarbonyl, sulfonate, sulfonyl, sulfoxide, ester, amide, cyano, carbonate, carbamate, urea, isourea, carboxamidine, guanidine, thioester, thioamide, thiocarbamate, thiourea, nitroguanidine, cyanoguanidine and xanthate; wherein said functional groups are separated from the atom to which $R_X^1$–$R_X^{12}$ is attached by at least two carbon atoms;

$R_X^4$, $R_X^5$, $R_X^{11}$ and $R_X^{12}$ may independently be hydroxy;

$R_X^1$ may optionally represent an additional bond, thereby completing an unsaturated linkage to $P_7$;

one or two of the substituents $R_X^1$–$R_X^{12}$ may optionally comprise the same or different values of $G^1$, as defined below;

wherein

Y and Y' are selected from the group consisting of:

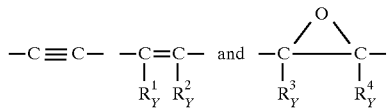

wherein $R_Y^1$ and $R_Y^2$, and $R_Y^3$ and $R_Y^4$, each pair being cis or trans relative to one another, may independently be hydrogen or a saturated or singly or multiply unsaturated, straight or branched acyclic substituent containing not more than 20 carbon atoms, not more than 16 halogen atoms, and not more than 6 heteroatoms selected from the group consisting of oxygen, nitrogen and sulfur, such that for any substituent the oxygen atoms total 4 of less, the nitrogen atoms total 4 or less, and the sulfur atoms total 2 or less, the heteroatoms being situated in functional group as defined for $R_X^1$–$R_X^{12}$;

$R_Y^1$ and $R_Y^2$ may also independently be a halogen;

one or two of the substituents $R_Y^1$–$R_Y^4$ may optionally comprise the same or different values of $G^1$, as defined below;

one of the substituents selected from the group consisting of $R_X^1$–$R_X^{12}$ and $R_Y^1$–$R_Y^4$ may be linked to either the atom in $P_7$ that carries the chain containing X, X', X", Y and/or Y' or to an atom in $P_7$ adjacent thereto, to form a 4–8 membered ring defined as for the analogous $R_1^1$–$R_6^{12}$-containing ring above;

wherein $Z^1$ is selected from the group consisting of:

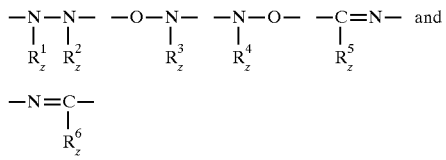

$Z^2$ is selected from the group consisting of:

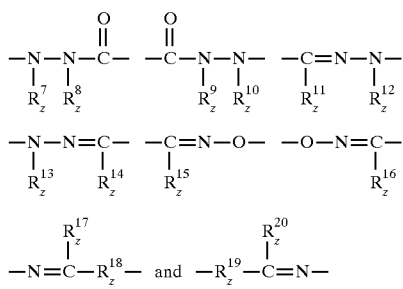

$Z^3$ is selected from the group consisting of:

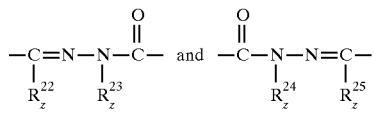

$Z^4$ and $Z^{4'}$ independently are:

and $Z^5$ and $Z^{5'}$ independently are selected from the group consisting of:

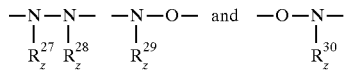

wherein $R_Z^{26}$ may be any of the values specified for $R_X^1$–$R_X^{12}$ above;

$R_Z^{18}$ and $R_Z^{19}$ may independently be selected from the group consisting of —O—, —S— and —$NR_Z^{21}$— wherein $R_Z^{21}$ may be selected from the group consisting of hydrogen, $C_{1-4}$ alkyl, 2-hydroxyethyl, 2-hydroxy-n-propyl, 2-acetoxyethyl and 2-acetoxy-n-propyl;

$R_Z^{17}$ and $R_Z^{20}$ may independently be hydrogen or a substituent selected from the group consisting of $C_{1-4}$ alkyl, $C_{1-4}$ alkoxy, $C_{1-4}$ alkylthio, phenoxy or thiophenoxy wherein each phenyl group may optionally be substituted by moieties selected from the group consisting of methyl, hydroxy, hydroxymethyl, thiol, carboxy, carboxymethyl, amino, methoxy, halogen and nitro, and amino optionally mono- or disubstituted by $C_{1-4}$ alkyl or monosubstituted by a substituent selected from the group consisting of cyano, nitro and phenyl (optionally substituted by moieties selected from the group consisting of halogen, hydroxy, hydroxymethyl, thiol, carboxy, carboxymethyl, amino and nitro);

$R_Z^1$–$R_Z^{16}$, $R_Z^{22}$–$R_Z^{25}$ and $R_Z^{27}$–$R_Z^{30}$ may independently be hydrogen or a saturated or unsaturated substituent selected from the group consisting of $C_{1-6}$ alkyl, $C_{1-6}$ halogenated alkyl, cyclohexyl and phenyl or benzyl wherein each phenyl group may optionally be substituted by moieties selected from the group consisting of methyl, ethyl, hydroxy, hydroxymethyl, thiol, carboxy, carboxymethyl, amino, methoxy, nitro, cyano, trifluoromethyl and halogen;

$R_Z^1$–$R_Z^4$, $R_Z^7$, $R_Z^{10}$, $R_Z^{12}$, $R_Z^{13}$ and $R_Z^{27}$–$R_Z^{30}$ may also be independently selected from the group consisting of $C_{1-6}$ acyl, $C_{1-6}$ halogenated acyl, $C_{2-6}$ monohydroxyacyl and $C_{2-6}$ hydroxyalkyl;

$R_Z^5$ and $R_Z^6$ may also be independently selected from the group consisting of $C_{1-6}$ hydroxyalkyl, $C_{1-6}$ alkoxy and $C_{1-6}$ hydroxyalkoxy;

$R_Z^8$, $R_Z^9$, $R_Z^{23}$ and $R_Z^{24}$ may also independently be $C_{2-6}$ hydroxyalkyl;

one of the substituents $R_Z^1$–$R_Z^{17}$, $R_Z^{20}$, $R_Z^{21}$, $R_Z^{22}$ and $R_Z^{25}$ may be linked to either the atom in $P_7$ that carries the chain containing $Z^1$, $Z^2$ or $Z^3$ or to an atom in $P_7$ adjacent thereto, to form a saturated or unsaturated or aromatic, carbocyclic or heterocyclic 4–8 membered ring containing 0–4 identical or different hetero ring members selected from the group consisting of O, S, =N— and NH, the ring being optionally substituted on its carbon and/or NH members by 1–8 identical or different substituents selected from the group consisting of halogen, hydroxy, methoxy, ethoxy, methyl, ethyl, cyano, azide, nitro, hydroxymethyl, 1-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

$R_Z^{26}$ may comprise $G^1$ as defined below, and/or an optional ring may be formed between $R_Z^{26}$ and $P_7$ as described above for $R_1^1$–$R_6^{12}$;

$R_Z^1$, $R_Z^4$, $R_Z^7$, $R_Z^{26}$ or $R_Z^{27}$ may comprise an additional bond, thereby completing an unsaturated linkage to $P_7$;

only one of the substituents $R_Z^1$–$R_Z^{25}$ may be substituted or unsubstituted phenyl or benzyl;

wherein

M and M' are independently selected from the group consisting of:

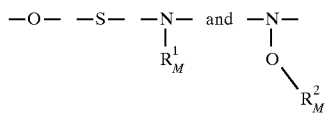

wherein $R_M^1$ and $R_M^2$ may independently be hydrogen or a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, in which the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, ester, amide, cyano, nitroguanidine and cyanoguanidine;

$R_M^1$ may optionally comprise an additional bond, thereby completing an unsaturated linkage to $P_7$;

$R_M^1$ or $R_M^2$ may optionally comprise the same or different values of $G^1$, as defined below;

$R_M^1$ or $R_M^2$ may be linked to either the atom in $P_7$ that carries the chain containing M and/or M' or to an atom in $P_7$ adjacent thereto, to form a 4–8 membered ring defined as for the analogous $R_1^1$–$R_6^{12}$-containing ring above;

wherein

Q, Q' and Q''' are independently selected from the group consisting of:

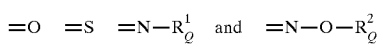

and wherein Q'' is selected from the group consisting of:

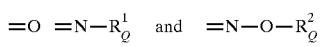

wherein $R_Q^1$ and $R_Q^2$ may independently be hydrogen or a saturated or singly or multiply unsaturated, straight or branched acyclic substituent containing 1–20 carbon atoms, not more than 16 halogen atoms, and not more than 6 heteroatoms selected from the group consisting of oxygen, nitrogen and sulfur, in which the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, ester, amide, cyano, nitroguanidine and cyanoguanidine;

$R_Q^1$ and/or $R_Q^2$ may optionally comprise the same or different values of $G^1$, as defined below;

$R_Q^1$ may be linked to either the atom in $P_7$ that carries the chain containing Q and/or Q' or to an atom in $P_7$ adjacent thereto, to form a 4–8 membered ring defined as for $R_1^1$–$R_6^{12}$-containing ring above;

wherein $R^Q$–$R^{Q'''}$ are independently selected from the group consisting of:

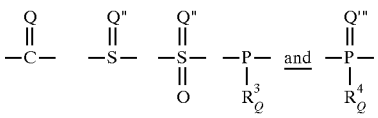

wherein $R_Q^3$ and $R_Q^3$ may independently be selected from the group consisting of halogen, hydrogen and a saturated or singly or multiply unsaturated straight or branched acyclic substituent containing 1–20 carbon atoms, not more than 16 halogen atoms, and not more than 6 heteroatoms selected from the group consisting of oxygen, nitrogen and sulfur, in which the oxygen atoms total 4 or less, the nitrogen atoms total 4 or less, and the sulfur atoms total 2 or less, the heteroatoms being situated in functional groups selected from the group consisting of hydroxy, amino, thiol, nitro, azide, ether, thioether, aldehyde, keto, carboxy, ester, amide, cyano, nitroguanidine and cyanoguanidine;

$R_Q^3$ and/or $R_Q^3$ may optionally comprise the same or different values of $G^1$, as defiined below one of $R_Q^3$ and $R_Q^4$ may be linked to either the atom in $P_7$ bonded to the chain that carries $R_Q$ or to an atom in $P_7$ adjacent thereto, to form a 4–8 membered ring defined as for $R_1^1$-$R_6^{12}$-containing ring above;

wherein $G^1$ and $G^2$ independently comprise a group containing 1–3 fused or separate, saturated or unsaturated or aromatic, carbocyclic or heterocyclic 4–8 membered rings, each ring containing 0–4 identical or different hetero ring members selected from the group consisting of —O—, —S—, —S(O)—, —S(O)$_2$—, —C(O)—, —NH— and =N—, each ring being optionally substituted on its carbon and/or NH members by 1–8 identical or different substituents, selected from the group consisting of halogen, hydroxy, methoxy, ethoxy, methyl, ethyl, cyano, azide, nitro, hydroxymethyl, 1-hydroxyethyl, 2-hydroxyethyl, 2-hydroxy-2-propyl, $CF_3$, $OCF_3$, SH, $SCH_3$, $SOCH_3$, $SCF_3$, COOH, $COOCH_3$, $COCH_3$, CH=O, acetoxy, amino, mono- or dialkylamino totaling 1–4 carbon atoms inclusive, acetamido, N-methylacetamido, carboxamido, N-alkylated carboxamido containing 1–4 carbon atoms inclusive, hydroxyacetyl and hydroxyacetoxy;

wherein for $G^1$ the optional second and third rings may be fused to the first ring and/or to one another or may be separate rings connected to one another and/or to the atom bearing $G^1$ by a single or double bond or by an intervening substituted or unsubstituted, linear or branched, saturated or unsaturated chain containing not more than 8 carbon atoms, not more than 8 halogens, and not more than 4 heteroatoms selected from the group consisting of oxygen, nitrogen, silicon, boron, arsenic, phosphorus, selenium and sulfur;

and wherein for $G^2$ the first ring is singly or doubly bonded to $P_7$ or to a component atom of the $S_6$ chain connecting $P_7$ and $G^2$, and the optional second and third rings may be fused to the first ring or to one another or may be separate rings connected to one another and/or to the first ring by single or double bonds or by an intervening substituted or unsubstituted, linear or branched, saturated or unsaturated chain containing not more than 8 carbon atoms, not more than 8 halogens, and not more than 4 heteroatoms selected from the group consisting of oxygen, nitrogen, silicon, boron, arsenic, phosphorus, selenium and sulfur;

wherein $E_1$ is selected from the group consisting of =O, =S, =NH, =NOR$_E^8$ wherein R$_E^8$ is hydrogen or a $C_1-C_8$ normal or branched alkyl radical, =N—NH$_2$, hydrogen, halogen, —OH, —SH, —NH$_2$, —NH—NH$_2$, —N$_3$, —CN, —NO, —NO$_2$, —NHOH, —ONH$_2$,

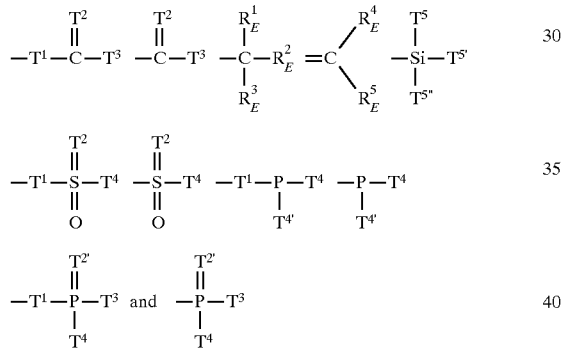

wherein $T^1$ is selected from the group consisting of —O—, —S— and —NH—;

$T^2$ is selected from the group consisting of =O, =S and =N—R$_E^6$ wherein R$_E^6$ is selected from the group consisting of hydrogen, hydroxy, cyano and nitro;

$T^{2'}$ is selected from the group consisting of =O and =S;

$T^3$, $T^4$ and $T^{4'}$ may independently be selected from the group consisting of —OH, —NH$_2$, —SH, —N$_3$, —NH—NH$_2$ and —NH—OR$_E^7$ wherein R$_E^7$ is selected from the group consisting of hydrogen, $C_{1-3}$ alkyl and $C_{1-3}$ acyl;

$T^3$ may also be hydrogen or halogen;

$T^5$ is selected from the group consisting of hydrogen, halogen, and hydroxy;

$T^{5'}$ and $T^{5''}$ are independently hydrogen or hydroxy;

R$_E^1$ is selected from the group consisting of hydrogen, halogen, hydroxy, nitro, nitroso, cyano, azide, —NH$_2$, —NH—OH, —SH, —O—NH$_2$, —NH—NH$_2$, —T$^1$—C(=T$^2$)—T$^3$, —C(=T$^2$)—T$^3$, —SiT$^5$T$^{5'}$T$^{5''}$, —T$^1$—S(=O)(=T$^2$)—T$^4$, —S(=O)(=T$^2$)—T$^4$, —T$^1$—P(—T$^4$)—T$^{4'}$, —P(—T$^4$)—T$^{4'}$, —T$^1$—P(=T$^2$)(—T$^3$)—T$^4$ and —P(=T$^2$)(—T$^3$)—T$^4$;

R$_E^2$ and R$_E^3$ may individually be selected from the group consisting of hydrogen, —C(=T$^2$)—T$^3$, cyano, nitro, azide, halogen and a $C_1-C_{15}$ straight or branched chain, saturated or unsaturated or aromatic-containing alkyl moiety optionally containing not more than 10 halogen atoms and not more than 4 heteroatoms selected from the group consisting of oxygen, nitrogen and sulfur;

if R$_E^1$ is cyano or —C(=T$^2$)—T$^3$, then R$_E^2$ or R$_E^3$ may optionally be selected from the group consisting of —SiT$^5$T$^{5'}$T$^{5''}$, —T$^1$—P(=T$^2$)(—T$^3$)—T$^4$ and —P(=T$^2$)(—T$^3$)—T$^4$; and R$_E^4$ and R$_E^5$ are individually selected from the group consisting of hydrogen, halogen, cyano, nitro, —C(=T$^2$)—T$^3$, —T$^1$—C(=T$^2$)—T$^3$, —CR$_E^1$R$_E^2$R$_E^3$, —SiT$^5$T$^{5'}$T$^{5''}$, —S(=O)(=T$^2$)—T$^4$ and —P(=T$^2$)(—T$^3$)—T$^4$.

13. A composition of claim 12 wherein $S_xE_1$ of the compound, taken together, is selected from the group consisting of:

(i) a moiety selected from the group consisting of dihalomethyl, trihalomethyl, —N$_3$, —NH$_2$, —CN, —COOH, —CH=CHCOOH, —C≡CCOOH, —CSSH, —COSH, —SO$_2$H, —SO$_3$H, —PO$_3$H$_2$, —P(=O)(oR$_a^a$)OH, —P(=S)(R$_a^a$)OH, —P(=O)(OR$_a^a$)OH, —P(=S)(OR$_a^a$)OH, —CH=NOH, —CH=NOCH$_3$, —CH=N(—O)CH$_3$, —C(CH$_3$)=NOH, —CH=CHR$_a^a$, —C≡C—R$_a^a$, —CH$_2$C≡C—R$_a^a$, —Si(CH$_3$)$_2$OH, —Si(OH)$_2$CH$_3$, —Si(CH$_3$)$_2$F, —Si(CH$_3$)$_2$R$_a^a$, —CH$_2$Si(CH$_3$)$_2$R$_a^a$ and =CHR$_a^a$; and (ii) —CH$_2$— or —CH(CH$_3$)—, to either of which is bonded a moiety selected from the group consisting of —R$_a^a$, —F, —N$_3$, —NH$_2$, —CN, —COOH, —COSH, —CSSH, —Si(CH$_3$)$_2$OH, —Si(OH)$_2$CH$_3$, —Si(CH$_3$)$_2$F, —SO$_2$H, —SO$_3$H, —PO$_3$H$_2$, —P(=O)(R$_a^a$)OH, —P(=S)(R$_a^a$)OH, —P(=O)(OR$_a^a$)OH, —P(=S)(OR$_a^a$)OH, the o-, m- or p-isomer of —M—C$_6$H$_4$CH$_2$—T$^3$, the o-, m- or p-isomer of —C$_6$H$_4$CH$_2$—T$^3$, —SR$_a^a$, —SCH$_2$CH$_2$OH, —S(=O)CH$_2$CH$_2$OH, —S(CH$_2$)$_3$OH, —S(CH$_2$)$_4$OH, —SCH$_2$CH$_2$SH, —M—C(=T$^2$)—M'—R$_a^a$, —OCH$_2$C(=O)CH$_3$, —OCH$_2$C(=NOH)CH$_3$, the o-, m- or p-isomer of —M—C(=T$^2$)—M'—C$_6$H$_4$—T$^3$, the o-, m- or p-isomer of —M—C(=T$^2$)—M'—C$_6$H$_4$CH$_2$—T$^3$ and -imidazol-2-yl;

wherein

R$_a^a$ is hydrogen or $C_{1-12}$ linear or branched, saturated or unsaturated or aromatic hydrocarbon optionally substituted by not more than 16 halogens.

14. A composition of claim 12 wherein K$_7^2$ is NK$_7^6$, K$_7^5$ is NK$_7^8$ and $S_xE_1$ is bonded to carbon 5 forming P$_{7B}$:

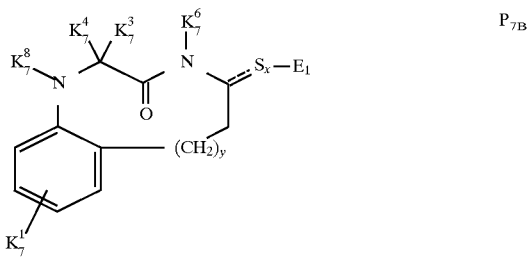

15. A composition of claim 14 wherein K$_7^4$ and K$_7^6$ are hydrogen, K$_7^8$ is methyl and y is 0 forming P$_{7BL}$

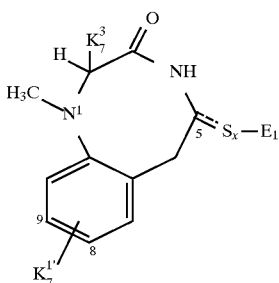

wherein $K_7^{1'}$ represents 1–2 identical or different substituents attached to carbons 8 and/or 9, which substituents are independently selected from the group consisting of hydrogen, halogen and a straight chain or branched chain, cyclic or acyclic, saturated or unsaturated or aromatic carbon- and/or heteroatom-containing moiety which, taken together, contain not more than 40 carbon atoms, not more than 24 halogen atoms and not more than 9 heteroatoms selected from the group consisting of oxygen, nitrogen, silicon, phosphorus and sulfur, the moieties being optionally connected to one another to form 1–2 additional carbocyclic or heterocyclic rings.

16. A composition of claim 15 wherein the compound is selected from the group consisting of:
(i) 11-O-(4'-hydroxyphenyl)-(2R,2S)-BL-V8-310;
(ii) 11-deoxy-11-(2'-hydroxyethylthio)-(2R,2S)-BL-V9-310;
(iii) 11-deoxy-11-cyano-(2S,5S)-BL-V8-310;
(iv) 11-deoxy-11-azido-(2S,5S)-BL-V8-310;
(v) 11-O-(N-methyl)carbamoyl-(2S,5S)-BL-V8-310;
(vi) 11-O-methanesulfonyl-(2S,5S)-BL-V8-310;
(vii) 11-deoxy-(2S,5S)-BL-V8-310 11-sulfonic acid;
(viii) 11-deoxy-11-oxo-BL-V8-310;
(ix) 5-des(hydroxymethyl)-5-carboxy-BL-V8-310;
(x) 11-deoxy-11-oxo-epi-BL-V9-310; and
(xi) 5-des(hydroxymethyl)-5-[2'-methoxycarbonyl)-(E)-vinyl]-epi-BL-V9-310.

17. A composition consisting of:
a physiologically acceptable pharmaceutical carrier; and
a compound comprising a phorboid-type pharmacological antagonist of the diacylglycerol binding site of protein kinase C, a phorboid-type noninflammatory agonist of the diacylglycerol binding site of protein kinase C, a phorboid-type pharmacological antagonist of a diacylglycerol binding site or a noninflammatory phorboid-type agonist of a diacylglycerol binding site, excluding compounds of the:
a) diterpene phorboid class;
b) indole, indene, benzofuran and benzothiophene phorboid class, further here defined by the mandatory presence of a substituted or unsubstituted six-atom chain connecting positions 3 and 4 of the indole, indene, benzofuran or benzothiophene skeleton to form an additional 9-membered ring and by the optional presence in this class of one or two nitrogen atoms at any of positions 5, 6 and 7 of the benzenoid ring portion of the skeleton;
c) bryostatin phorboid class;
d) polyacetate-derived phorboid class;
e) perylenequinone class; and
f) naphthodianthrone class.

18. A composition of claim 17 wherein the compound is a phorboid-type pharmacological antagonist of the diacylglycerol binding site of protein kinase C.

19. A composition of claim 17 wherein the compound is a noninflammatory phorboid-type agonist of the diacylglycerol binding site of protein kinase C.

20. A composition of claim 17 wherein the compound is a phorboid-type pharmacological antagonist of a diacylglycerol binding site.

21. A composition of claim 17 wherein the compound is a noninflammatory phorboid-type agonist of the diacylglycerol binding site.

22. A composition of claim 17 wherein compounds of the diaminobenzyl alcohol phorboid class are excluded.

23. A composition of claim 22 wherein compounds of the diacylglycerol-diacyloxtbutanol phorboid class are excluded.

24. A composition of claim 17 wherein the compound is selected from the diaminobenzyl alcohol phorboid class.

25. A composition of claim 17 wherein the compound is selected from the diacylglycerol-diacyloxybutanol phorboid class.

26. A composition of claim 17 wherein the compound is selected from the benzolactam phorboid class.

27. A method of treating inflammation in a mammal in need of anti-inflammatory or anti-psoriatic treatment comprising the step of administering a composition of claim 10 to said mammal.

28. A method of treating inflammation in a mammal in need of anti-inflammatory or anti-psoriatic treatment comprising the step of administering a composition of claim 11 to said mammal.

29. A method of treating a inflammation in mammal in need of anti-inflammatory or anti-psoriatic treatment comprising the step of administering a composition of claim 12 to said mammal.

30. A method of modulating protein kinase C activity comprising the step of contacting protein kinase C, in vitro or in vivo, with a composition of claim 10.

31. A method of modulating protein kinase C activity comprising the step of contacting protein kinase C, in vitro or in vivo, with a composition of claim 11.

32. A method of modulating protein kinase C activity comprising the step of contacting protein kinase C, in vitro or in vivo, with a composition of claim 12.

33. A method of modulating protein kinase C activity comprising the step of contacting protein kinase C, in vitro or in vivo, with a composition of claim 13.

34. A method of modulating protein kinase C activity comprising the step of contacting protein kinase C, in vitro or in vivo, with a composition of claim 17.

35. A method for treating a mammal infected with a virus which comprises administering to a mammal in need of such treatment an antivirally effective quantity of a composition of claim 13; provided that, said composition does not include compounds wherein $S_xE_1$, taken together, is selected from the group consisting of:
(i) a moiety selected from the group consisting of —COOH, —CH=CHCOOH, —C≡CCOOH, —CSSH, —COSH, —SO$_2$H, —SO$_3$H, —PO$_3$H$_2$, —P(=O)(R$_a^a$)OH, —P(=S)(R$_a^a$)OH, —P(=O)(OR$_a^a$)OH and —P(=S)(OR$_a^a$)OH; and
(ii) —CH$_2$— or —CH(CH$_3$)—, to either of which is bonded a moiety selected from the group consisting of —COOH, —COSH, —CSSH, —SO$_2$H, —SO$_3$H, —PO$_3$H$_2$, —P(=O)(R$_a^a$)OH, —P(=S)(R$_a^a$)OH, —P(=O)(OR$_a^a$)OH and —P(=S)(OR$_a^a$)OH.

36. A method of claim 35 wherein said virus is a retrovirus.

37. A method of claim 36 wherein said retrovirus is a Human Immunodeficiency Virus.

38. A method of claim 35 wherein the composition contains, in addition, one or more pharmaceuticals selected from the group consisting of:
   (i) a nucleoside analog;
   (ii) a tetrahydroimidazo benzodiazepin-2(1H)-one derivative; and
   (iii) a protease inhibitor.

39. A method of producing a phorboid antagonist or a non-inflammatory agonist ligand selective for one or more phorboid receptors and/or protein kinase C subtypes, comprising the step of replacing a hydroxymethyl or 1-hydroxyethyl group of a parent compound with $S_oE_o$, which parent compound:
   a. binds reversibly or irreversibly to a diacylglycerol-type receptor; and/or
   b. activates any form of the enzyme protein kinase C; and
   c. contains an hydroxymethyl or 1-hydroxyethyl group bonded to a carbon atom; and wherein
   $S_o$—$E_o$ represents a substituent which is either i) singly or doubly bonded to the carbon atom of the parent compound in place of the hydroxymethyl or 1-hydroxyethyl group; or ii) singly or doubly bonded to a carbon atom immediately adjacent to the carbon atom to which the hydroxymethyl or 1-hydroxyethyl group was bound in the parent compound; and wherein
   $S_o$ is an organic, substituted or unsubstituted, saturated or unsaturated or aromatic, straight or branched, acyclic or ring-containing and/or ring-carrying chain of atoms which separates the parent-compound moiety (the parent compound without the hydroxymethyl or 1-hydroxyethyl group) and $E_o$ by a linear count of at least two but not more than 12 atoms and contains and/or carries not more than 9 heteroatoms selected from the group selected from oxygen, nitrogen, silicon, sulfur, phosphorus, arsenic, boron and selenium, and carries not more than 16 halogen atoms; provided that the total number of atoms does not exceed 35; and wherein
   $E_o$ is selected from the group consisting of hydrogen, halogen and a saturated or singly or multiply unsaturated group containing up to 15 carbon atoms and optionally containing 1 to 12 halogen atoms and/or optionally containing 1 to 6 heteroatoms selected from the group consisting of oxygen, nitrogen, silicon, sulfur, phosphorus, arsenic, boron and selenium; or wherein
   $S_oE_o$, taken together, is selected from the group consisting of hydrogen, halogen, thionic sulfur atom, ketonic oxygen atom, hydroxy, amine and thiol, singly or doubly bonded to the carbon atom of the parent compound in place of the hydroxymethyl or 1-hydroxyethyl group.

* * * * *